United States Patent [19]

Nakanishi et al.

[11] Patent Number: 5,492,836
[45] Date of Patent: Feb. 20, 1996

[54] METHOD FOR DETERMINING THE STRUCTURE OF OLIGOSACCHARIDE LINKAGES AND AUTOMATED INSTRUMENTATION THEREOF

[75] Inventors: Koji Nakanishi, New York, N.Y.;
Harold V. Meyers, Belmont, Mass.;
William T. Wiesler, Boulder, Colo.;
Makoto Ojika, Ama, Japan

[73] Assignee: The Trustees of Columbia University in the City of New York, New York, N.Y.

[21] Appl. No.: 665,311

[22] Filed: Mar. 6, 1991

Related U.S. Application Data

[63] Continuation-in-part of Ser. No. 441,157, Nov. 21, 1989, abandoned.

[30] Foreign Application Priority Data

Nov. 21, 1990 [WO] WIPO ...................... PCT/US90/06821

[51] Int. Cl.$^6$ .......................... G01N 33/00; G01N 21/00; F01N 3/10
[52] U.S. Cl. .......................... 436/94; 436/171; 436/173; 435/4; 422/70; 422/82.05; 422/82.09
[58] Field of Search .......................... 436/94, 171, 173; 435/4; 422/70, 82.05, 82.09

[56] References Cited

U.S. PATENT DOCUMENTS 5,104,508   4/1992   Williams et al. .................... 204/182.8

*Primary Examiner*—David A. Redding
*Attorney, Agent, or Firm*—John P. White

[57] ABSTRACT

The invention provides a method for determining the structure of a carbohydrate sample, comprising perbenzoylating a carbohydrate sample with a perbenzoylating agent to protect free hydroxyl groups in the carbohydrate sample; cleaving the glycosidic linkages of the perbenzoylated carbohydrate sample by contacting the carbohydrate sample with an amount of $BrCH_2COBr/H_2O$ effective to cleave the carbohydrate sample; treating the resulting product with AgOAc and methanol or AgOTf/TMU and methanol to effect glycosidation; treating the resulting product with thiourea to remove bromoacetate groups; subjecting the resulting product to effect methoxycinnamoylation of free hydroxyl groups; separating the resulting benzoates with high-pressure liquid chromatography; performing mass, ultraviolet and circular dichroic spectroscopy on the separated benzoates; and comparing the spectra so obtained with reference spectra or calculated values to identify the structure of the carbohydrate. The invention also provides an apparatus for automatically determining the structure of a carbohydrate molecule such as an oligosaccharide.

18 Claims, 136 Drawing Sheets

1 ml vol

I: CBAA  II: ABAC  III: ABCA
IV: AACC  V: CACA  VI: CAAC

METHOD FOR DETERMINING THE STRUCTURE OF OLIGOSACCHARIDE LINKAGES AND AUTOMATED INSTRUMENTATION THEREOF

This invention was made with support under Grant Number GM 34509 from the National Institute of Health, U.S. Department of Health and Human Resources. Accordingly, the U.S. Government has certain rights in the invention. This application is a continuation-in-part of U.S. Ser. No. 441,157, filed Nov. 21, 1989 now abandoned, the contents of which are hereby incorporated by reference into the present application.

BACKGROUND OF THE INVENTION

This invention relates to a method for determining the structure of carbohydrates and more particularly to a method for cleaving and reacting oligosaccharides to give bichromophoric derivatives, separating the derivatives and measuring their characteristics using spectrophotometric methods and determining the structure of the derivatives by spectrophotometric methods. The invention also relates to novel laboratory apparatus which can automatically carry out the structural determination of microscale quantities of oligosaccharides and carbohydrates.

The automatic analysis of amino acid content in protein and peptide samples is known and automatic instruments are available commercially to accomplish this task on samples of unknown structure. An example of such a system is Applied Biosystems Model 420A. In this system, a protein sample is deposited on a glass slide, hydrolyzed and "derivatized" using reagents dispensed by the system. The derivatives of the sample are extracted and delivered to the separation system where they are separated in a micro liquid chromatography column. An ultraviolet detector detects each amino acid present and determines its concentration. The data is displayed by a computer or stored for further analysis.

Likewise, an automated system exists for sequencing nucleic acids, and U.S. Pat. No. 4,811,218 discloses such an apparatus. According to that patent, the apparatus makes use of an enzymatic method of sequencing originally developed by Smith. The patent discloses an improved detecting apparatus capable of sequencing more than one clone at a time.

Neither of these instruments is applicable to structural or analytical work involving sugars. Increasing interest in the structure and properties of such compounds has created a demand for sophisticated yet simplified analysis of oligosaccharides and other types of sugars. Unfortunately, oligosaccharide structure is more difficult to determine because it involves ascertaining the structure of the saccharide subunits and their absolute configuration, and finally their anomeric structure.

SUMMARY OF THE INVENTION

The invention provides a method for determining the structure of a carbohydrate sample, comprising perbenzoylating a carbohydrate sample with a perbenzoylating agent to protect free hydroxyl groups in the carbohydrate sample; cleaving the glycosidic linkages of the perbenzoylated carbohydrate sample by contacting the carbohydrate sample with an amount of $BrCH_2COBr/H_2O$ effective to cleave the carbohydrate sample; treating the resulting product with silver acetate (AgOAc) and methanol or AgOTf/TMU (silver triflate/tetramethylurea) and methanol to effect glycosidation; treating the resulting product with thiourea to remove bromoacetate groups; subjecting the resulting product to effect methoxycinnamoylation of free hydroxyl groups; separating the resulting benzoates with high-pressure liquid chromatography; performing mass, ultraviolet and circular dichroic spectroscopy on the separated benzoates; and comparing the spectra so obtained with reference spectra or calculated values to identify the structure of the carbohydrate.

The invention also provides an apparatus for use in determining the structure of a carbohydrate, comprising at least one reaction vessel for reacting a carbohydrate sample with reagents to cleave the carbohydrates into subunits and introduce chromophoric entities onto the subunits; means for introducing the reagents into the reaction vessel; means for removing a sample from the reaction vessel; means for separating benzoates resulting from introduction of chromophoric entities onto the subunits; means for delivering a sample of the separated benzoates to each of a plurality of spectrophotometric instruments; means for determining the mass spectrum of a sample of the resulting benzoates; means for determining the ultraviolet spectrum of a sample of the resulting benzoates; means for determining the circular dichroic spectrum of a sample of the resulting benzoates; and means for comparing the mass, ultraviolet and circular dichroic spectra to reference spectra and values in order to determine the structure of the sample carbohydrate.

The invention further provides a method for cleaving a carbohydrate comprising contacting carbohydrate sugar molecule with an amount of a mixture of $BrCH_2COBr$ and water effective to cleave the glycosidic linkages.

DETAILED DESCRIPTION OF THE PREFERRED EMBODIMENT

Figure 1A:
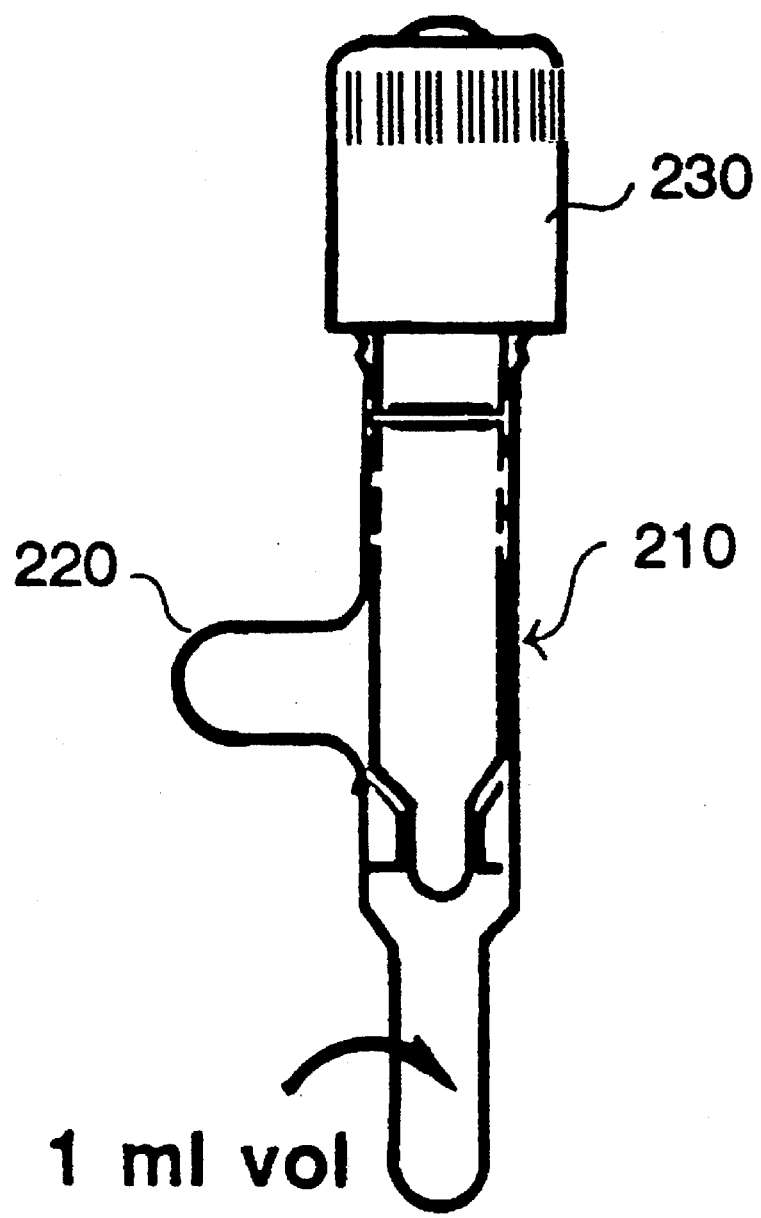
FIG. 1a is a cross sectional view of a bromoacetobrominolysis reaction for use in the present invention.

Throughout this application, various publications are referenced by Arabic numerals within parentheses. Full citations for these publications may be found at the end of the specification immediately preceding the claims. The disclosures of these publications in their entireties are hereby incorporated by reference into this application in order to more fully describe the state of the art as known to those skilled therein as of the date of the invention described and claimed herein.

This invention provides a method for determining the structure of a carbohydrate sample, comprising perbenzoylating a carbohydrate sample with a perbenzoylating agent to protect free hydroxyl groups in the carbohydrate sample; cleaving the glycosidic linkages of the perbenzoylated carbohydrate sample by contacting the carbohydrate sample with an amount of bromoacetyl bromide ($BrCH_2COBr$) and water effective to cleave the carbohydrate sample; treating the resulting product with AgOAc and methanol or AgOTf/TMU and methanol to effect glycosidation; treating the resulting product with thiourea to remove bromoacetate groups; subjecting the resulting product to effect methoxycinnamoylation of free hydroxyl groups; separating the resulting benzoates with high-pressure liquid chromatography; performing mass, ultraviolet and circular dichroic spectroscopy on the separated benzoates; and comparing the spectra so obtained with reference spectra or calculated values to identify the structure of the carboydrate. The method is particularly adapted for use with oligosaccharides, but is applicable to polysaccharides and complex carbohydrates.

The perbenzoylating agent may be para-bromobenzoyl chloride, and perbenzoylation should preferably be carried out in the presence of silver triflate and dimethylaminopyridine.

The cleavage step should preferably be performed in a glass tube sealed with a Teflon (PTFE) spindle valve, and the ratio of $BrCH_2COBr$ to water should be between 1:1.2 and 4:1, although a ratio between about 1:2 and about 1:0.8 appears most preferred. The cleavage step can be carried out at a temperature between about 0° C. and about 75° C. depending upon the particular oligosaccharide involved.

The methoxycinnamoylation step may be accomplished using para-methoxycinnamoyl chloride in the presence of dimethylamino pyridine and silver triflate.

This invention also provides an apparatus for use in determining the structure of a carbohydrate, comprising at least one reaction vessel for reacting a carbohydrate sample with reagents to cleave the carbohydrates into subunits and introduce chromophoric entities onto the subunits; means for introducing the reagents into the reaction vessel; means for removing a sample from the reaction vessel; means for separating benzoates resulting from introduction of chromophoric entities onto the subunits; means for delivering a sample of the separated benzoates to each of a plurality of spectrophotometric instruments; means for determining the mass spectrum of a sample of the resulting benzoates; means for determining the ultraviolet spectrum of a sample of the resulting benzoates; means for determining the circular dichroic spectrum of a sample of the resulting benzoates; and means for comparing the mass, ultraviolet and circular dichroic spectra to reference spectra or calculated values in order to determine the structure of the sample carbohydrate.

The reaction vessel for effecting cleavage is prefereably a glass tube having a Teflon (PTFE) spindle valve as a closure, and the means for separating benzoates is preferably a high pressure liquid chromatograph.

The means for comparing the mass, ultraviolet and circular dichroic spectra with reference spectra or calculated values comprises means for converting mass, ultraviolet and circular dichroic spectra into a series of spectral signals; means for storing reference spectra or calculated values in the form of a plurality of reference signals; and means activated by the spectral signal for comparing the series of spectral signals to each of the reference signals to determine whether a substantial similarity exists between the spectral signals and the reference signals and to indicate the structure of a carbohydrate sample based upon a substantial similarity between the spectral signals and the reference signals. A digital computer can be programmed to make the necessary comparisons.

The invention also provides a method for cleaving a carbohydrate comprising contacting a carbohydrate sugar molecule with an amount of a mixture of $BrCH_2COBr$ and water effective to cleave the glycosidic linkages in the carbohydrate molecule.

The ratio of $BrCH_2COBr$ to water may be between 1:1.2 and 4:1, although a ratio of $BrCH_2COBr$ to water of between about 1:1.2 and about 1:0.8 is preferred.

The method is applicable to oligosaccharides, polysaccharides, complex carbohydrates, and may also be used for derivatizing monosaccharides.

The CD, UV, MS instruments can be standard models used in the laboratory, and samples can be injected robotically using robotic interfaces, such as those sold by Zymark. UV measurements can be performed on a Perkin Elmer 320 UV spectrophotometer. CD spectra can be recorded on a JASCO 500A spectropolarmeter driven by a JASCO DP500N Data Processor. The curves should preferably be normalized to $1.0 \times 10^{-5}M$ and smoothed using a DFT (Discrete Fourier Transfer) or FIR (Finite duration Impulse Response filter) procedure, as is known in the art to those who manipulate and smooth spetrophometric curves. Mass spectrophotometry can be performed on a mass spectrophotometer made by Hewlett-Packard or JEOL Company of Japan. The use of FAB mass spectrophotometer (Fast Atom Bombardment) can provide additional information about the sequence from oligosaccharide, polysaccharide or complex saccharides.

Alternatively, an integrated instrumentation system can be used combining the high pressure liquied chromatograph, and the UV, MS and CD spectrophotometers into one more compact table top unit. This can be done by utilizing less precise spectrophotometer, as opposed to high resolution analytical intruments. By "stripping down" the instruments to include only the basic parts necessary to achieve resolution adequate for the purposes of determining sugar structure, and packaging them with the necessary computer hardware and software to control these functions, much of the size and expense usually associated with these instruments can be avoided. In this way, a more compact and less expensive instrument can be provided.

Figure 25:
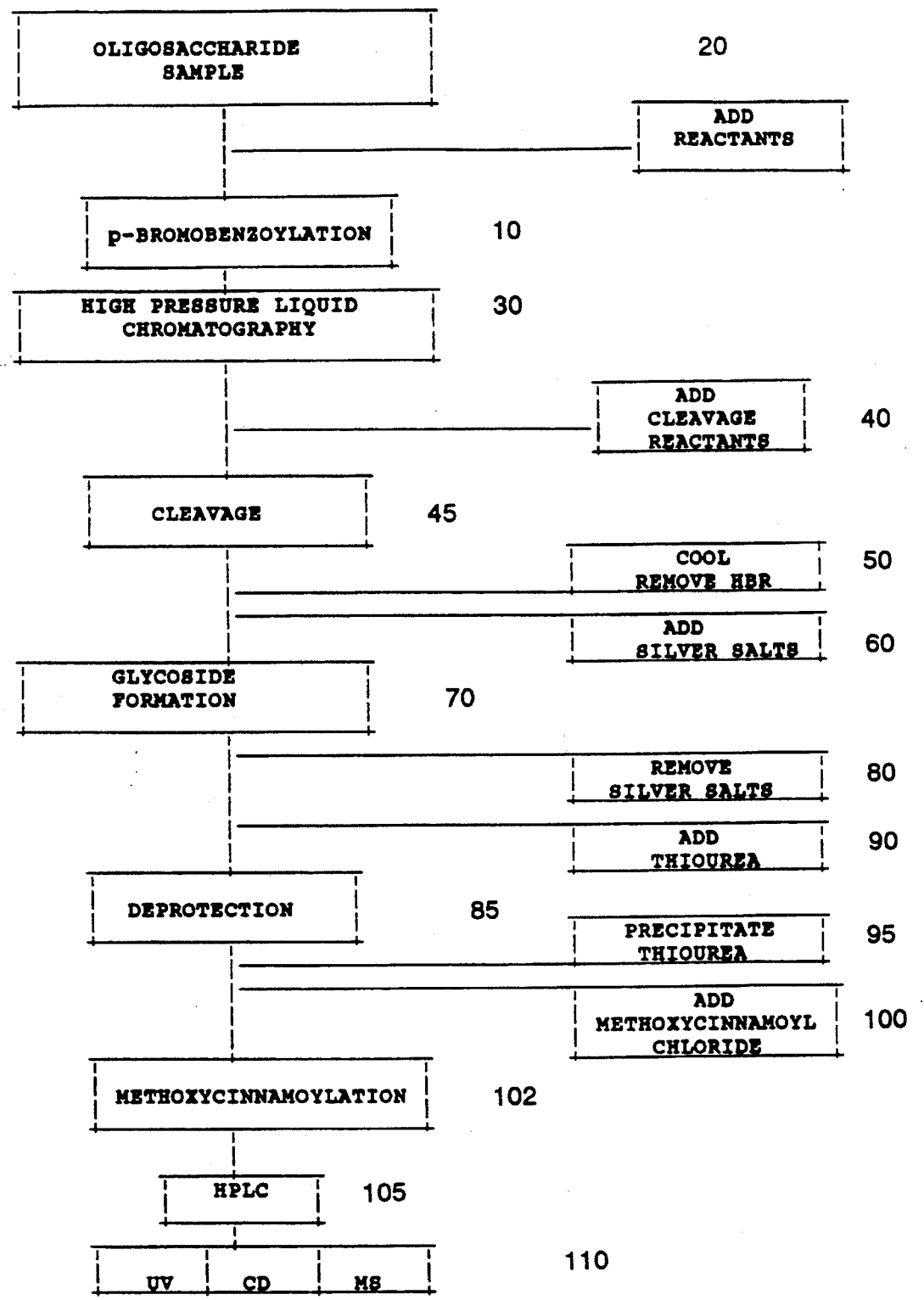
FIG. 25 is a flow chart for the automatic analysis of carbohydrates according to the present invention.

An example of the automated instrumentation for use in carrying out the method of the present invention will now be discussed with reference to FIG. 25, which illustrates diagramatically an automated apparatus for carrying out the method of the present invention, generally designated by the reference numeral 10. A sample of an oligosaccharide, for example, is weighed and introduced into a light protected reaction vessel manually to start the process. To the oligosaccharide sample, p-bromobenzoyl chloride, silver triflate, and a catalytic amount of DMAP, are added by a pumping mechanism or by robotics 20. The resulting product mixture containing the peracylated or perbenzoylated oligosaccharide is removed from the reaction vessel automatically after completion of the reaction, usually about 12 h, and purified using high-pressure liquid chromatography 30. The purified perbenzoylated oligosaccharide can optionally be made into a powder by lyophilizing the product with benzene.

The purified peracylated oligosaccharide can now be transferred to the 1 ml reaction vessel depicted in FIG. 1a. The perbenzoylated oligosaccharide is dissolved in a mixture of bromoacetylbromide and water (preferably 1:0.8 on a molar basis, which may be added through a pumping mechanism or using robotics 40 into a 1 ml glass tube covered with a Teflon spindle valve. The cleavage reaction 45 proceeds at 60° C. for 12 h. The flask is transferred robotically 50 to a dry ice acetone bath where it is cooled to −78° C. The accumulated HBr is removed by vacuum, also applied robotically 50.

To the solid residue containing $BrCH_2CO_2H$ is added dry methanol preferably under argon, then silver acetate or a mixture of silver triflate/tetramethylurea (2:1) is added robotically 60 with stirring in the dark, and the glycoside formation 70 reaction is allowed to proceed. After completion of the reaction silver salts are removed by filtration 80, the filtrate contracted and the residue, which was suspended in hexane/EtOaC (2:1) is passed through a Pasteur pepette filled with slurry of activity II neutral $Al_2O_3$ in hexane/EtOAC (2:1). The $Al_2O_3$ column is washed with EtOAC (5 ml), and the eluate and washings were concentrated to give a residue which can be lyophilized with benzene.

In the deprotection step 85, the product is added to methanol, and thiourea is added robotically 90 with stirring at room temperature. After the $AgNO_3$ in $CH_3CN$ is added robotically 95 to precipitate the thiourea. The mixture is diluted with $CH_2Cl_2$ and passed over a Pasteur pipette filled with $SiO_2$. The $SiO_2$ column is washed with $CH_2Cl_2/MeOH$ (9:1) and the eluate and washings are concentrated to dryness, then lyophilized with benzene to give an amorphorous powder.

The methoxycinnamoylation step 102 proceeds automatically as follows: the powder is dissolved in pyridine, and p-methoxycinnamoyl chloride, AgOTf, and DMAP (cat) are added robotically 100 under argon. The reaction proceeds for about 12 h in the dark, then one drop of water is added with additional stirring. The mixture is concentrated to dryness, suspended in hexane/EtOAC (2:1), then passed through a Pasteur pipette filled with neutral $Al_2O_3$ slurry (activity II) in hexane/EtOAC (2:1). The eluate and washings are concentrated to afford a residue which is HPLC-purified 105. Purified products are isolated and samples are injected into by UV, CD, and MS spectrophotometers 110 for analysis.

The use of robotics to handle the wet chemistry procedures such as adding reagents, moving test tubes, capping and uncapping reaction vessels or tubes, agitating, weighing, controlling temperature, and atmospheric filtration, transferring sample to a column can all be controlled automatically through a series of robots (not shown). The use of robotics to automate laboratory procedures is well known in the art. Zymark Corporation, Hopkington, Mass., makes a line of robotic devices for use in automating laboratory procedures. These robotic modules or building blocks can be grouped together and computer controlled to provide an automated progression of steps in which the foregoing procedures for oligosaccharide cleavage and analysis can be carried out. The *Laboratory Robotics Handbook* (1988) by Zymark, the contents of which is incorporated herein by reference, provides an overview of the state of the art in laboratory robotics from which a person of ordinary skill can assemble the robots and controllers necessary to carry out the process automatically.

Preferably, the cleavage reaction should be carried out in a glass tube such as that shown in FIG. 1a. This glass tube 210 is preferably and conveniently made from a high vacuum valve manufactured by VWR Scientific and available from Kontes, a vendor of laboratory glassware known to those skill in the art. To make the tube for use with the cleavage reaction, the side arm 220 is removed using a torch and the orifice is sealed. The PTFE or Teflon spindle valve 230 sold with the high vacuum valve can be used to seal the tube and prevent the escape of HBr gas.

This invention is illustrated in the Experimental Details section which follows. This section is set forth to aid in an understanding of the invention but is not intended to, and should not be construed to, limit in any way the invention as set forth in the claims which follow.

Due to the large number of sugar derivatives, a simple, four symbol descriptor is used herein to designate the substituents at positions 2, 3, 4, and 6, respectively, of the pyranose sugar indicated (2, 3, 4 for a pentopyranose or 6-deoxyhexopyranose sugar) as follows: O=free alcohol, A=acetate, brA=bromoacetate, B=p-bromobenzoate, C=p-methoxycinnamate and NB=N-(p-bromobenzamide).

Recent years have seen a rapid growth in the understanding of the important and varied roles of oligosaccharides from glycoproteins and glycolipids (1). These oligosaccharides play a particularly important biological role on cell surfaces, and have been implicated as the antigenic determinants in a number of systems. Cell-cell recognition, cellular differentiating during development, and the attachment of viruses to cells during infection are all processes in which the cell-surface oligosaccharides are involved. Structurally diverse oligosaccharides are also constituents of other bioactive glycoconjugates such as saponins (2).

Determination of linkage structure in oligosaccharides has long relied upon methylation analysis by GLC/MS of partially methylated alditol acetates (3). These monosaccharide residues are obtained by hydrolysis of permethylated oligosacchrides, reduction of the anomeric center, and acetylation of the remaining hydroxyls which were originally involved in linkages. Methylation analysis generally requires a minimum of 25 nmol of material, although capillary GLC with smaller quantities have been reported (4). The analysis relies heavily on chromatographic separation and comparison of derivatized monosaccharide GLC retention times with a large bank of synthetic standards, few of which are commercially available. Linkage analysis generally follows a sugar component analysis, and an additional analysis for determination of monosaccharide absolute configuration may be performed.

An alternative to methylation analysis based upon UV and CD spectroscopic analysis of HPLC-separated components bearing UV-active chromophores has been under development in our laboratory for several years (5–9). The pursuit of alternative methodology is justified by several important advantages which it can offer over conventional methods. First, as a spectroscopic method, it does not rely on direct comparisons with synthetic standards, and thus would be more accessible to non-specialists in fields outside of carbohydrate chemistry; instead, components are identified by CD, a widely used and readily available technique in biology and biochemistry. Second, only nanomole quantities of chromophorically derivatized sugar components are required for CD measurements, and these spectra are compared with the 150 reference CD data given below. Finally, CD spectra provide more structural information than that obtained by methylation analysis. In most cases, the CD spectra indicate the identity of the component sugar, its linkage pattern, and its absolute configuration. Low resolution MS and HPLC retention time provide additional information regarding the presence of various functional groups such as NAc, NBz, OAc, or the absence of oxygen functions (deoxy sugars).

Recent CD studies showed that the CD spectra of pyranosides bearing a combination of p-bromobenzoate (max 245 nm) and p-methoxycinnamate (max 311 nm) chromophores were characteristic for each type of sugar and substitution pattern (9–12). Therefore, we envisioned using these two different exciton-coupling chrmophores to selectively tag free hydroxyls and those originally involved in glycosidic linkages as shown diagramatically below:

By simple analogy to methylation analysis, this roughly corresponds to using the p-bromobenzoate chromophore in place of the methyl groups of methylation analysis, and p-methoxycinnamate chromophores instead of acetates to tag hydroxyls liberated from glycosidic linkages. Degradation of oligosaccharides with the selective introduction of these chromophores can be achieved by a variety of procedures. The resulting UV-active monocaccharide subunits are then separated by HPLC and subjected to UV, CD, and MS analysis. The ratio of the two chromophores present are readily determined by UV, thus indicated the number of other sugar residues to which the particular sugar was linked; the CD spectra of the individual components serve to identify the sugars and their chromophore substitution patterns, the latter representing the linkage patterns of each monosaccharide component in the original oligosaccharide. After UV and CD, samples are subjected to MS for further structural analysis if necessary.

A complete CD spectral library for the identification of all types of pyranoside sugar components obtainable from oligosaccharides is contained in the figures. The utility of these spectra is demonstarated by a number of model studies in which known oligosaccharides have been derivatized to the appropriate chromophoric sugar subunits for spectral analysis. Derivatization procedures based upon a novel glycosidic cleavage reaction are presented and shown to be applicable on a nanomole scale.

The CD database is presently restricted to pyranoside components, as CD calculations are not straightforward for the conformationally flexible furanosides (see Ref. 19, p. 143–145). Thus, spectral data for furanoside components must be obtained experimentally, after which it can be used for comparison purpose.

Preliminary efforts to obtain bichromophoric derivatives of the type shown above involved an initial peralkylation of oligosaccharides with either the benzyl or allyl protecting groups. Earlier studies used only a single chromophore that resists conventional glycosidic cleavage conditions, p-phenylbenzyloxy (max 253 nm), to tag the free hydroxyl groups; the substitution pattern is then derived from the amplitudes of the exciton-split curve (5–9). However, the monochromophoric approach suffers from the low perphenylbenzylation yield, difficulty in cleavage of glycosidic Scheme 1

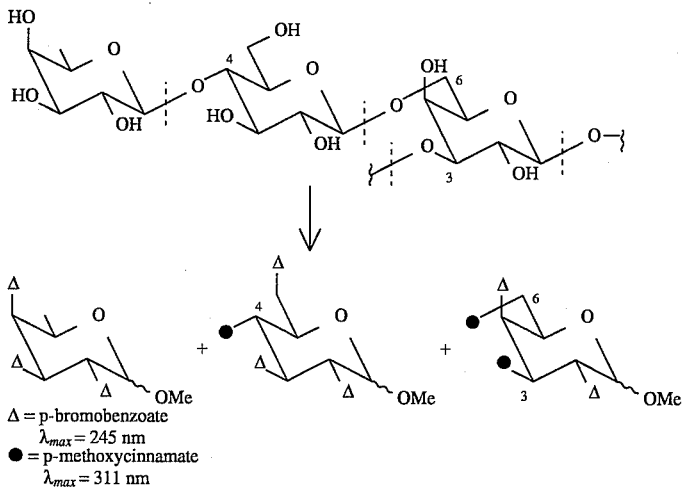

$\Delta$ = p-bromobenzoate
 $\lambda_{max}$ = 245 nm
● = p-methoxycinnamate
 $\lambda_{max}$ = 311 nm linkages, and the necessity for identifying the sugar units separately. Glycosidic linkages in the peralkylated oligosaccharides were subsequently cleaved under methanolysis conditions using a Teflon bomb in a microwave oven. The mixture of cleavage products was then per-p-bromobenzoylated (tagging linkage hydroxyls), deprotected, and finally cinnamoylated (tagging originally free hydroxyls). When the benzyl protecting group was used, deprotection/cinnamoylation could be achieved in a single pot in high yields. The oligosaccharide is perbenzylated, the glycosidic bonds are cleaved by methanolysis in microwave oven, the liberated hydroxyls p-bromobenzoylated, and the benzylated groups are converted into methoxycinnamates by a one-pot microreaction (90%) consisting of two steps: treatments with $FeCl_3/CH_2Cl_2$, rt, 1 h(8), followed by MeOCnCl/ AgOTf/Pyr, rt, 1 h. However, several drawbacks made the five step sequence unattractive, and it remained difficult to carry out this procedure on submilligram quantitites.

A more straightforward approach to bichromophoric derivatization involves the direct cleavage of per-p-bromobenzoylated oligosaccharides, thus eliminating protection/deprotection steps; importantly, perbenzoates can be prepared in high yields, and furthermore, their lipophilic properties greatly facilitate purification by HPLC when the starting oligosaccharide is contaminated. While methanolysis of perbenzoylated oligosaccharides was found to be sluggish and to result in undesired acyl migration or ester hydrolysis, acetobrominolysis conditions (AcOH/HBr/ acetyl bromide) [13] were found to be ideally suited for degradation of perbenzoylated oligosaccharides [14]. We have developed two variations of the acetobrominolysis reaction which are suitable for oligosaccharide perbenzoates.

Trifluroacetobrominolysis—Acetobrominolysis conditions (HBr in acetic acid) applied to lactose octa-p-bromobenzoate were found to effect glycosidic cleavage with concomitant acetylation of the linkage hydroxyls. It is at these linkage positions where introduction of the methoxycinnamate chromophore is desired. While acetate groups are not readily removable in the presence of benzoates, a variety of haloacetates can be deprotected and replaced with the second chromophore.

The trifluoracetate group represents one type of labile acetate, and thus the acetobrominolysis reaction was tried with trifluoracetic acid as the solvent. This procedure, identified as scheme 2, is shown diagramatically below:

Scheme 2

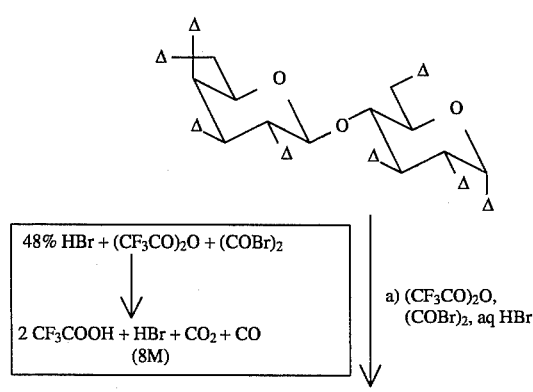

Scheme 2 (continued)

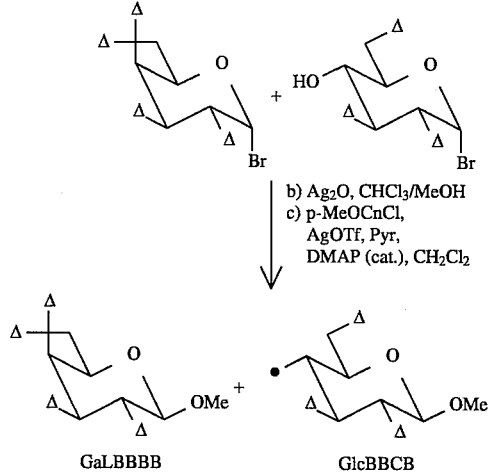

Anhydrous 8M $HBr/CF_3CO_2H$ reagent was generated by combining 48% aqueous HBr with $(CF_3CO)_2O$ and oxalyl bromide (41:79:130 v/v) [9]. Treatment of lactose octa-p-bromobenzoate with this reagent for 30 min at 100° C. in a sealed tube afforded two glycosyl bromide products, GalBBBB and GlcBBOB, the latter bearing a free alcohol at the linkage position: A cautionary note concerning the use of oxalyl bromide is warranted; as CO, $CO_2$ and HBr are liberated from oxalyl bromide during the cleavage reaction, dangerous pressures may be generated. However, the reactions can be safely carried out in the heavy glass reaction vessels utilized in these studies (See FIG. 1a). The transient presence of a trifluroacetate group at the hydroxyl involved in the glycosidic linkage, which is presumable lost during workup, accounts for the absence of acyl migration products. Addition of stoichiometric amounts of $H_2O$ to varying ratios of $(CF_3CO)_2O$ and $(COBr)_2$ enabled manipulation of the HBr concentration; an 8M $HBr/CF_3CO_2H$ solution was optimal for clean, complex cleavage reactions. After removal of the HBr gas and $CF_3CO_2H$ under reduced pressure, the bromosugars were converted to their methyl glycosides with $Ag_2O$. Cinnamoylation of the mixture gives GalBBBB and G1BBCB, the CD curves of which agreed well with synthetically prepared standards. This three-step reaction sequence was similarly applied to stachyose tetradeca-p-bromobenzoate and stevioside undeca-p-bromobenzoate [9]. However, application to oligosaccharides containing deoxypyranose (e.g., quinovose), pentopyranose (e.g., xylose, arabinose), branched hexopyranose and amino sugars gave multiple decomposition products, thus limiting the utility of these cleavage conditions.

Bromoacetobrominolysis—A cleavage reaction amenable to hexopyranoses and deoxysugars, including branched sugars, and amino sugars was uncovered when $CF_3CO_2H$ was replaced with $BrCH_2CO_2H$ [14].

Step a)-Cleavage of glycosidic bond.

Bromoacetyl bromide/water mixtures were found to cleave glycosidic linkages in per-p-bromobenzoylated oligosaccharides with concomitant protection of liberated hydroxyls in bromoacetate esters. Thus, benzoyl migration is prevented and the integrity of the linkage points is maintained. Cleavage reactions were conveniently performed in glass tubes (1.1 or 3.3 ml capacity) fitted with Teflon screw caps to confine HBr during the reactions. Reaction tubes for these high pressure reactions are conveniently prepared from gas flow controllers commonly used for flash chromatography (Aldrich) by cutting and sealing the bottom and side-arm as shown in FIG. 1a. Optimal utilization of the BrCH$_2$COBr/H$_2$O reagent required varying both the time and temperature of the cleavage reaction. Cleavage rates are dependent upon the particular sugars and linkages. In general, β linkages are cleaved more rapidly than α linkages. Terminal and 6-linked residues; 2- and 4-linked residues are the most difficult to liberate. This is consistent with observed rate of acetolysis of pyranose-containing disaccharides [15].

b) Conversion of α-bromo pyranosides into β-methyl pyranosides, and c) deprotection of bromoacetyl group. Methods b1) and c1) are applicable only to oligosaccharides containing no amino sugars, e.g., digitonin (Scheme 4); however, revised methods b2) and c2) are more general and can be employed when amino sugars are present, e.g., sarasinoside C, (Scheme 5).

b1 and c1). After removal of BrCH$_2$CO$_2$H with aq NaHCO3, the mixture was immediately converted to stable β-methyl glycosides with Ag$_2$CO$_3$/AgoTf in MeOH/CHCl$_3$. Deprotection of bromoacetates with thiourea [16] yielded the mixture of β-methyl pyranosides. Aminoethanethiol hydrochloride/NaHCO$_3$ (excess) in MeOH/CHCl$_3$ can also be used to effect bromoacetate deprotection.

b2 and c2). These more general schemes differ only slightly in the sense that the bromosugars were converted into the methyl glycosides with AgOAc or AgOTf rather than with Ag$_2$CO$_3$, and that AgNo$_3$ was employed for removal of thiourea. The usage of Ag$_2$CO$_3$ in cases where 2-deoxy-2-N-acetylated sugars are present tend to lead to hydrolysis of the NAc group; it is also advantagious (in general) to remove the thiourea by precipitation with AgNO$_3$ because some amino sugars coelute with thiourea on silica gel.

d) Cinnamoylation. Free hydroxyl groups involved in glycosidic linkages are cinnamoylated in high yield.

Lactose octabenzoate was subjected to these cleavage and derivatization reactions to provide the same chromophoric products as obtained using the trifluoracetobrominolysis approach (Scheme 2). The four steps shown diagramatically below as Scheme 3 are efficient and convenient, as purification is required only after the final step to separate the subunits for spectroscopic analysis.

Scheme 3

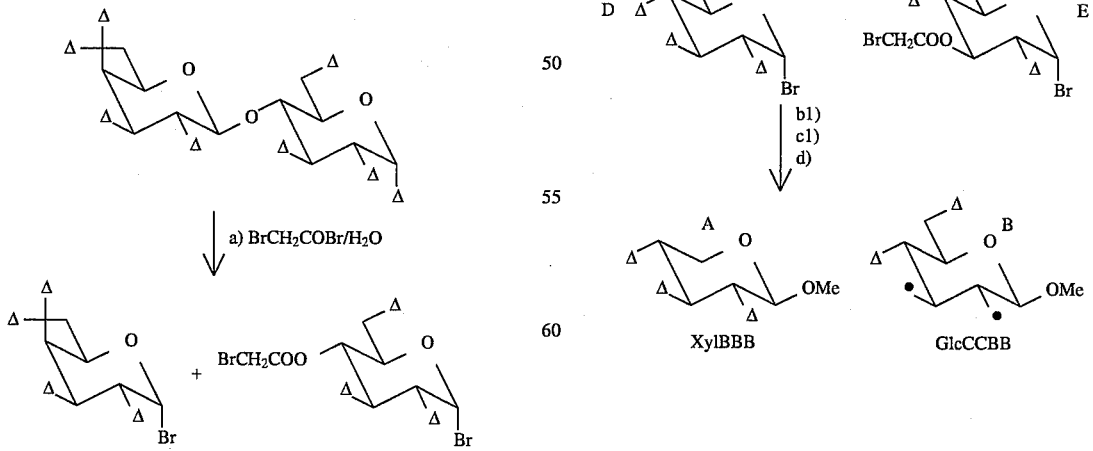

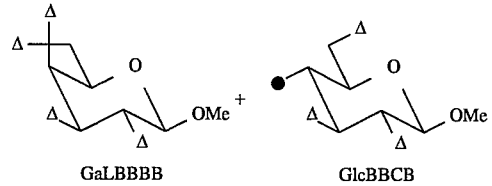

The earlier version of this general procedure, steps a/b1/c1/d was applied to digitonin heptadeca-p-bromobenzoate [14] as illustrated below:

Scheme 4

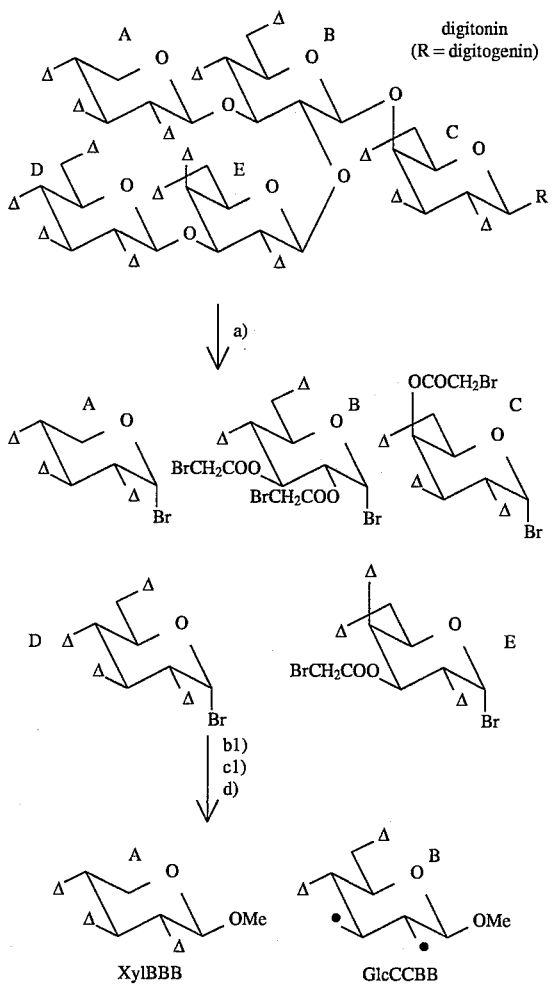

-continued
Scheme 4

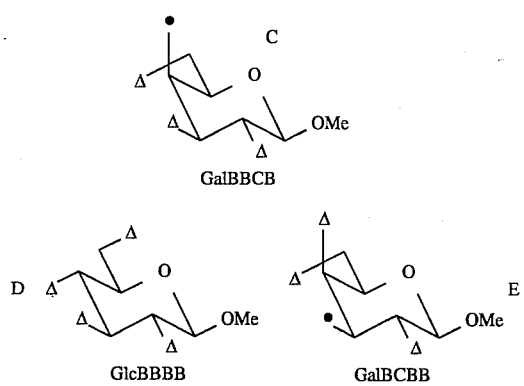

Treatment of its heptadeca-p-bromobenzoate (300 μg, 70 nmol), in $BrCH_2COBr/H_2O$ (1:1 molar ratio), which generates a 9.5M $HBr/BrCH_2CO_2H$ solution, for 12 h at 60° C., gives the α-bromoglycosides of Xy1BBB, Glc(brA)₂BB, GlcBBBB, GalB(brA)BB and GalBB(brA)B. Deprotection of bromoacetates with thiourea and subsequent cinnamoylation provided the bichromophoric mixture Xy1BBB, GlcCCBB, GlcBBBB, GalBCBB and GalBBCB in 41%, 69%, 94%, 35%, and 31% overall yields, respectively. Yields of the MPLC separated components were determined by UV. Concentration of each in a given volume of acetonitrile were calculated using the previously determined extinction coefficients (see Experimental Part).

The resulting degradation products were separated by HPLC (FIG. 1b) and characterized by CD (FIG. 1c–g). As can be seen in FIG. 1, excellent agreement was found between CD spectra of these components and synthetic standards which had been previously prepared [5, 6, 9].

For oligosaccharides containing N-acetyl sugars, e.g., sarasinoside C, the more general methods b2/c2 shown below were employed:

Scheme 5

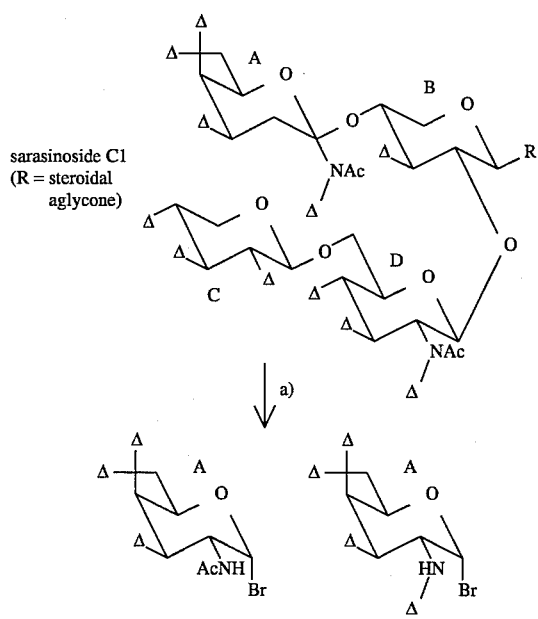

-continued
Scheme 5

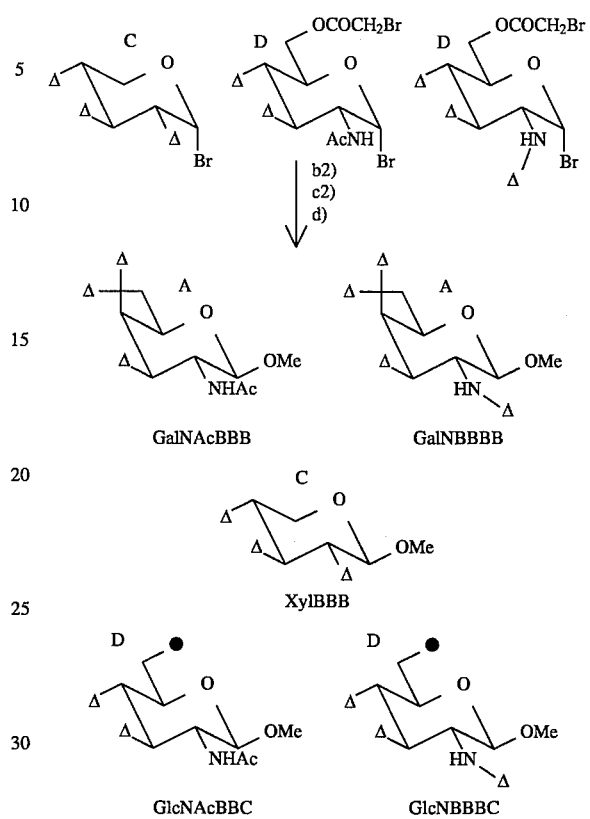

Benzoylation of N-acetyl sugars under standard conditions produce varying amounts of imide products. For example, benzoylation of sarasinoside $C_1$ shown above resulted in complete N-benzoylation to give the undeca-p-bromobenzoate. Cleavage with stoichiometric $BrCH_2COBr/H_2O$ (50° C., 12 h) followed by glycosidation with AgOTf/TMU in MeOH, deprotection, and cinnamoylation, resulted in five major products obtained from HPLC shown in FIG. 2. An aqueous $NaHCO_3$ workup to remove the $BrCH_2CO_2H$ after the cleavage step where 2-deoxy-2-N-acetate 1-bromo pyranoside were obtained led to some decomposition of the unstable 1-bromosugar intermediate; hence, the glycosidation step was performed in the presence of $BrCH_2CO_2H$. The use of $Ag_2O$ or $Ag_2CO_3$ in the glycosidation step leads to hydrolysis products (i.e., δ-lactol formation) because $H_2O$ is generated from these silver reagents in the presence of $BrCH_2CO_2H$; mercury salts [e.g., $Hg(CN)_2/HgBr_2$] were also successfully employed to effect glycosidation, but they were difficult to remove afterwards. Each N-acetylated sugar was found to give rise to two products—one N-acetate and one N-benzoate.

Loss of the N-acetate group during cleavage predominates over N-benzoate deprotection, providing GalNBBBB and GlcNBBBC as the major products, and GalNAcBBB and GlcNAcBBC as the minor products. Similar cleavage results were obtained with stoichiometric $BrCH_2COBr/H_2O=(1.0/0.8$ mol. eq.) (103 ml) (17 ml). The unstable, branched xylopyranose residue was not observed under any conditions. Synthetic methyl β-xylopyranoside 3-p-bromobenzoate 2,4-bis-bromoacetate was coinjected with the cleavage mixture after the glycosidation step to confirm the absence of this expected cleavage product. The terminal xylopyranose, however, provides the expected XylBBB. Higher cleavage temperatures and longer reaction times (e.g., 60° C.

24 h) led to decomposition of the terminal xylose residue, while lower temperatures (e.g., rt, 70 h) appeared to effect partial cleavage with stoichiometric $BrCH_2COBr/H_2O$.

A variety of model disaccharides and saponins bearing N-acetylated sugars have been examined with satisfactory results. Best results were obtained when a slight excess of $BrCH_2COBr$ over $H_2O$ was employed (1:0.8). However, certain cases are consistently prone to either decomposition or rearrangement. For example, 3- and 4-linked GlcNAc residues typically yield the expected cleavage products, while 3- and 4-linked GalNAc residues give rise to a single rearrangement product which has been identified as an N-acetylated furanosamine methyl glycoside. The 2-acetamide glycosyl bromides were found to be particularly sensitive to hydrolysis, making it important to maintain anhydrous conditions in the cleavage procedure.

3. HPLC Separation of Derivatization Products. EtOAc/hexane solvent systems and a 3 µm Hypersil analytical column were used throughout these studies. EtOAc/hexane (1:4) was sufficient for separation of simple two-component mixtures obtained from disaccharides such as lactose, while a less polar system (EtOAc/hexane, 1:7) was required for separation of residues obtained from digitonin. As seen above in FIG. 1B, the presence of methoxycinnamate groups results in longer retention times than bromobenzoate groups. Thus, tri- and tetrabenzoates elute from the column first, followed by tribenzoate monocinnamates ($B_3C$) and then dibenzoate dicinnamates ($B_2C_2$). Analogously, tricinnamate monobenzoates would follow.

Figure 1B:
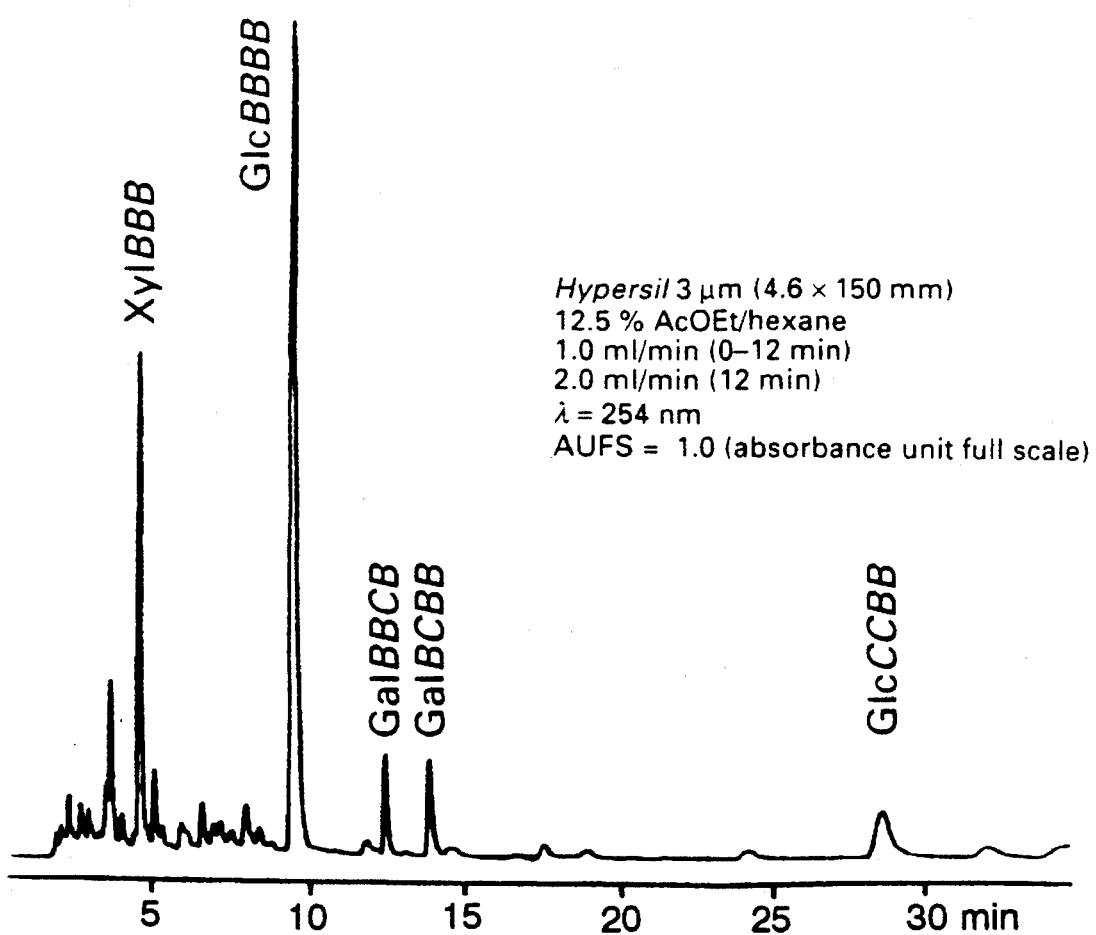
FIG. 1b–G are each HPLC(b) and CD spectra of products obtained from digitonin (solid line) compared to synthetic (c-f) or calculated (g) spectra.
Figure 1C:
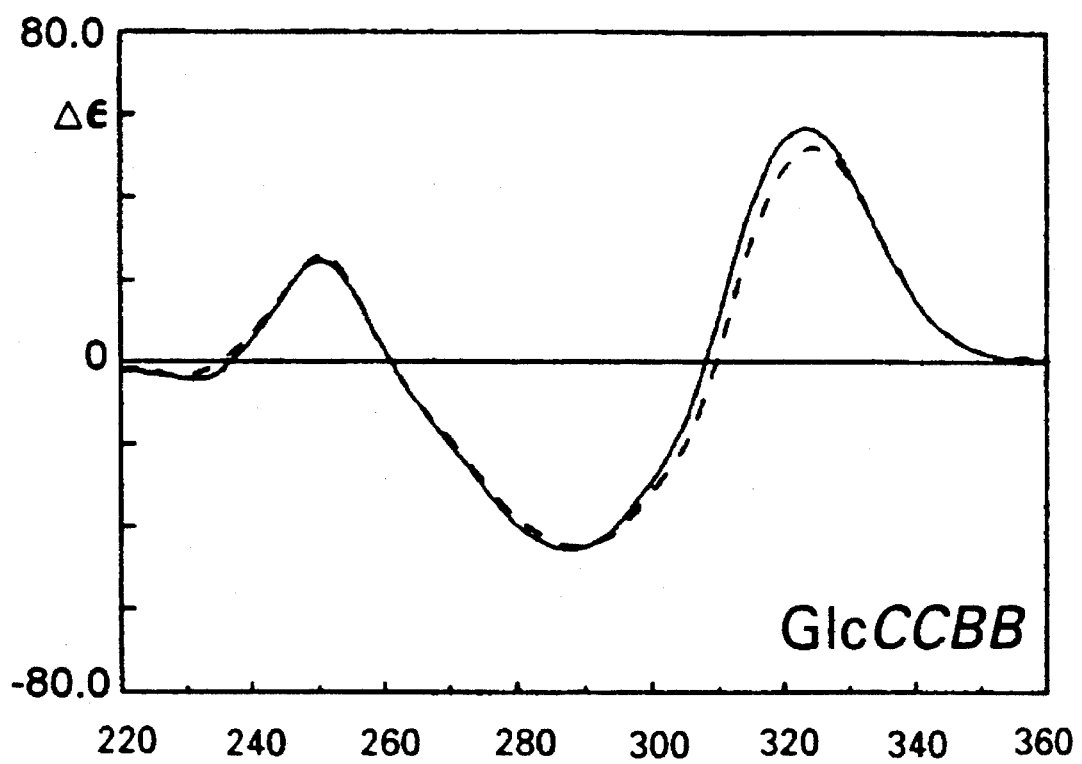
Figure 1D:
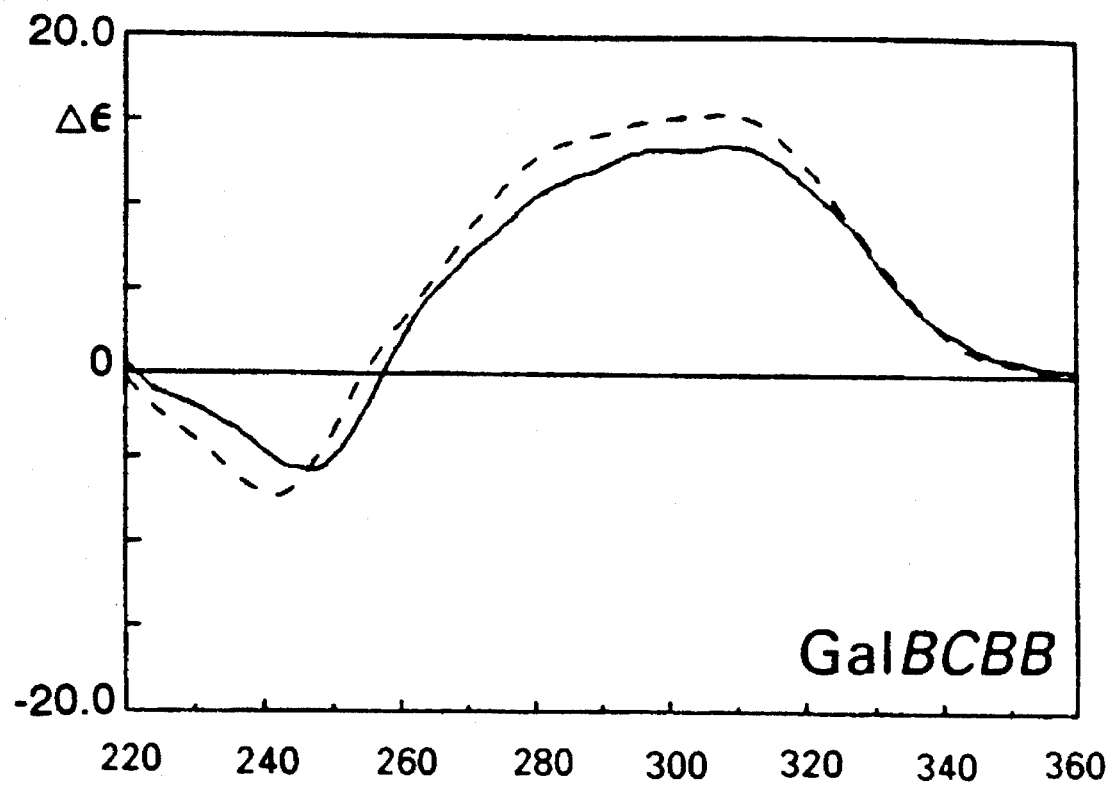
Figure 1E:
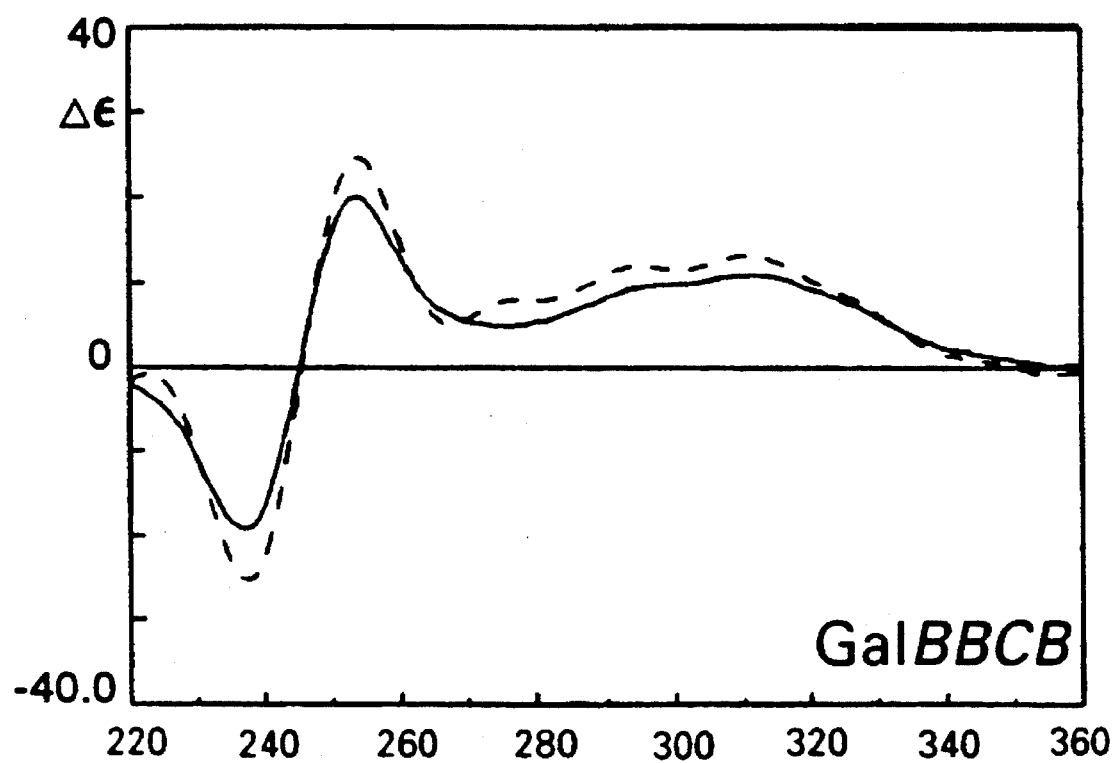
Figure 1F:
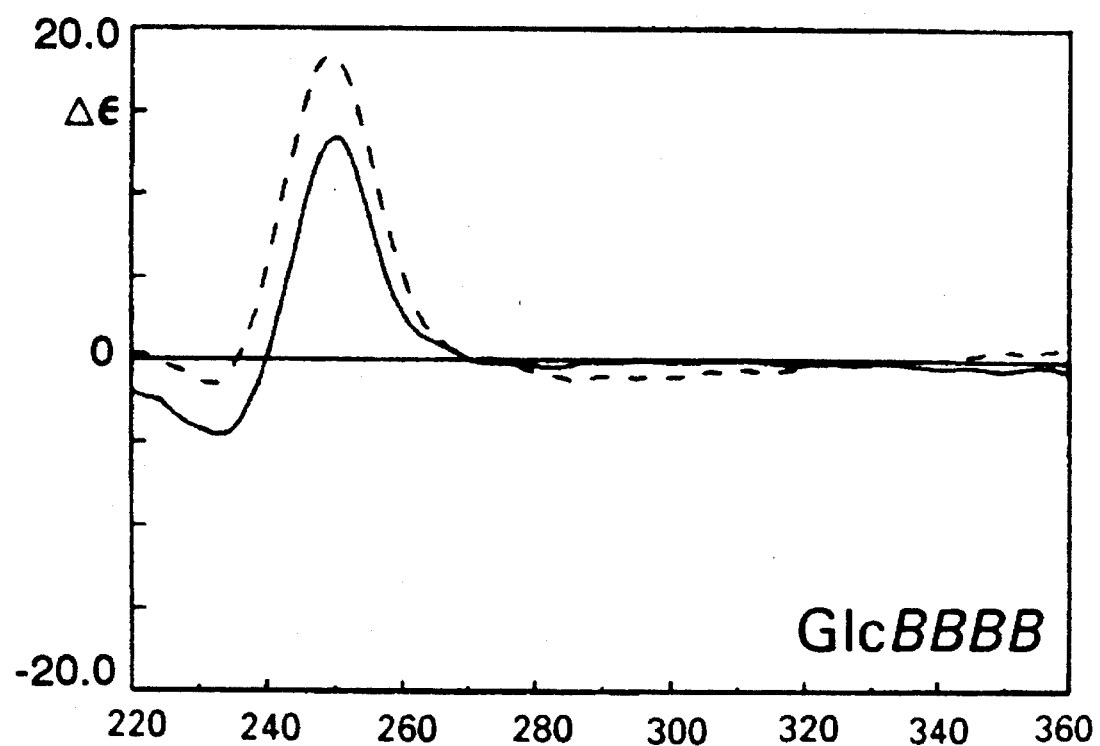
Figure 1G:
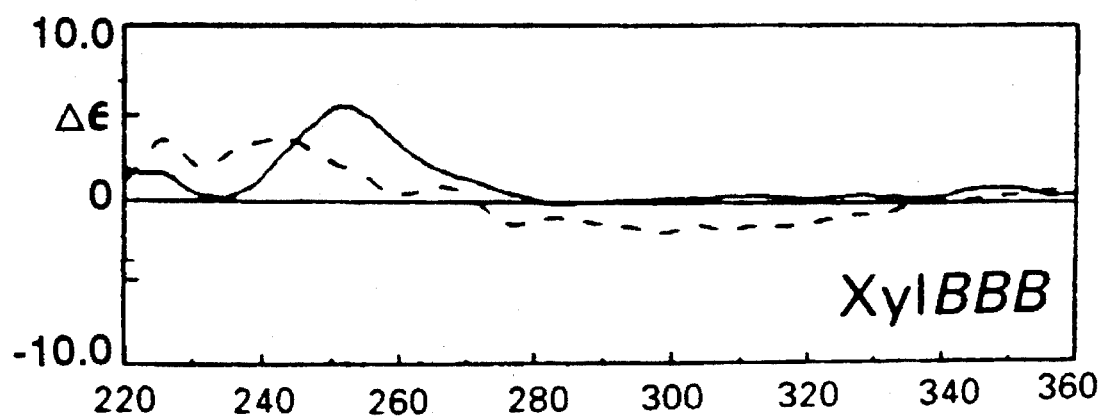
Figure 2:
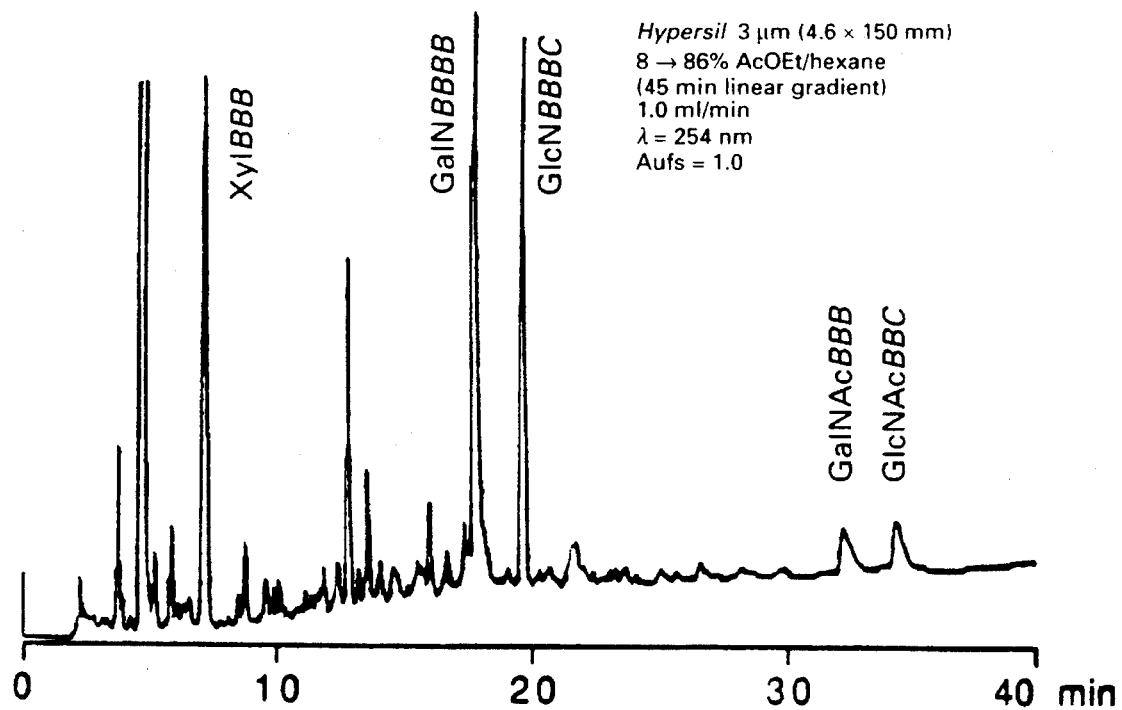
FIG. 2 contains an HPLC profile of derivitization products obtained from sarasinoside C, using gradient elution.

A second important determinant of HPLC elution order is the presence of amino sugars, which require the use of gradient solvent systems because of their increased polarity. Thus, for all studies involving N-acetylated sugars, a 45 min linear gradient from 8 to 86% EtOAc/hexane was employed. As seen in FIG. 2, N-benzoylated products elute before the corresponding N-acetylated products. While this type of gradient system provides good separation between different types of sugar derivatives, it is not expected to provide good separation between structural isomers of similar polarity. More complex component mixtures may require an initial gradient separation followed by one or more separations with isocratic solvent systems which are better suited to separate derivatives with similar substituents (e.g., GalB-BcB and GalBCBB, as shown in FIG. 1b).

In conventional methylation analysis, structural assignments rest in large degree upon comparison of GLC retention times. In the spectroscopic approach presented here, the HPLC retention time data can serve to supplement the spectral data. As more derivatives are examined, the elution profiles of these products can be catalogued and used to confirm structural assignments.

4. UV Spectral Analysis. After isolating components from HPLC, the products were then analyzed by UV in the range of 200–400 nm. HPLC retention times provide some indication of the type of sugar (Such as amino sugar) and the types of chromophores which may be present. The ratio of benzoate to cinnamate chromophores is determined by a simple analysis of UV spectra (Table 1).

Derivatives obtained from terminal sugar subunits have only bromobenzoate chromophores. These components have an absorption maxima of 245 nm and are essentially transparent above 300 nm. Products derived from sugars having a single linkage point again have absorption maxima at 245 nm in addition to a second, smaller absorption at 310 nm owing to the presence of a single methoxycinnamate chromophore. In products derived from branching sugars having two or three linkages, the 310 nm cinnamate absorption is greater or roughly equal to the benzoate absorption at 245 nm.

The ratio of absorbances at these two positions (i.e., $A_{245 nm}/A_{310 nm}$) has been quantified for a number of derivatives having combinations of three or four chromophores and are indicated in Table 1. A discrete range of ratios are observed for each class of compounds. For the monobenzoate di- and tricinnamates ($BC_2$ and $BC_3$), overlapping of observed ratios at values of 0.42–0.43 leads to some ambiguity. However, the tricinnamates are only expected from infrequently occurring sugar components which have three linkage points. Ambiguities can be resolved by subjecting the product to MS following CD analysis.

While not necessary in all cases, mass spectra must be obtained for products having only bromobenzoate chromophores as indicated by UV. In such cases, the UV provides no indication of the number of benzoate groups present which is crucial to the CD analysis. Low resolution MS can easily indicate the number of benzoates and the types of functional groups which are present. For example, 6-deoxyhexopyranoside and pentopyranoside derivatives having similar HPLC, UV, and CD can only be distinguished by MS.

5. Circular Dichroism Data Base. In our ongoing CD studies of bichromophoric sugar derivatives [10–12], we have found that derivatives bearing bromobenzoate and methoxycinnamate chromophores have highly characteristic CD spectra which are in accord with the principles of exciton coupling [19]. The accumulated data base currently consists of roughly 60 spectra of dichromophoric pyranosides, all of which have been prepared synthetically. Another 12 spectra of tri- or tetrachromophoric compounds obtained via derivatization of oligosaccharides completes the inventory at this time. The 72 dichromophoric derivatives are all the possible permutational isomers of α-methyl gluco-, galacto-, and mannopyranoside bearing two chromophores (bromobenzoates, methoxycinnamates, or one of each) and two acetate groups. The CD spectra of these 72 dichromophoric compounds represent the spectral contributions of all possible pairwise interactions which contribute to the spectra of tri- and tetrachromophoric derivatives in an additive fashion. These 72 spectra are referred to as the "basis set" because they can be algebraically summed to provide simulated spectra tri- and tetrachromophoric derivatives.

Figure 3:
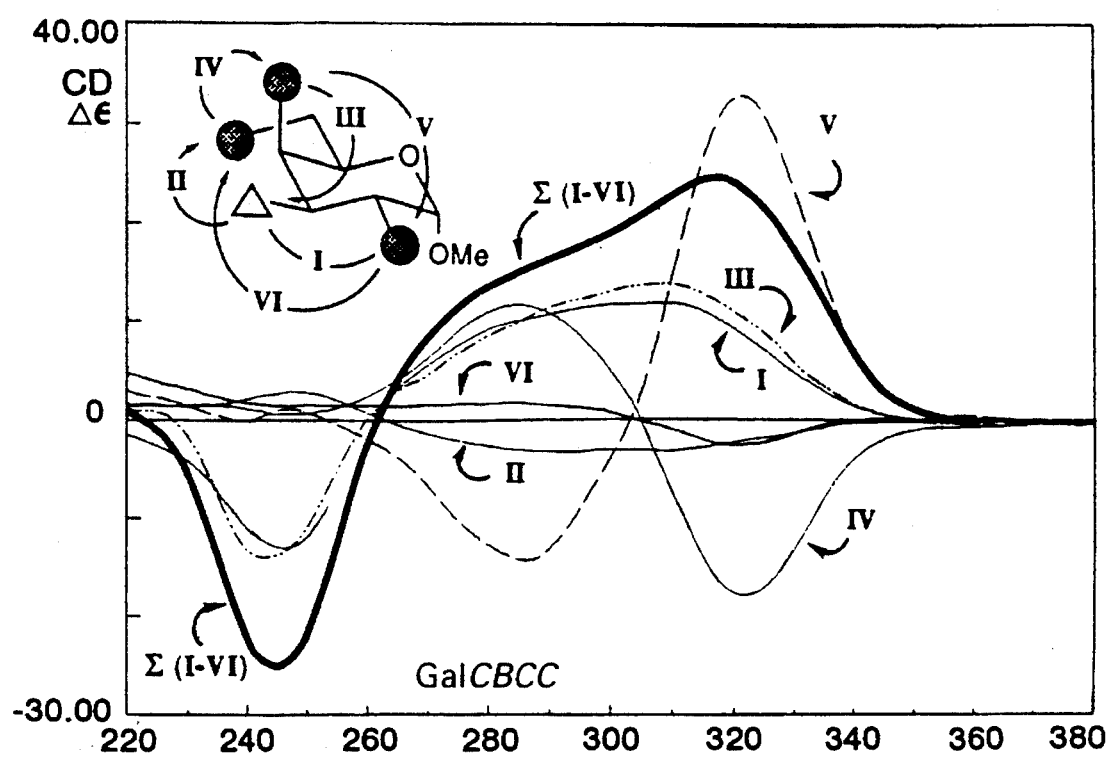
FIG. 3 contains CD curves of the six basis set derivatives and their sum for GALBCC.
Figure 4A:
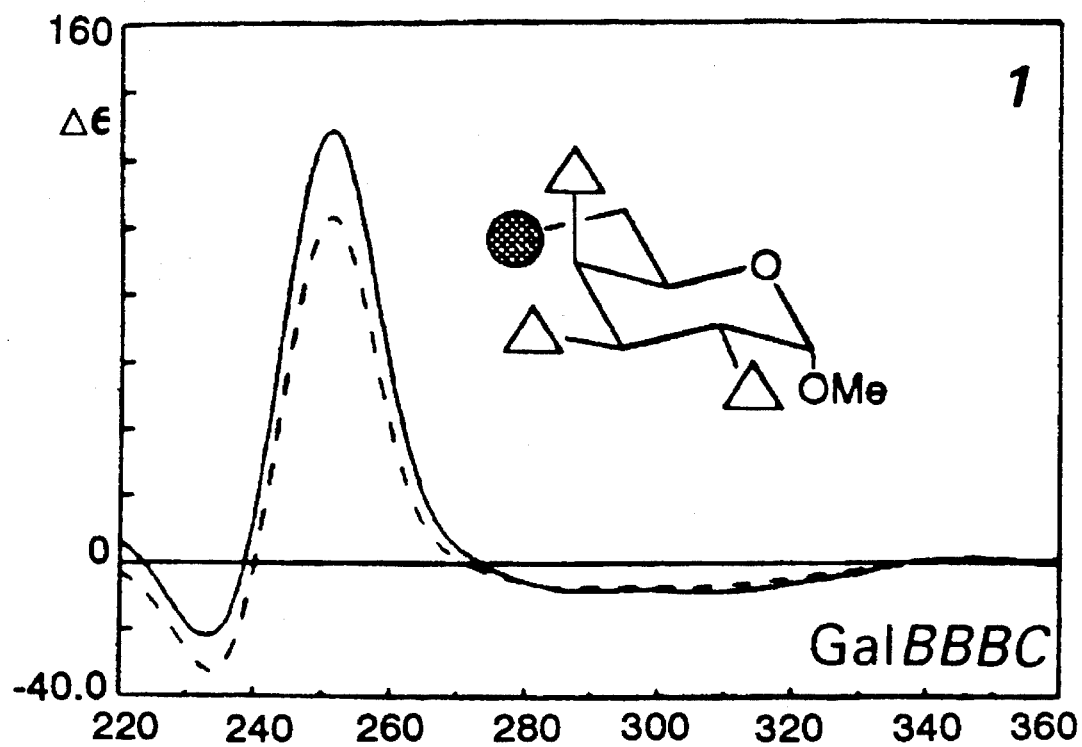
FIGS. 4a–f contains $B_3C$ circular dichroic (CD) spectra.
Figure 4B:
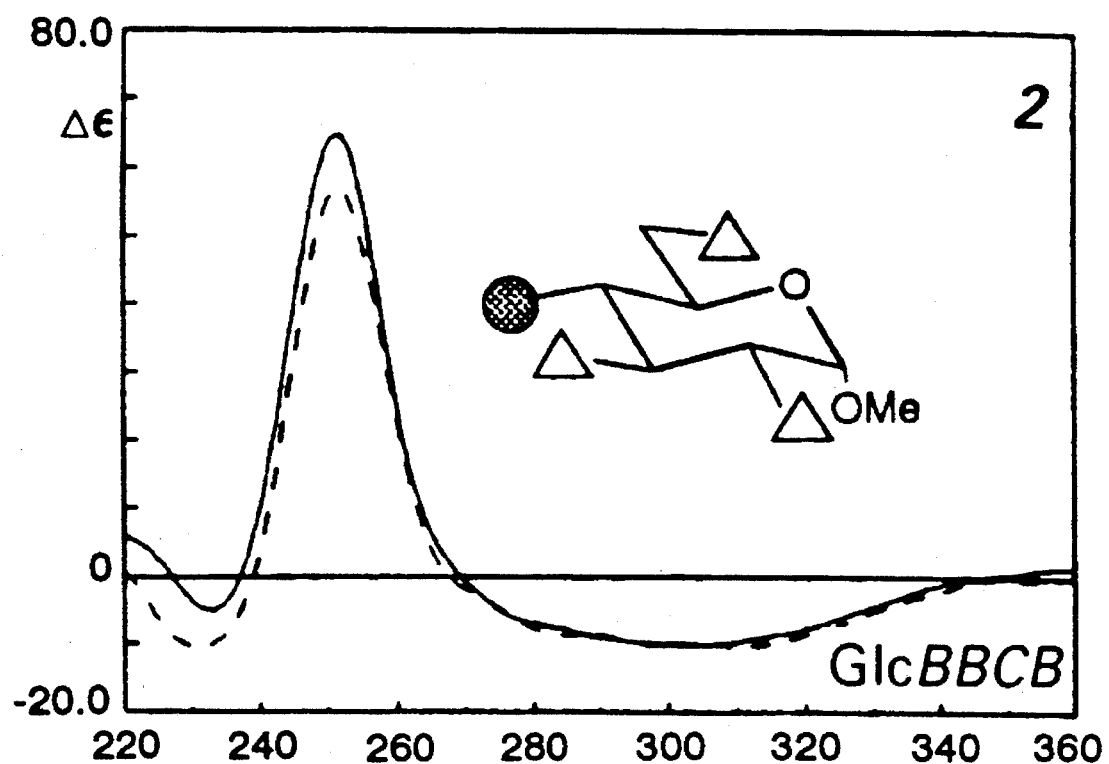
Figure 4C:
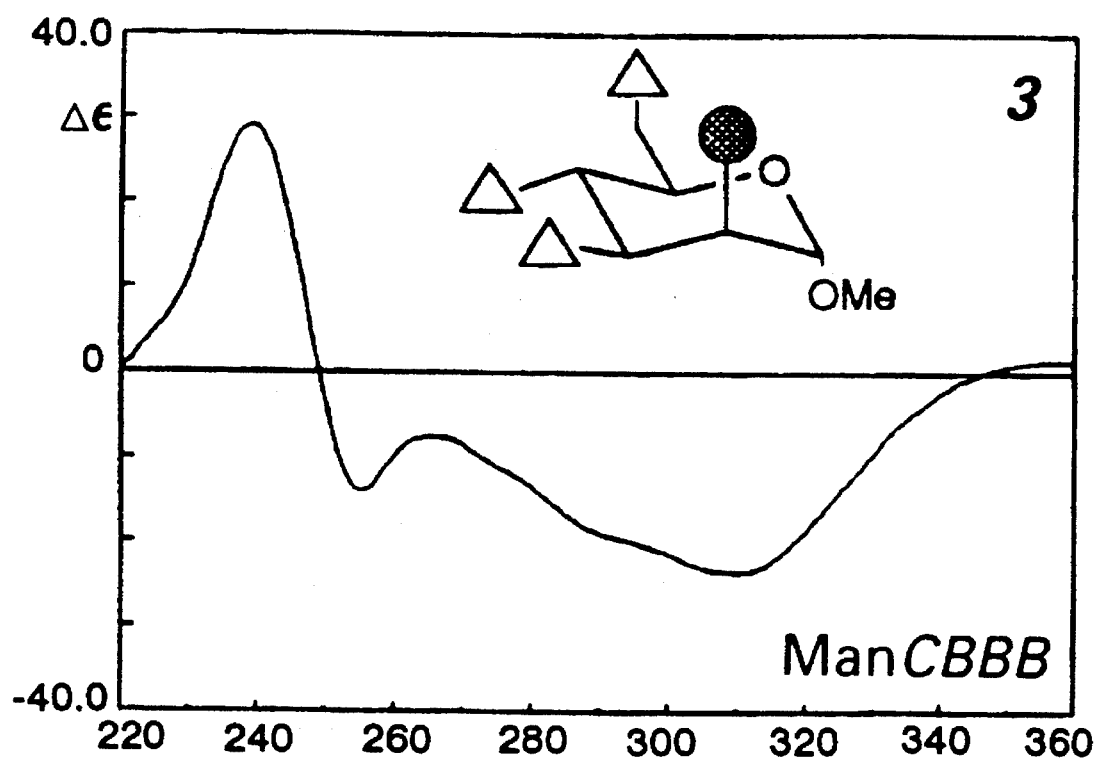
Figure 4D:
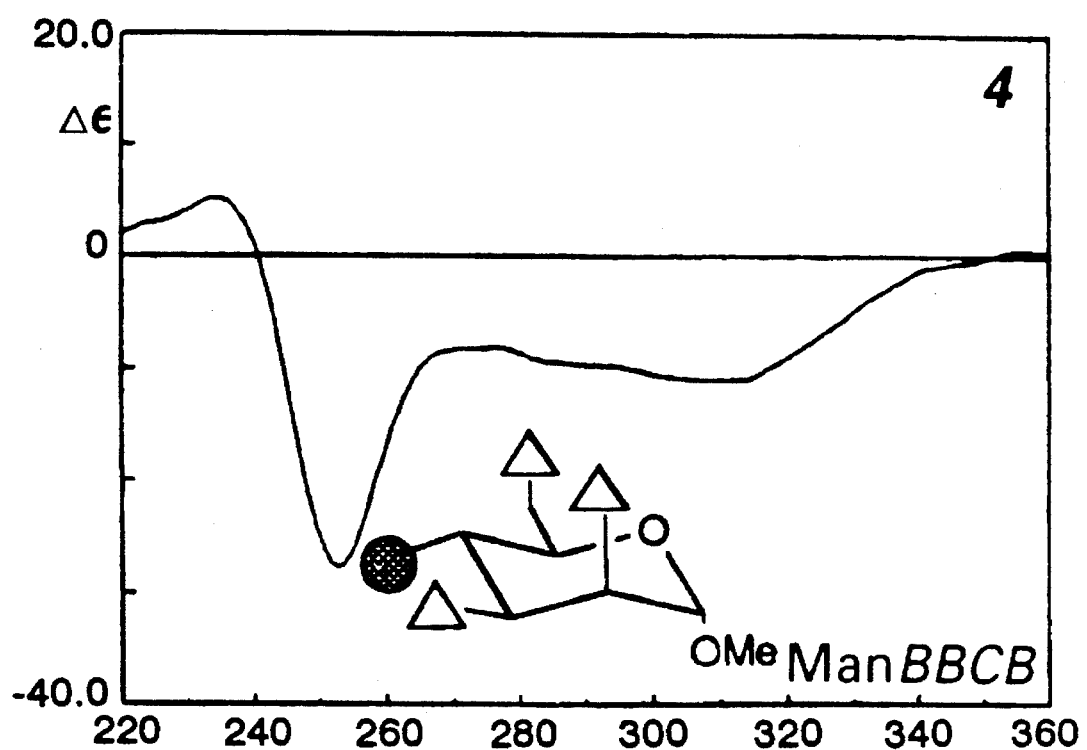
Figure 4E:
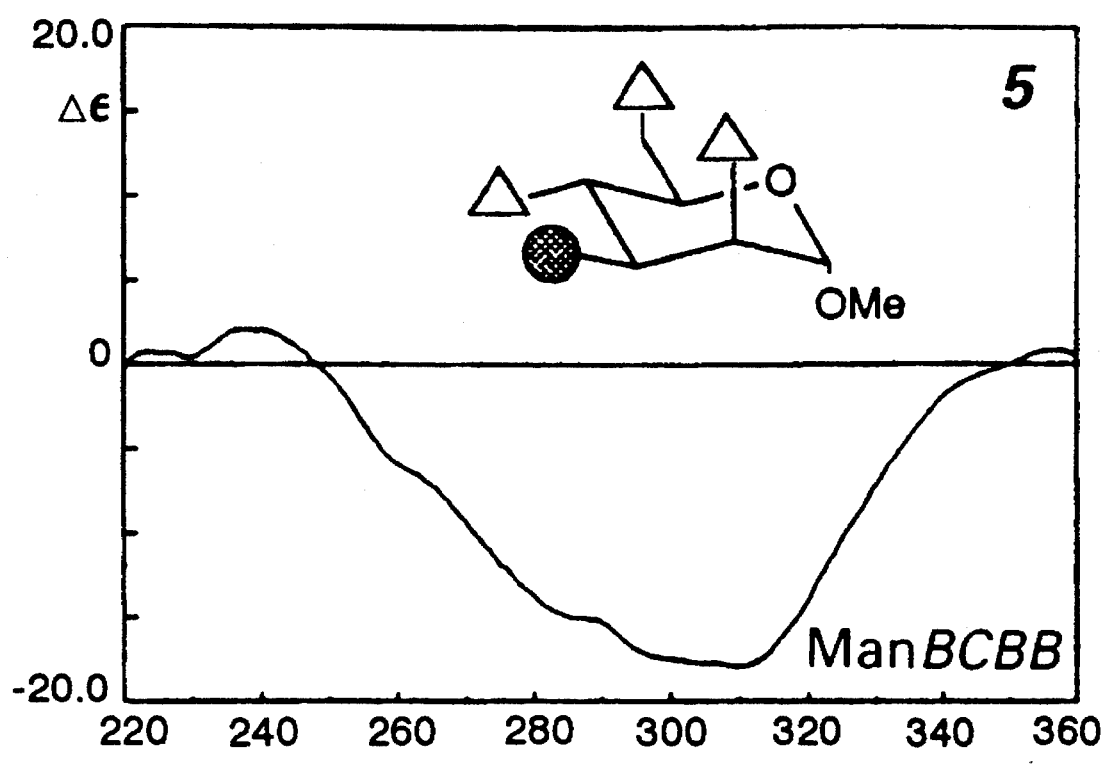
Figure 4F:
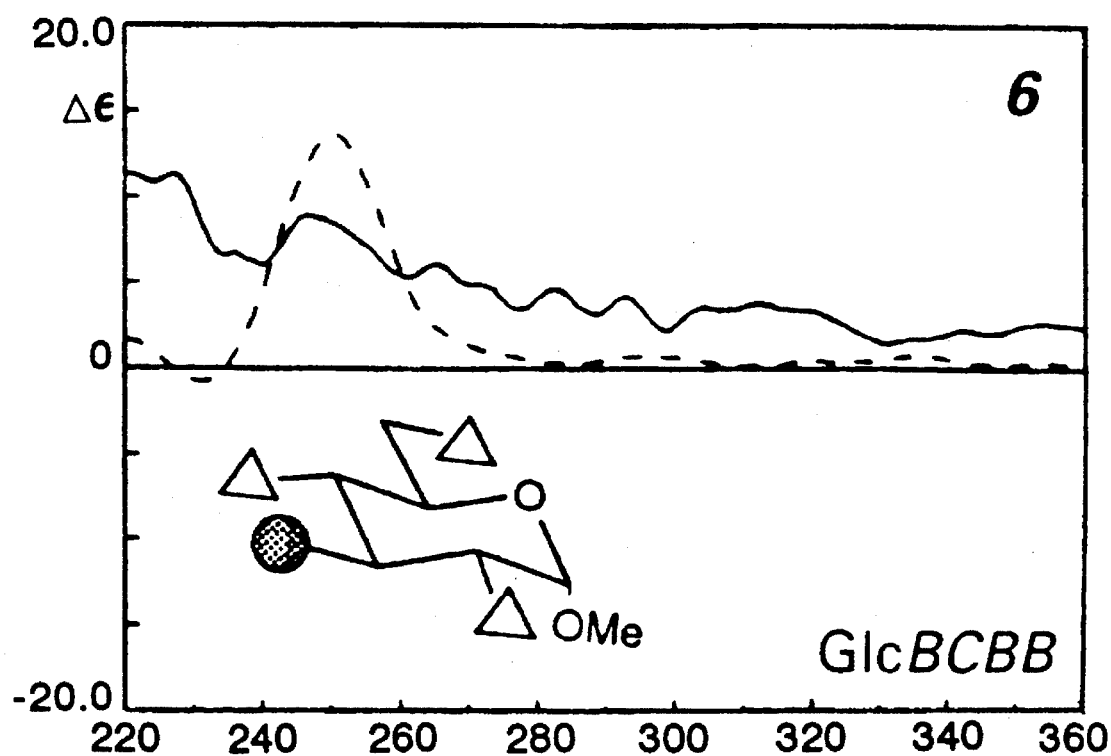
Figure 5A:
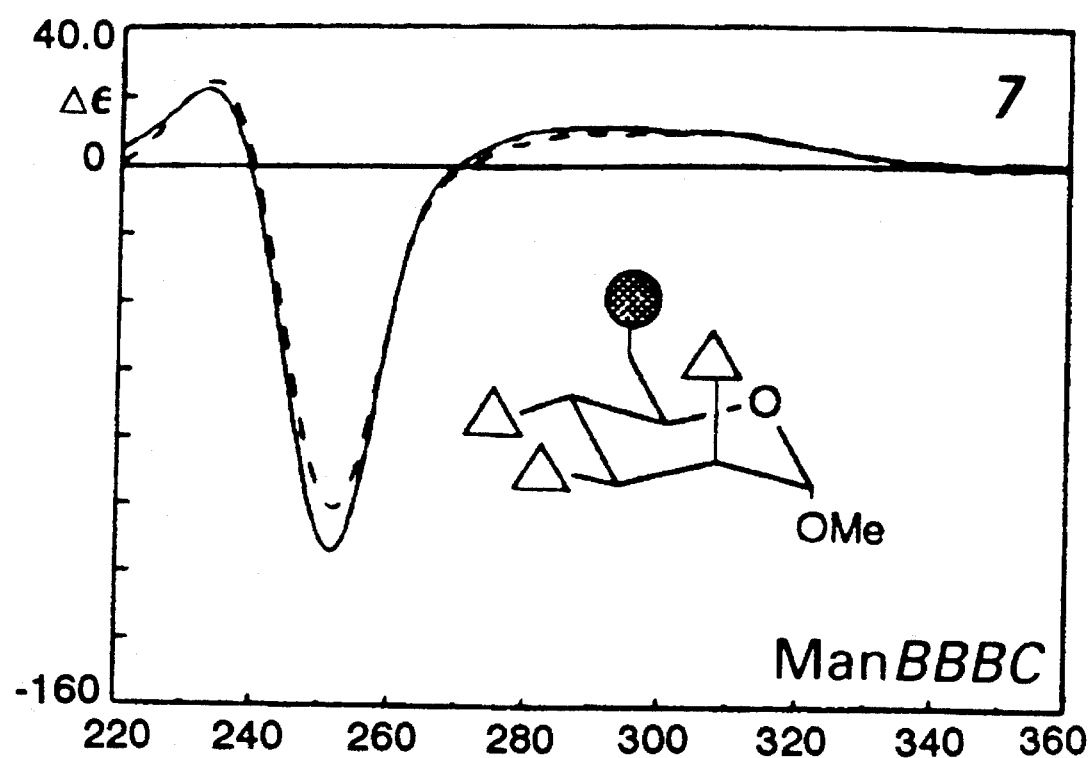
FIGS. 5a–f are a continuation of the $B_3C$ CD spectra of FIGS. 4a–f
Figure 5B:
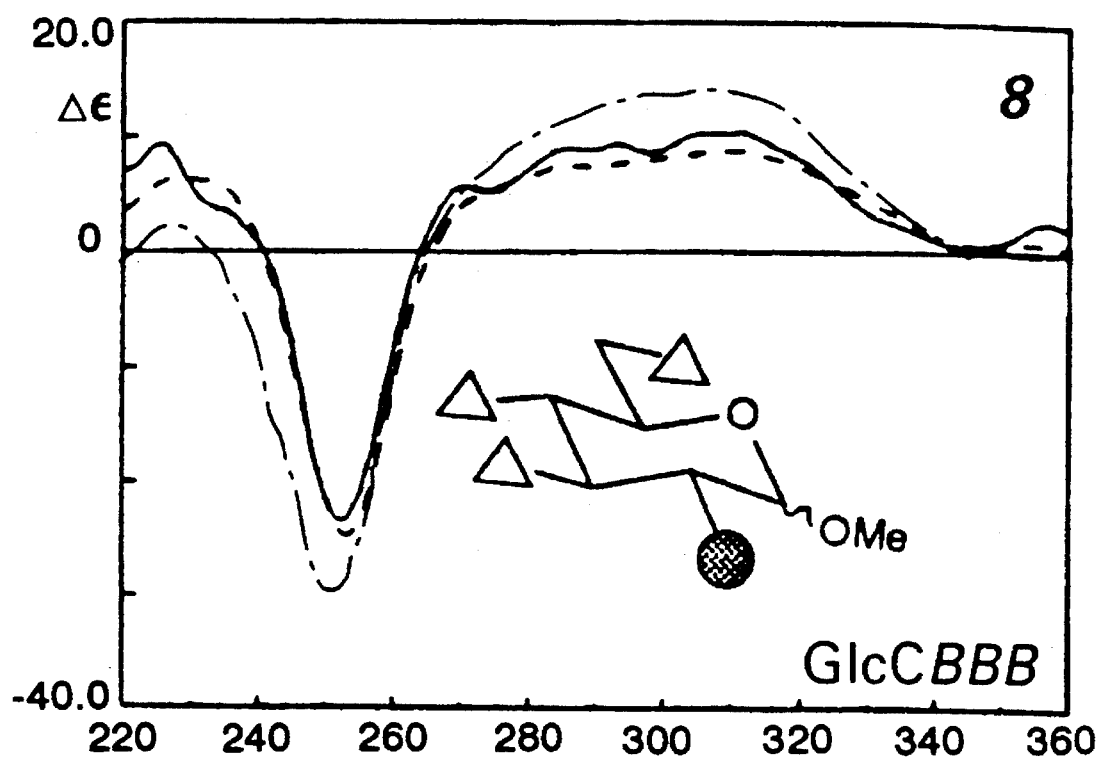
Figure 5C:
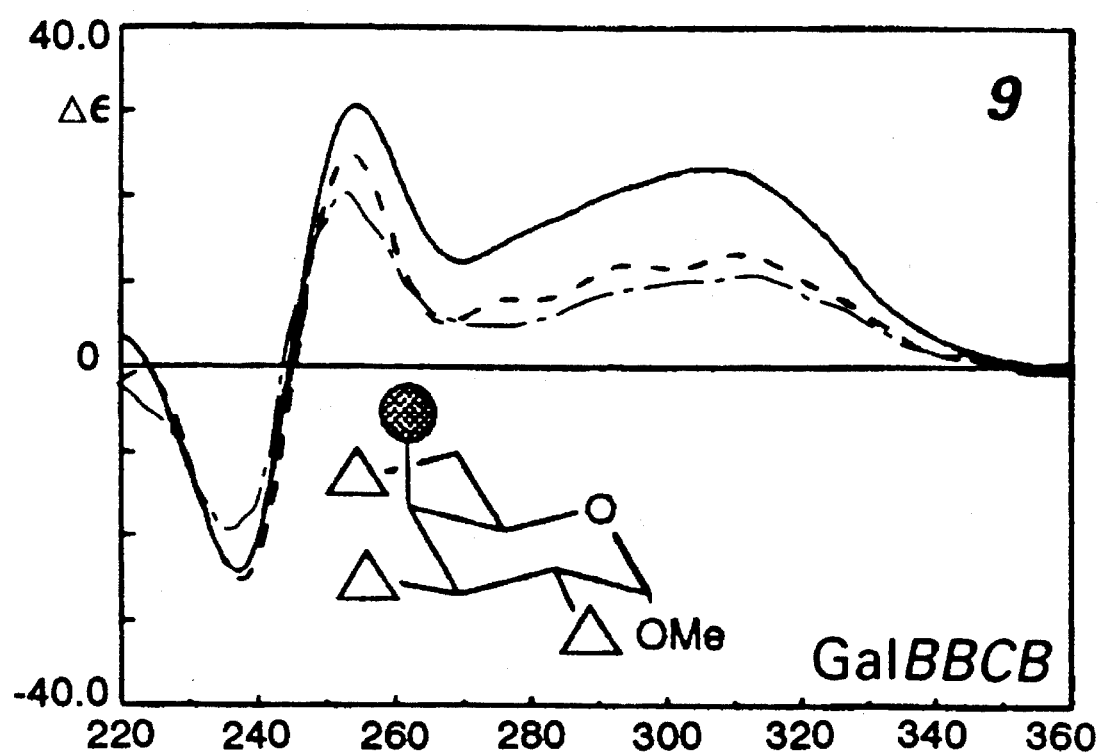
Figure 5D:
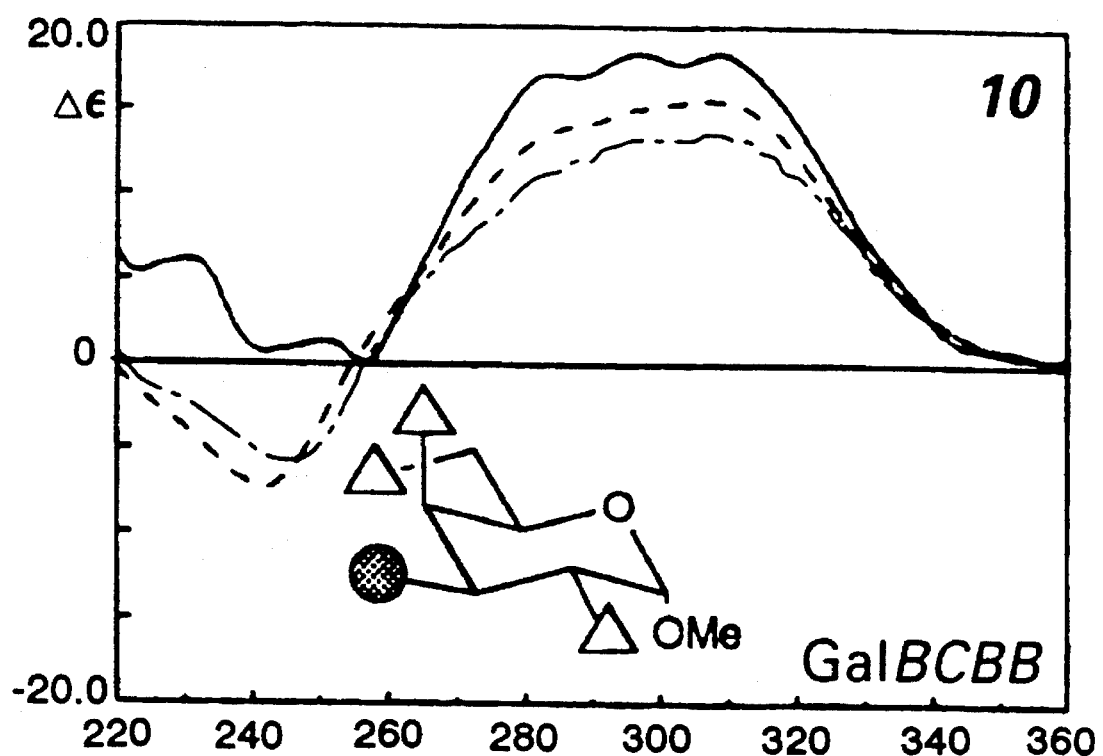
Figure 5E:
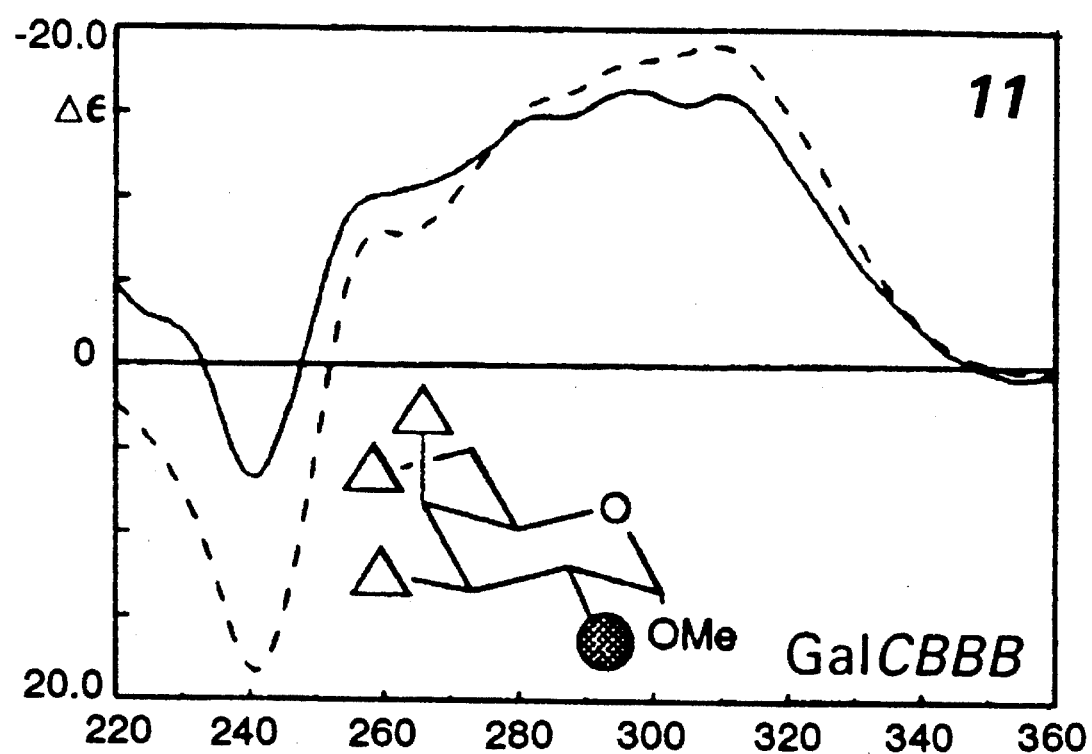
Figure 5F:
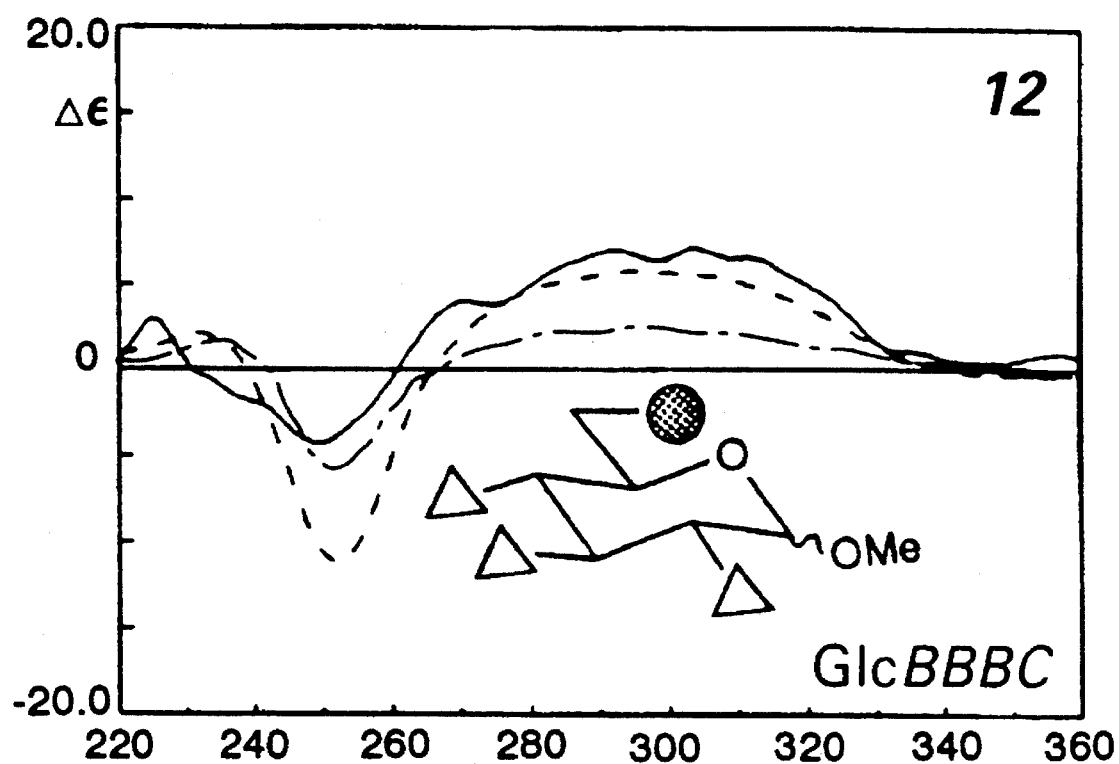

The 72 previously reported basis set spectra [10–12] have been digitally smoothed to improve the signal/noise ratio, and have been used to calculate CD curves for all possible tri- and tetrachromophoric pyranoside derivatives related to the glucose, galactose, and mannose parent sugars. The calculation procedure involves an algebraic summation of either the three (for trichromophoric derivatives) or six (for tetrachromophoric derivatives) basis set spectra which represent the constitutent pairwise two-chromophore interactions in the tri- and tetrachromophoric derivatives in question. For example, FIG. 3 shows the six basis set spectra corresponding to each of the six pairwise interactions in methyl galactopyranoside 4-p-bromobenzoate 2,3,6-tri-p-methoxycinnamate (Ga1CBCC). These include three spectra for benzoate/cinnamate interactions (I–III) and three for cinnamate/cinnamate interactions (IV–VI). Benzoate/cinnamate interactions give rise to Cotton effects around the absorption maxima of the two chromophores (245 and 311 nm). Cinnamate/cinnamate interactions result in tow Cotton effects centered around the cinnamate absorption maximum at 311 nm. The sum of these six spectra provides a satisfactory simulation of GalCBCC (see FIG. 6, spectrum 16, for a comparison of calculated vs. observed CDs). While none is present in this example, benzoate/benzoate interactions give rise to two Cotton effects around 245 nm (see, for example, CD spectra of GlcBBBB and XylBBB, FIG. 1f,g).

Figure 6A:
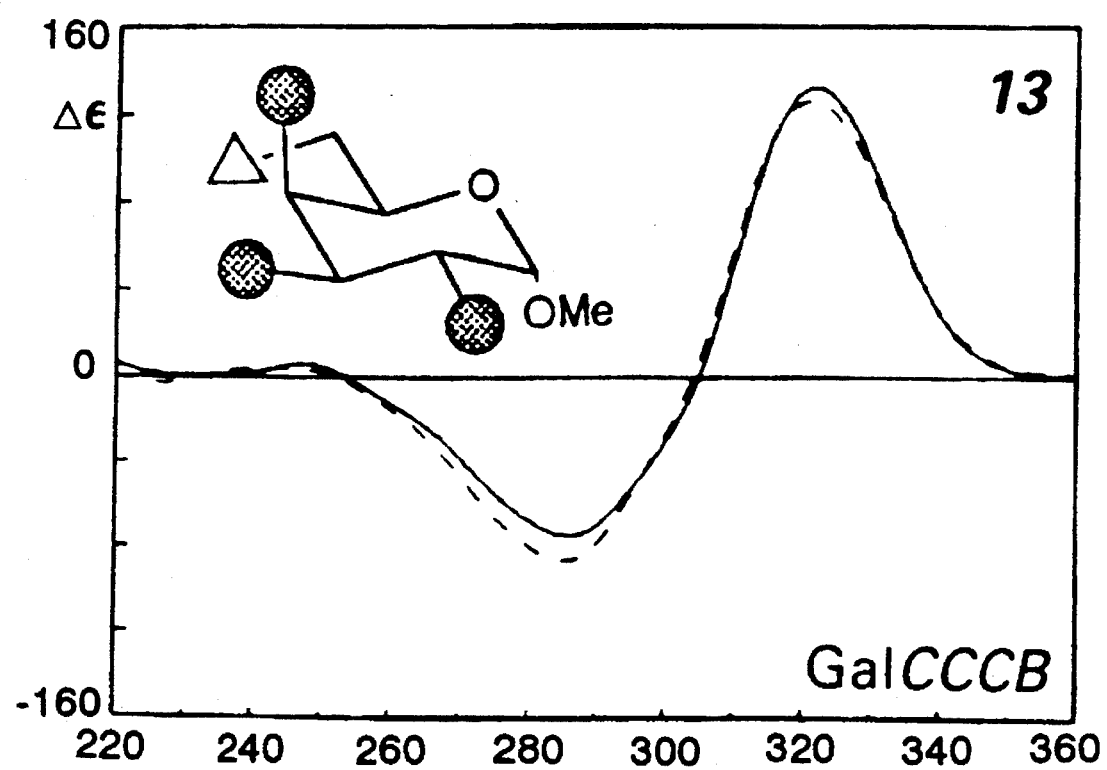
FIGS. 6a–f contain $BC_3$ CD spectra.
Figure 6B:
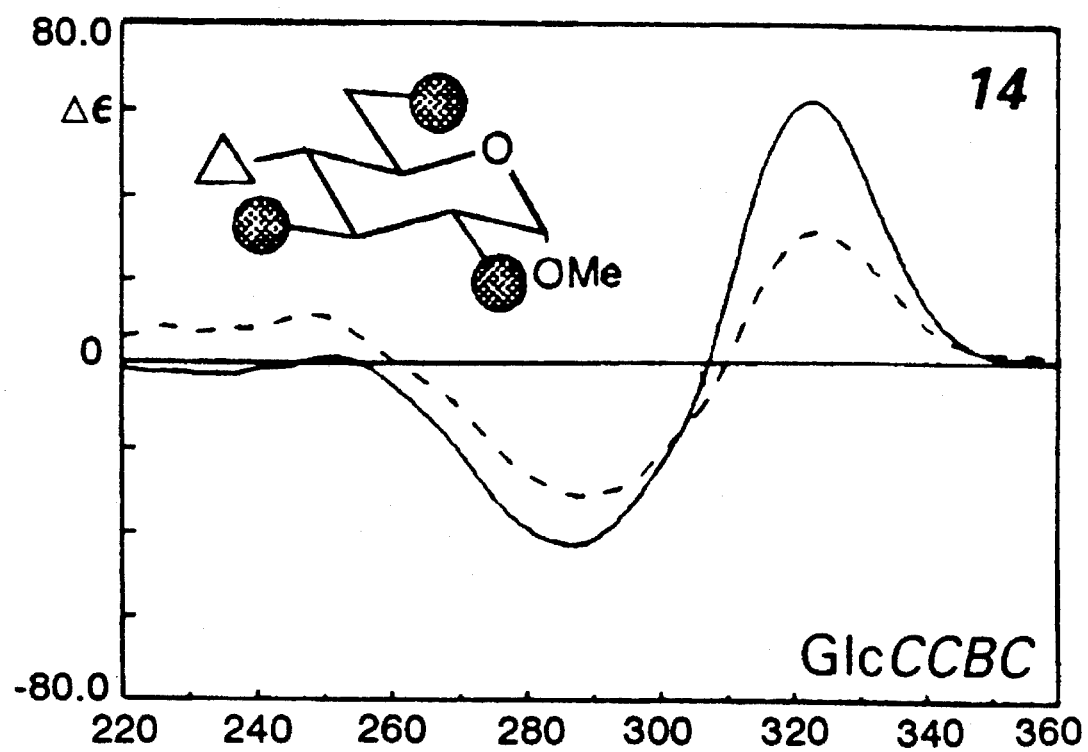
Figure 6C:
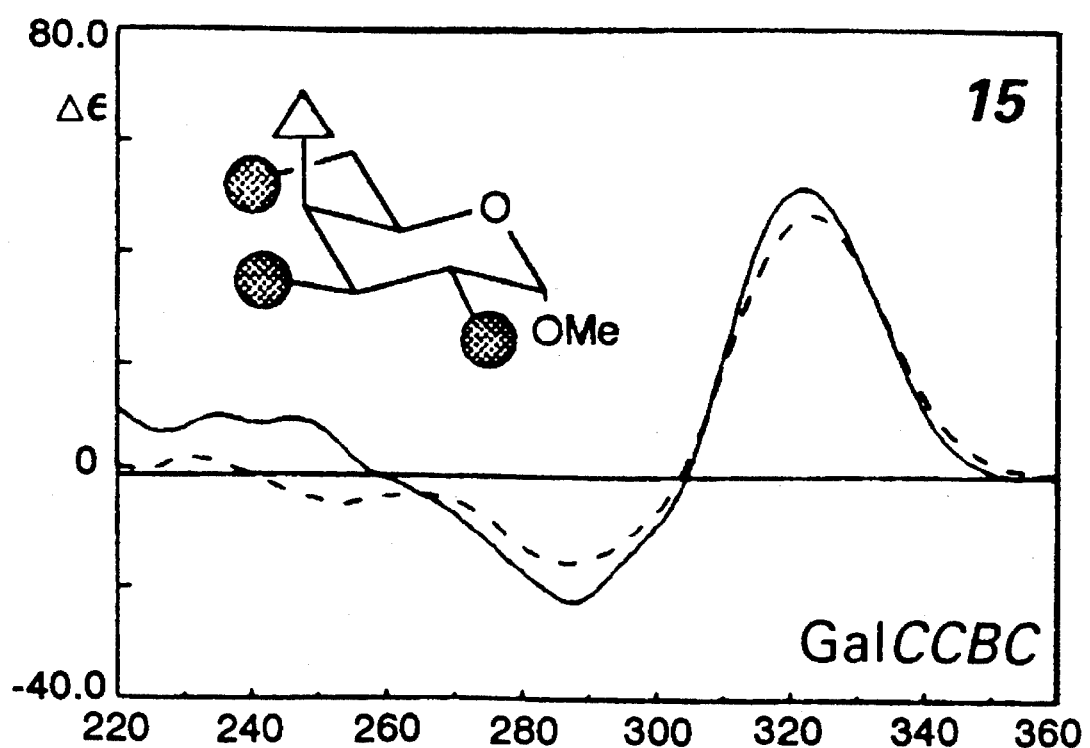
Figure 6D:
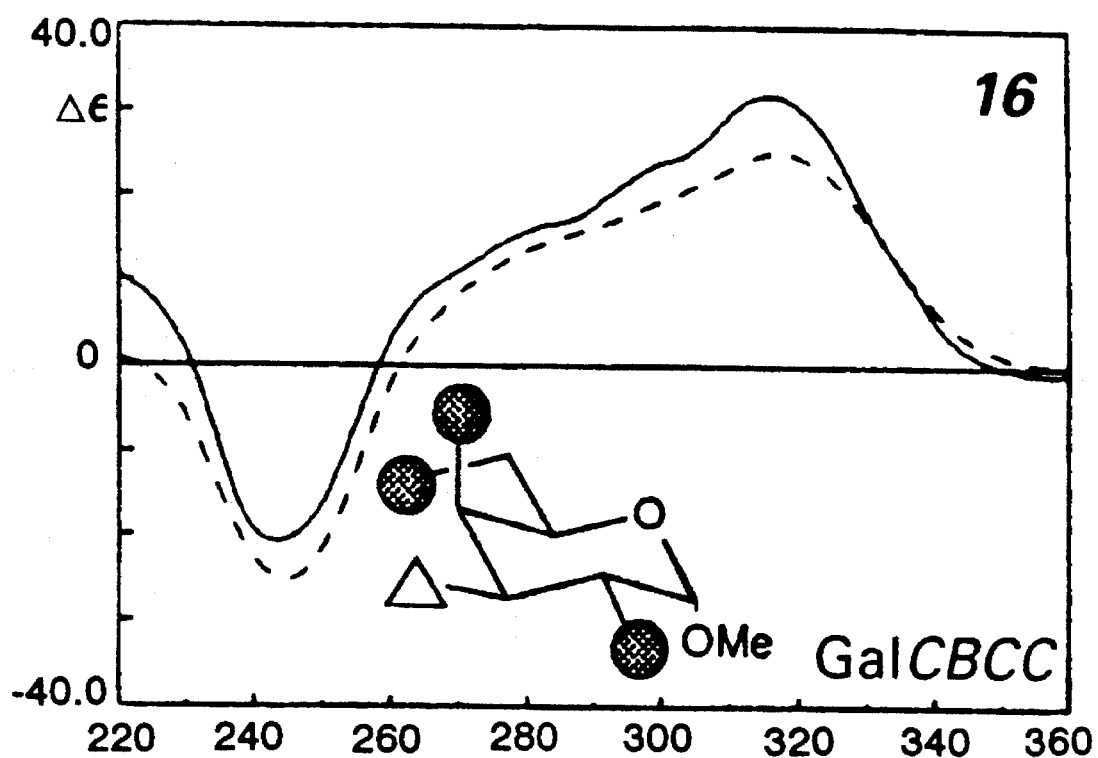
Figure 6E:
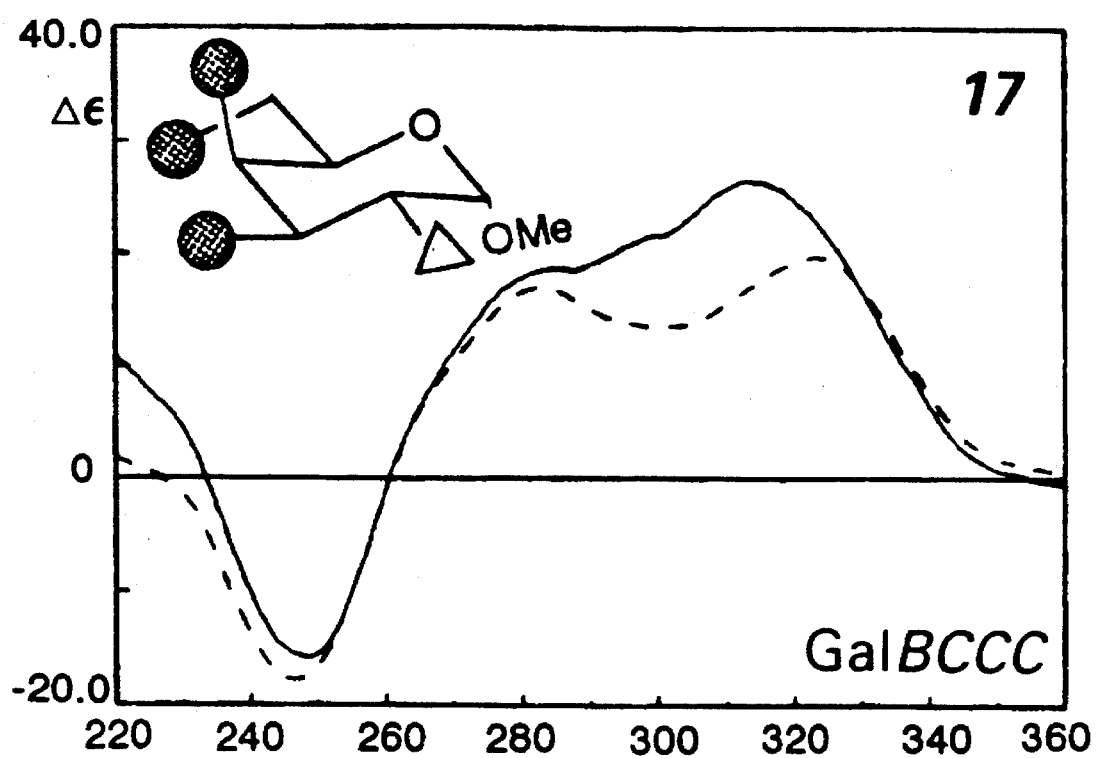
Figure 6F:
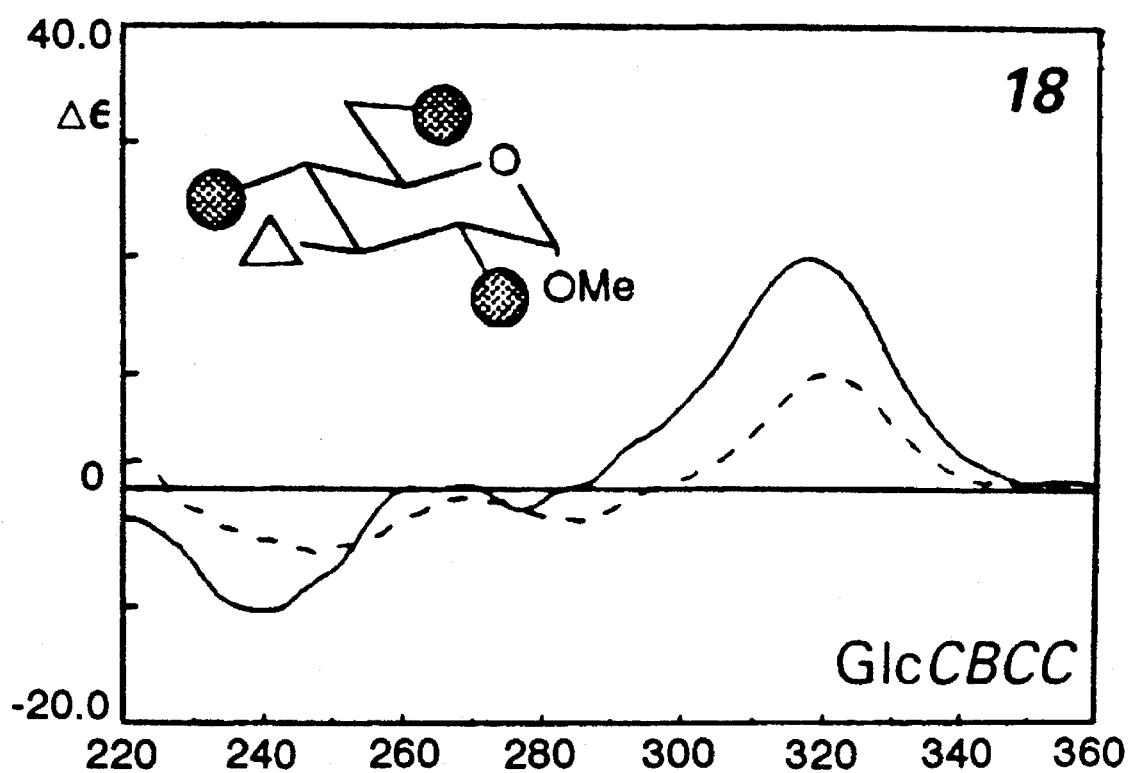
Figure 7A:
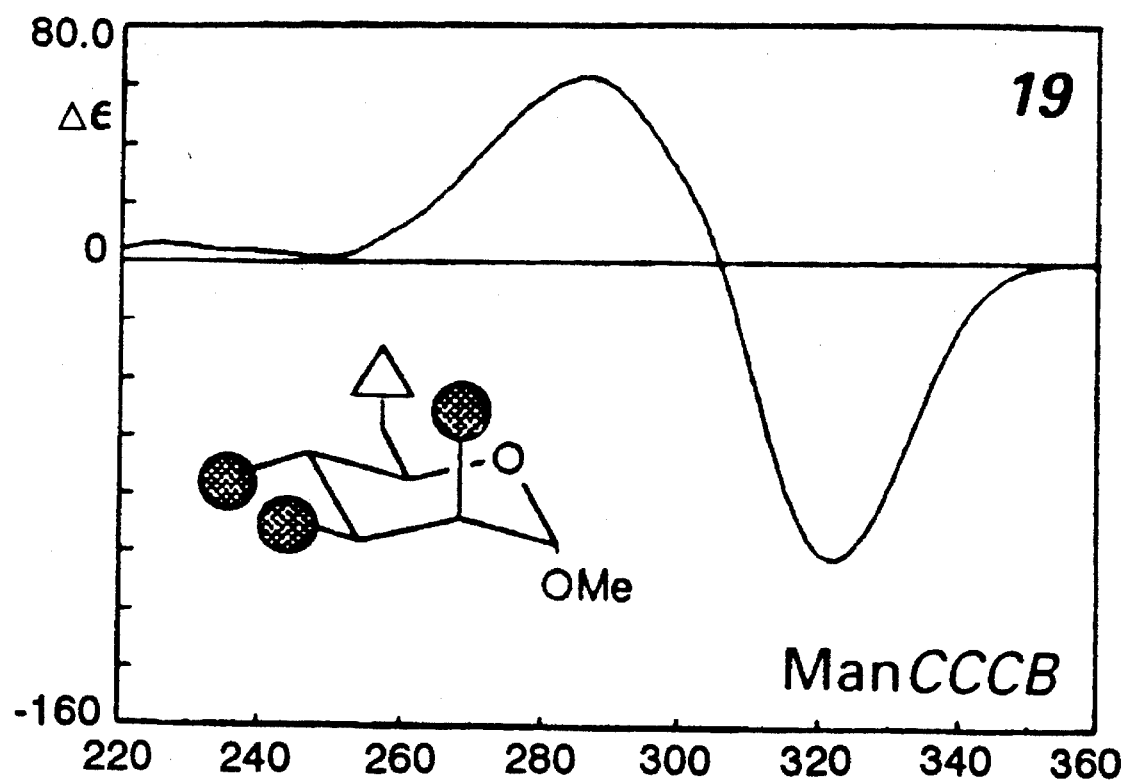
FIGS. 7a–f are a continuation of the $BC_3$ CD spectra of FIGS. 6a–f.
Figure 7B:
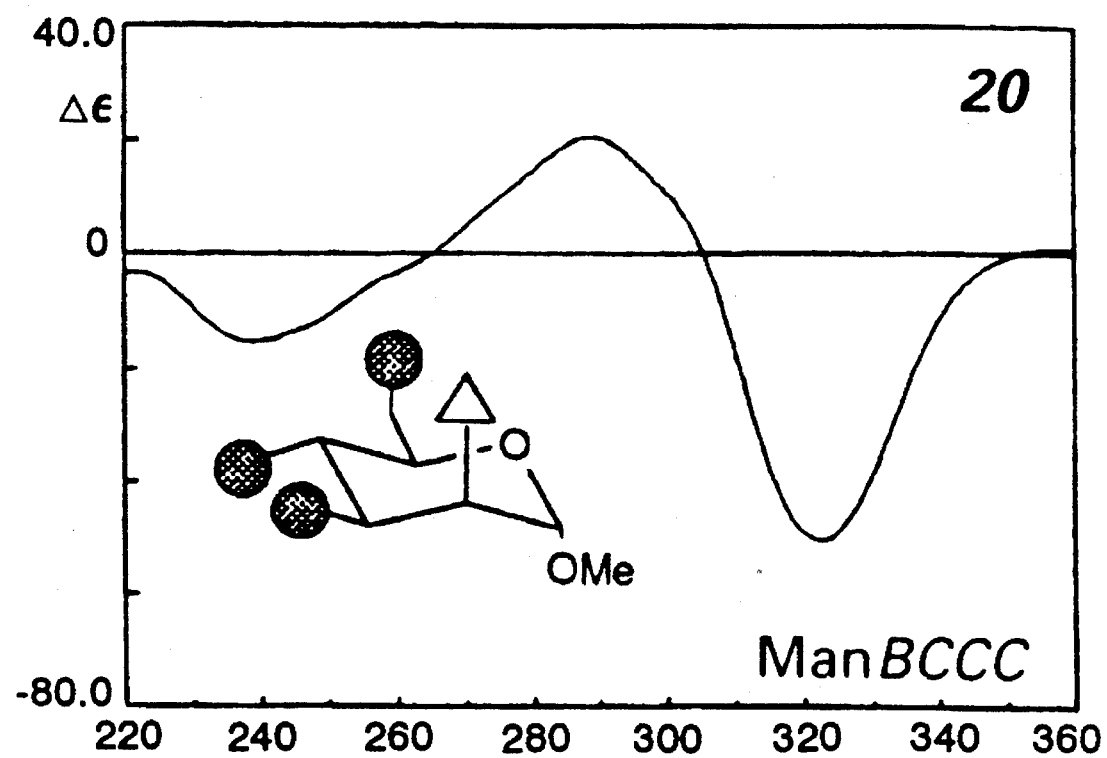
Figure 7C:
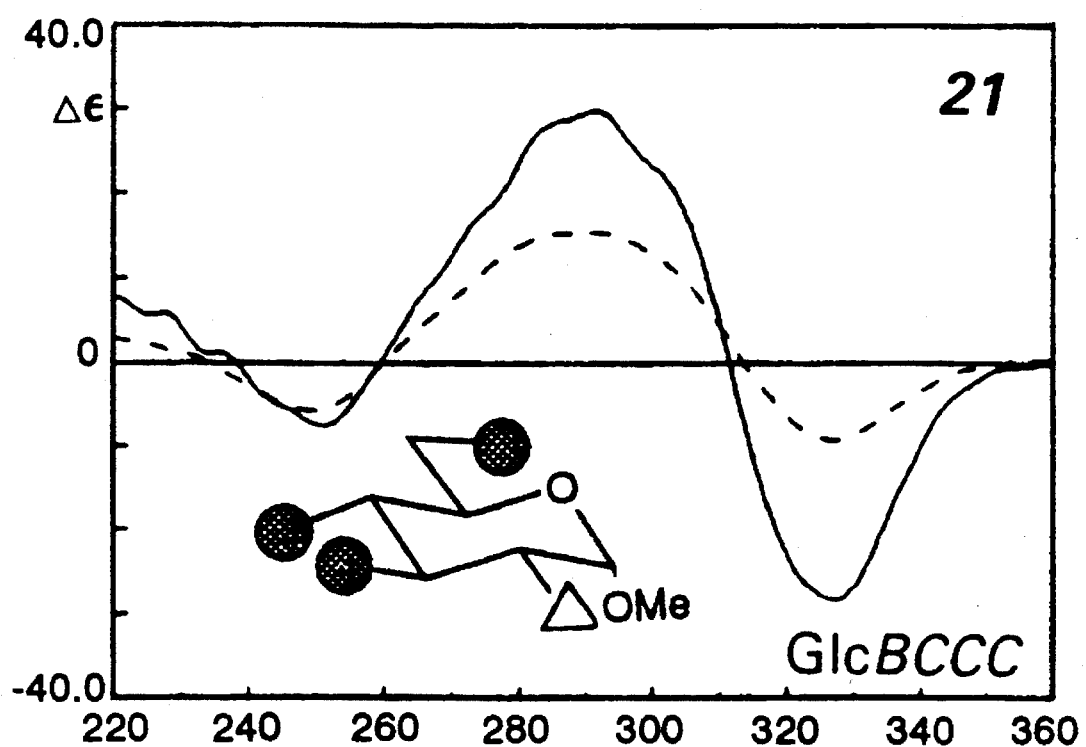
Figure 7D:
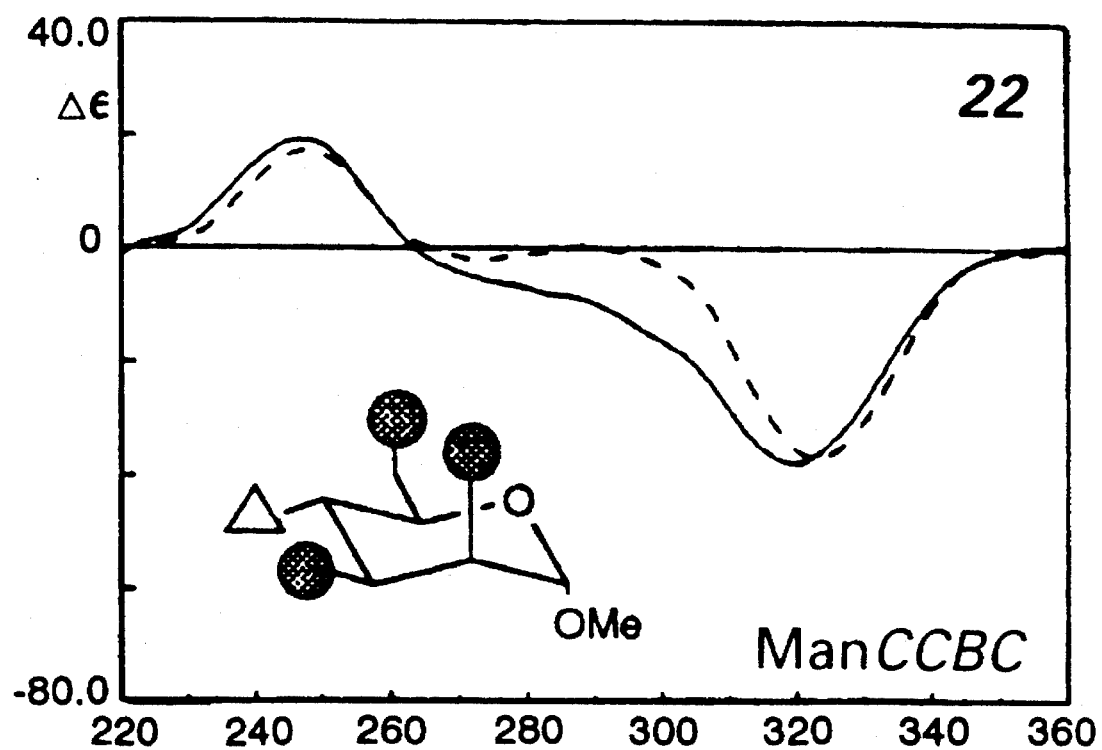
Figure 7E:
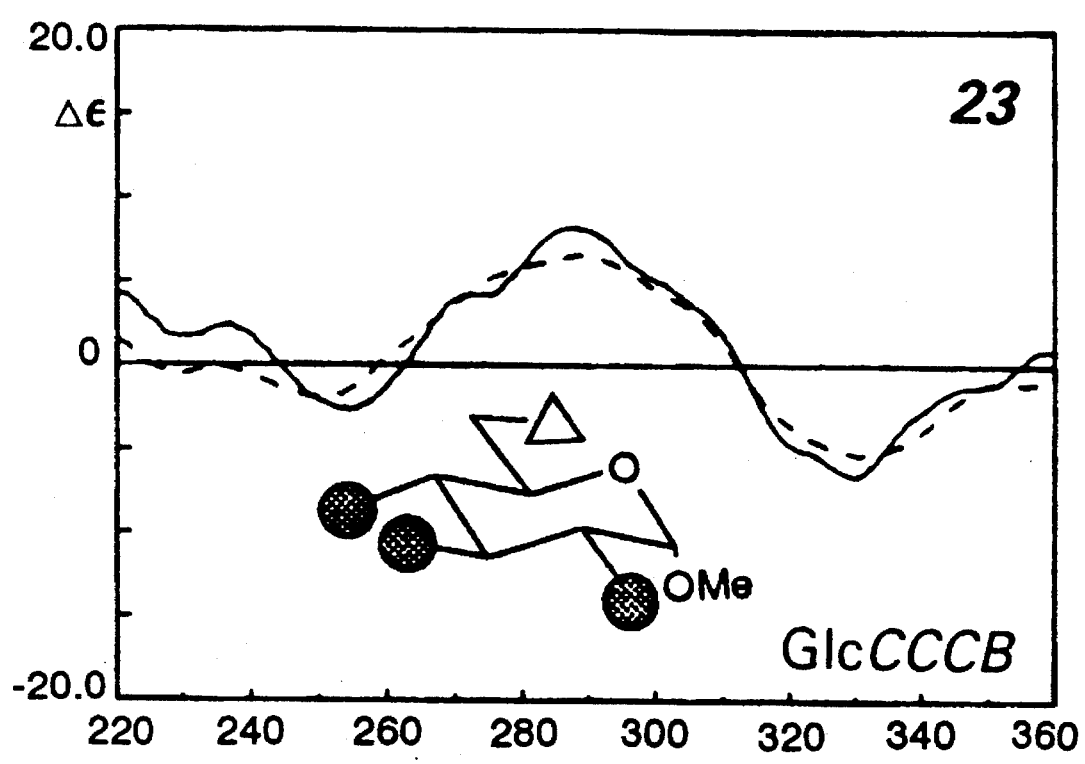
Figure 7F:
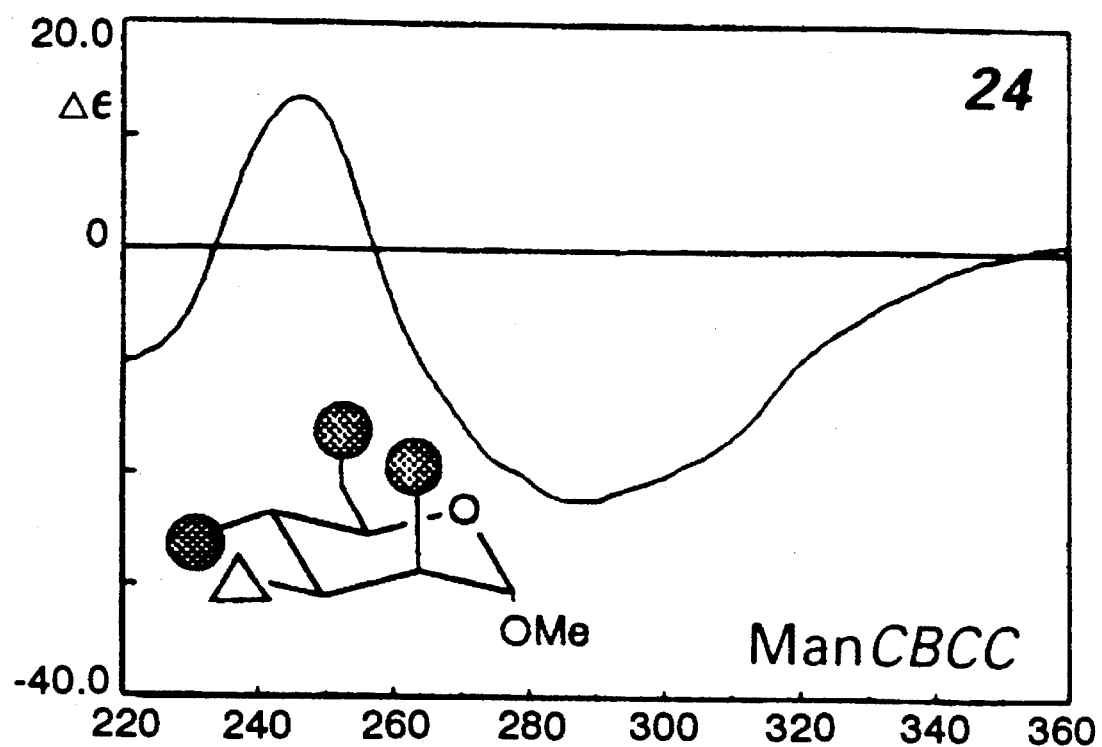
Figure 8A:
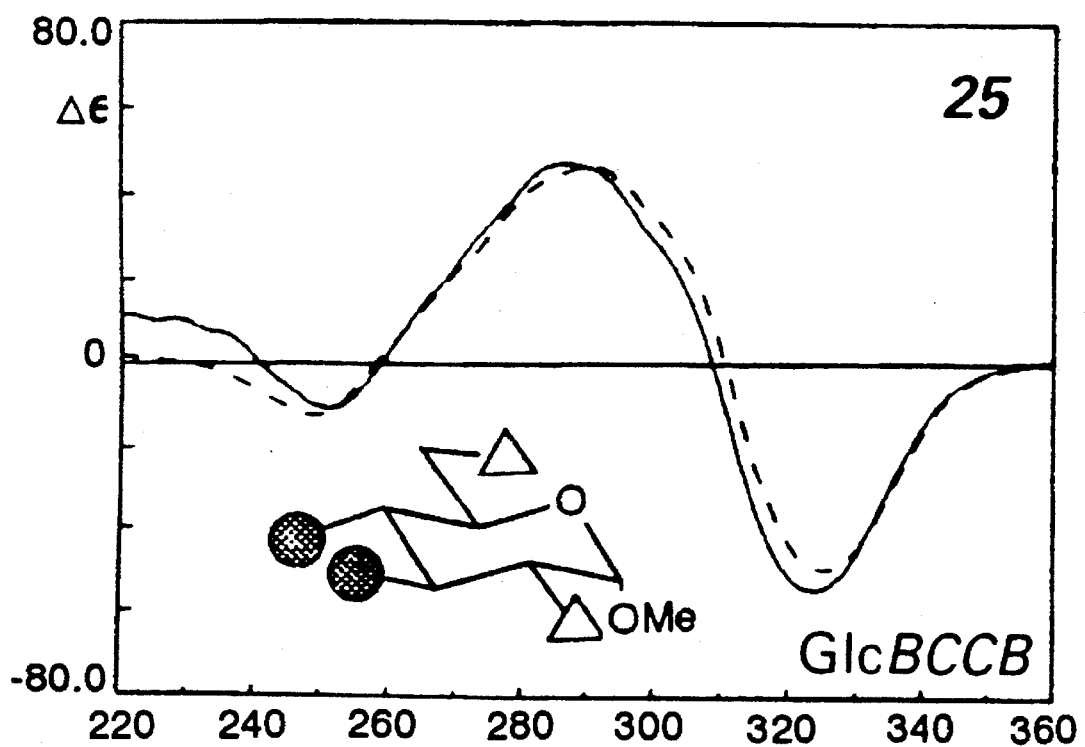
FIGS. 8a–f contain $B_2C_2$ CD spectra.
Figure 8B:
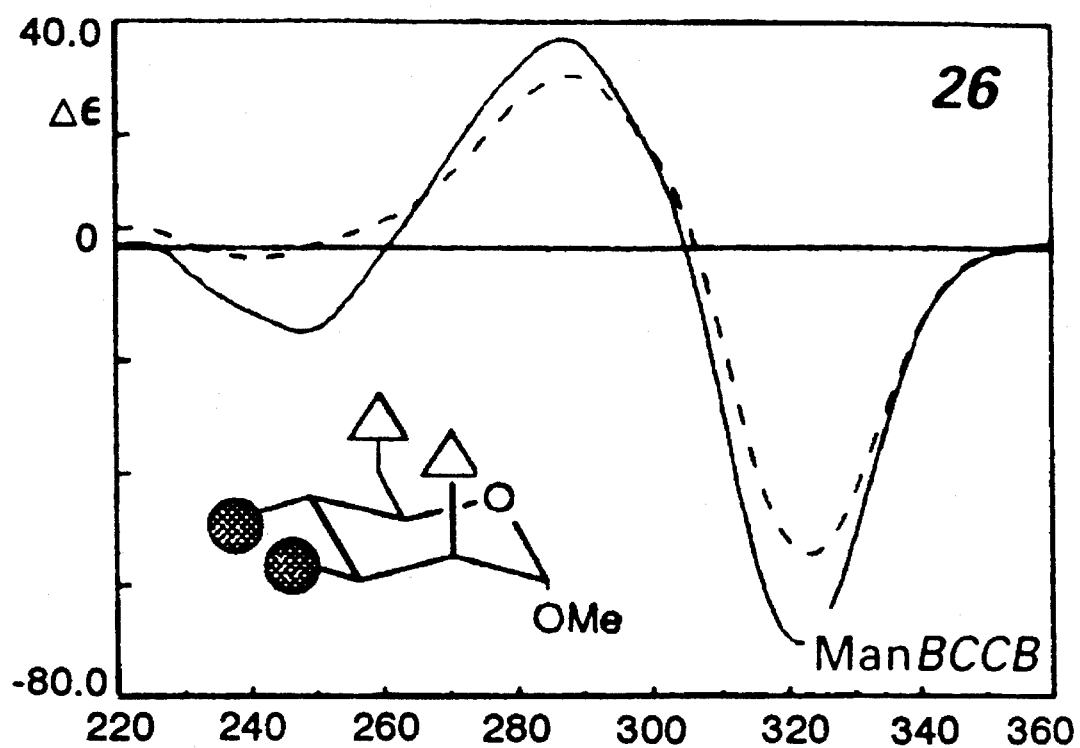
Figure 8C:
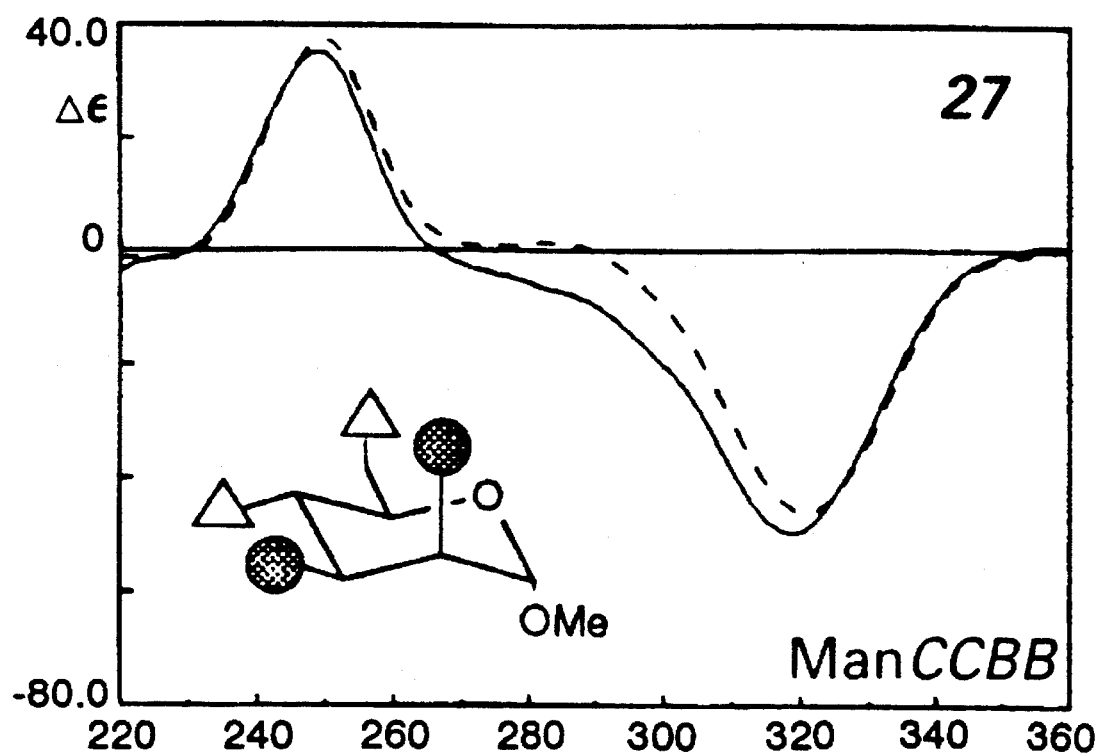
Figure 8D:
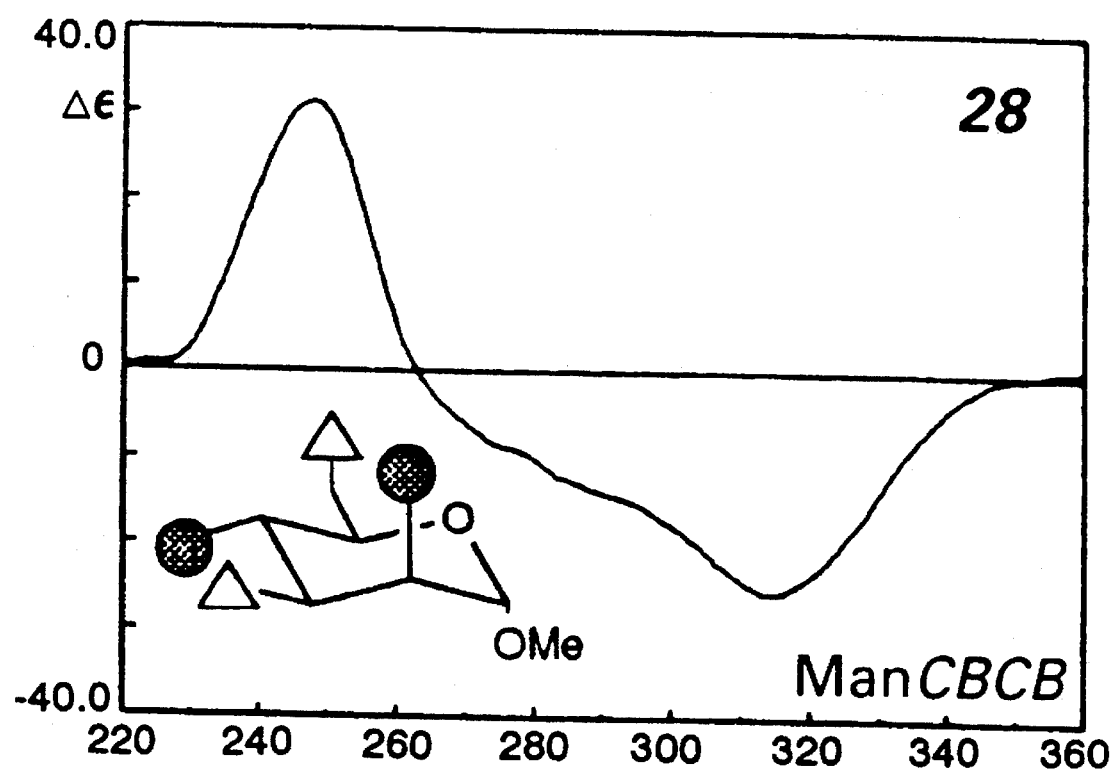
Figure 8E:
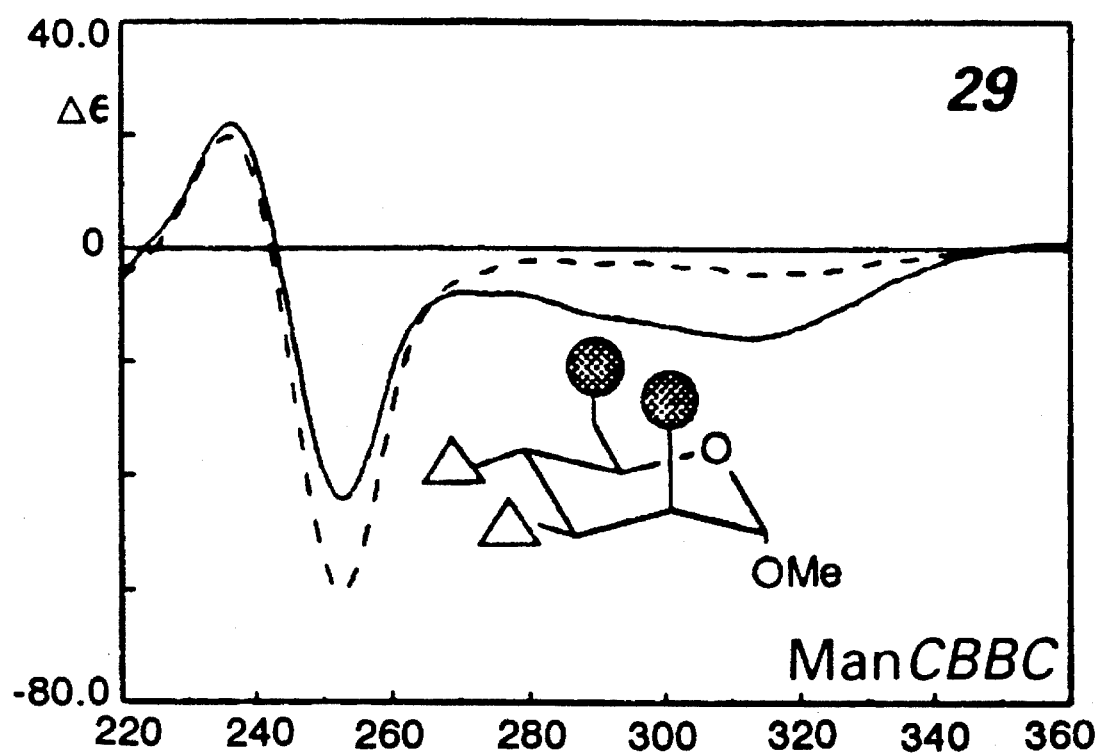
Figure 8F:
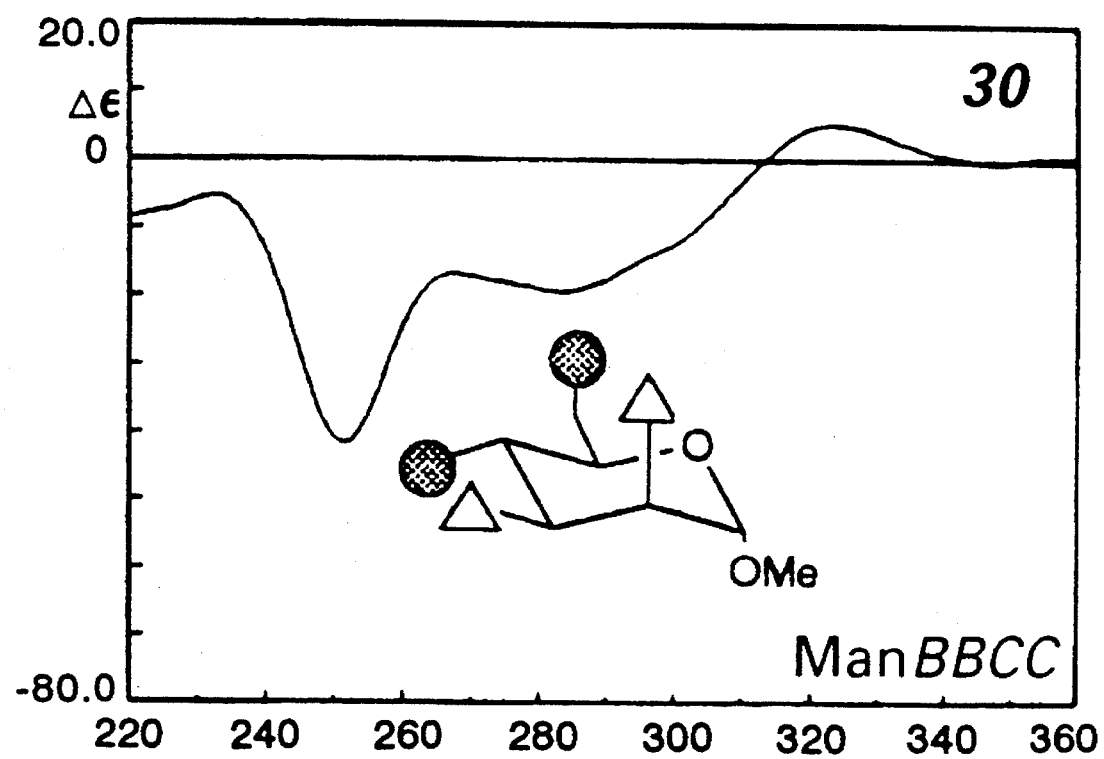
Figure 9A:
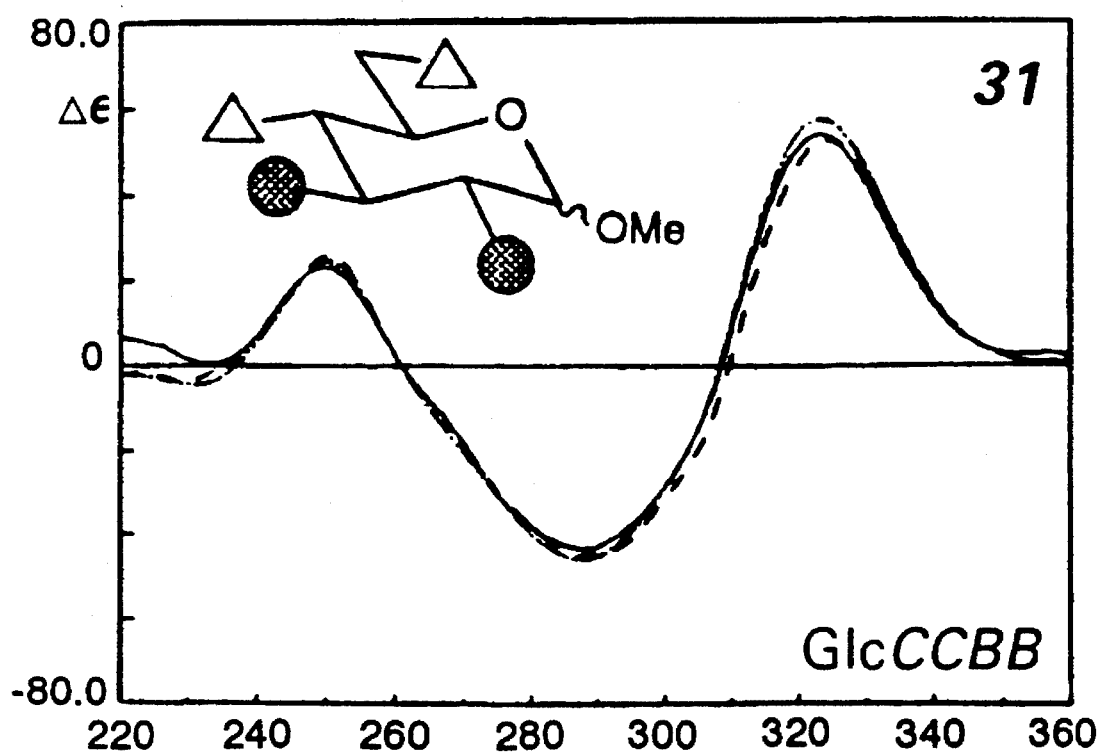
FIGS. 9a–f are a continuation of the $B_2C_2$ CD spectra of FIGS. 8a–f.
Figure 9B:
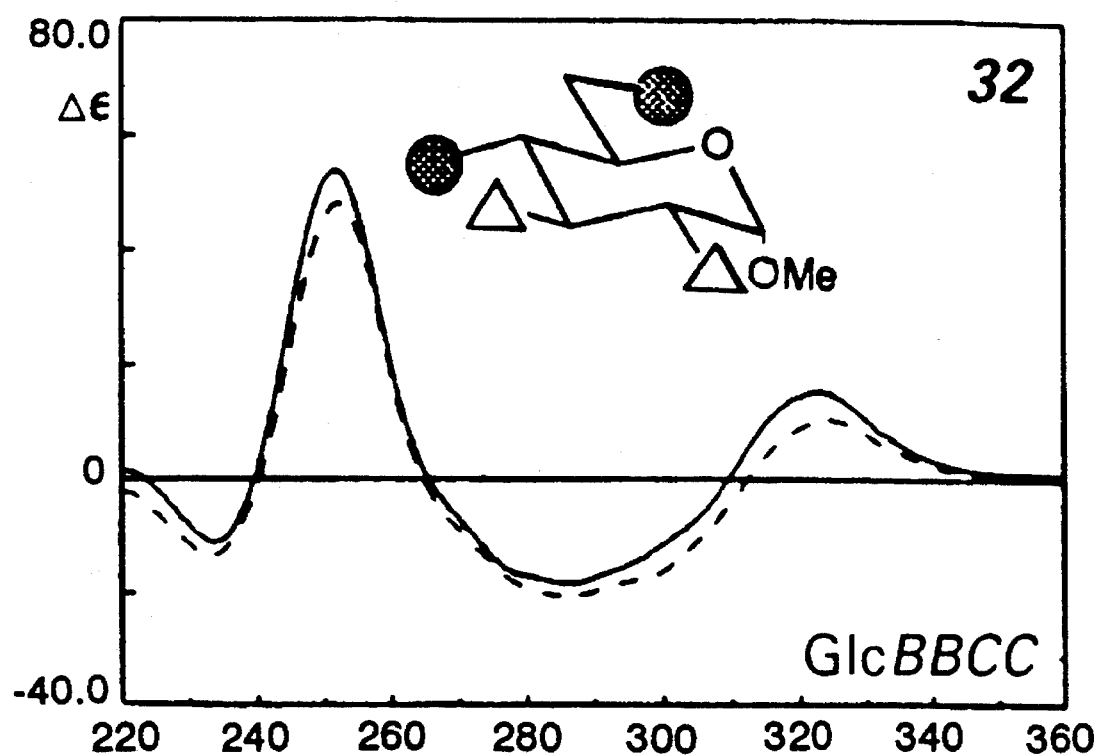
Figure 9C:
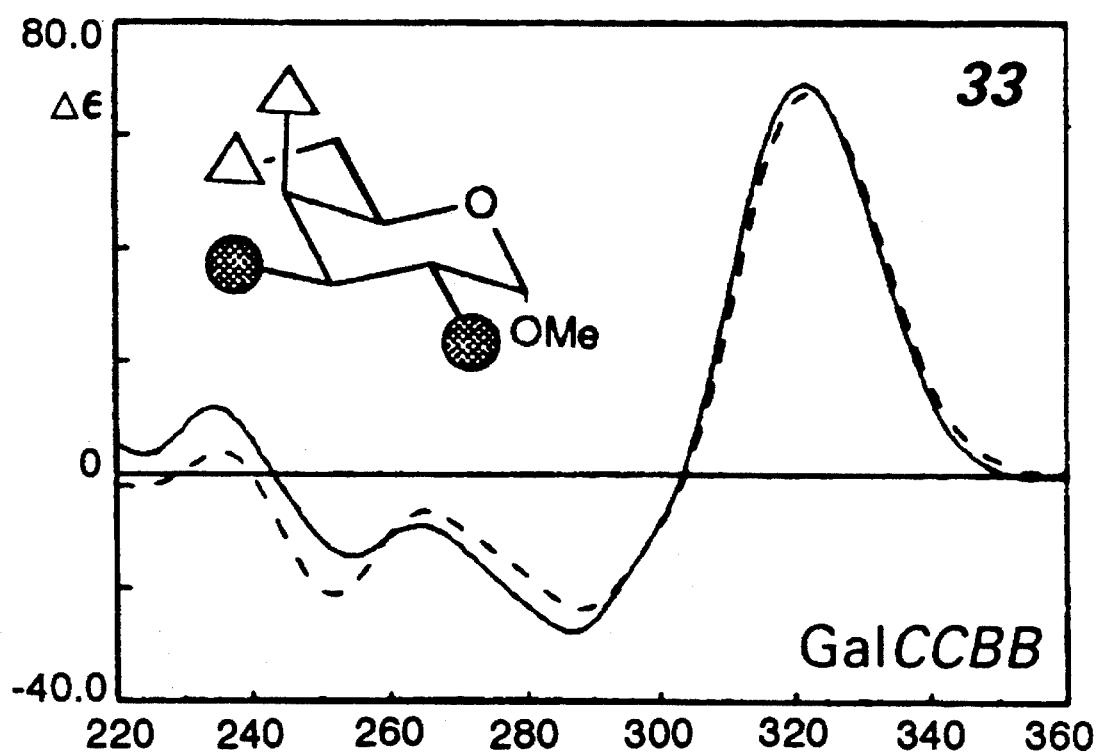
Figure 9D:
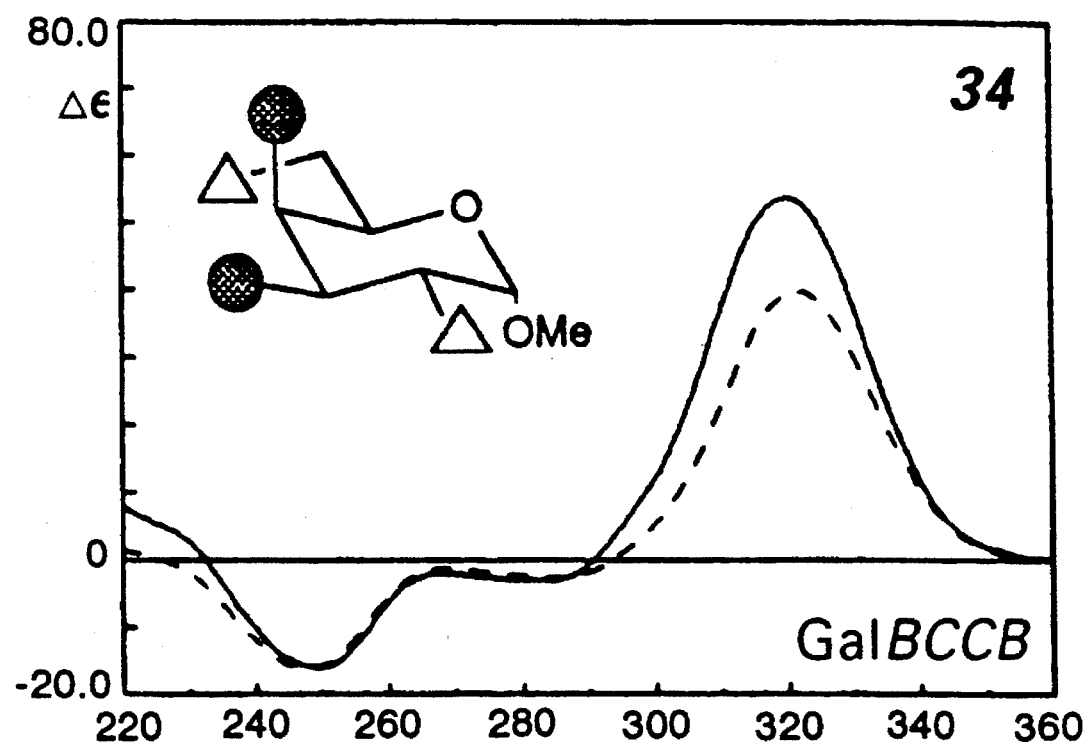
Figure 9E:
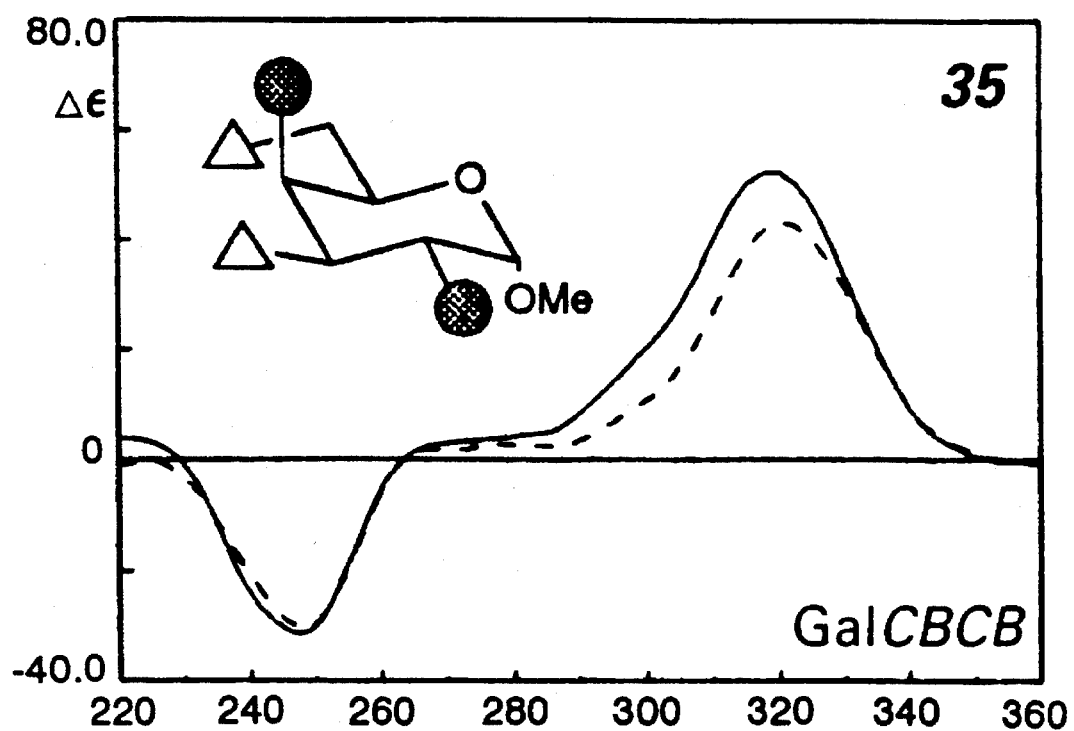
Figure 9F:
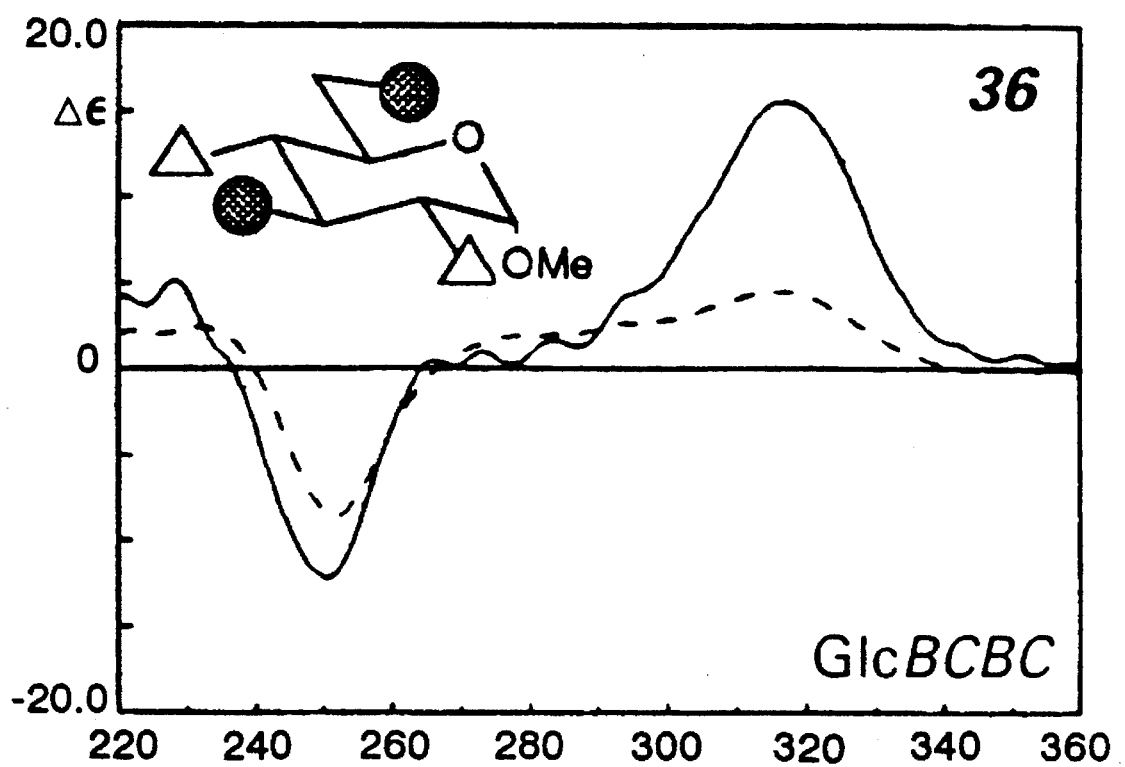
Figure 10A:
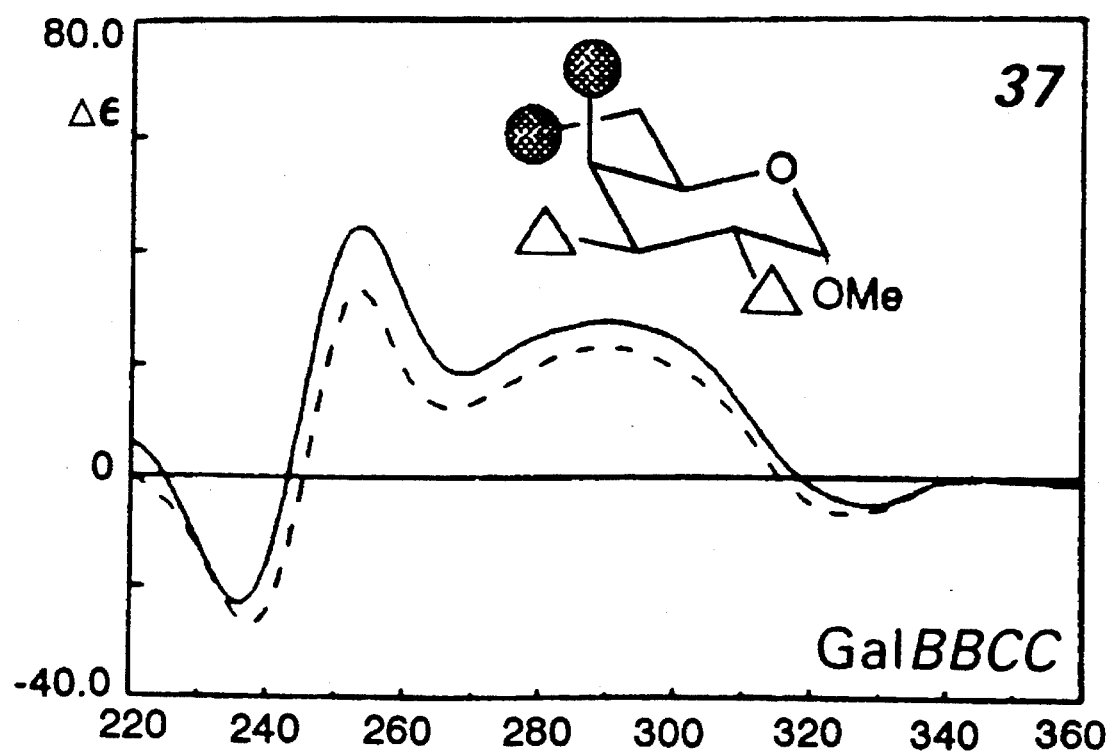
FIGS. 10a–f are a continuation of the $B_2C_2$ CD spectra of FIGS. 8a–f.
Figure 10B:
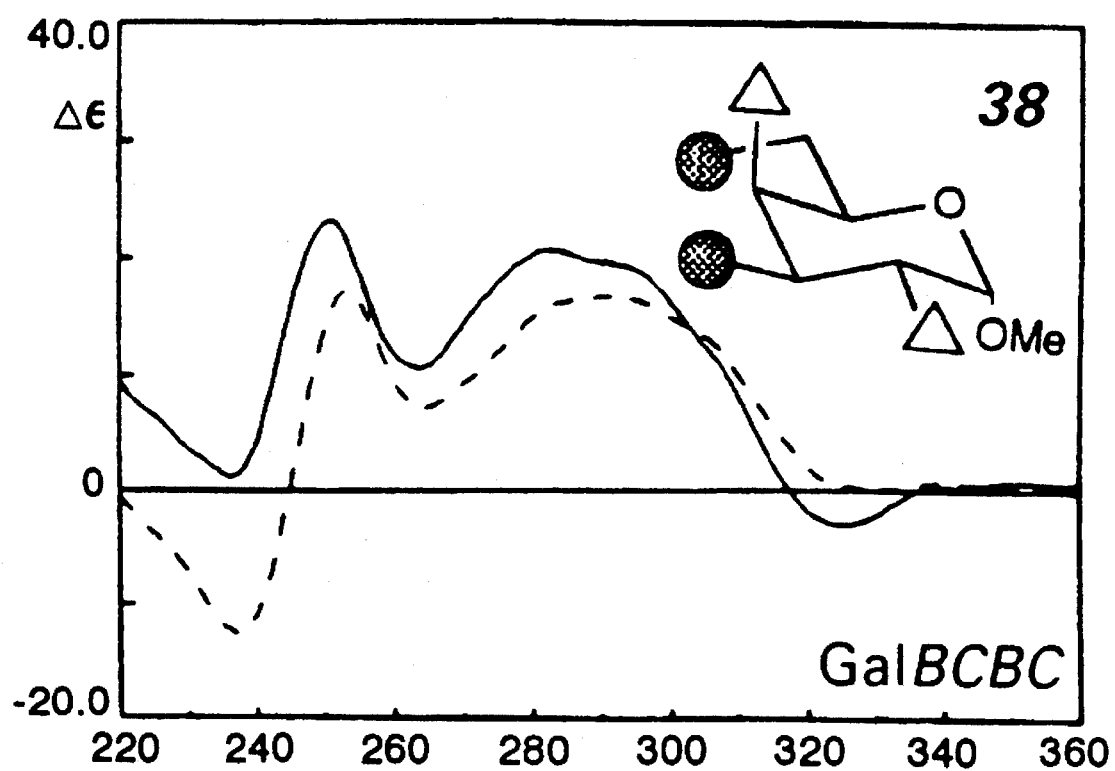
Figure 10C:
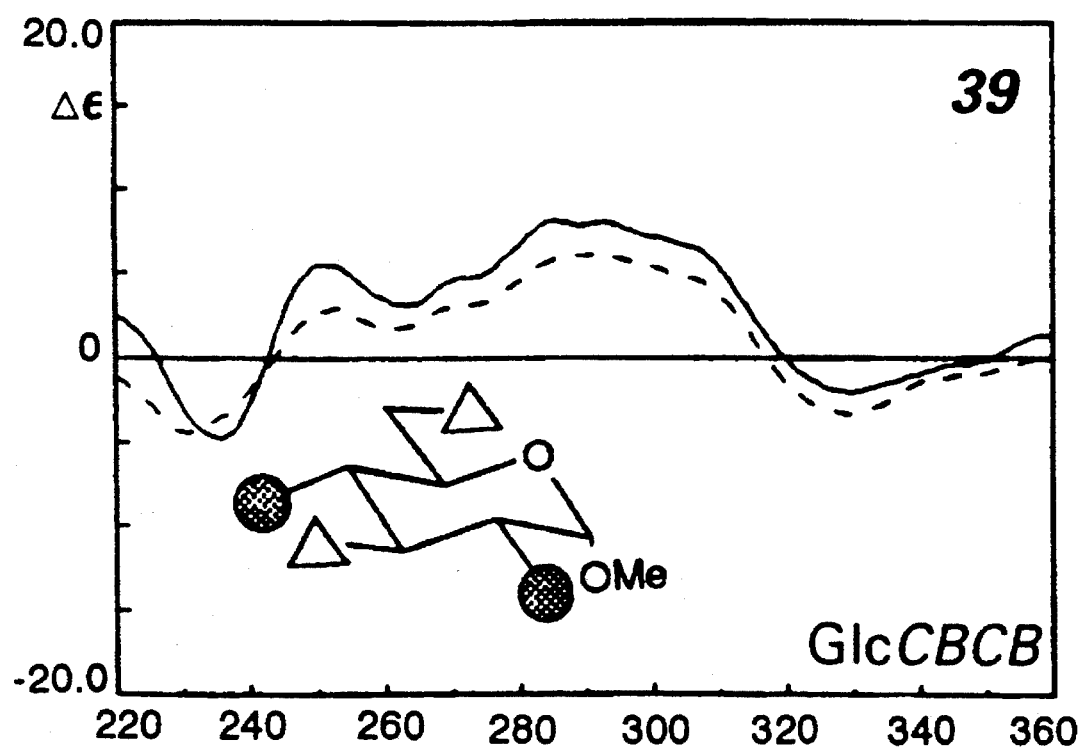
Figure 10D:
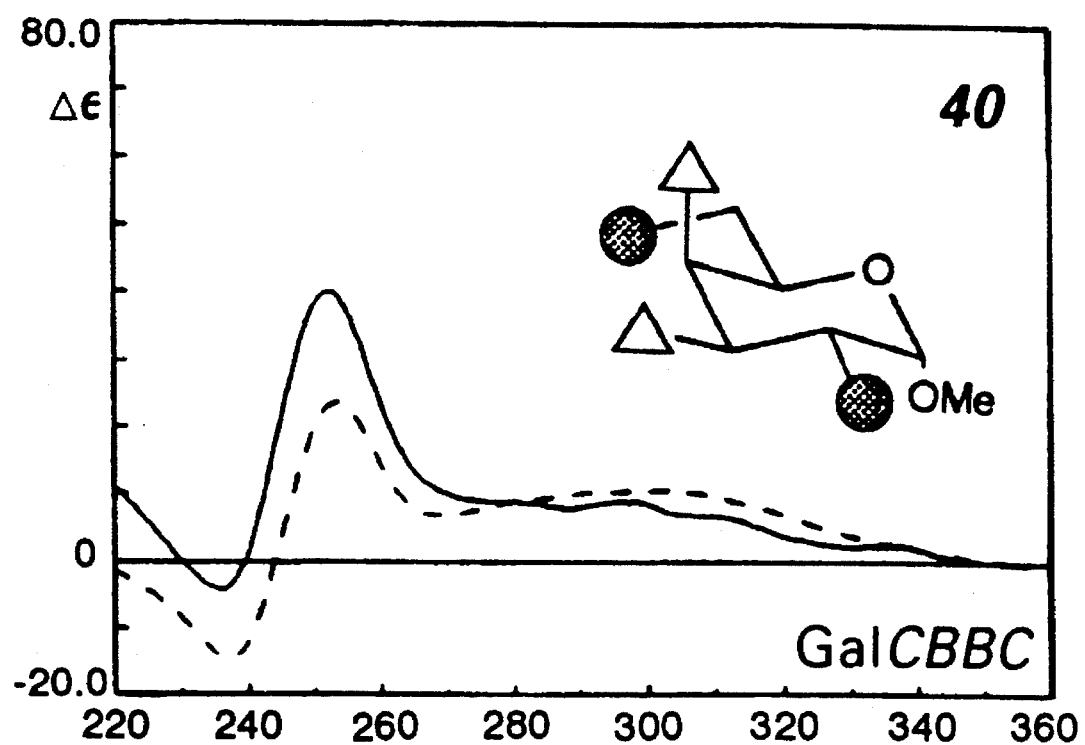
Figure 10E:
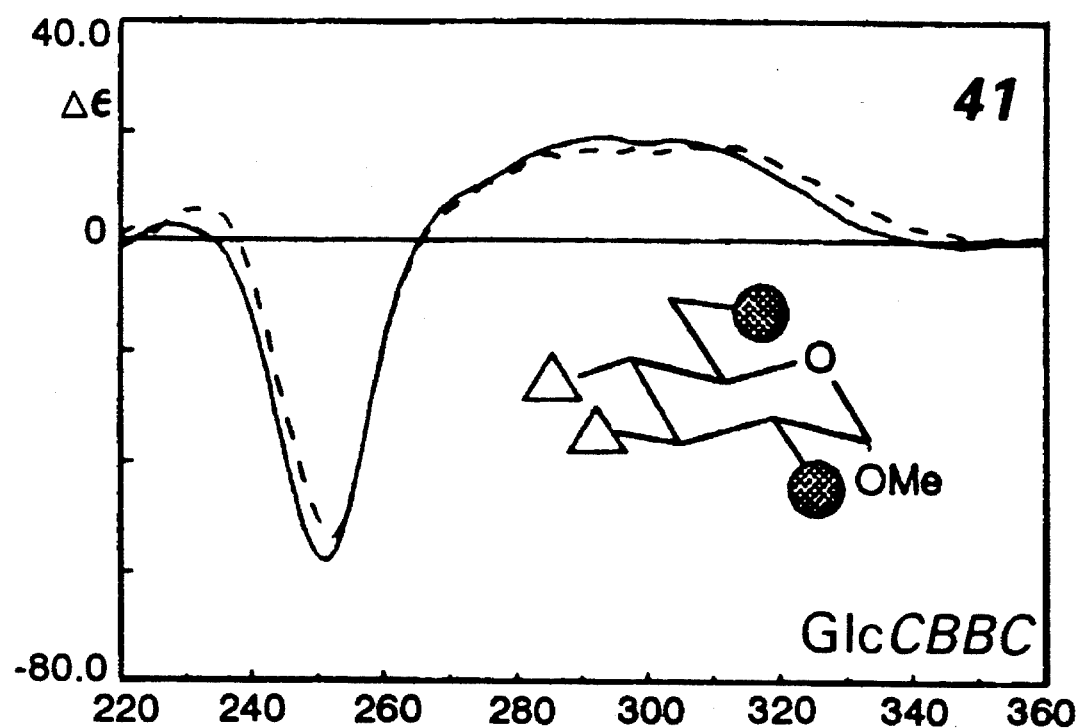
Figure 10F:
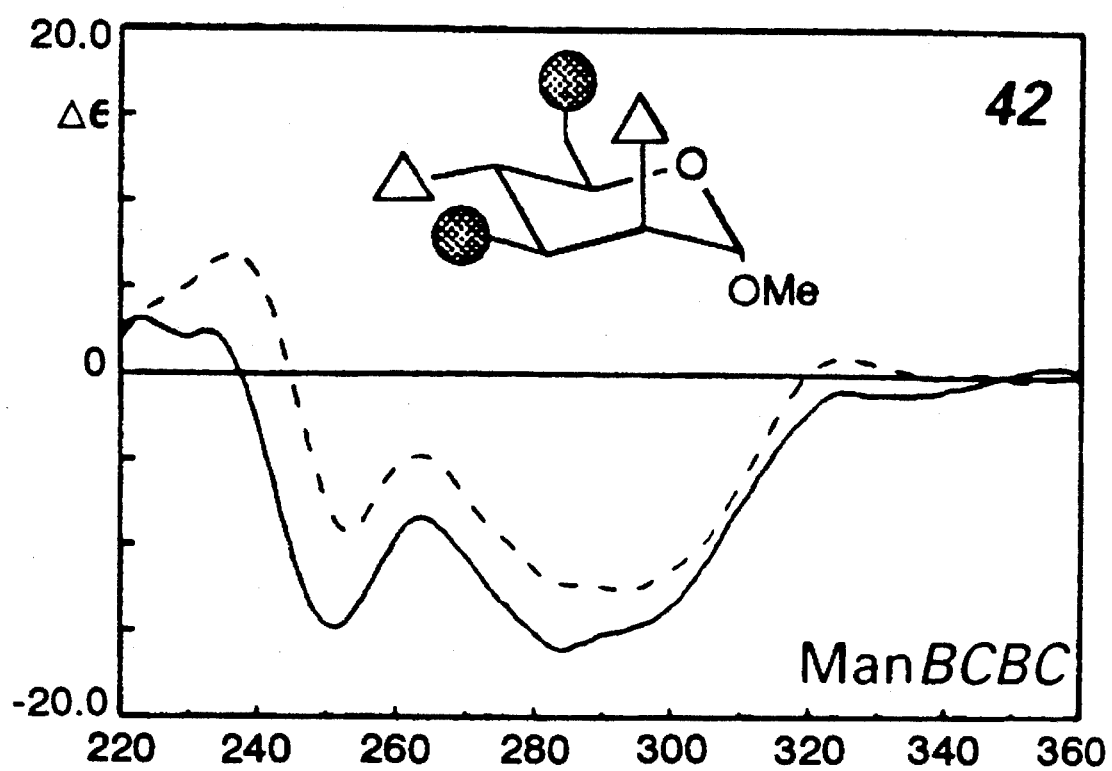
Figure 11A:
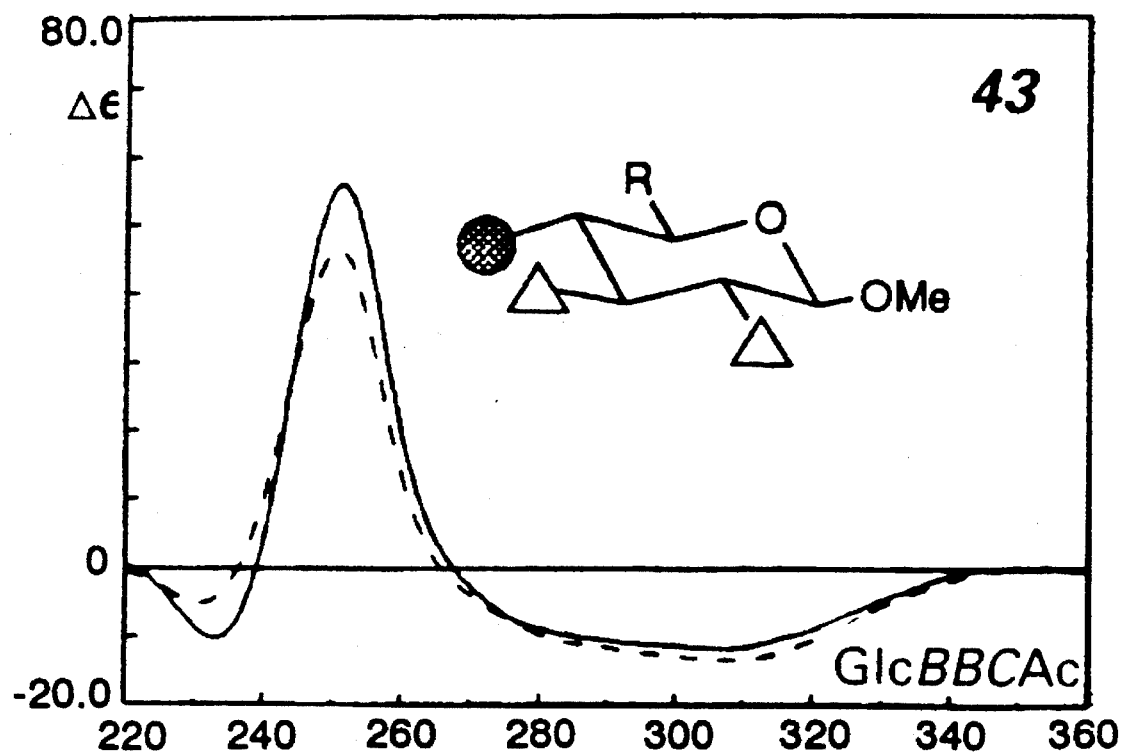
FIGS. 11a–f contain $B_2C$ CD spectra.
Figure 11B:
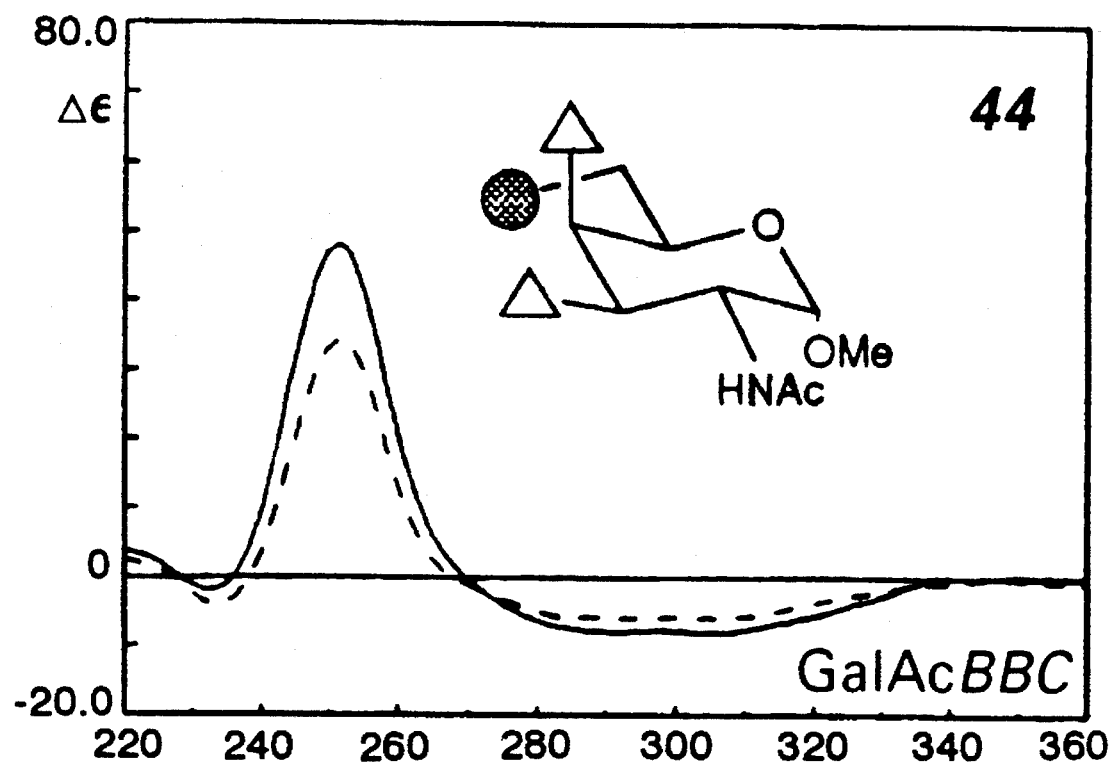
Figure 11C:
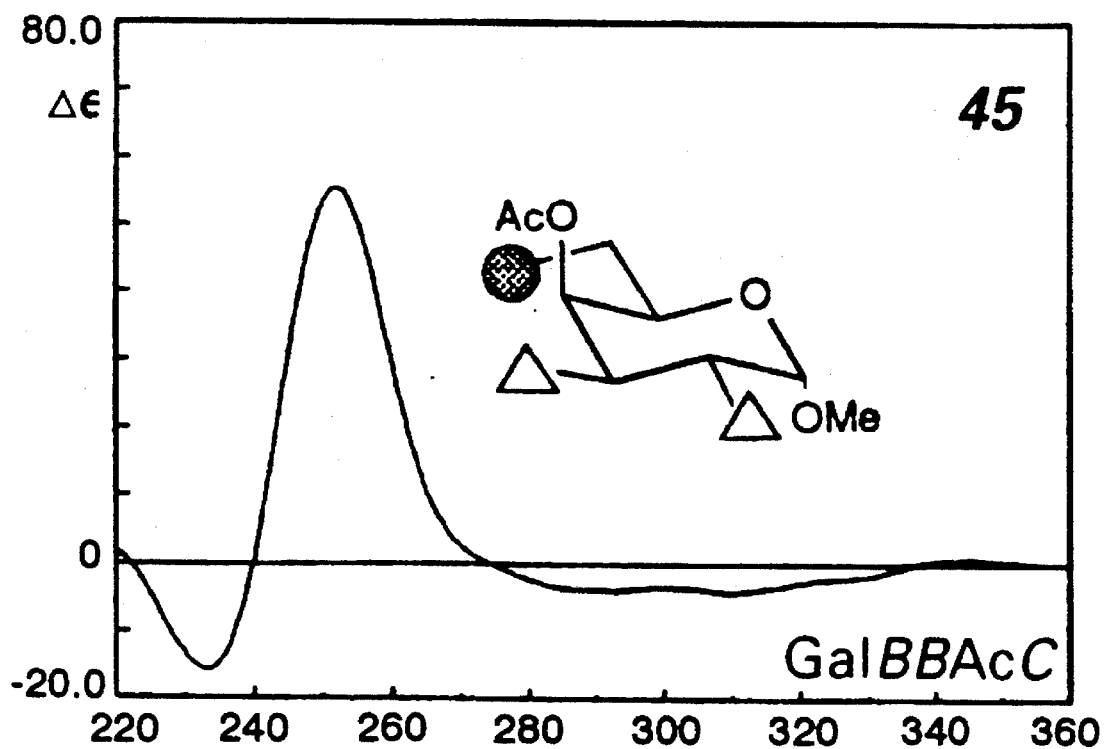
Figure 11D:
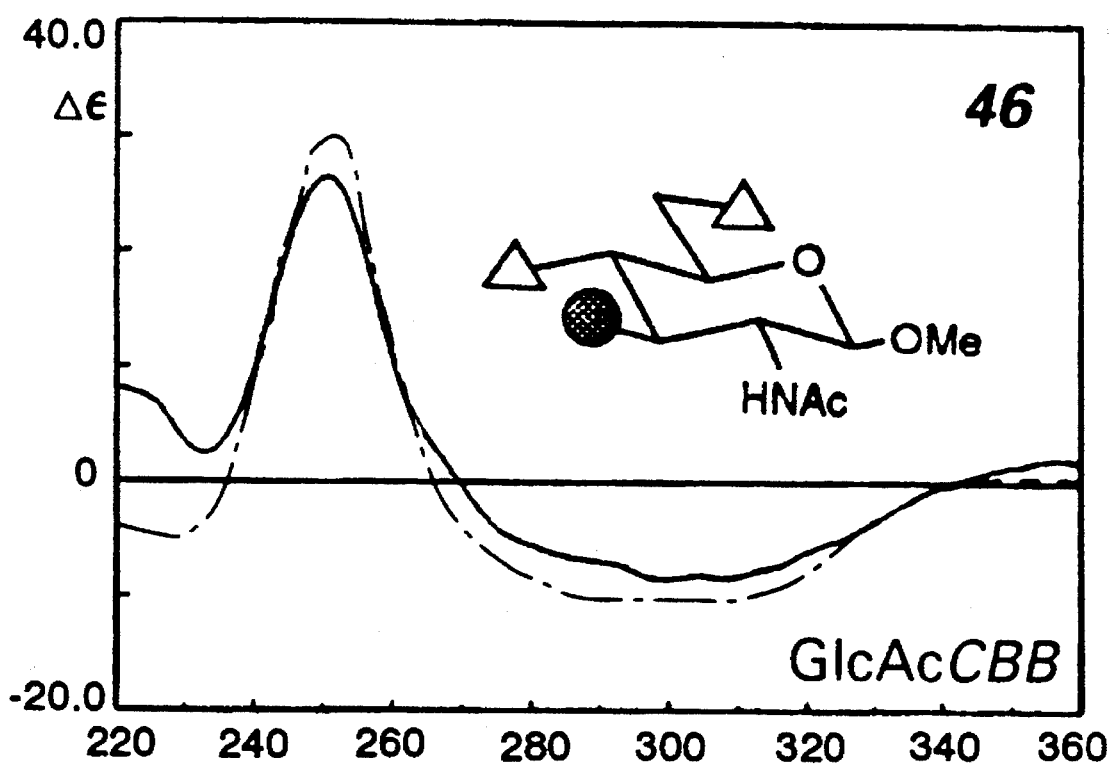
Figure 11E:
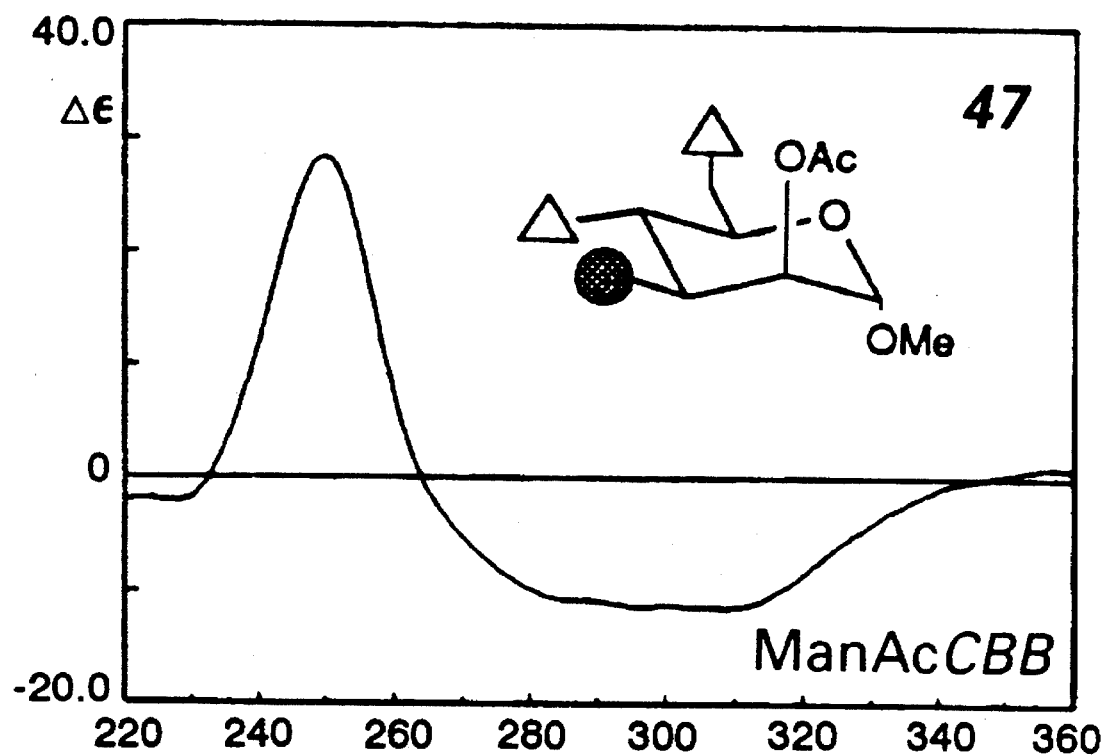
Figure 11F:
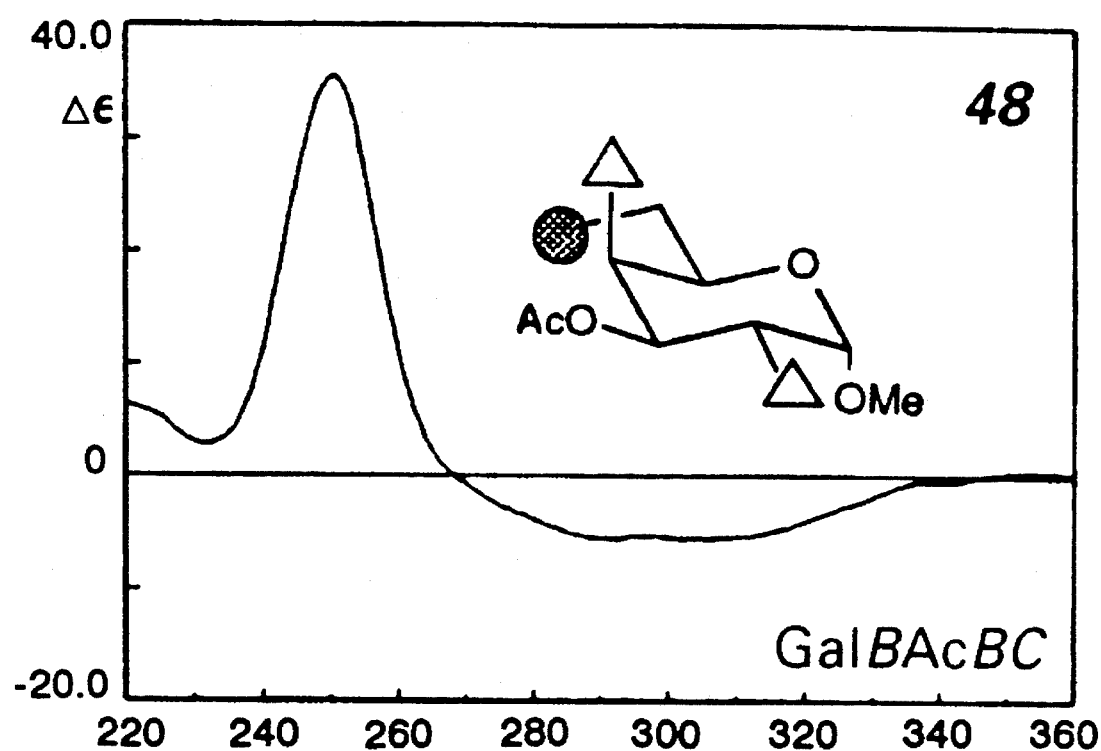
Figure 12A:
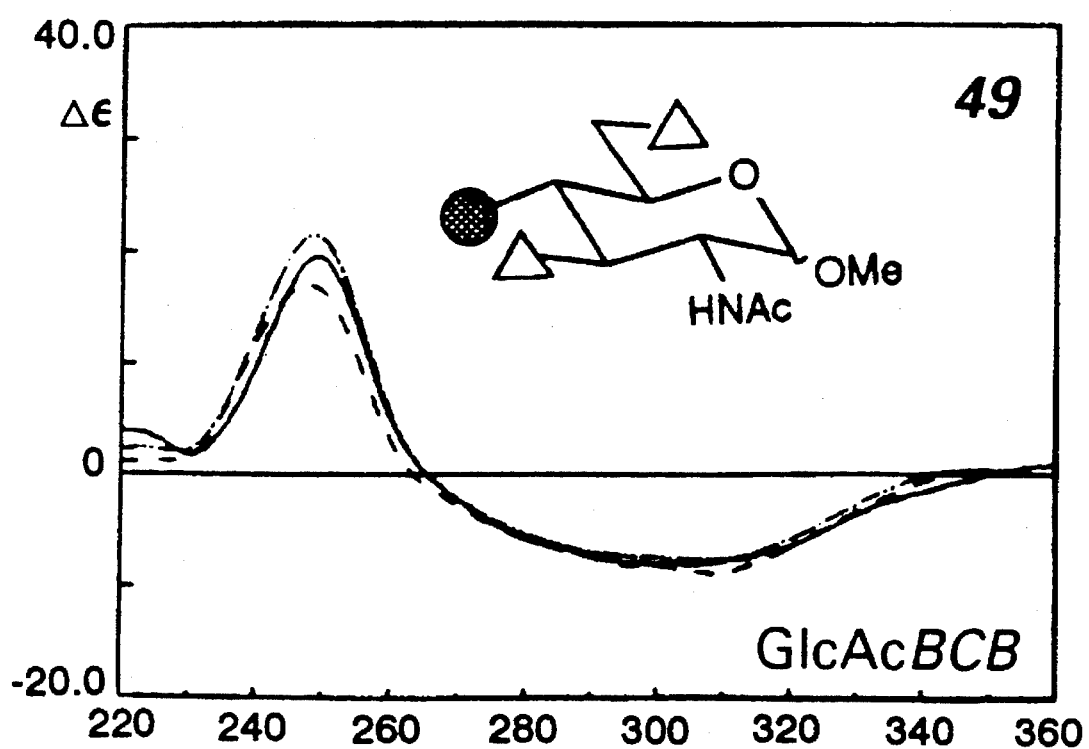
FIGS. 12a–f are a continuation of the $B_2C$ CD spectra of FIGS. 11a–f.
Figure 12B:
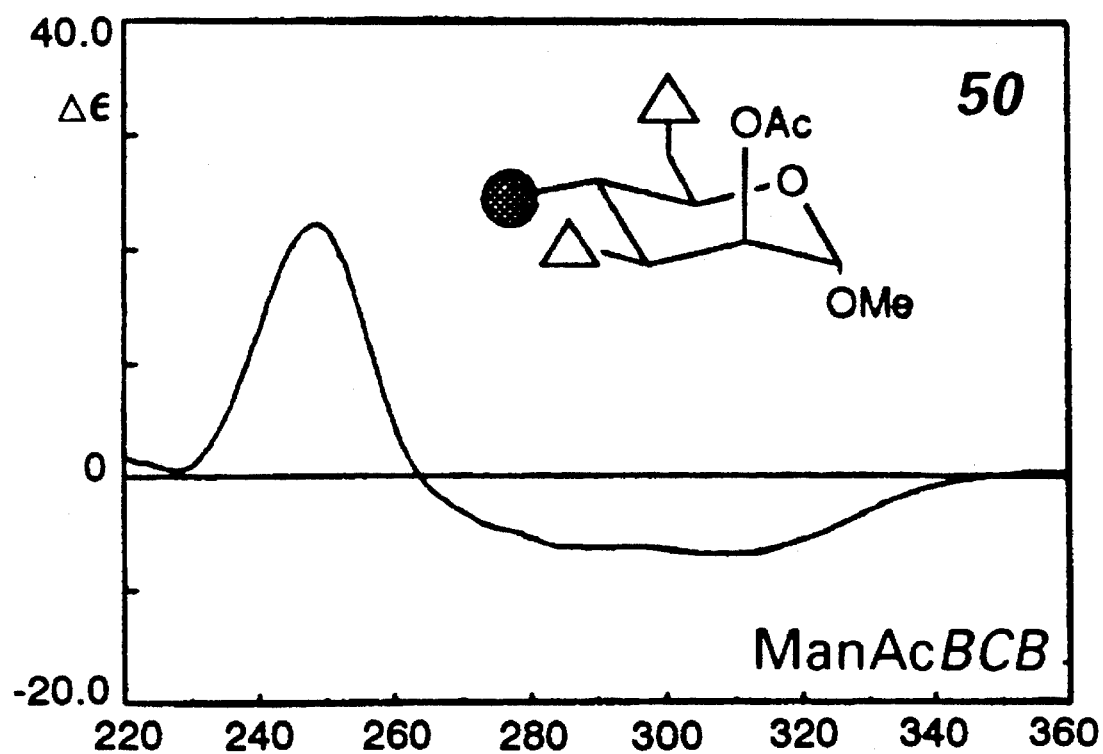
Figure 12C:
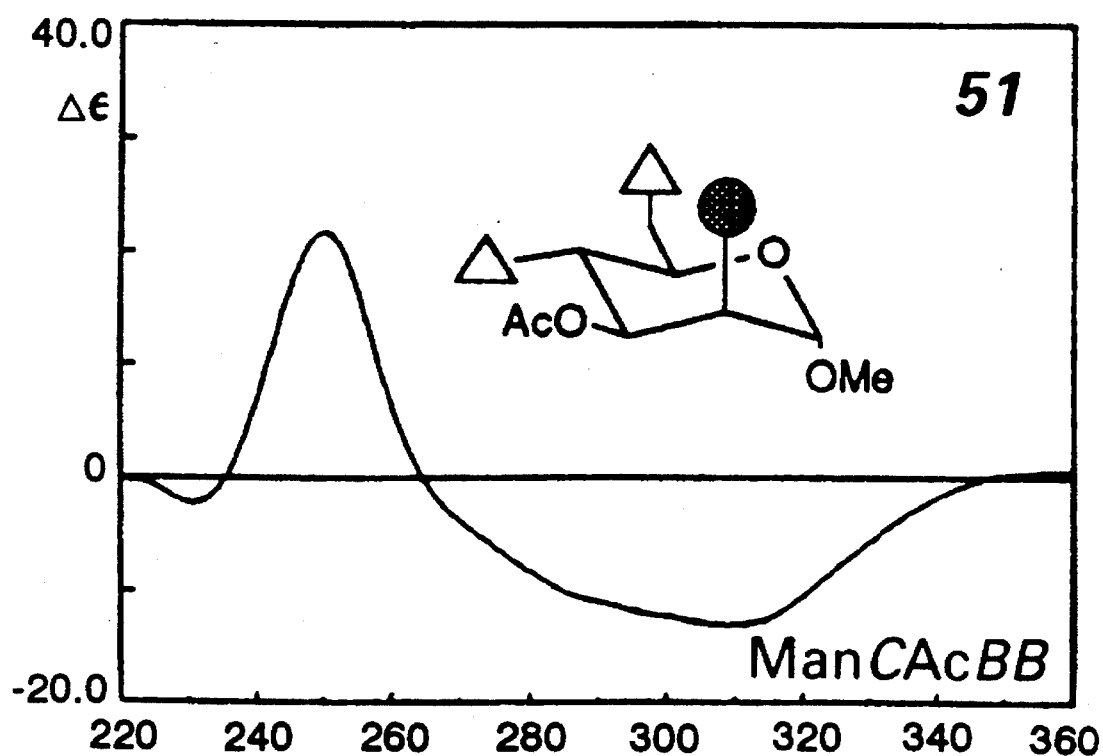
Figure 12D:
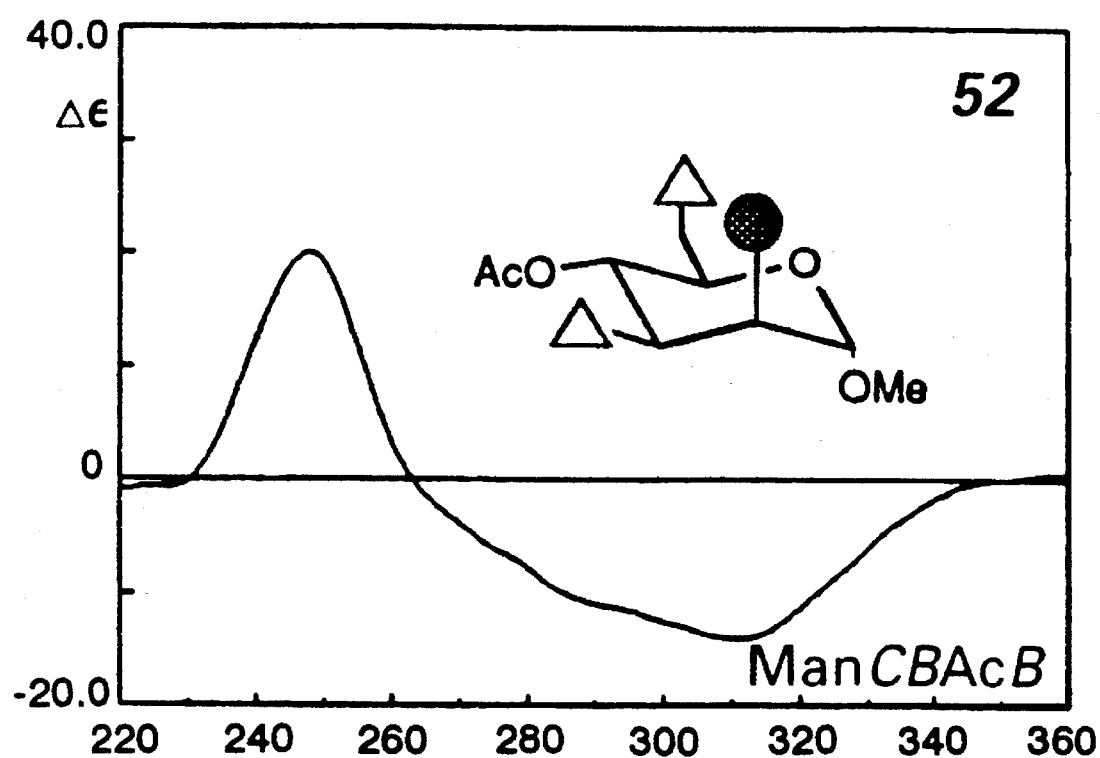
Figure 12E:
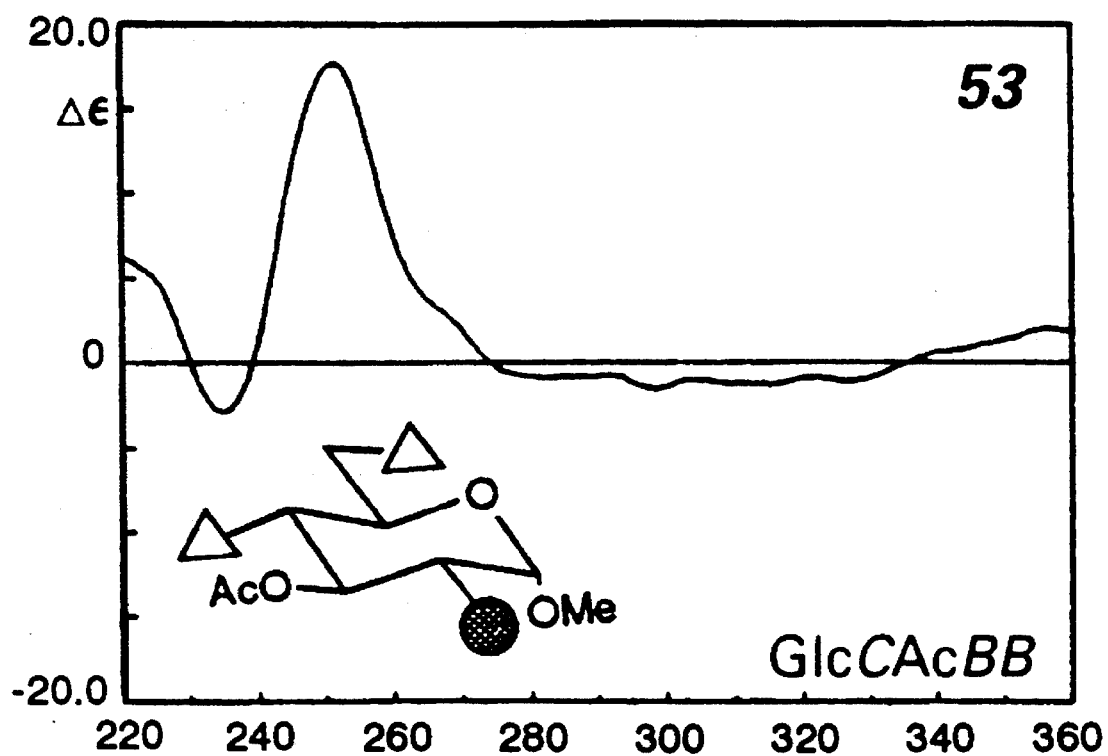
Figure 12F:
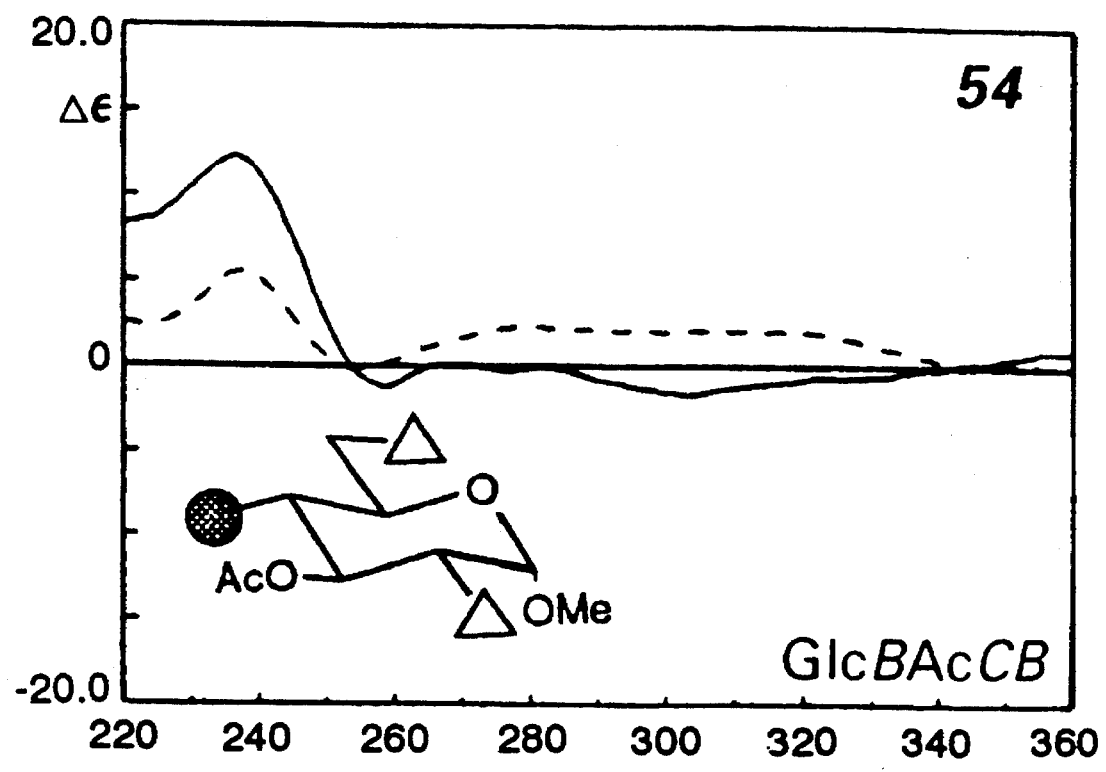
Figure 13A:
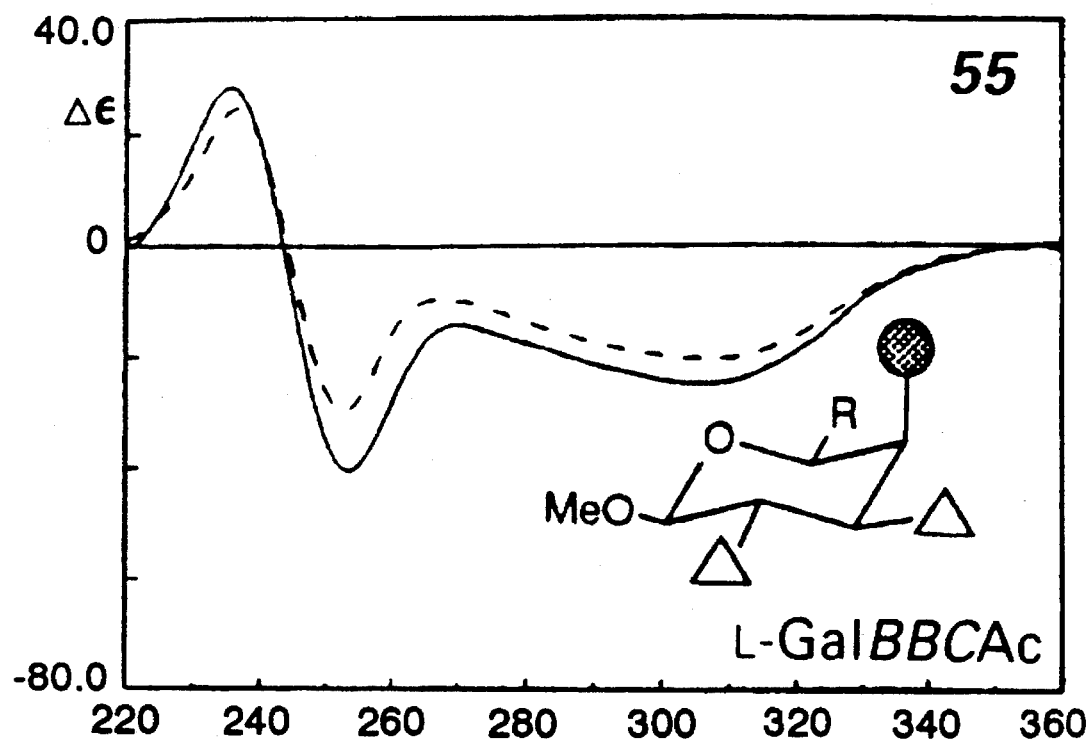
FIGS. 13a–f are a continuation of the $B_2C$ CD spectra of FIGS. 11a–f.
Figure 13B:
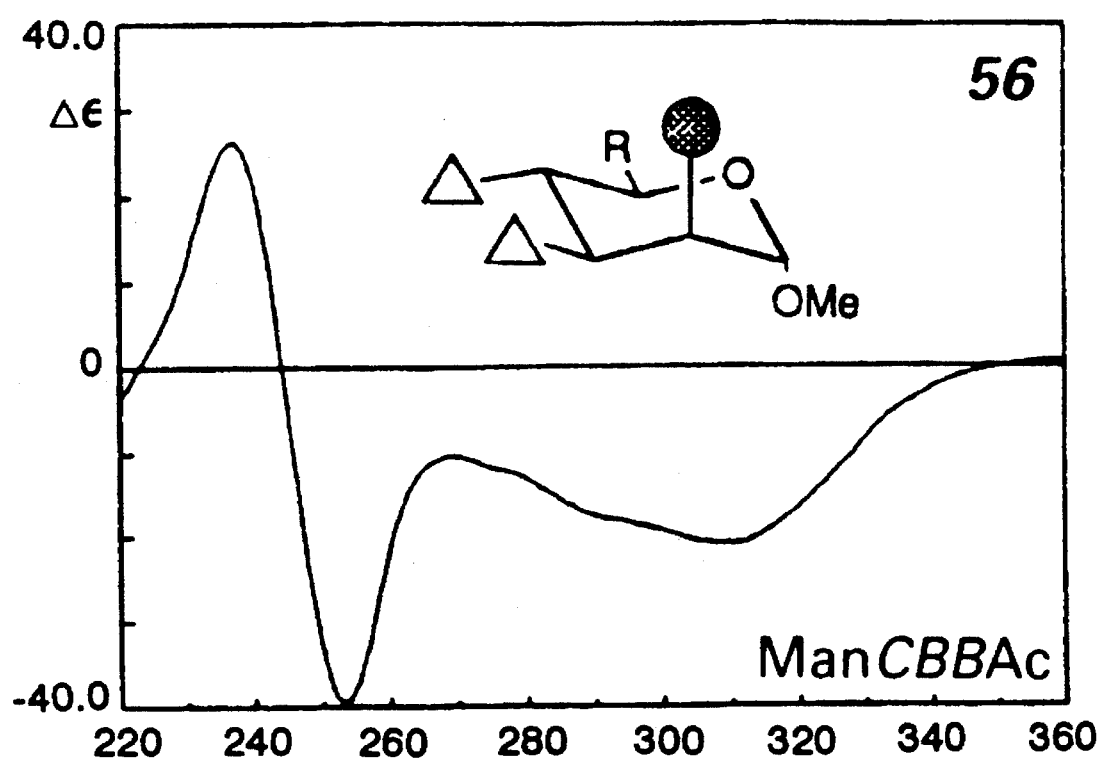
Figure 13C:
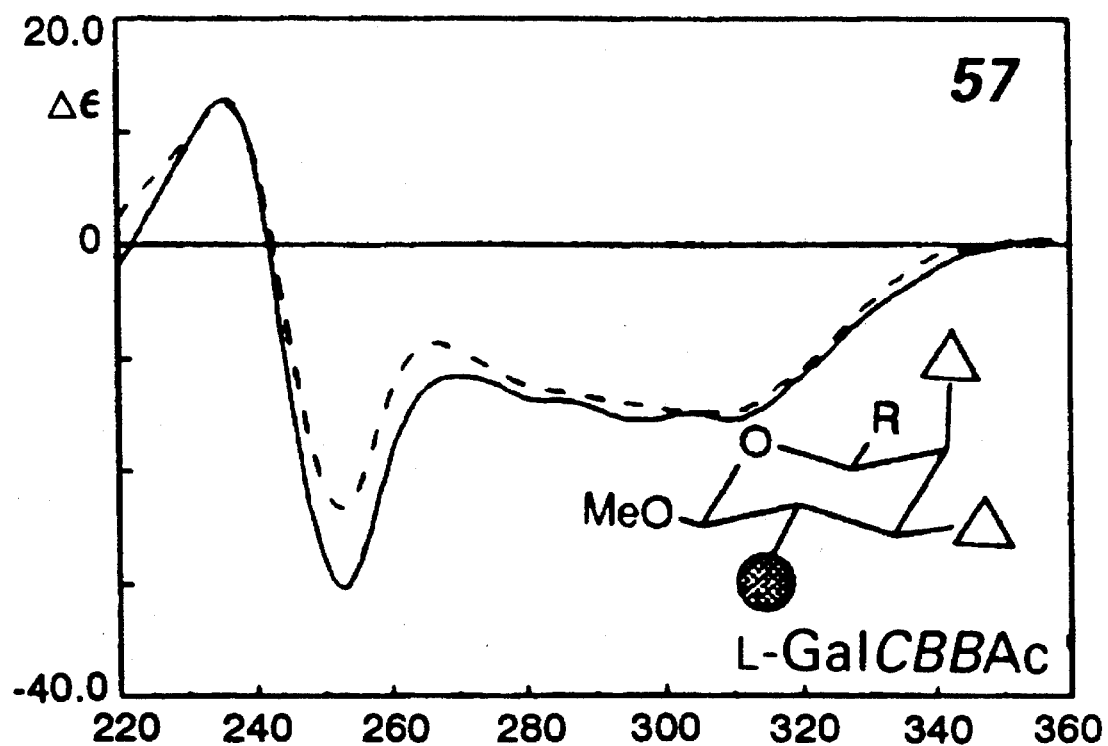
Figure 13D:
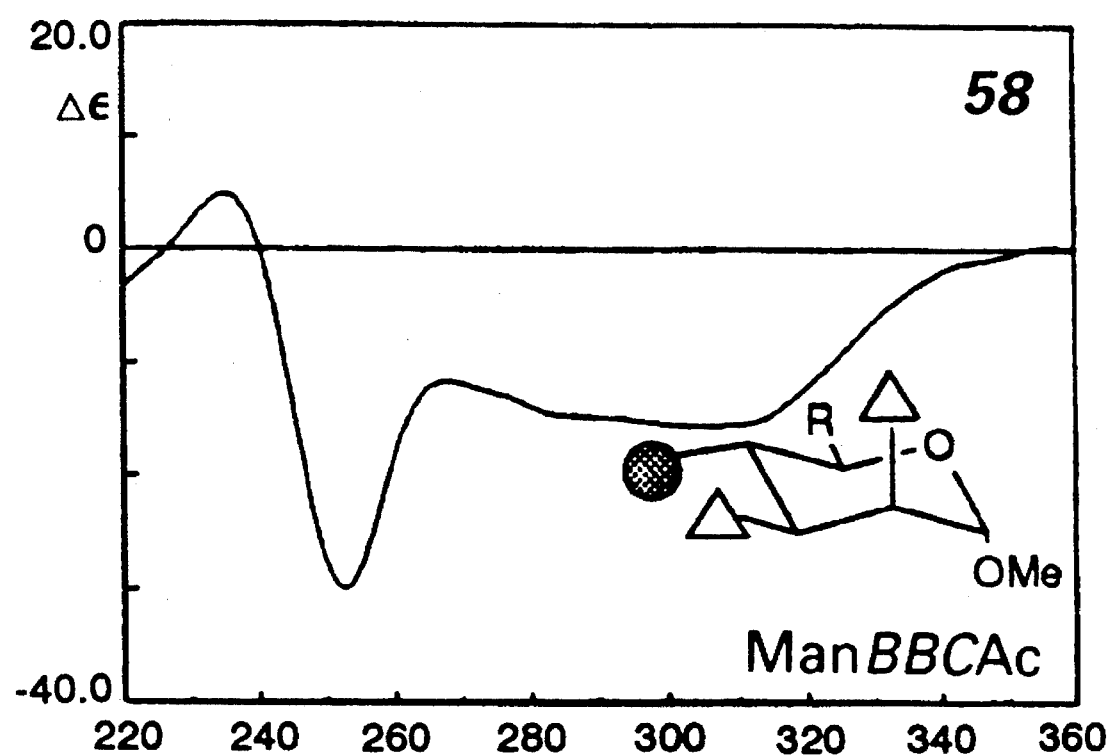
Figure 13E:
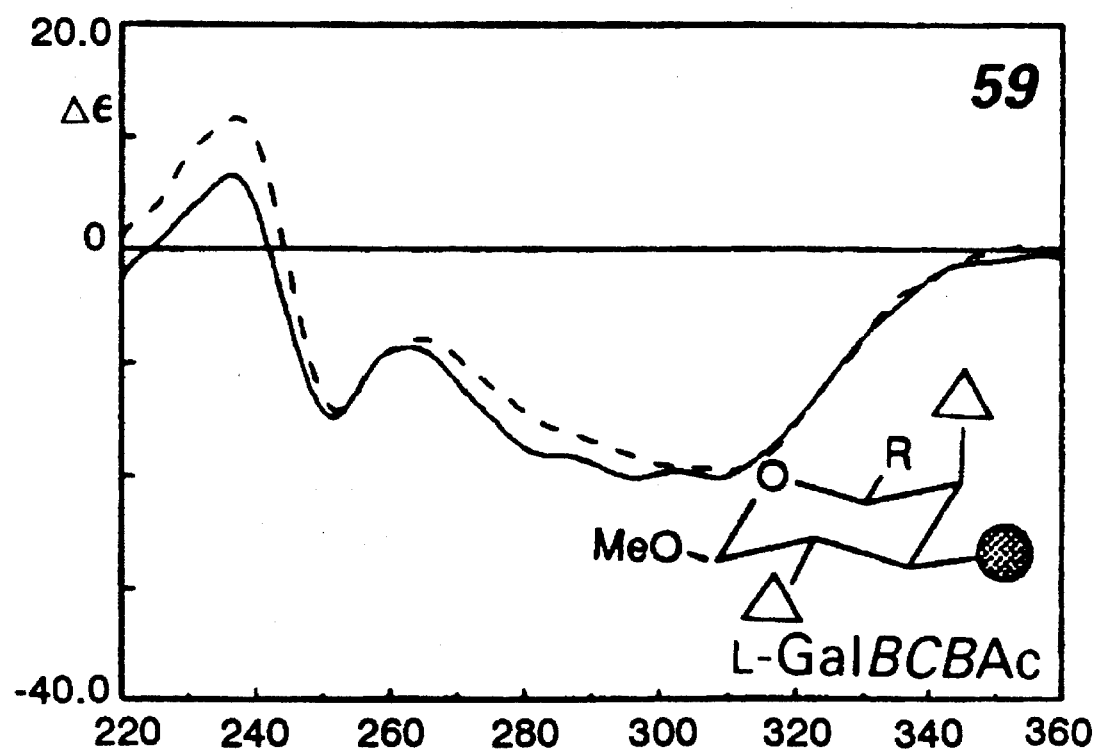
Figure 13F:
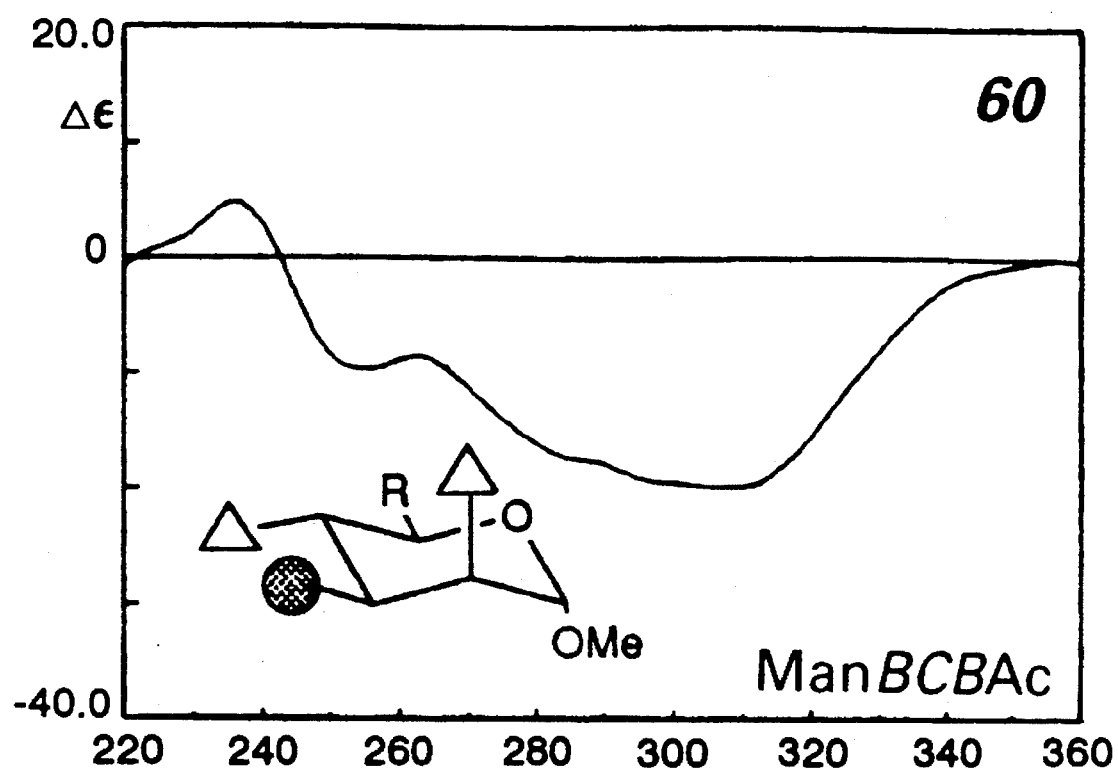
Figure 14A:
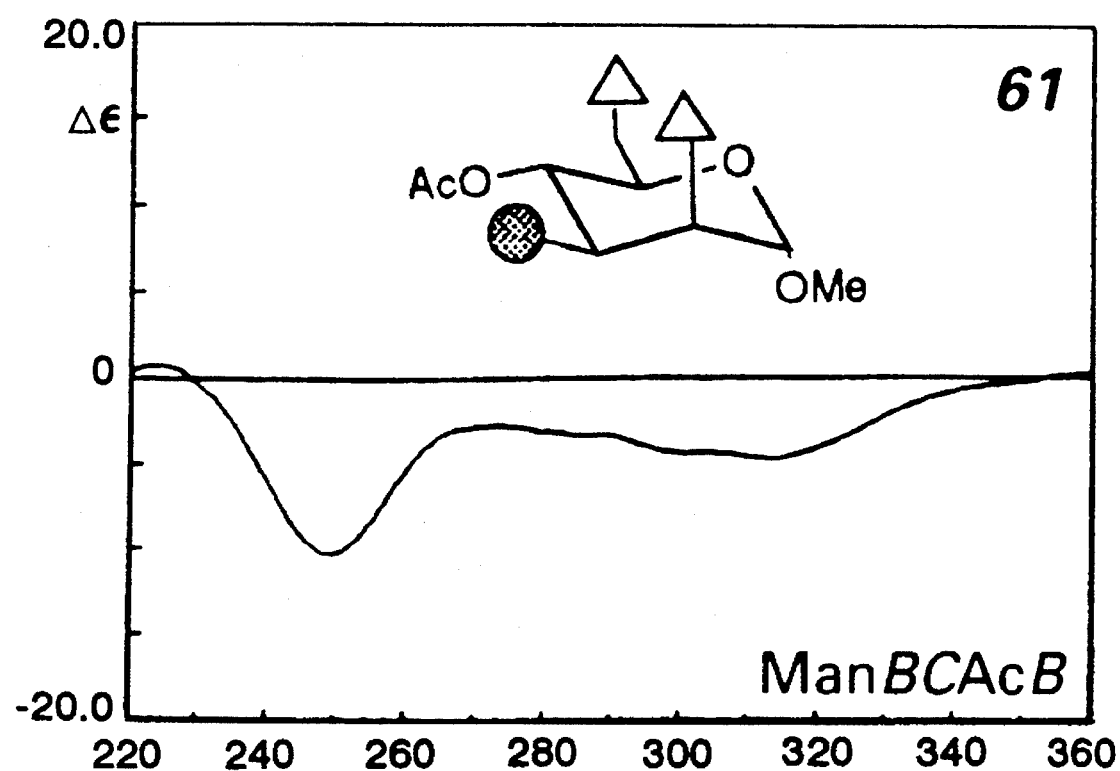
FIGS. 14a–f are a continuation of the $B_2C$ CD spectra of FIGS. 11a–f.
Figure 14B:
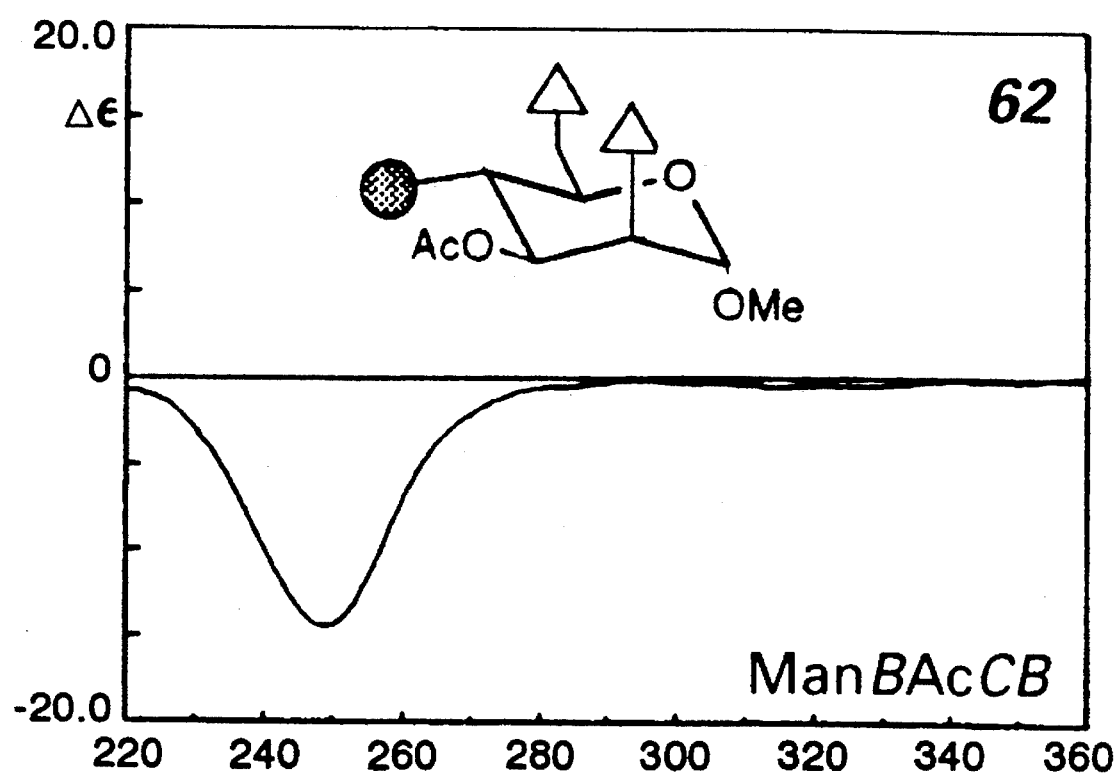
Figure 14C:
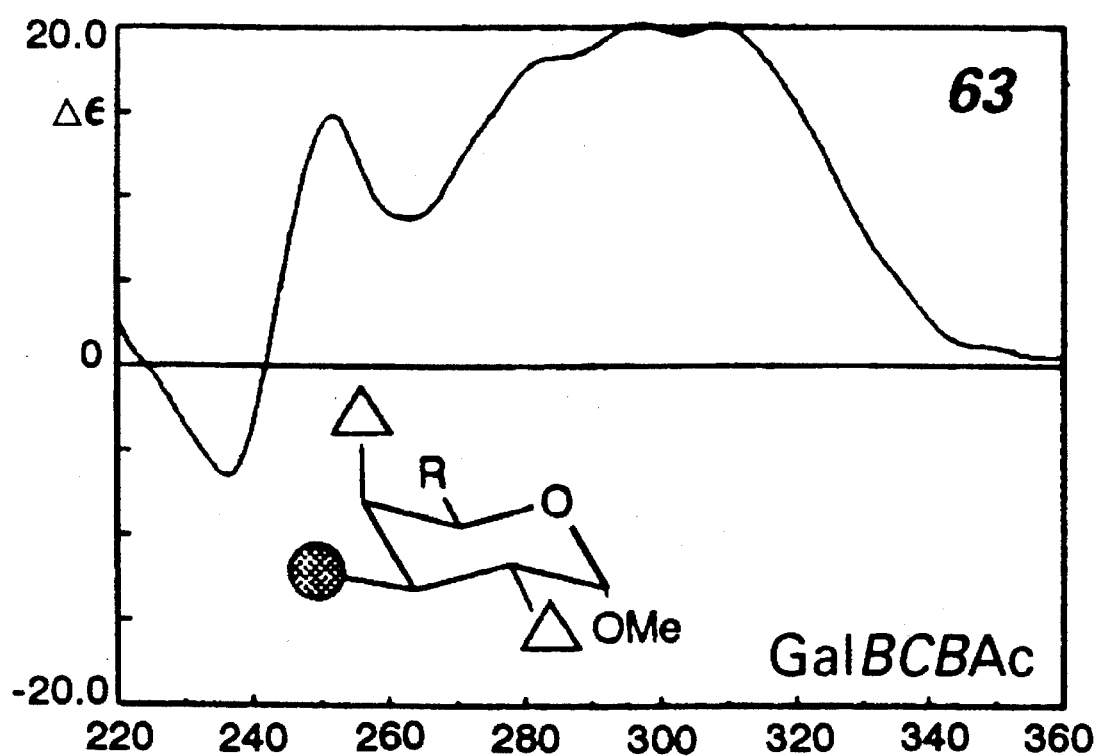
Figure 14D:
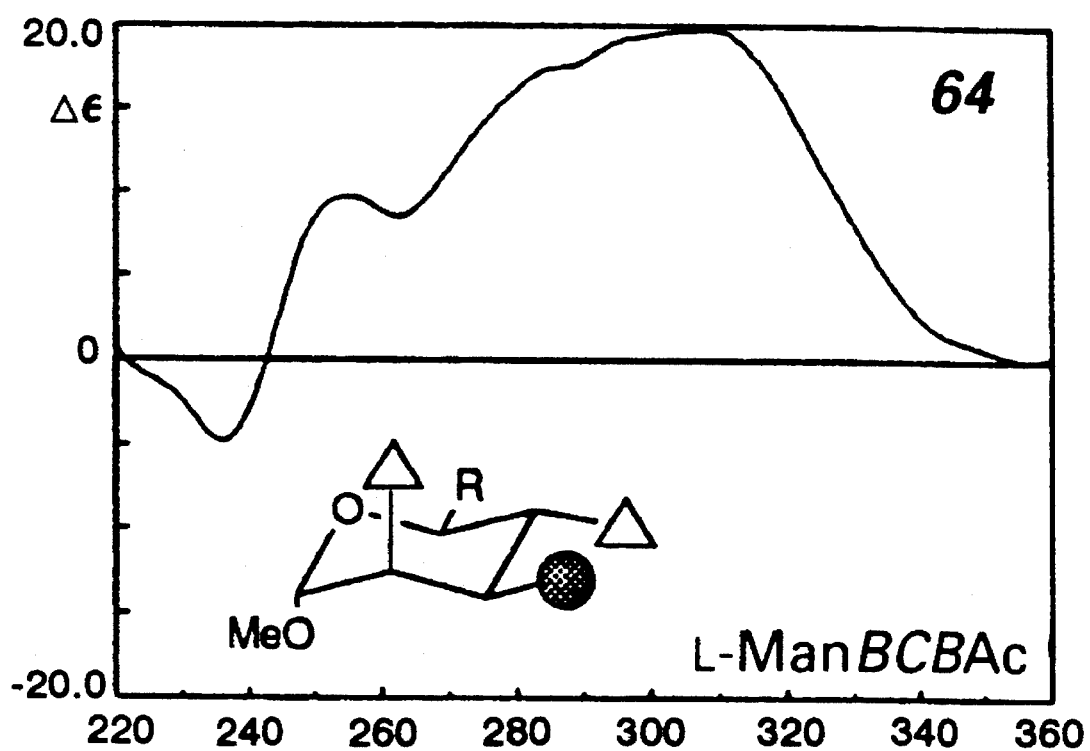
Figure 14E:
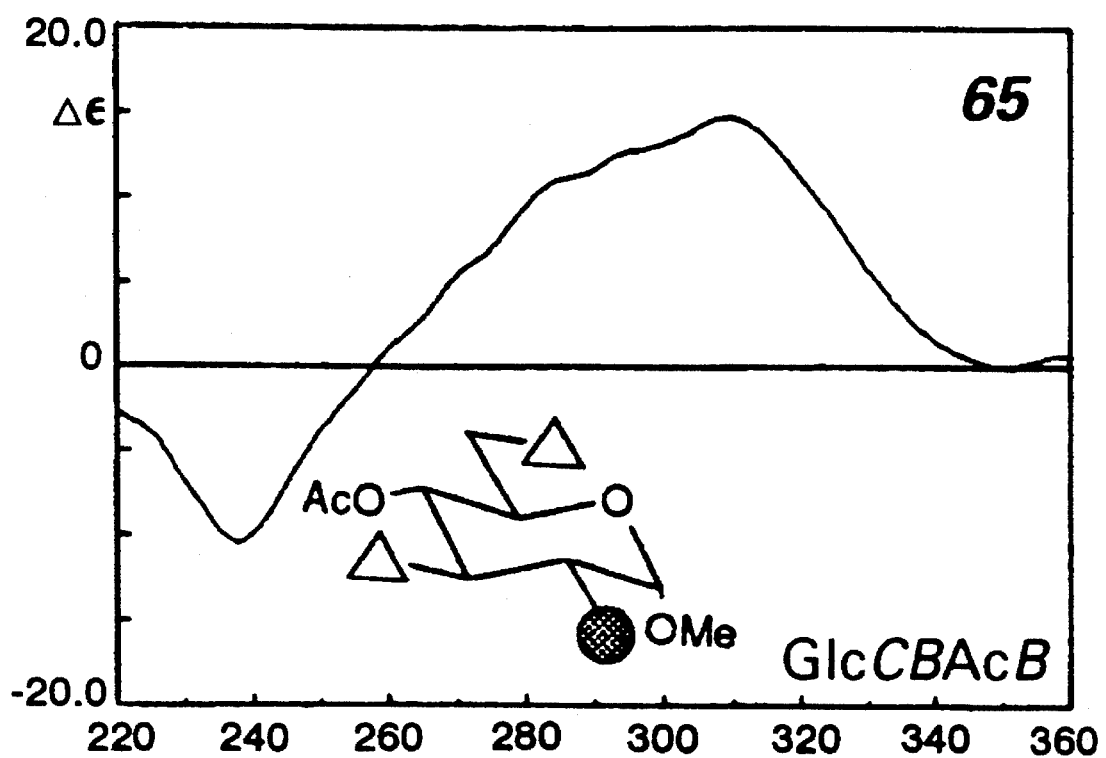
Figure 14F:
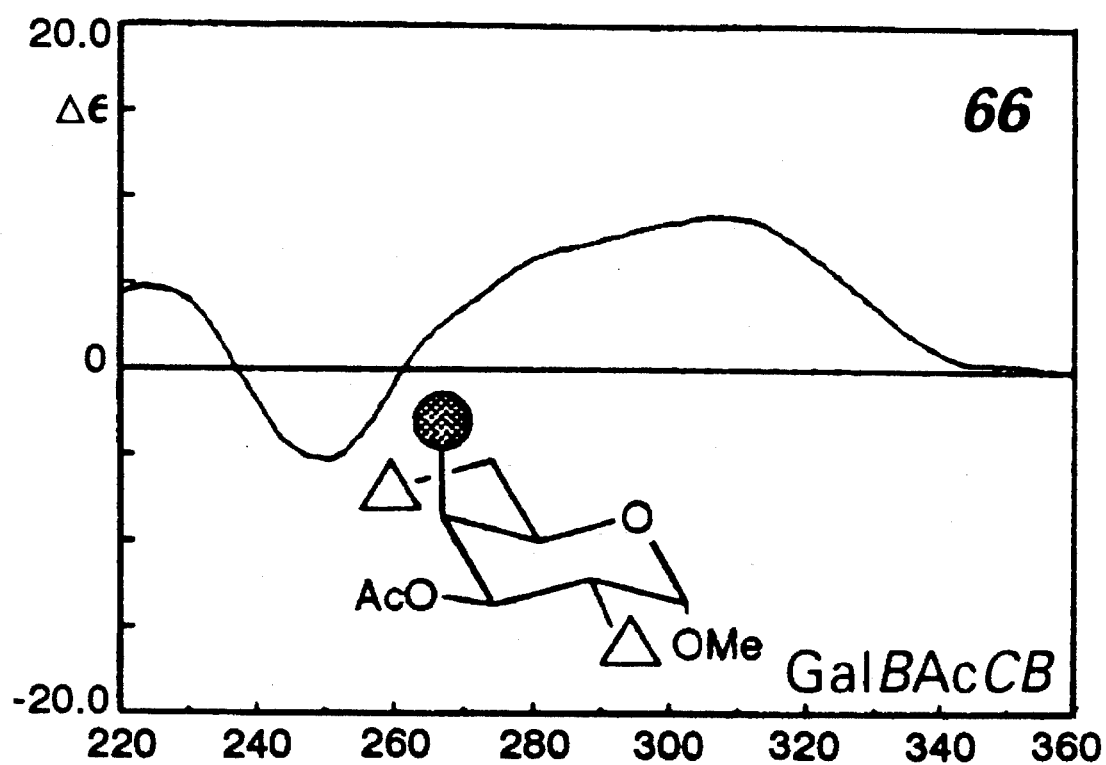
Figure 15A:
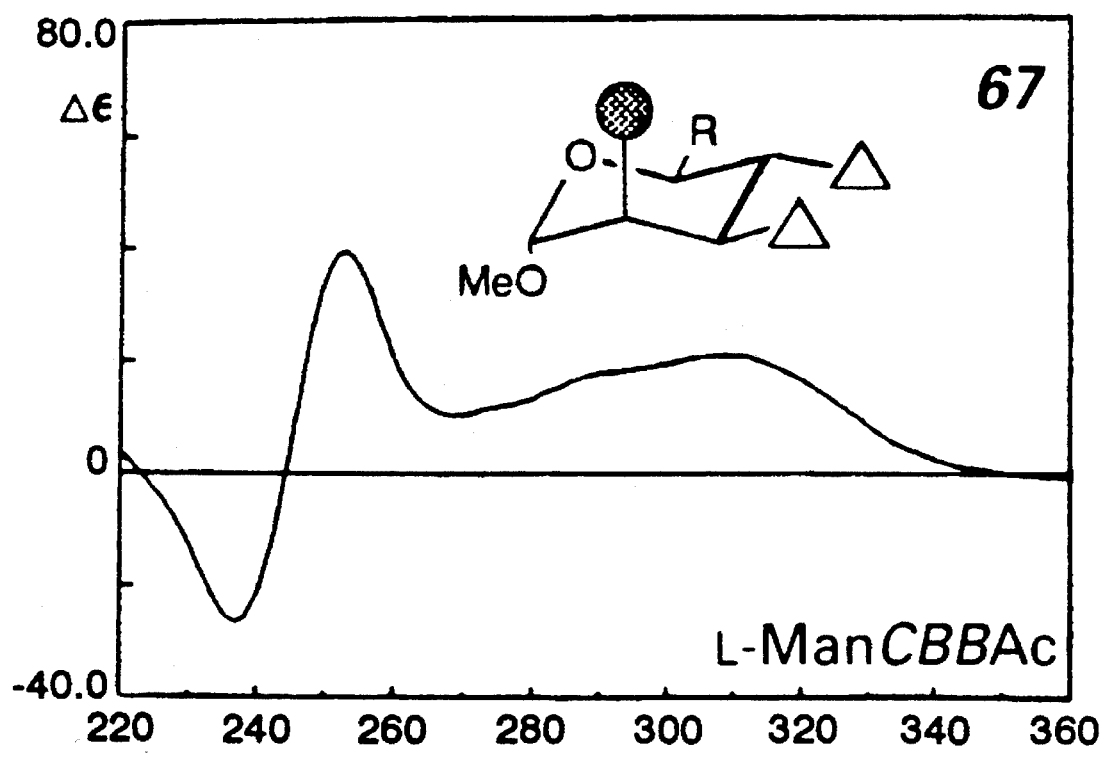
FIGS. 15a–f are a continuation of the $B_2C$ CD spectra of FIGS. 11a–f.
Figure 15B:
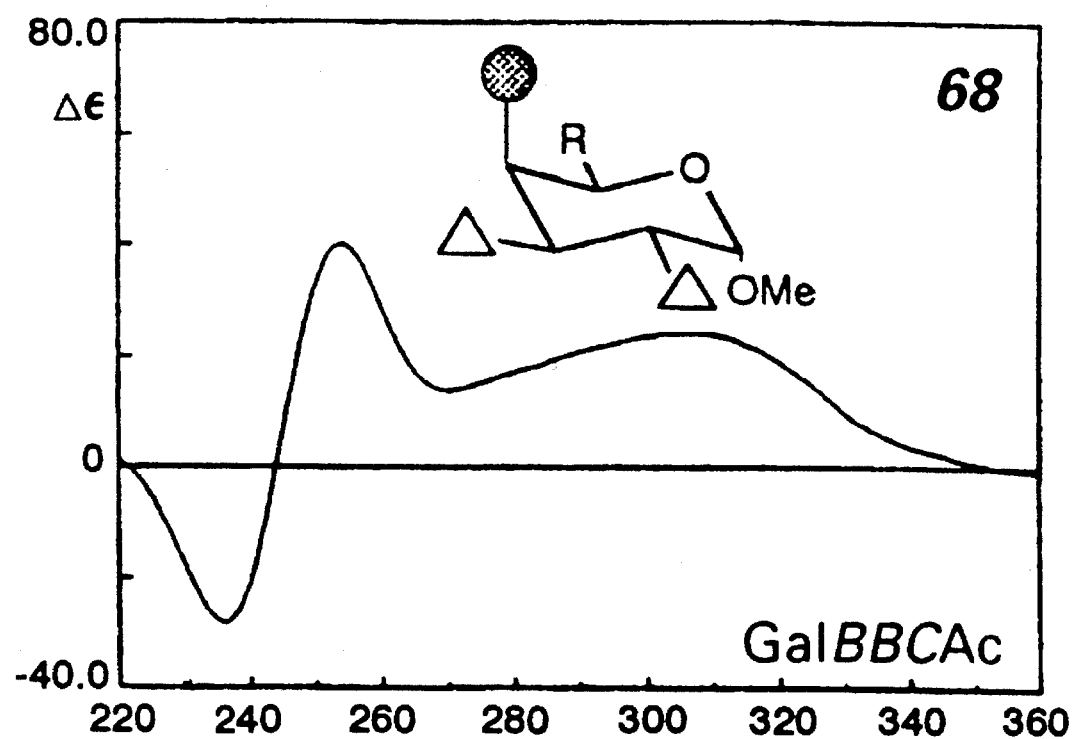
Figure 15C:
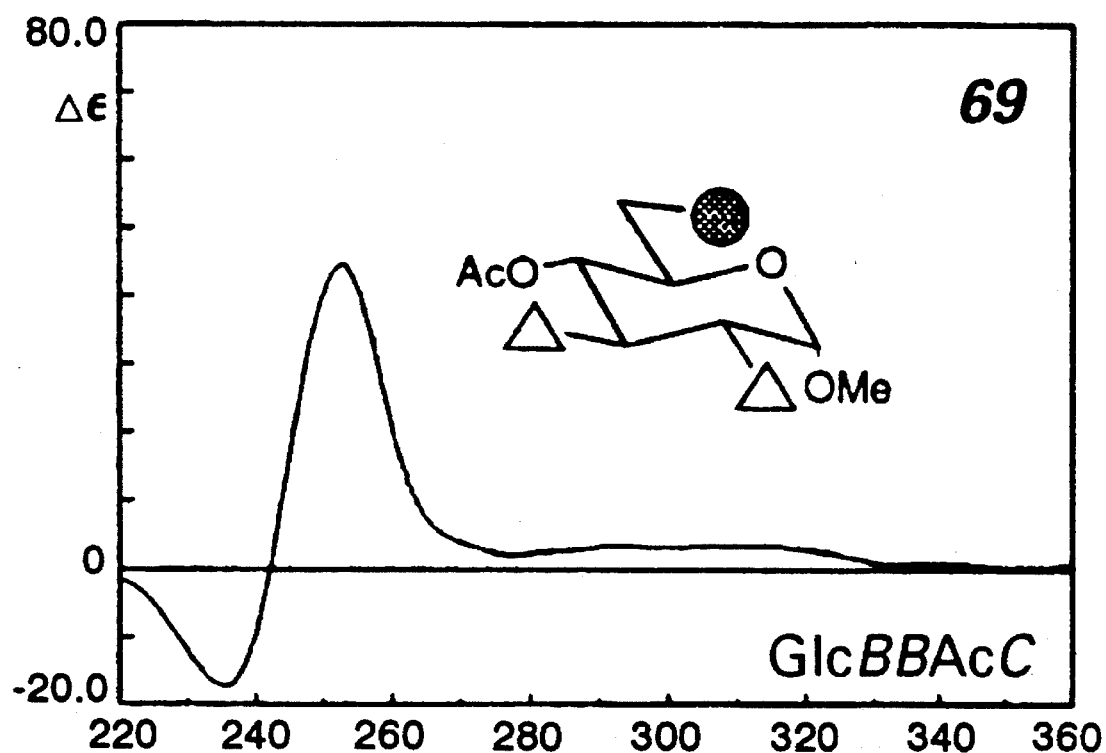
Figure 15D:
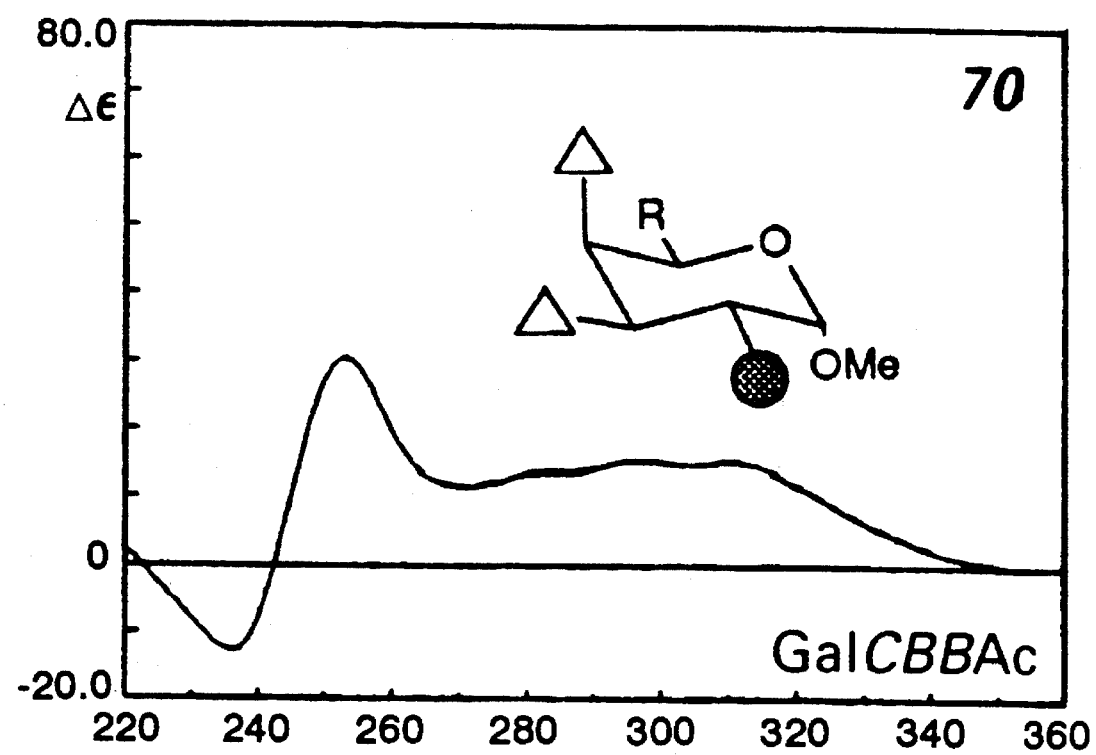
Figure 15E:
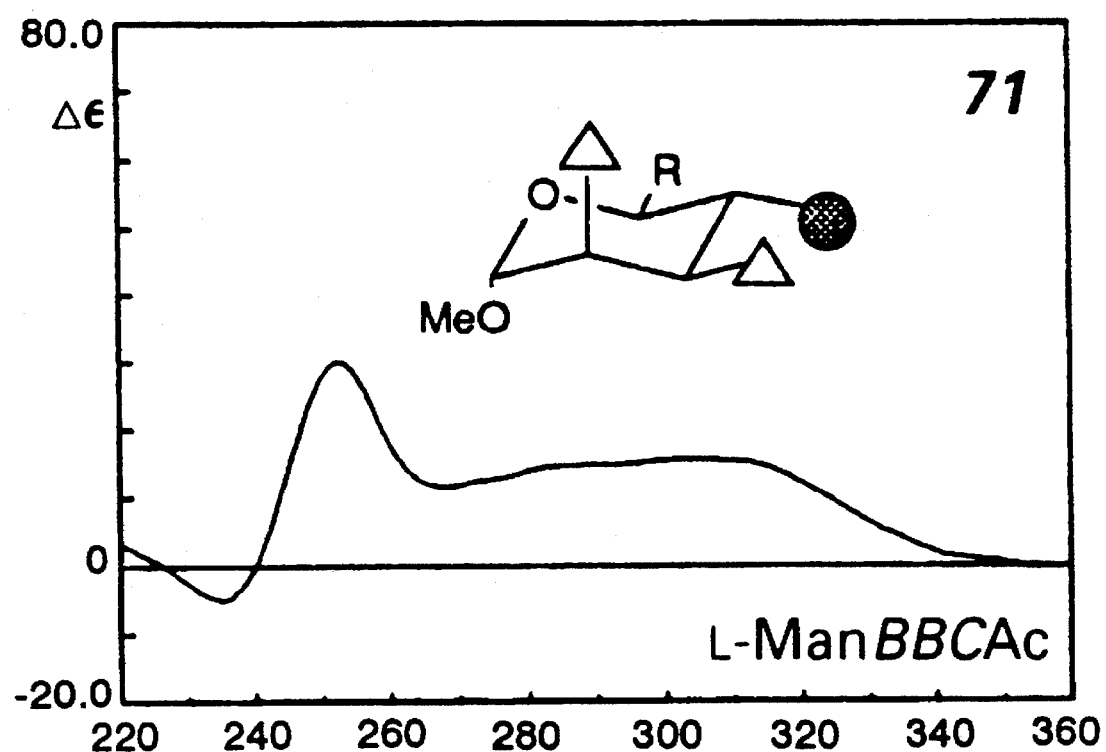
Figure 15F:
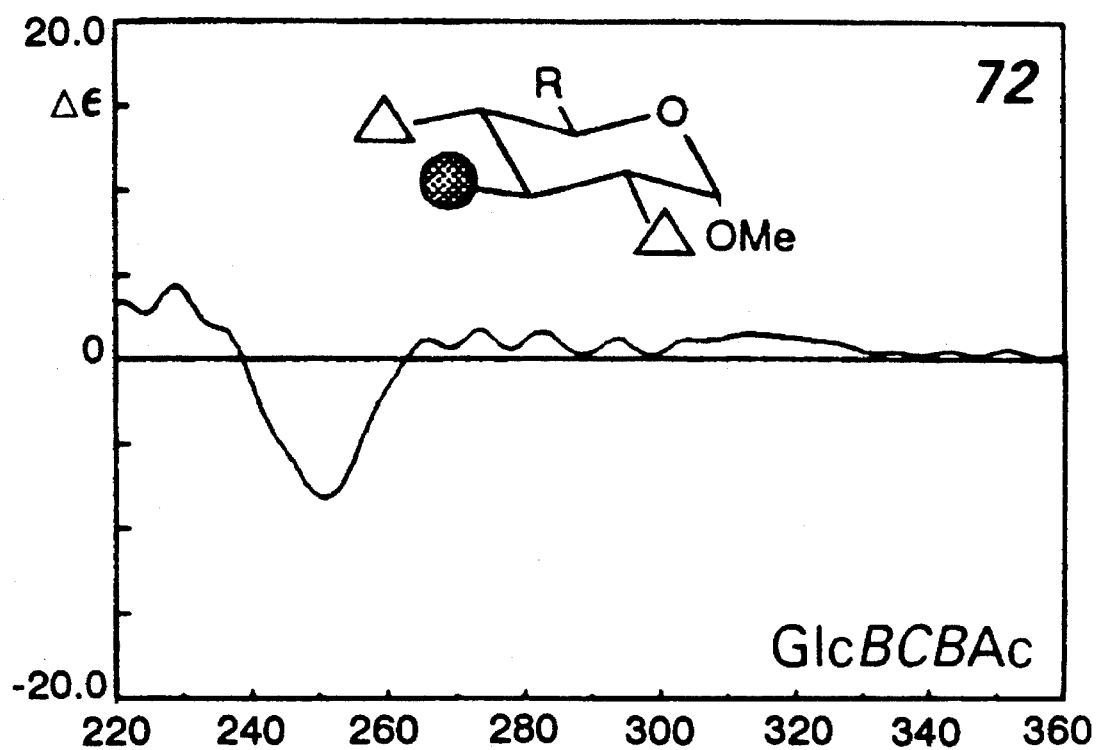
Figure 16A:
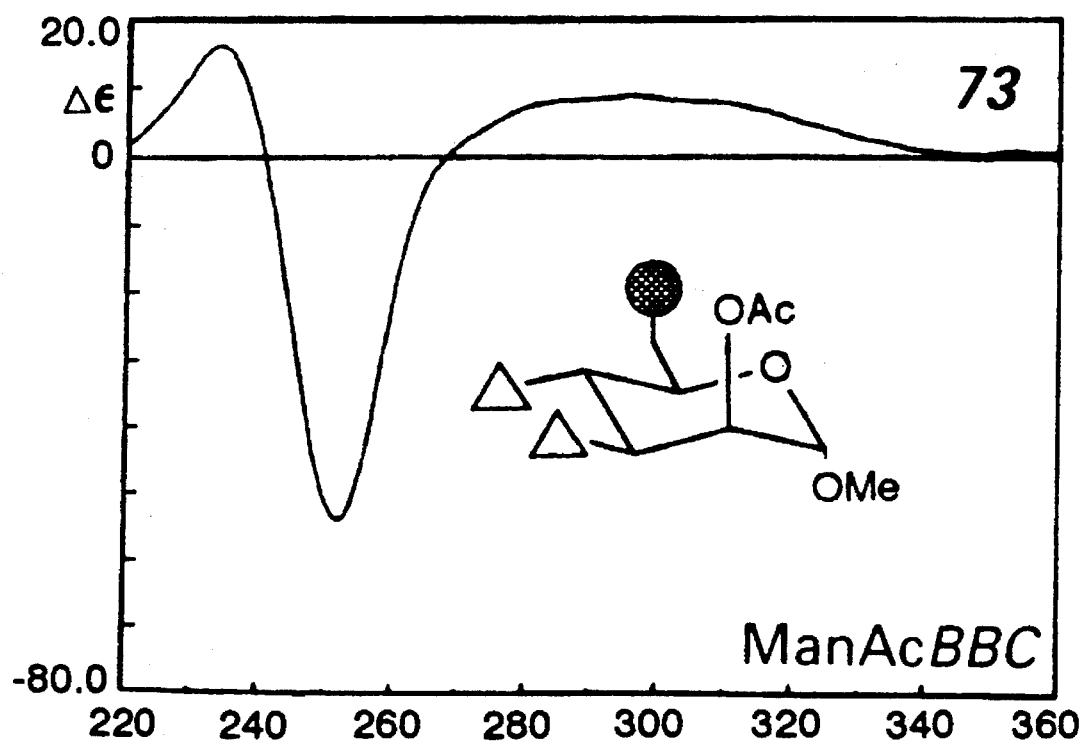
FIGS. 16a–f are a continuation of the $B_2C$ CD spectra of FIGS. 11a–f.
Figure 16B:
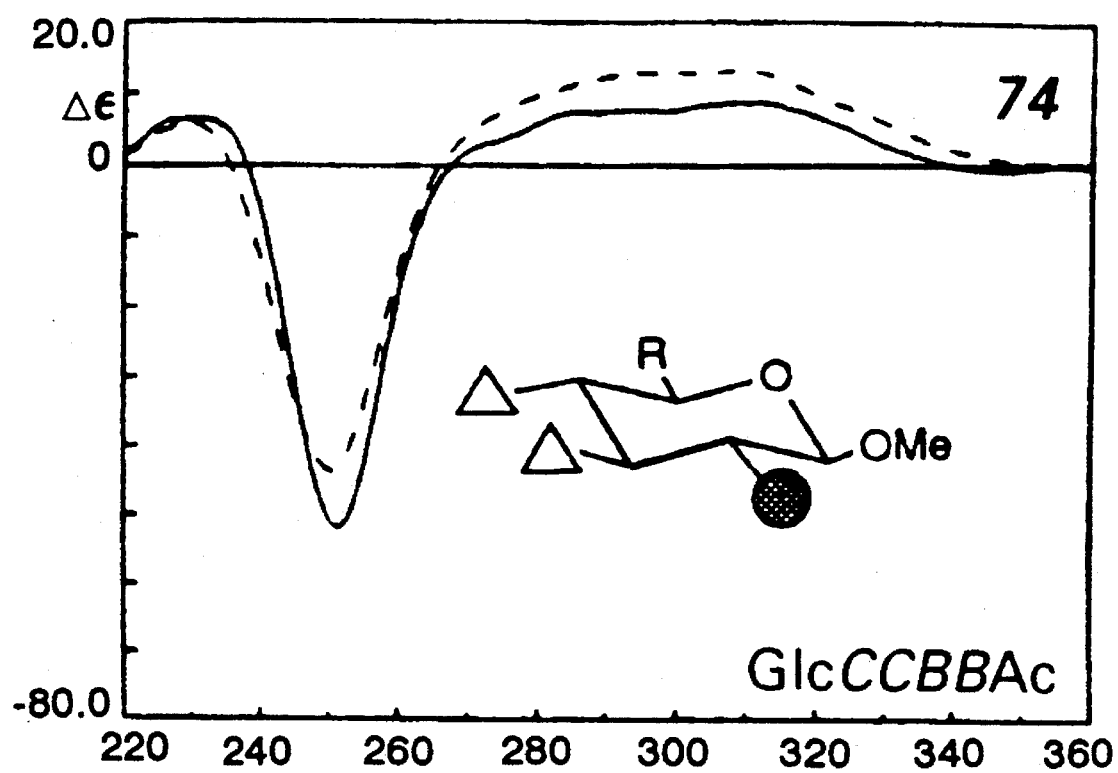
Figure 16C:
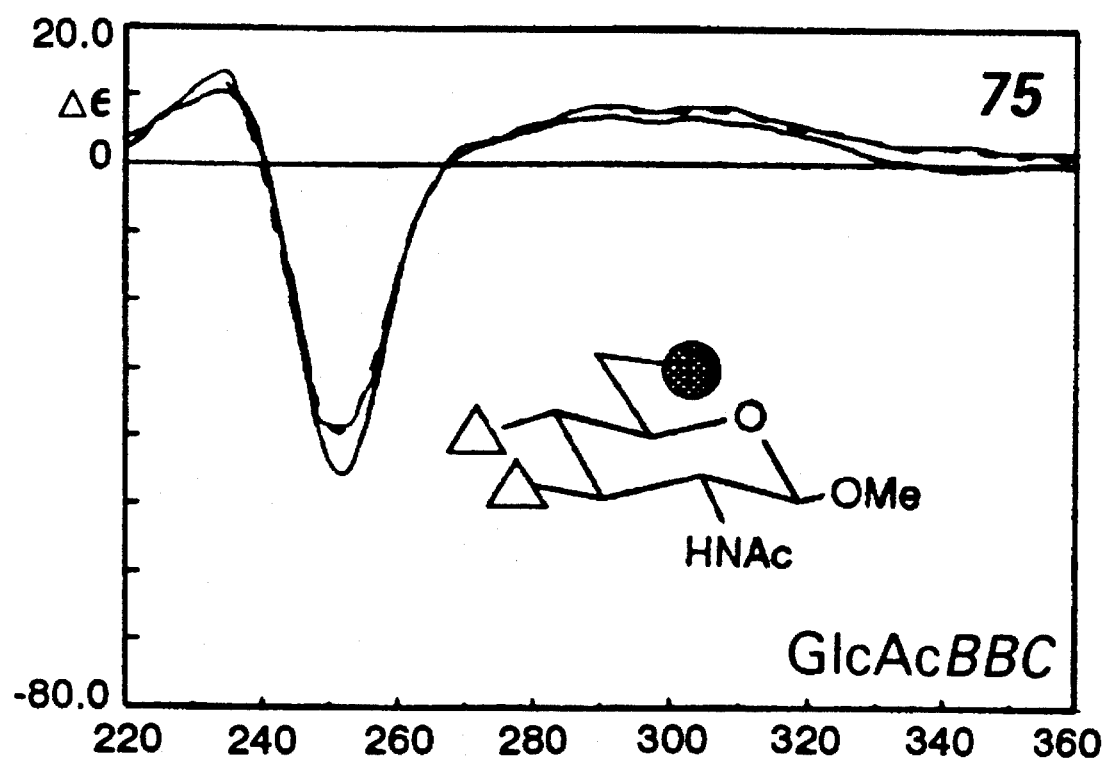
Figure 16D:
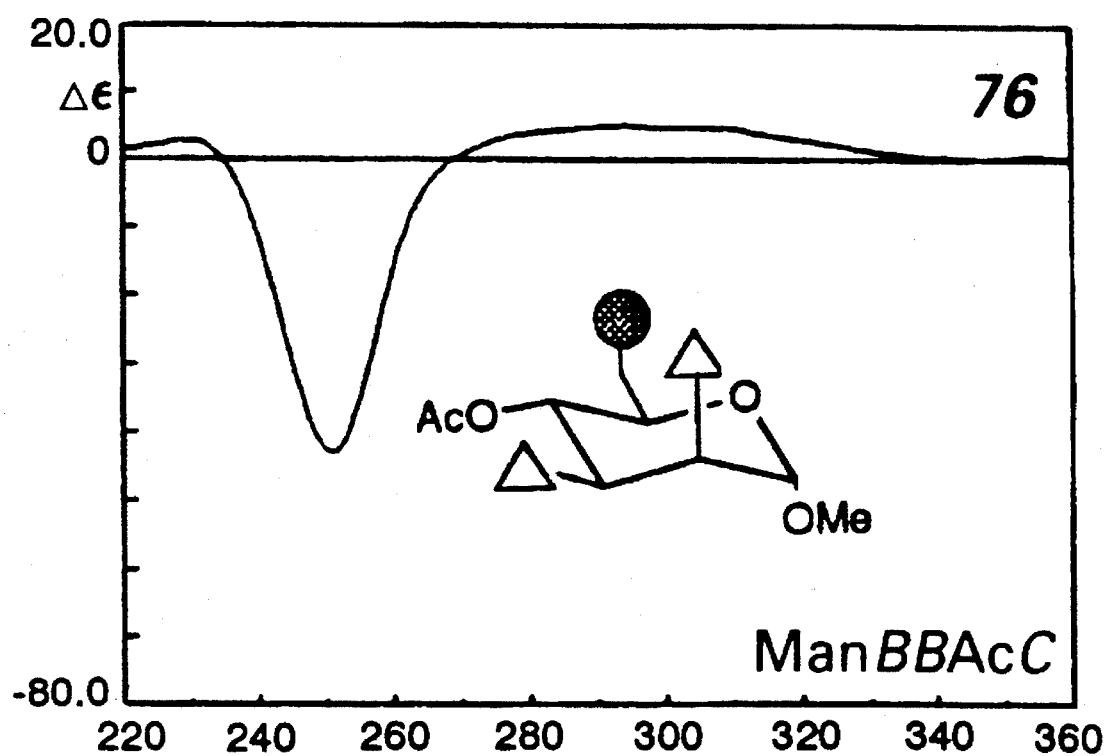
Figure 16E:
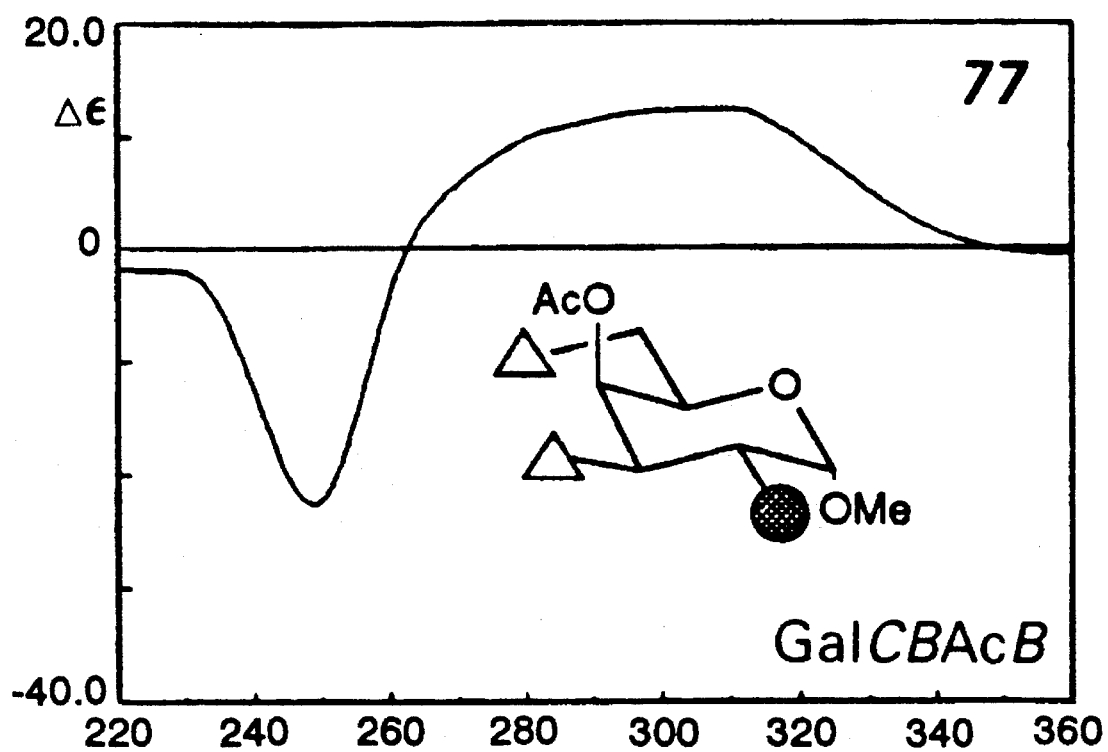
Figure 16F:
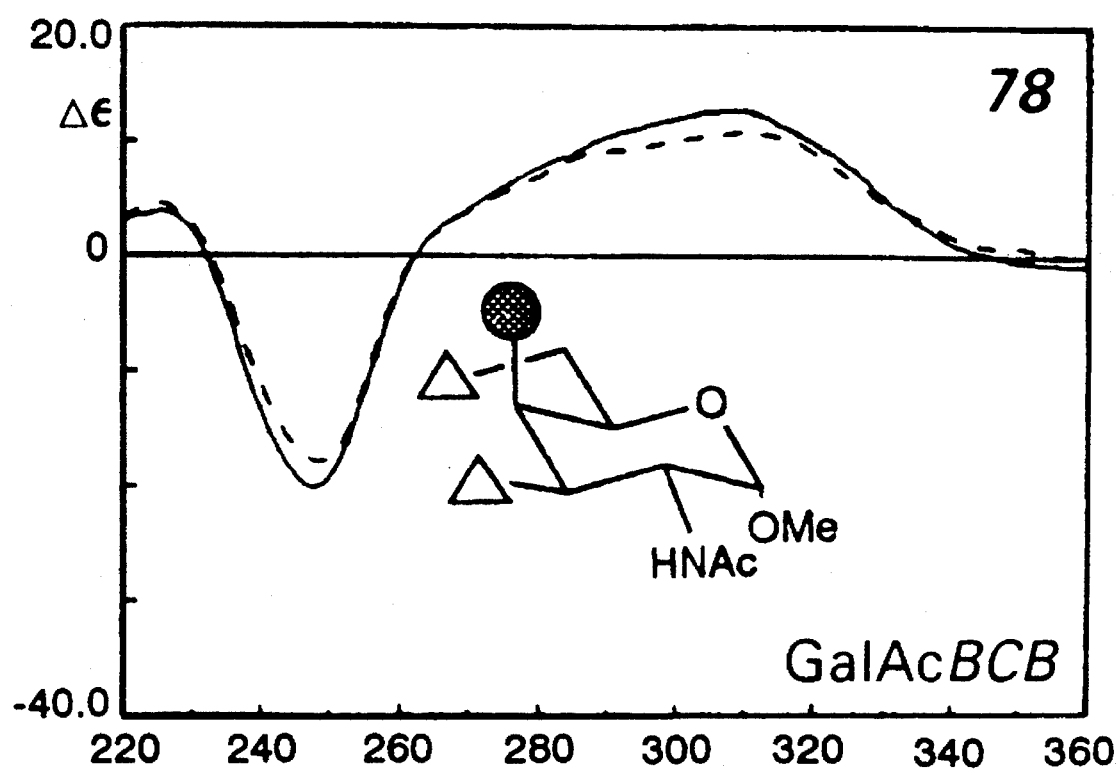
Figure 17A:
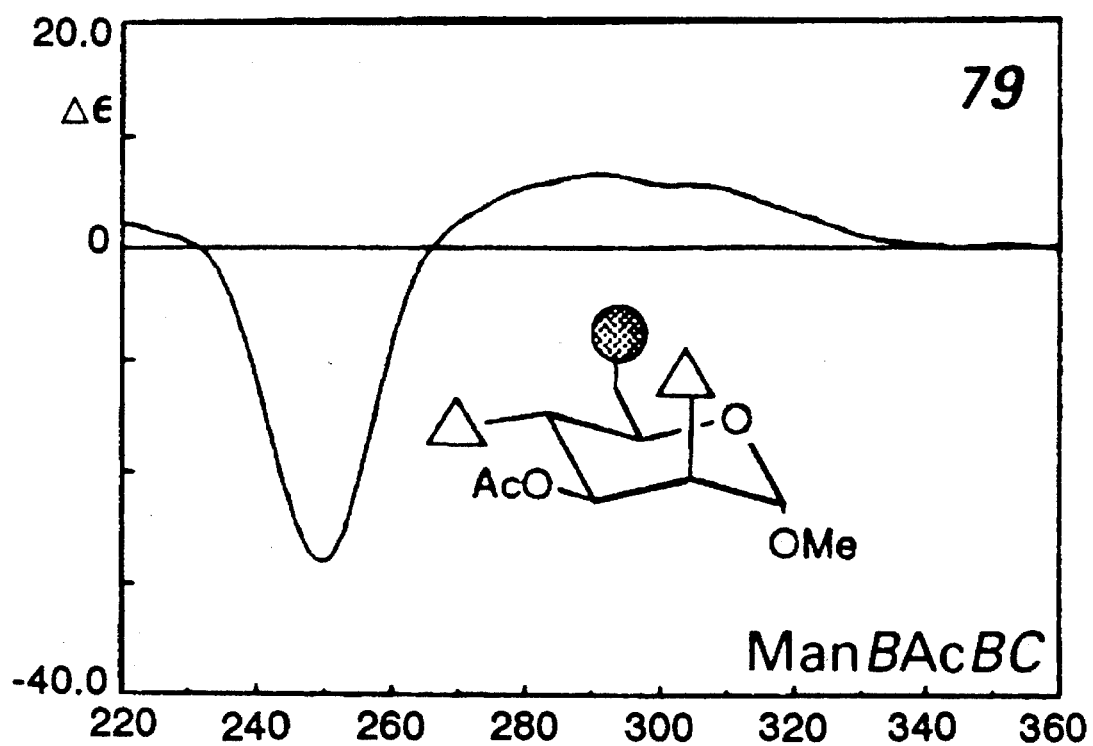
FIGS. 17a–f are a continuation of the $B_2C$ CD spectra of FIGS. 11a–f.
Figure 17B:
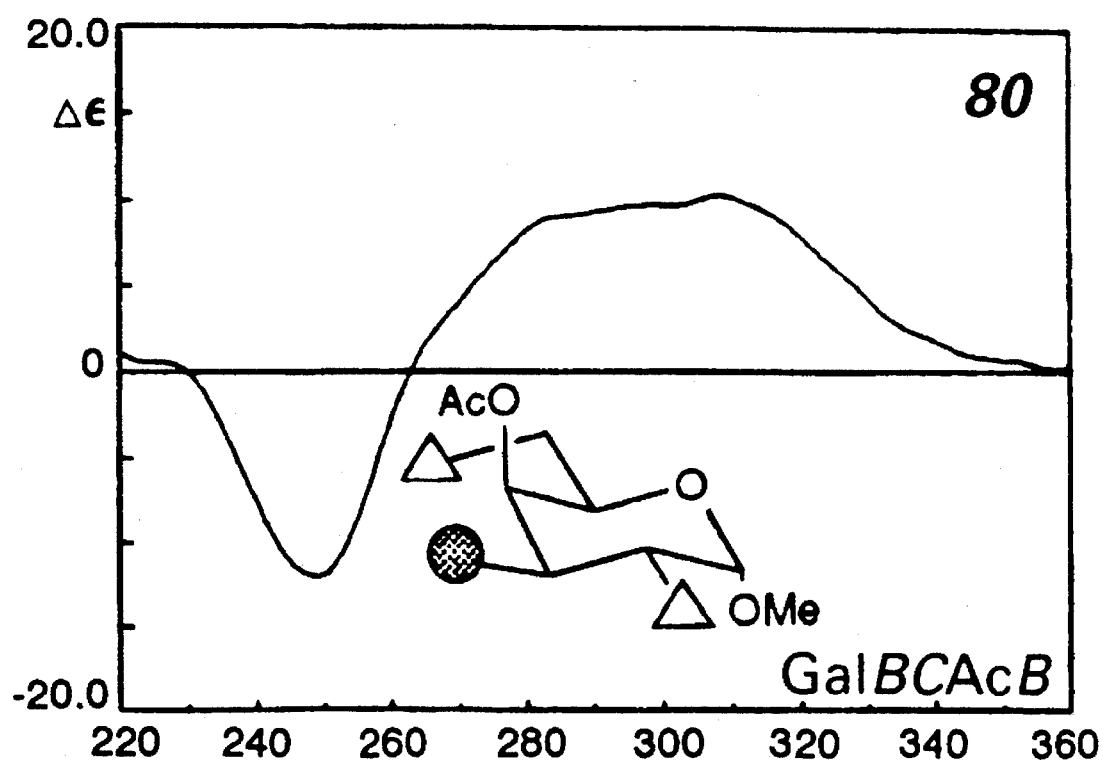
Figure 17C:
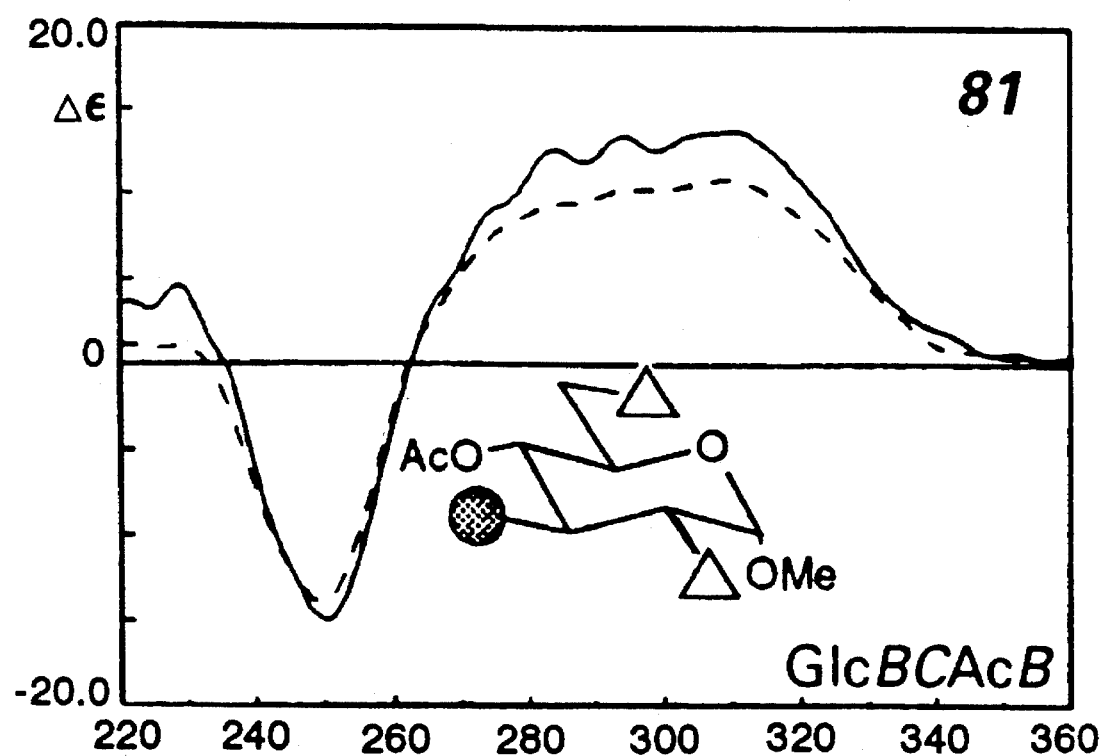
Figure 17D:
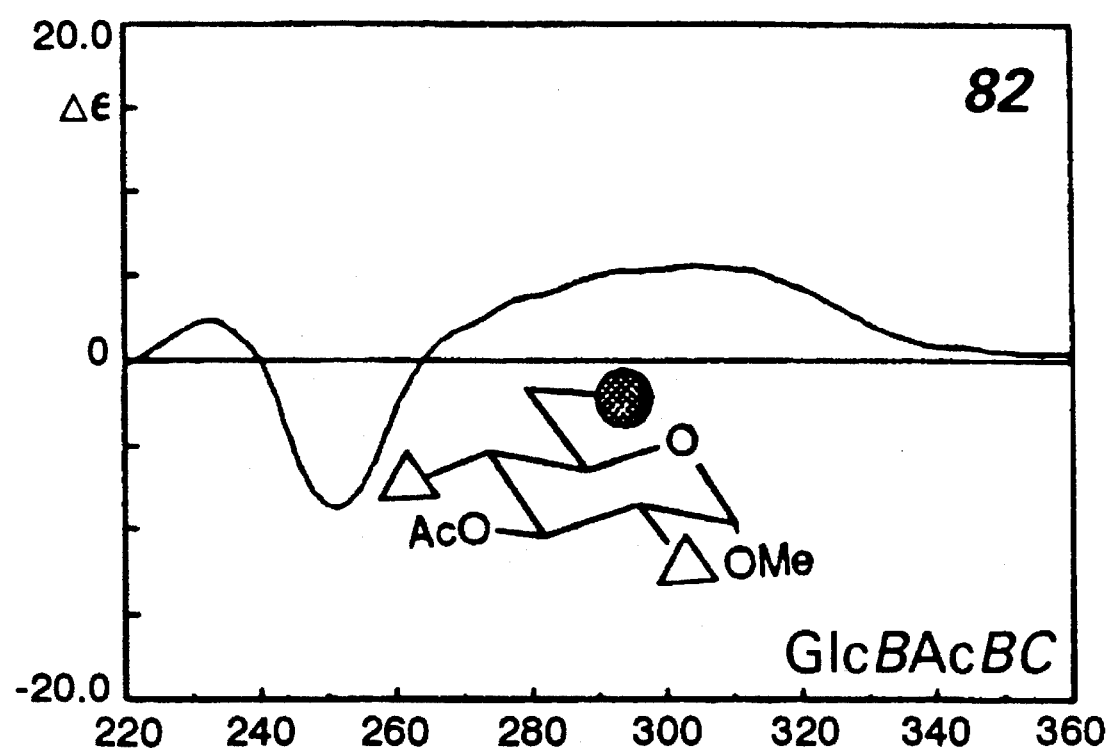
Figure 17E:
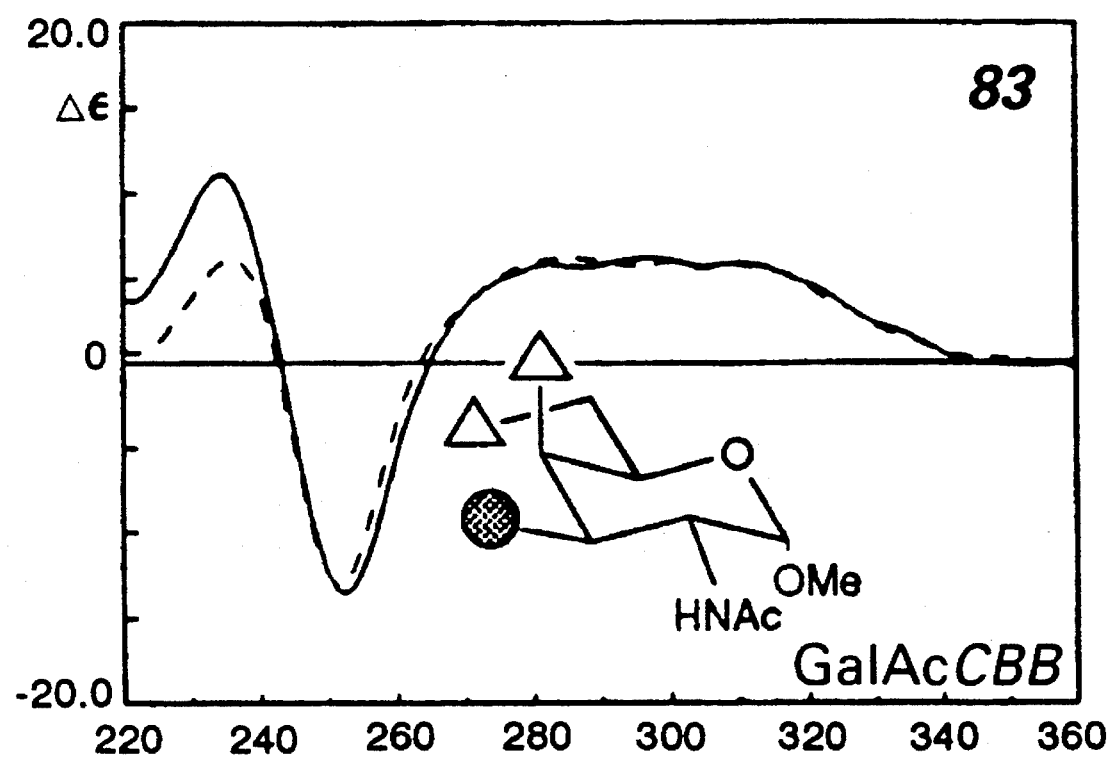
Figure 17F:
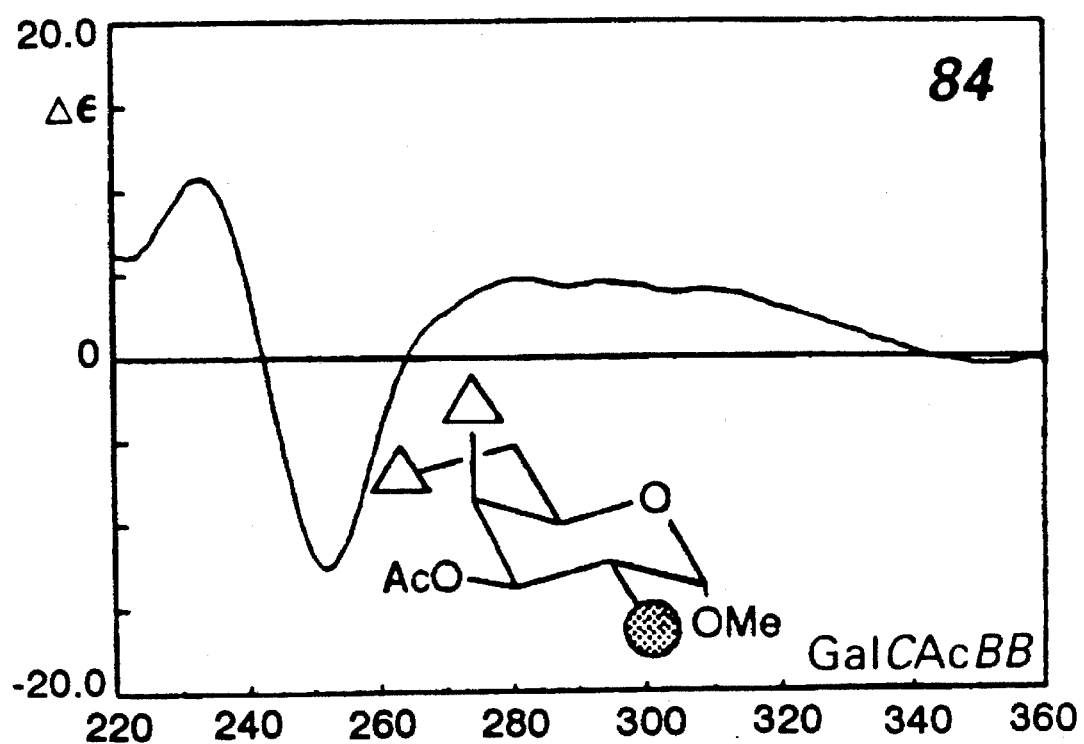
Figure 18A:
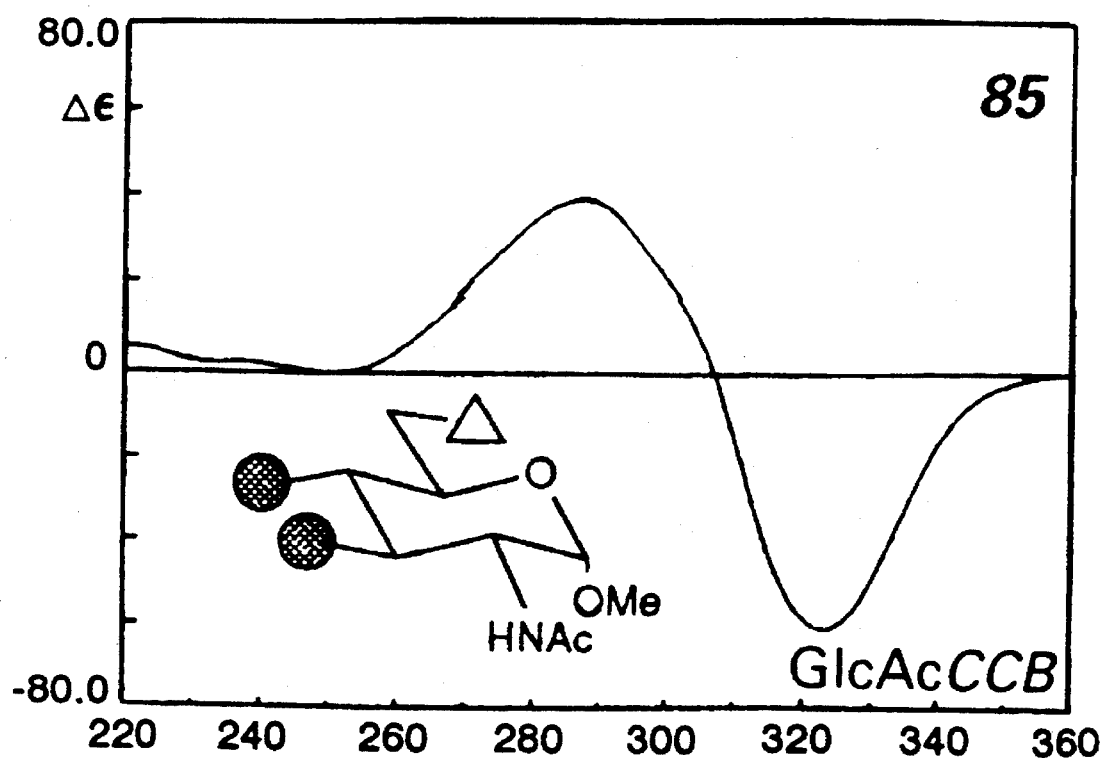
FIGS. 18a–f contain the $BC_2$ CD spectra.
Figure 18B:
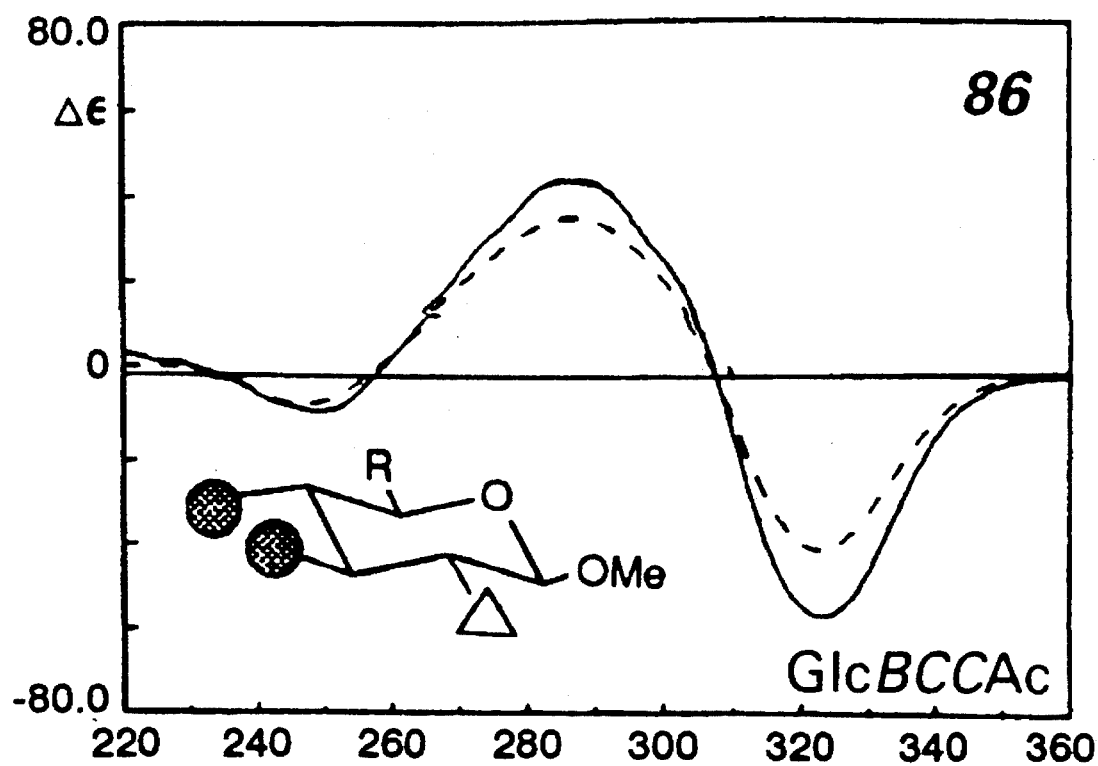
Figure 18C:
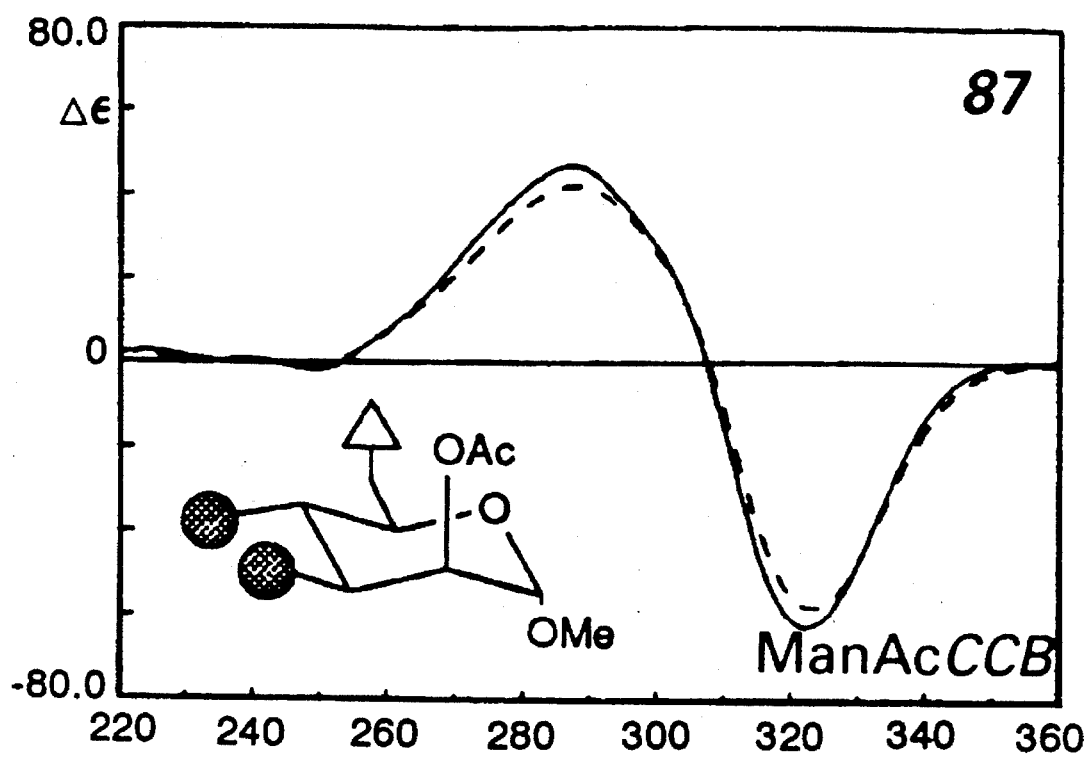
Figure 18D:
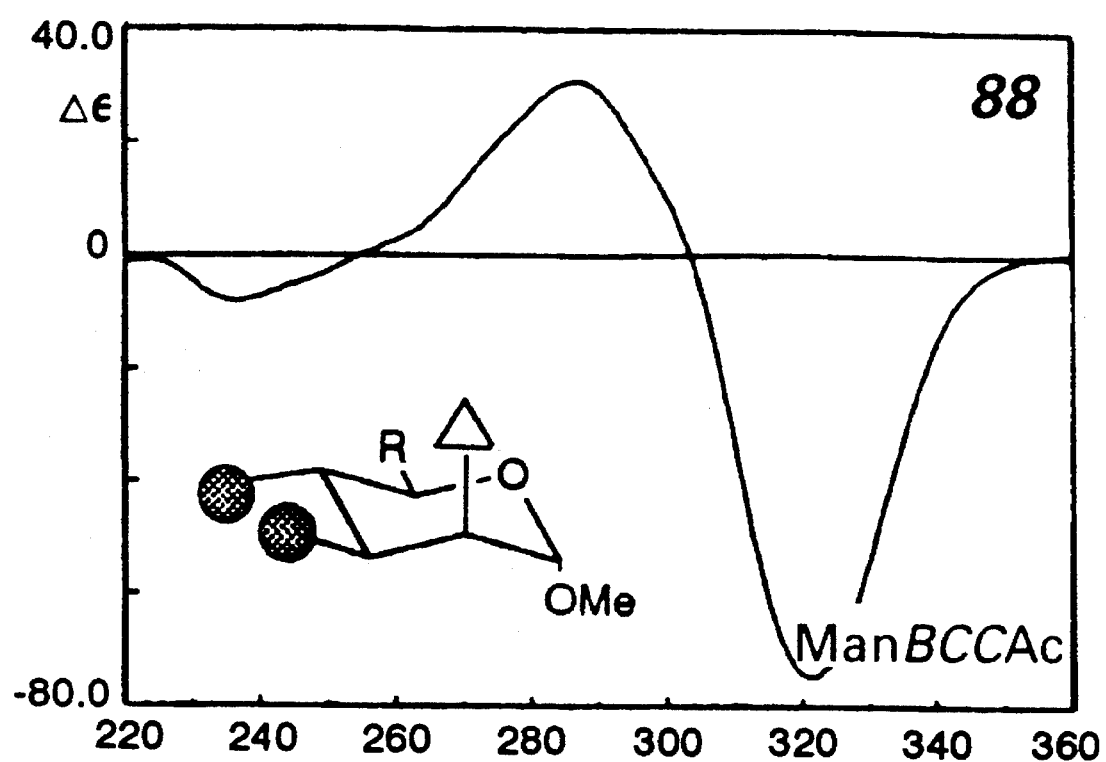
Figure 18E:
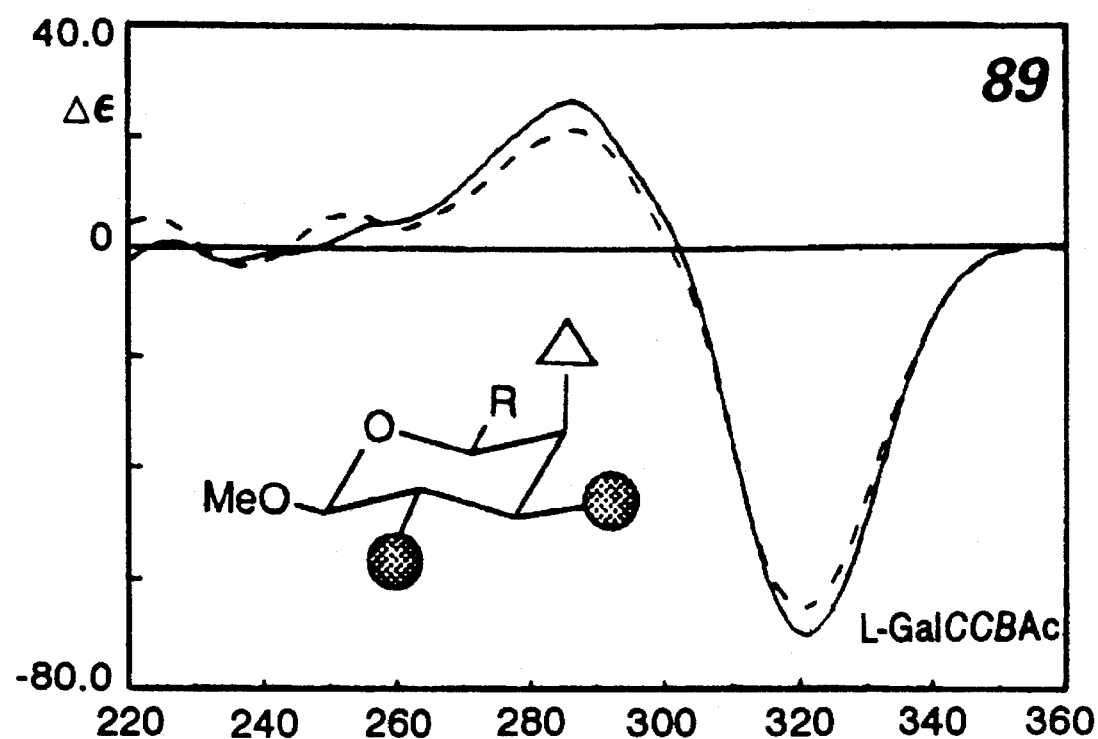
Figure 18F:
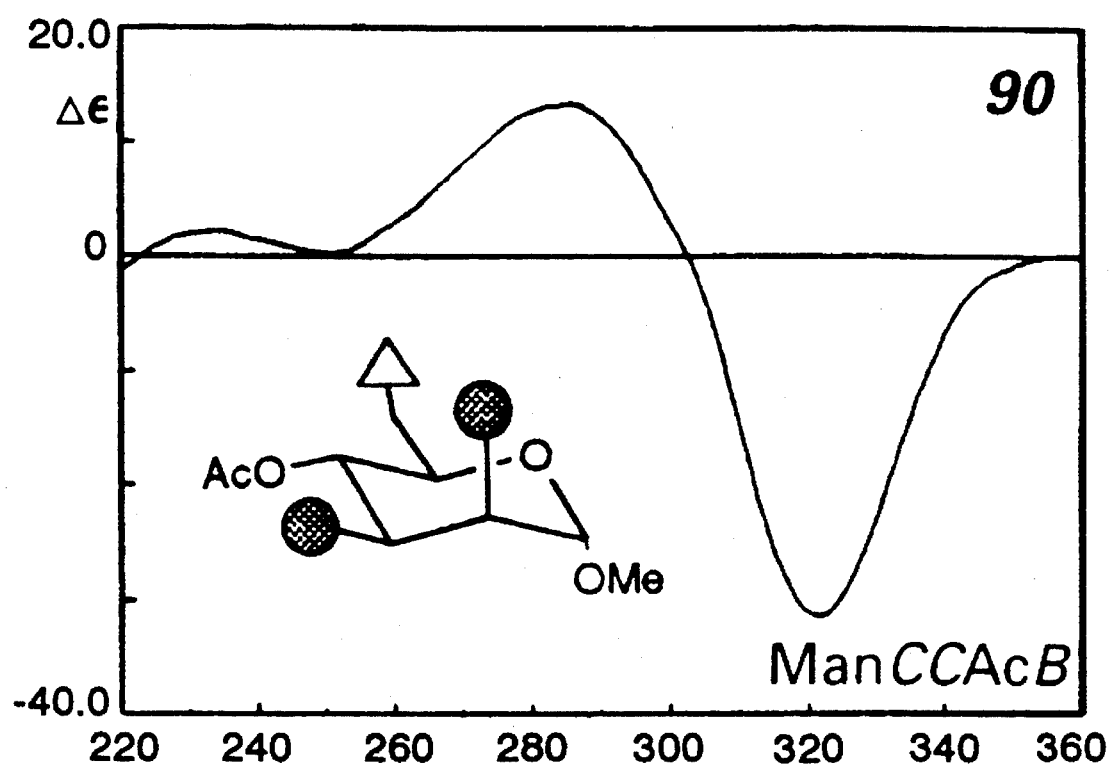
Figure 19A:
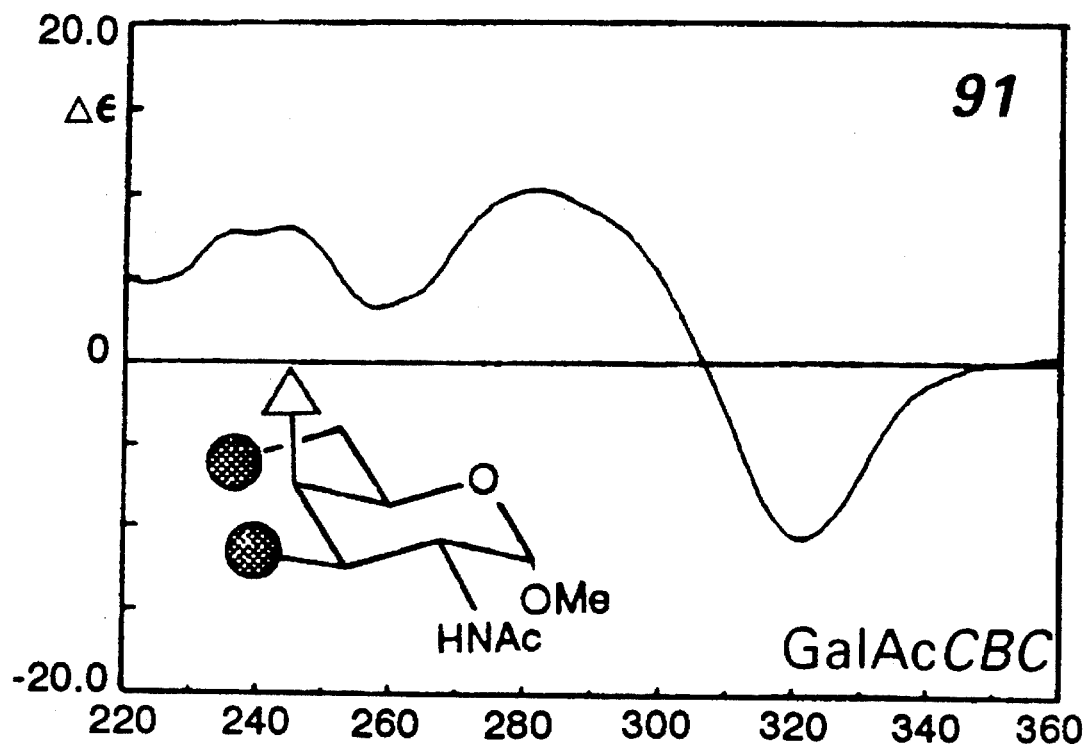
FIGS. 19a–f are a continuation of the $BC_2$ CD spectra of FIGS. 18a–f.
Figure 19B:
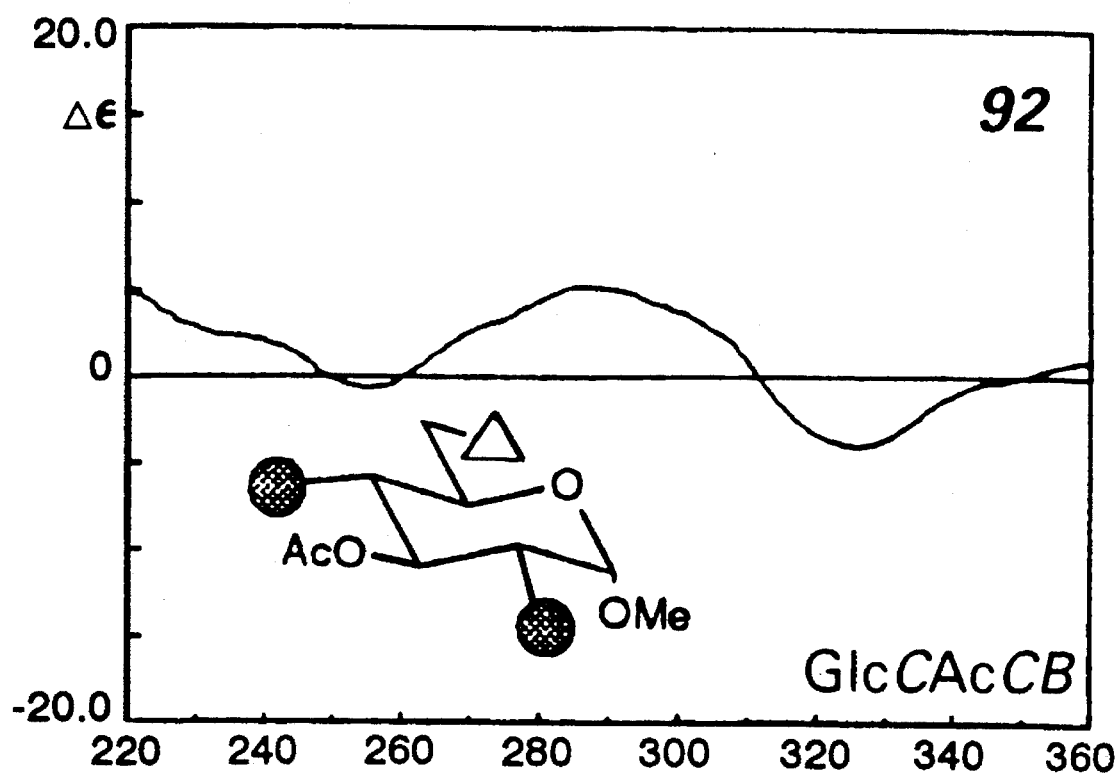
Figure 19C:
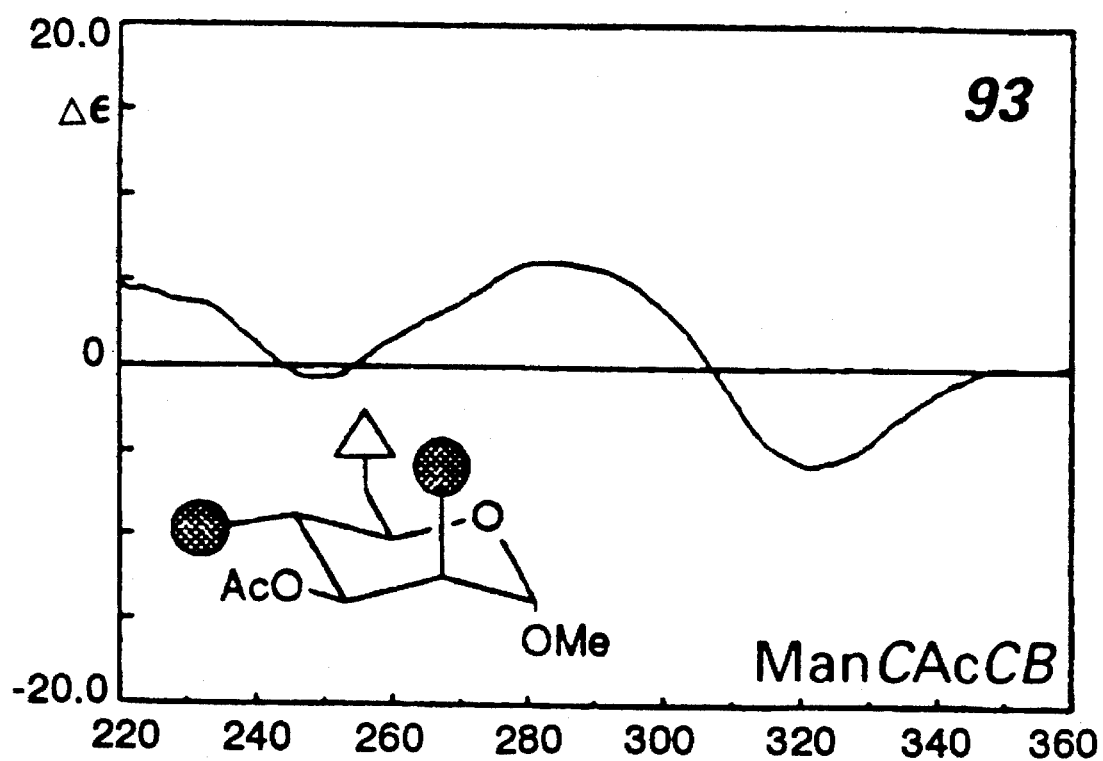
Figure 19D:
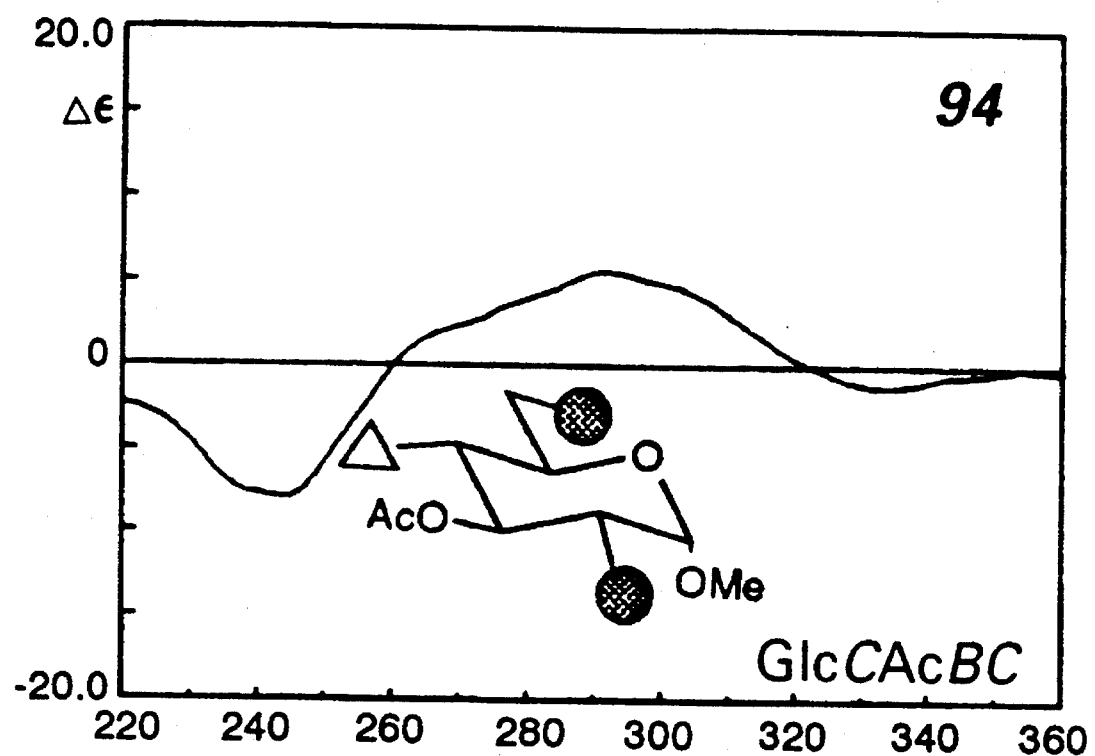
Figure 19E:
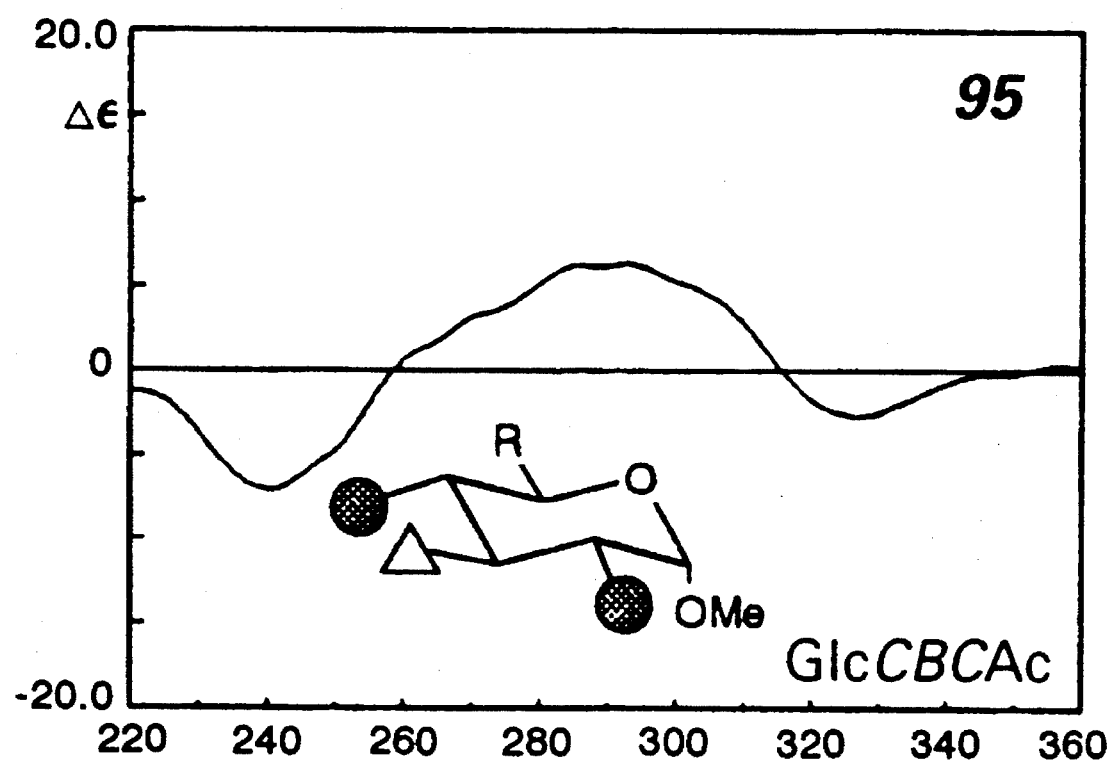
Figure 19F:
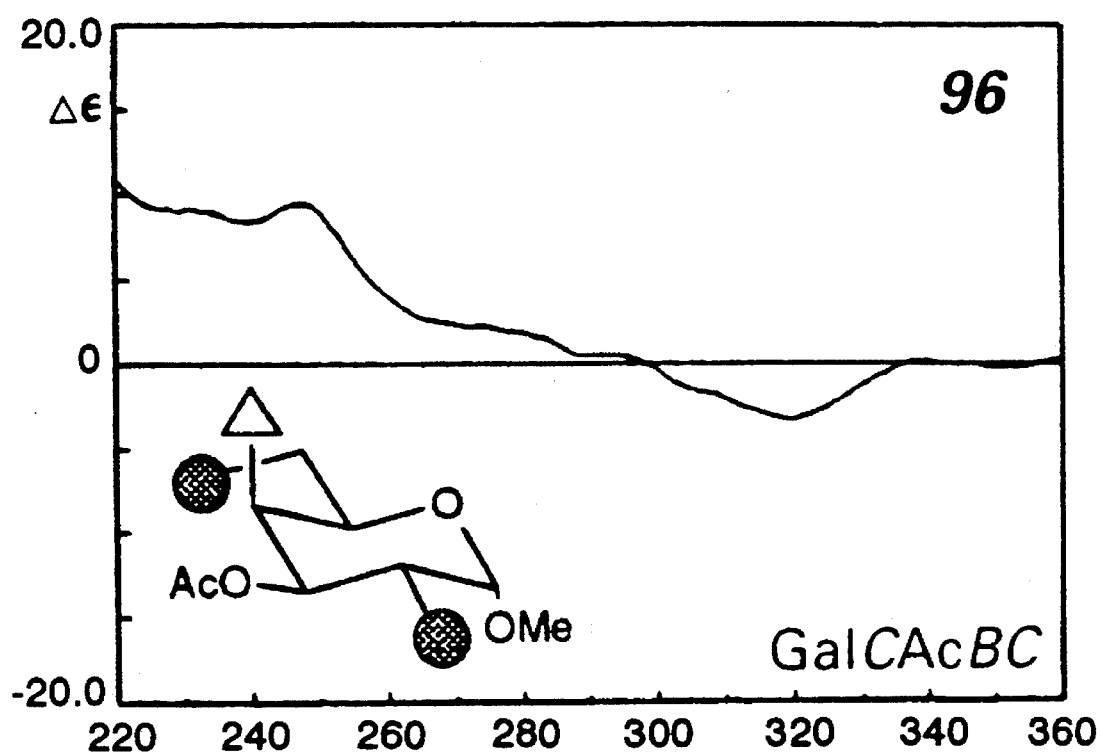
Figure 20A:
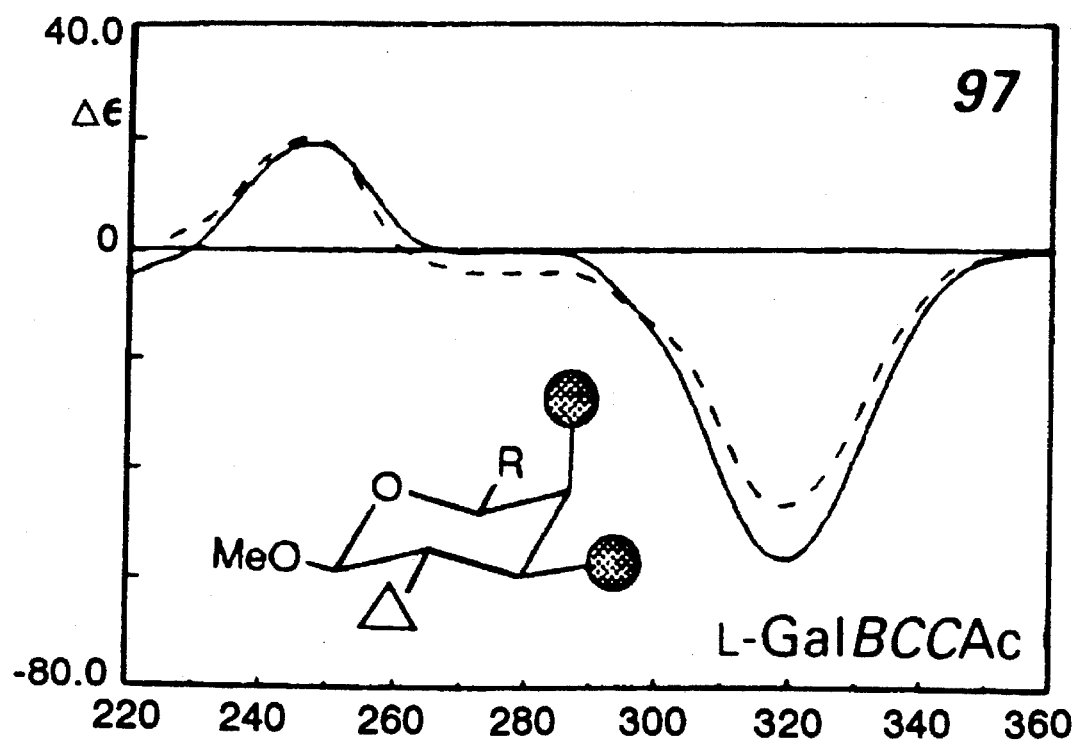
FIGS. 20a–f are a continuation of the $BC_2$ CD spectra of FIGS. 18a–f.
Figure 20B:
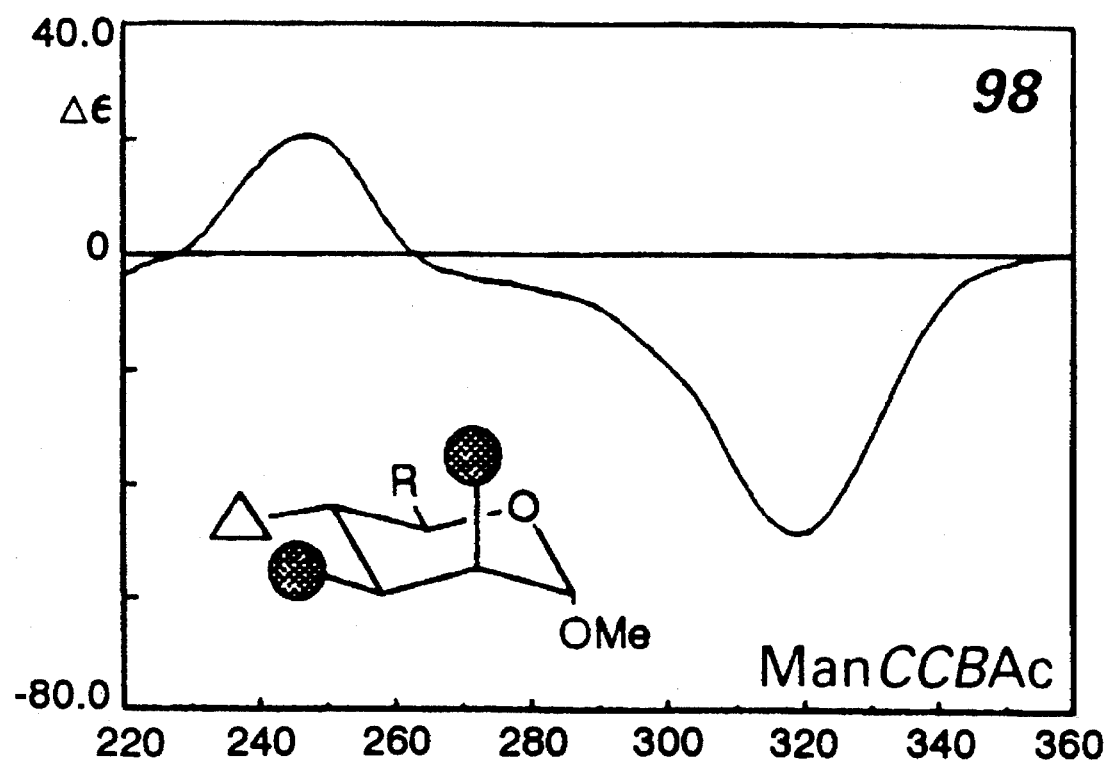
Figure 20C:
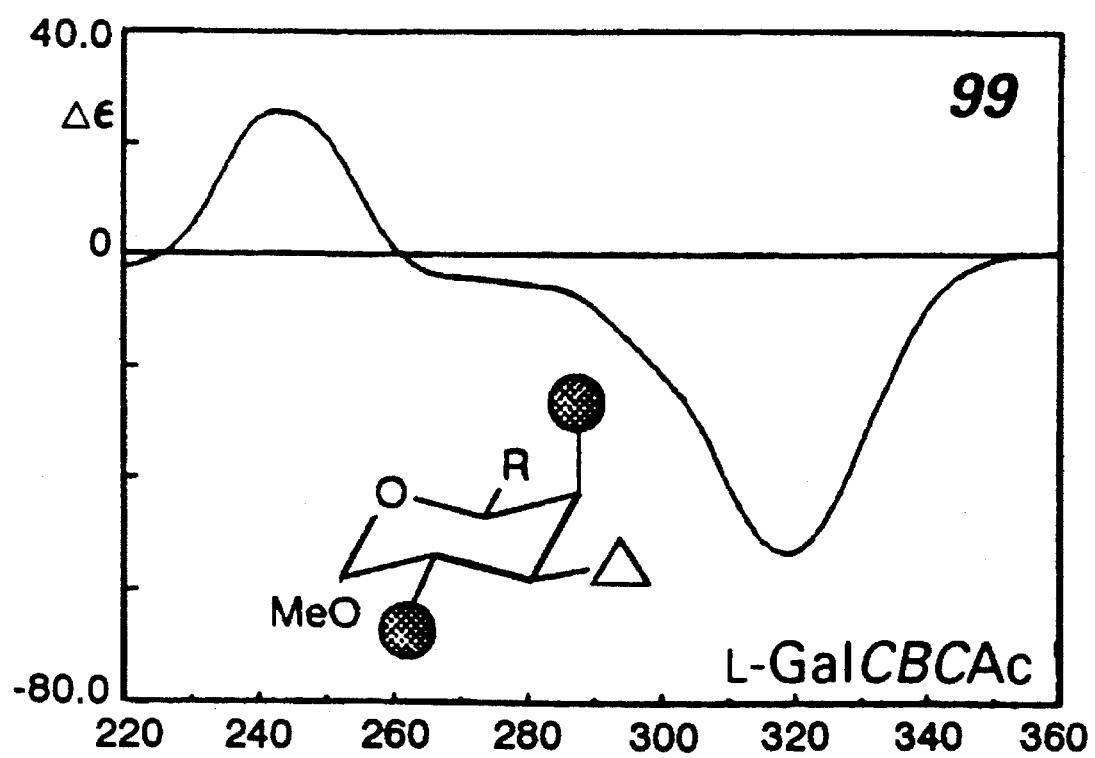
Figure 20D:
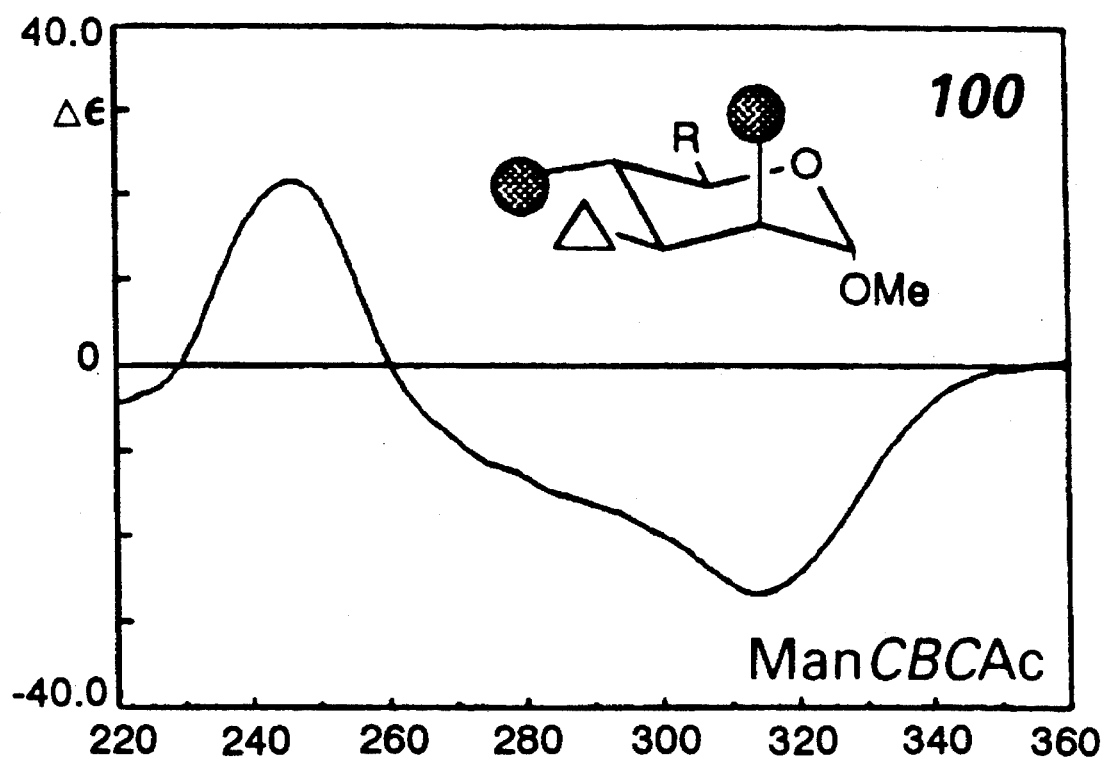
Figure 20E:
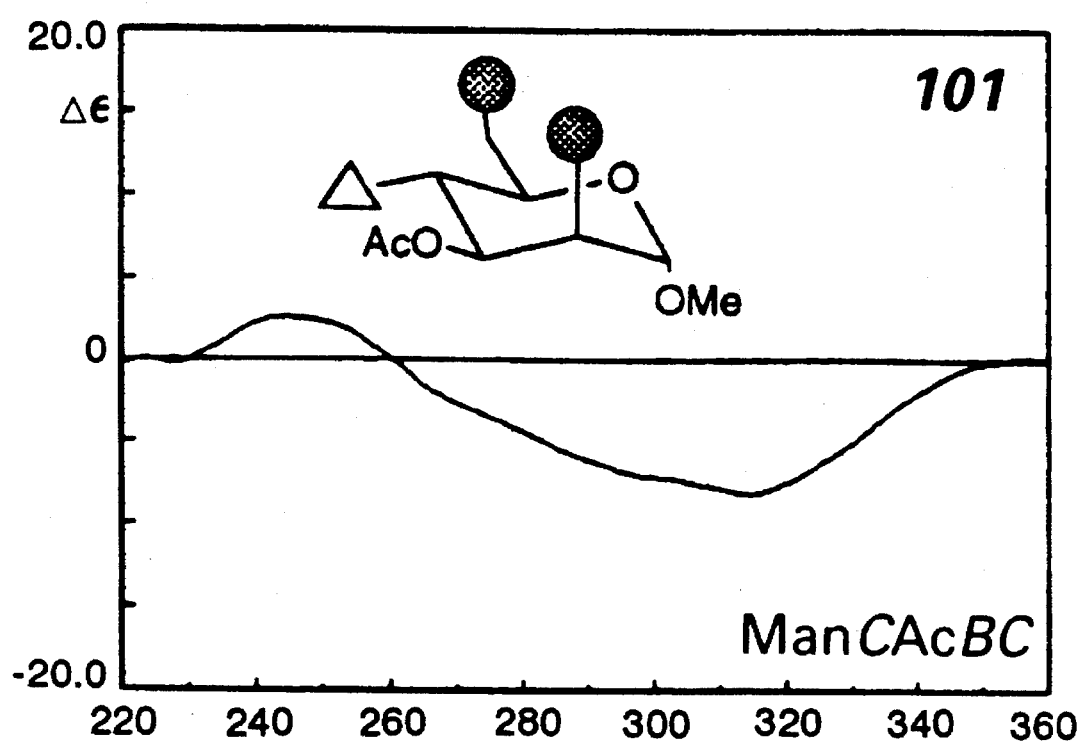
Figure 20F:
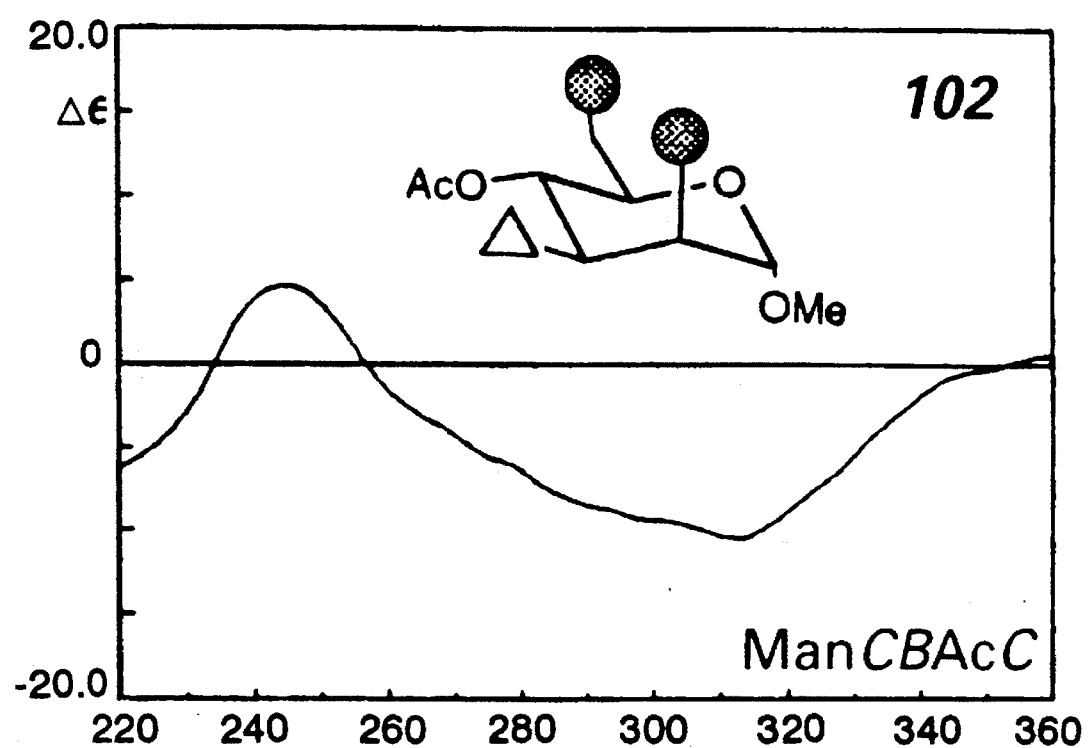
Figure 21A:
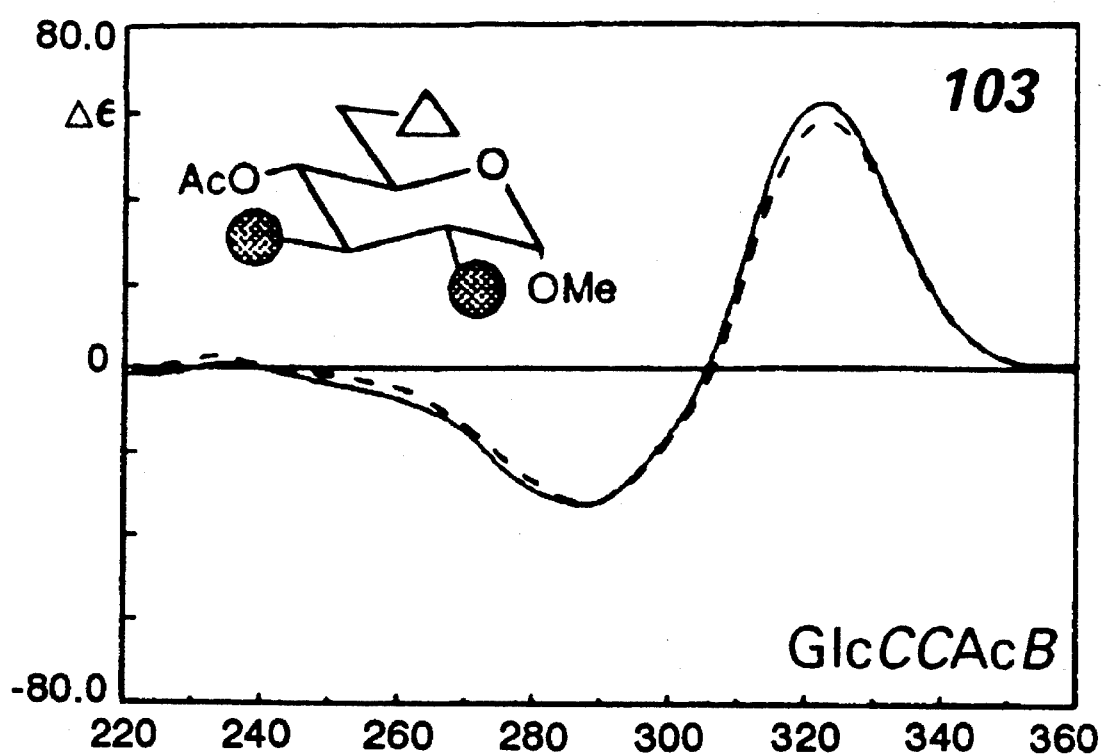
FIGS. 21a–f are a continuation of the $BC_2$ CD spectra of FIGS. 18a–f.
Figure 21B:
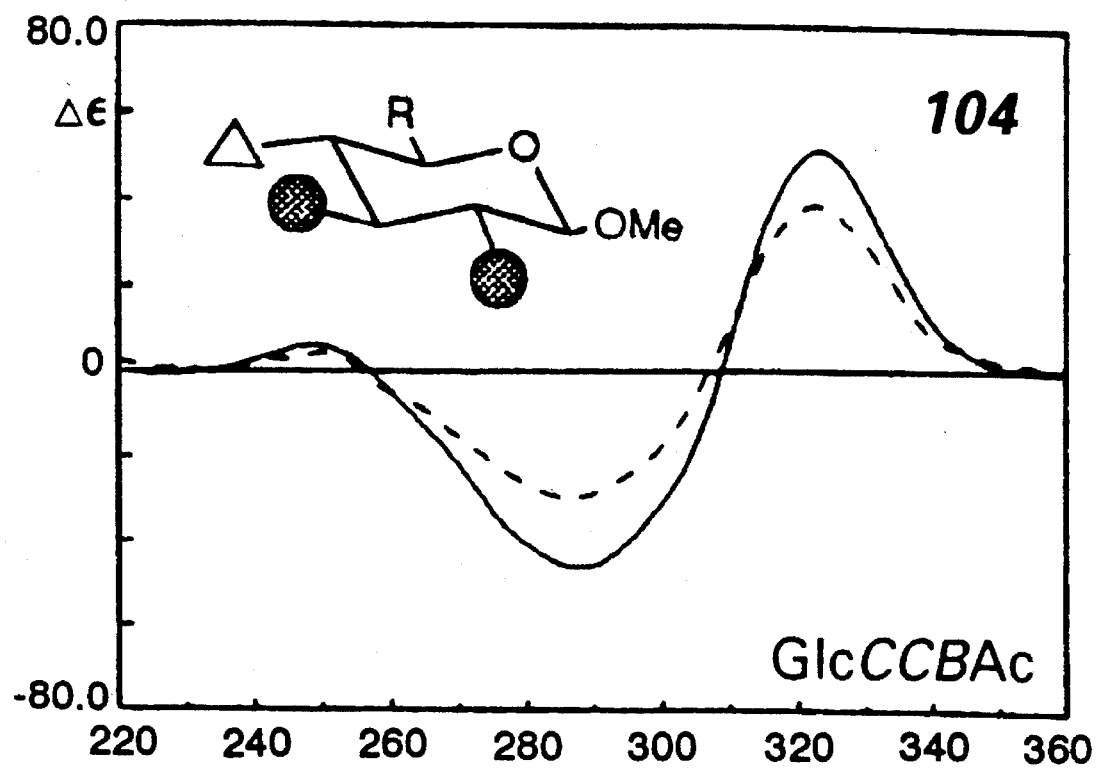
Figure 21C:
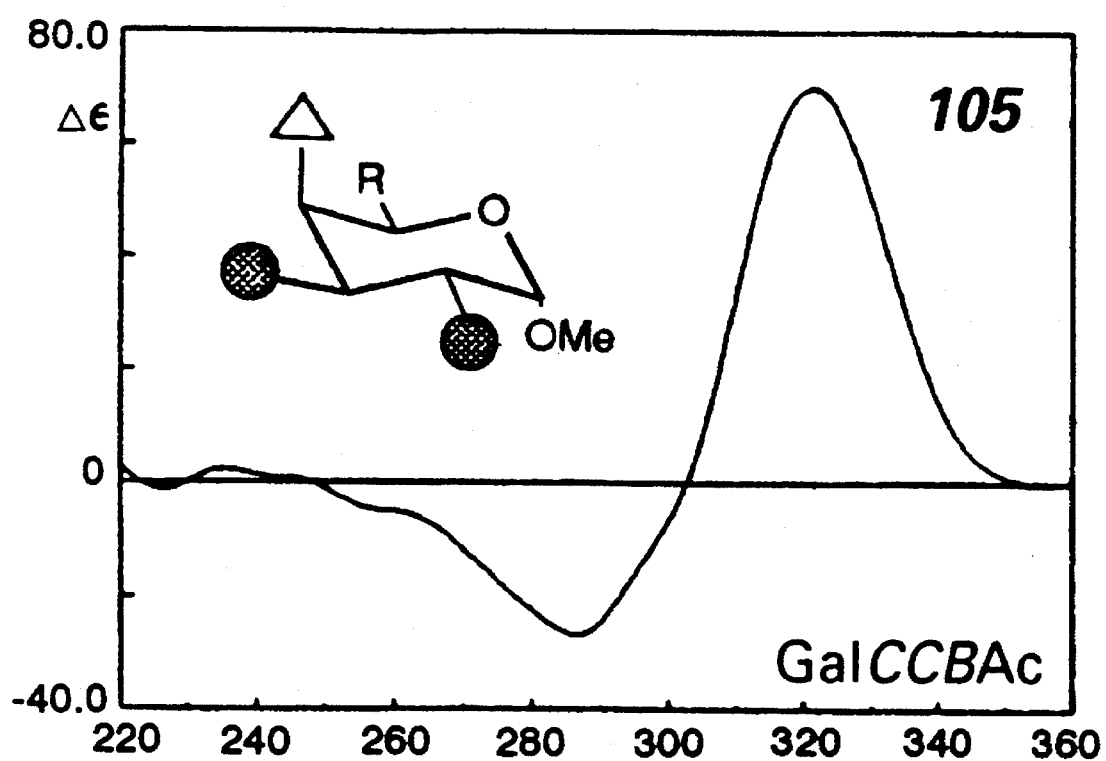
Figure 21D:
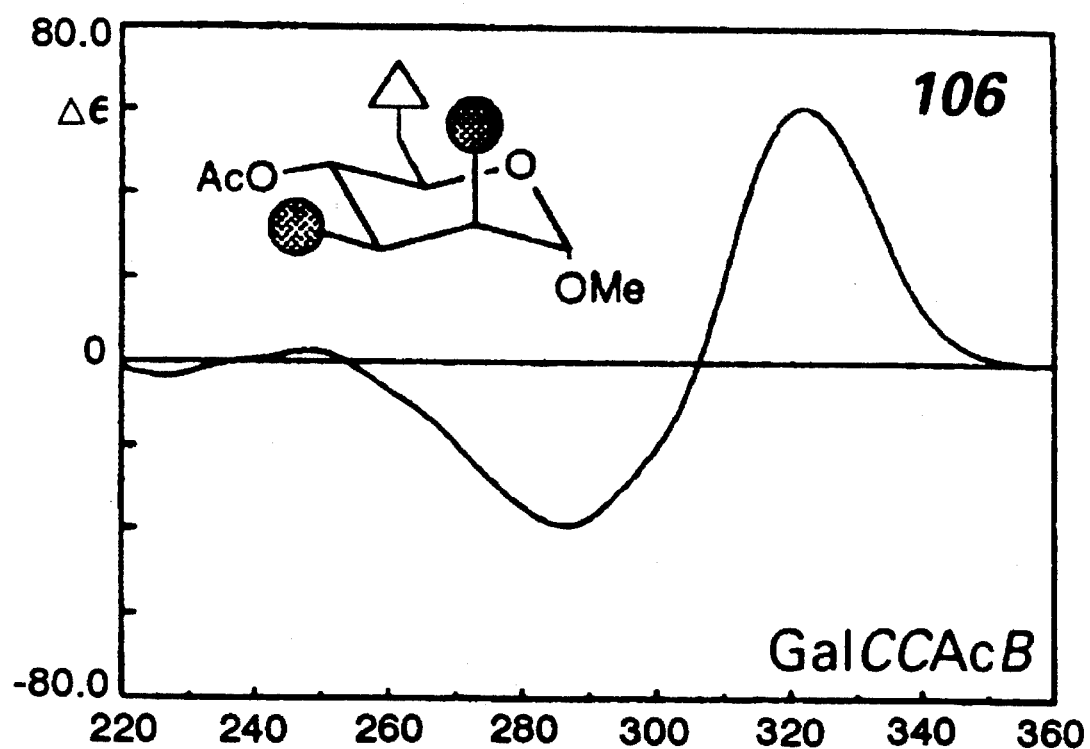
Figure 21E:
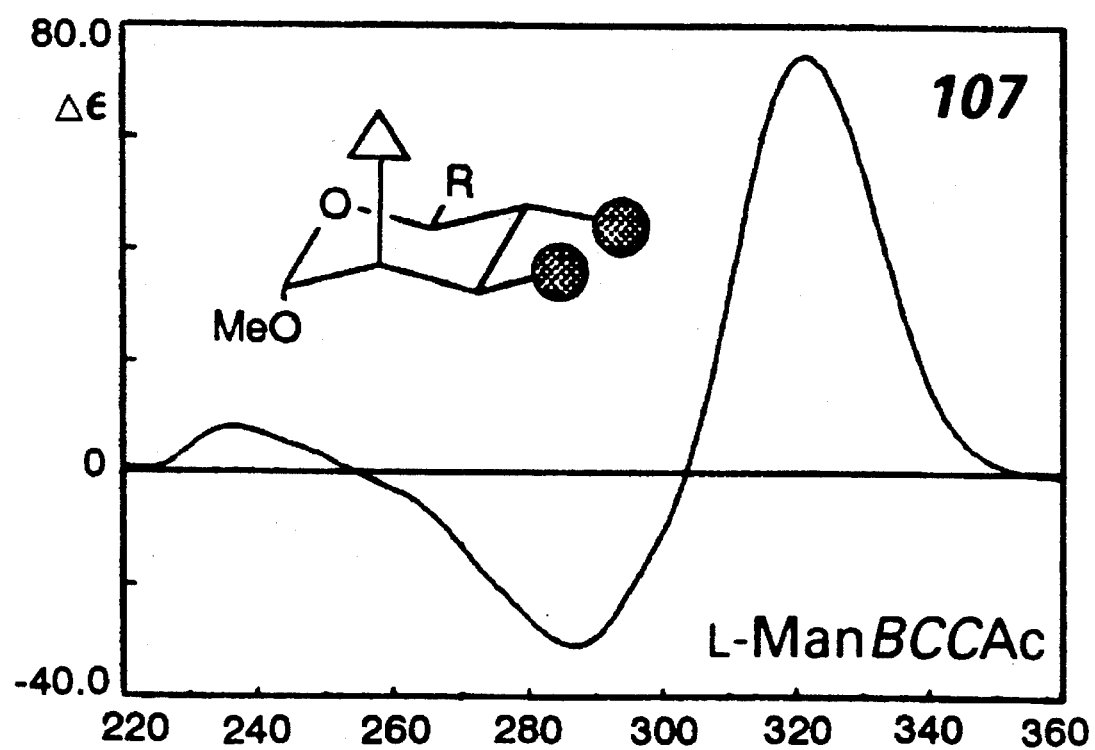
Figure 21F:
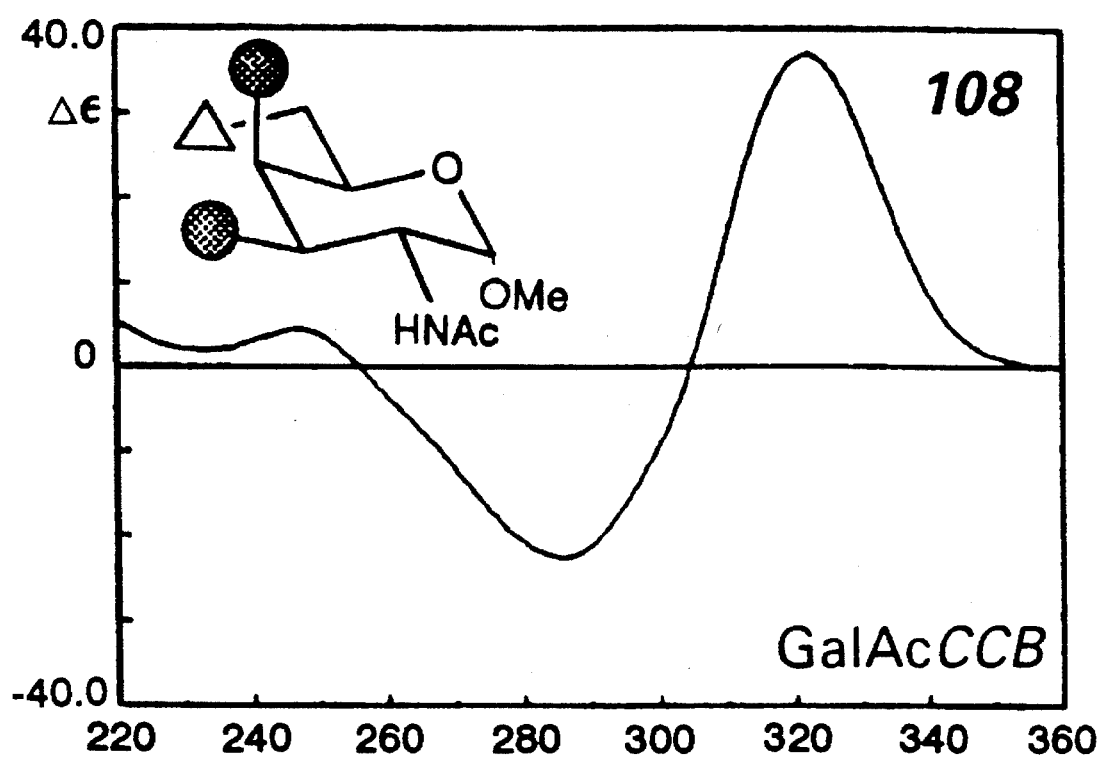
Figure 22A:
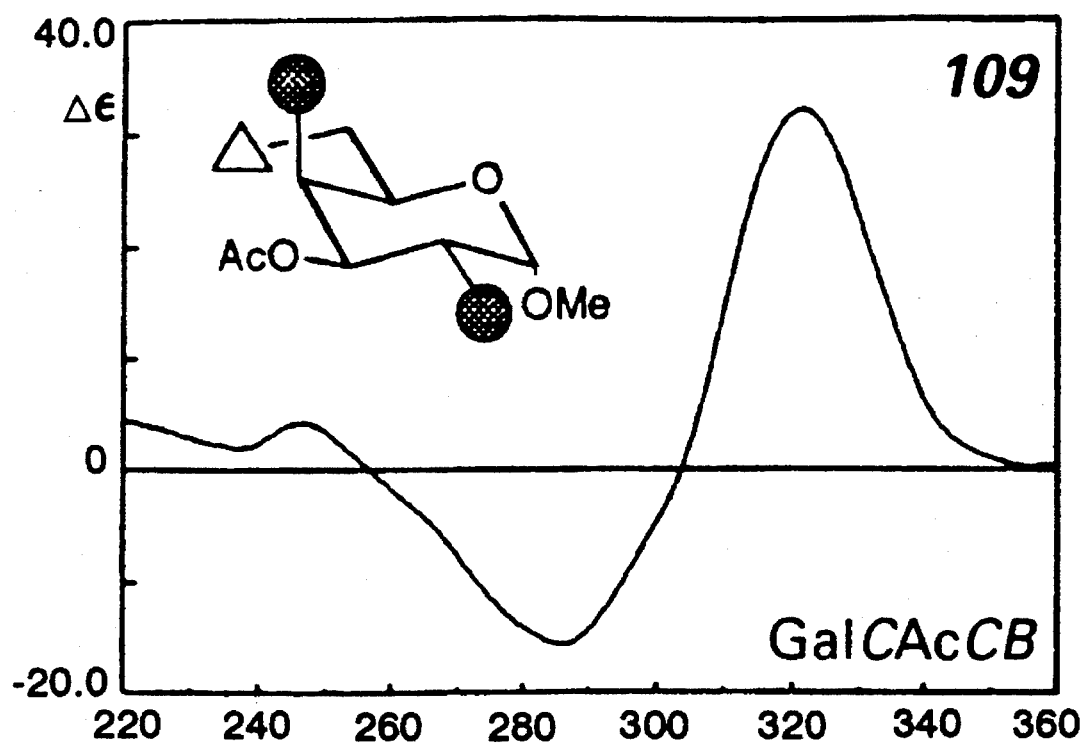
FIGS. 22a–f are a continuation of the $BC_2$ CD spectra of FIGS. 18a–f.
Figure 22B:
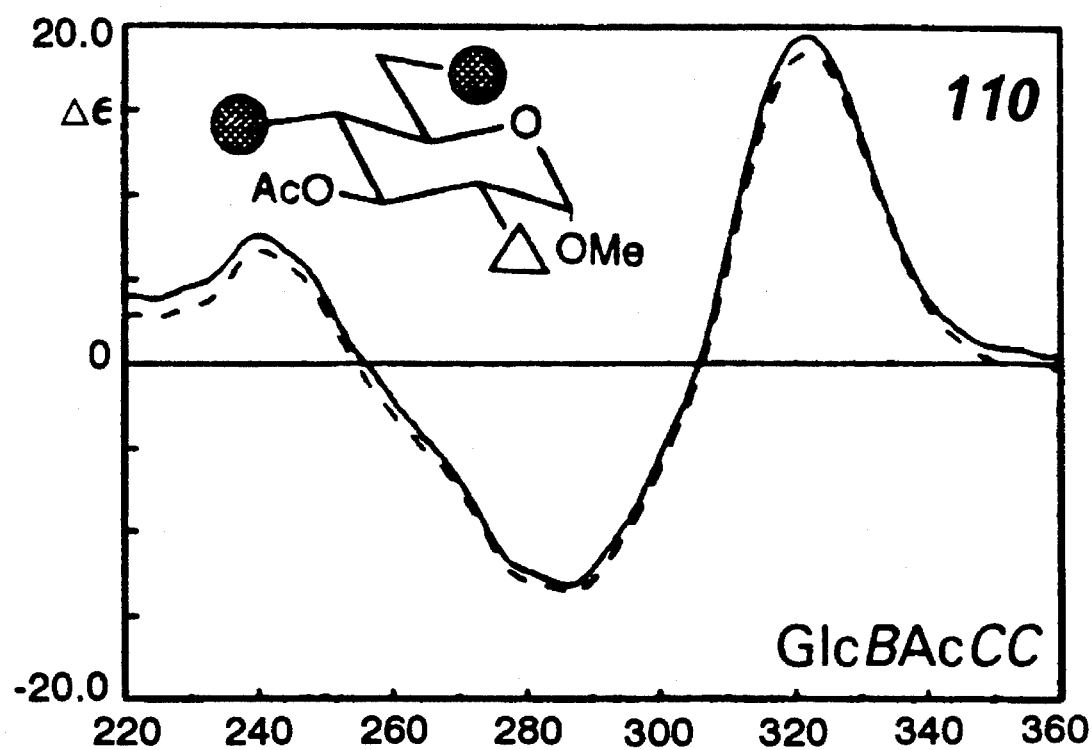
Figure 22C:
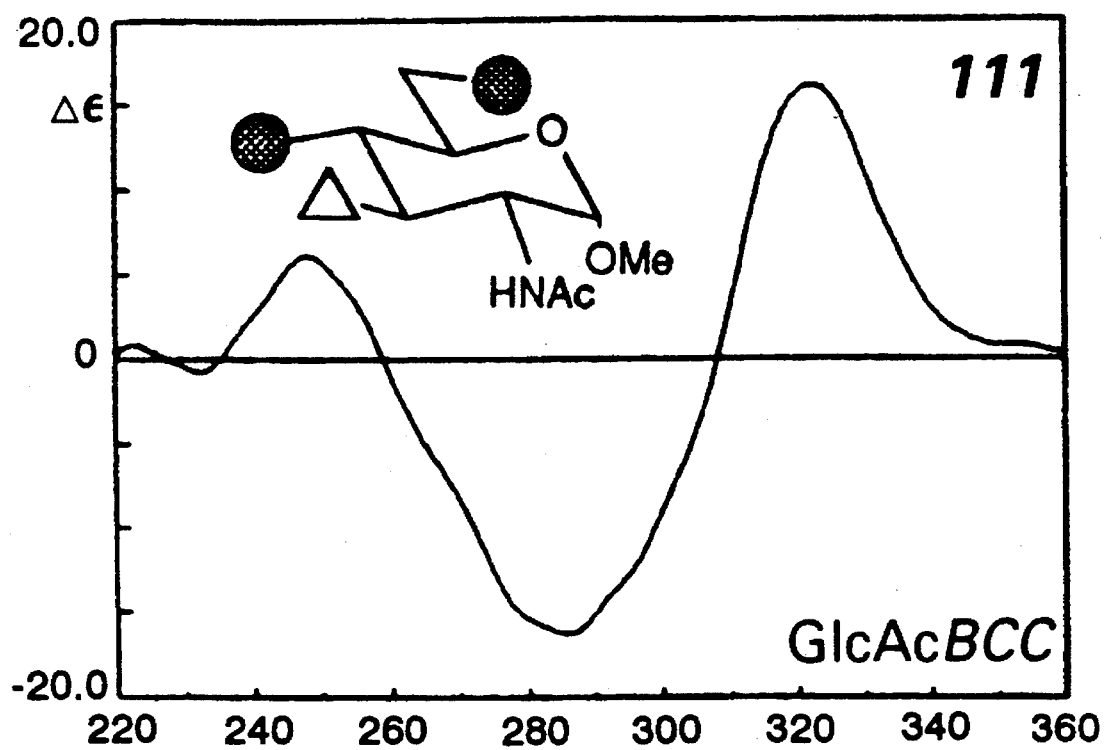
Figure 22D:
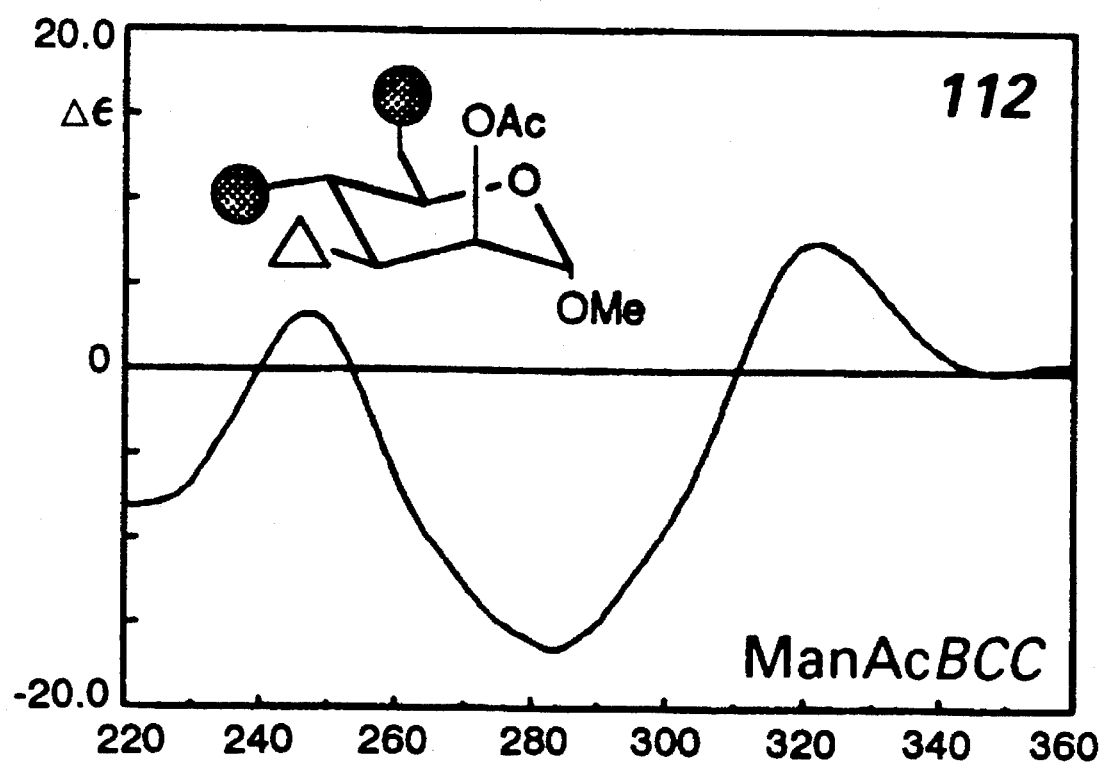
Figure 22E:
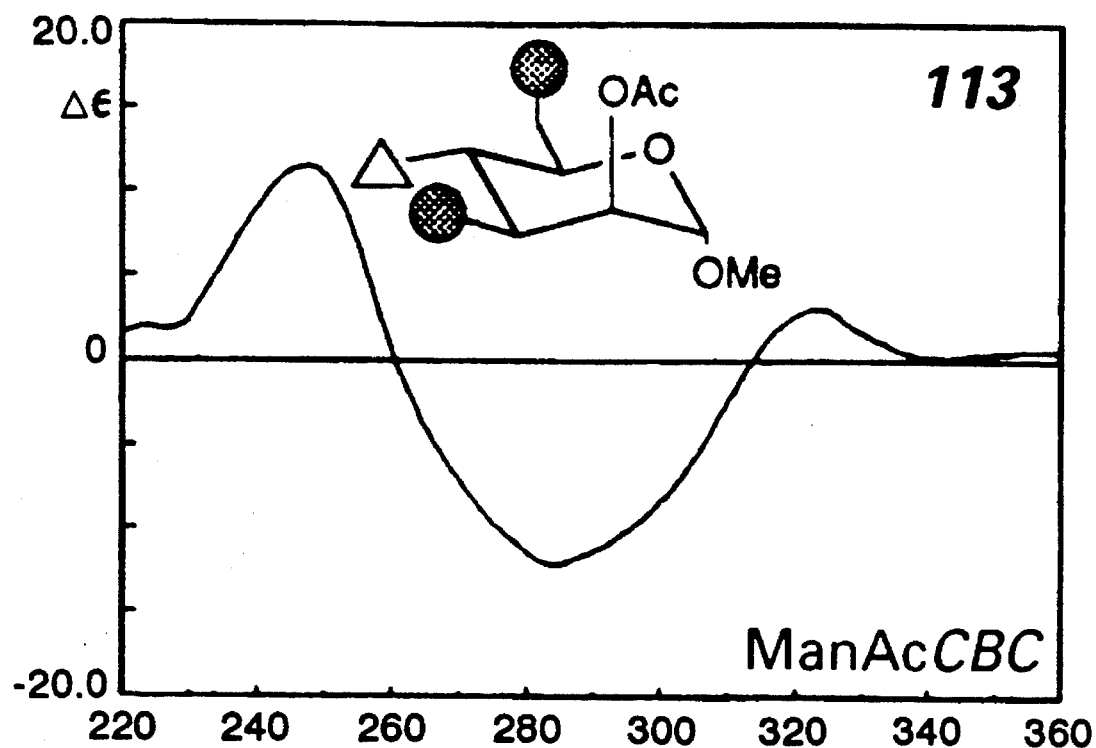
Figure 22F:
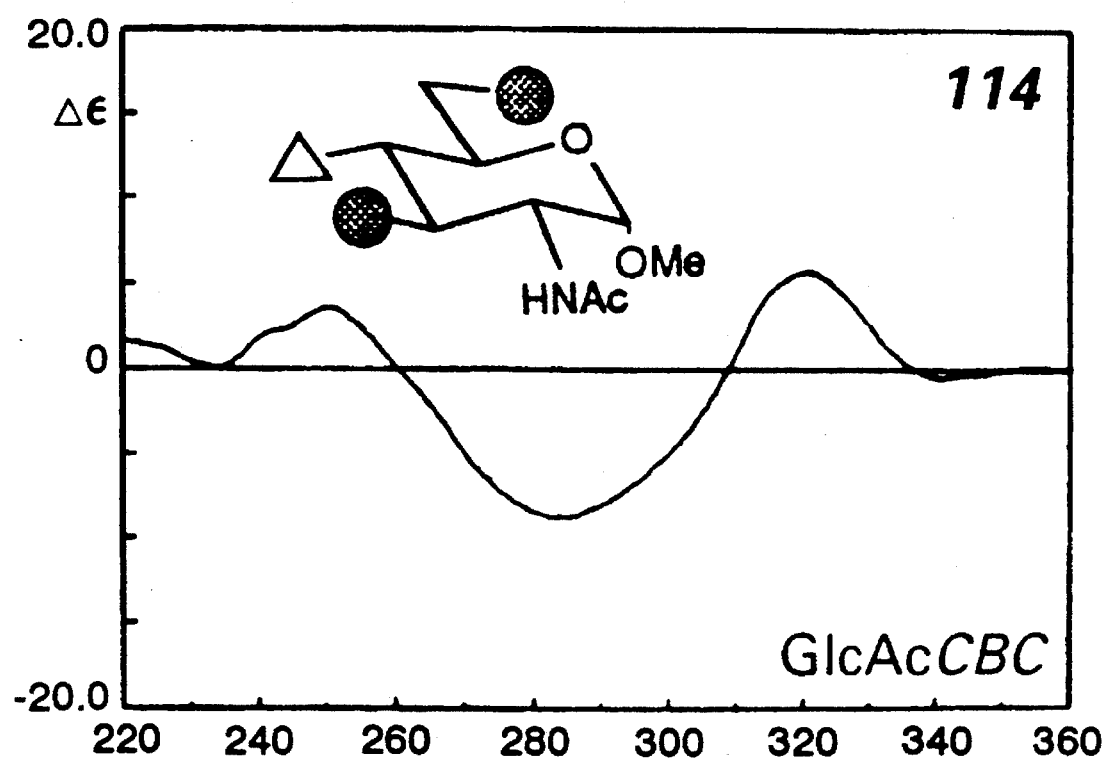
Figure 23A:
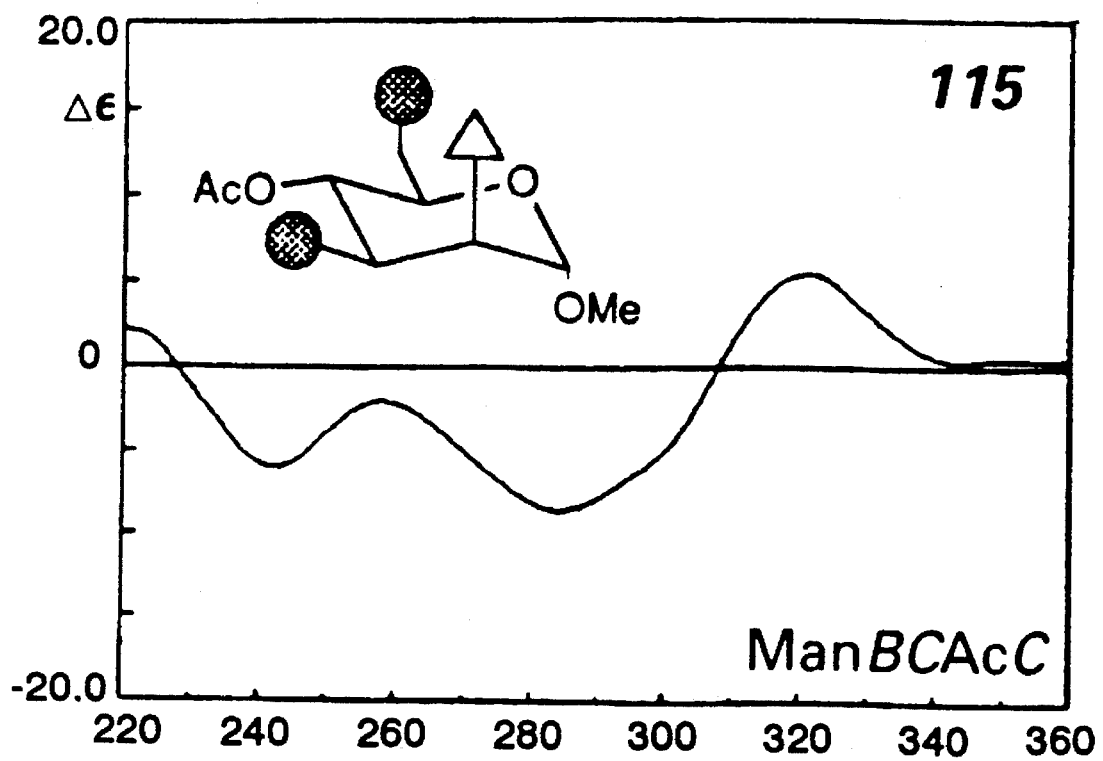
FIGS. 23a–f are a continuation of the $BC_2$ CD spectra of FIGS. 18a–f.
Figure 23B:
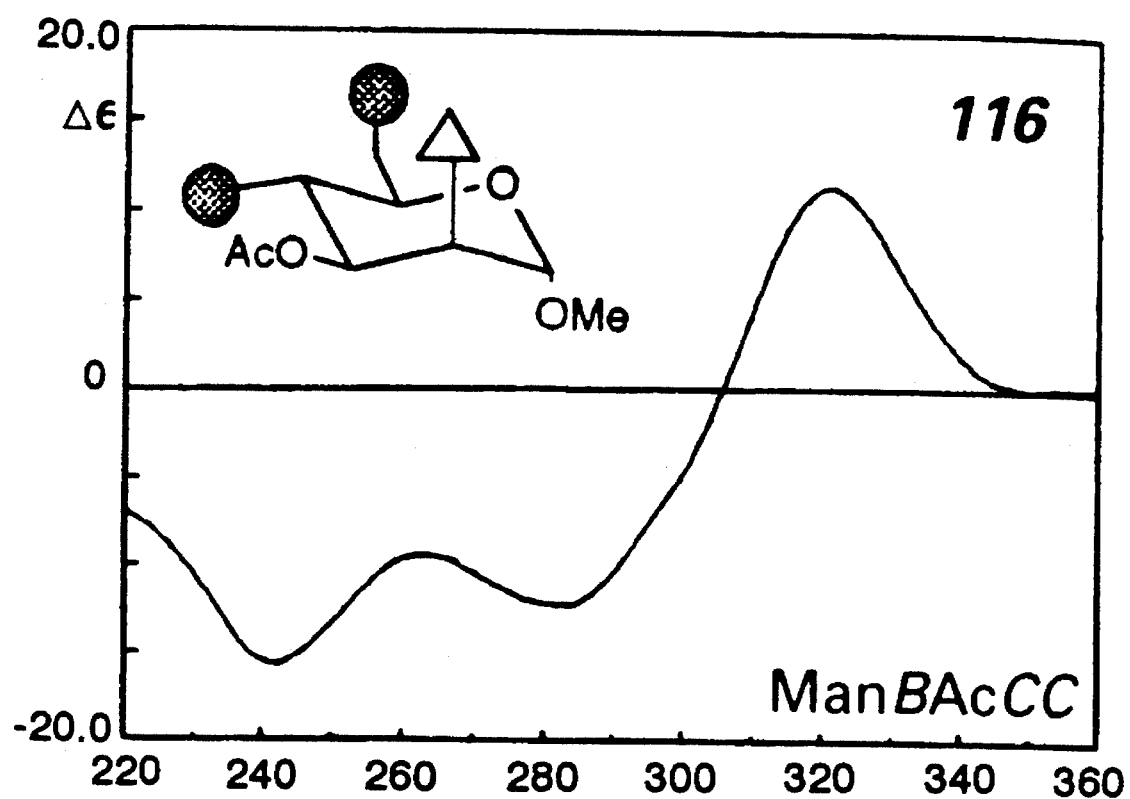
Figure 23C:
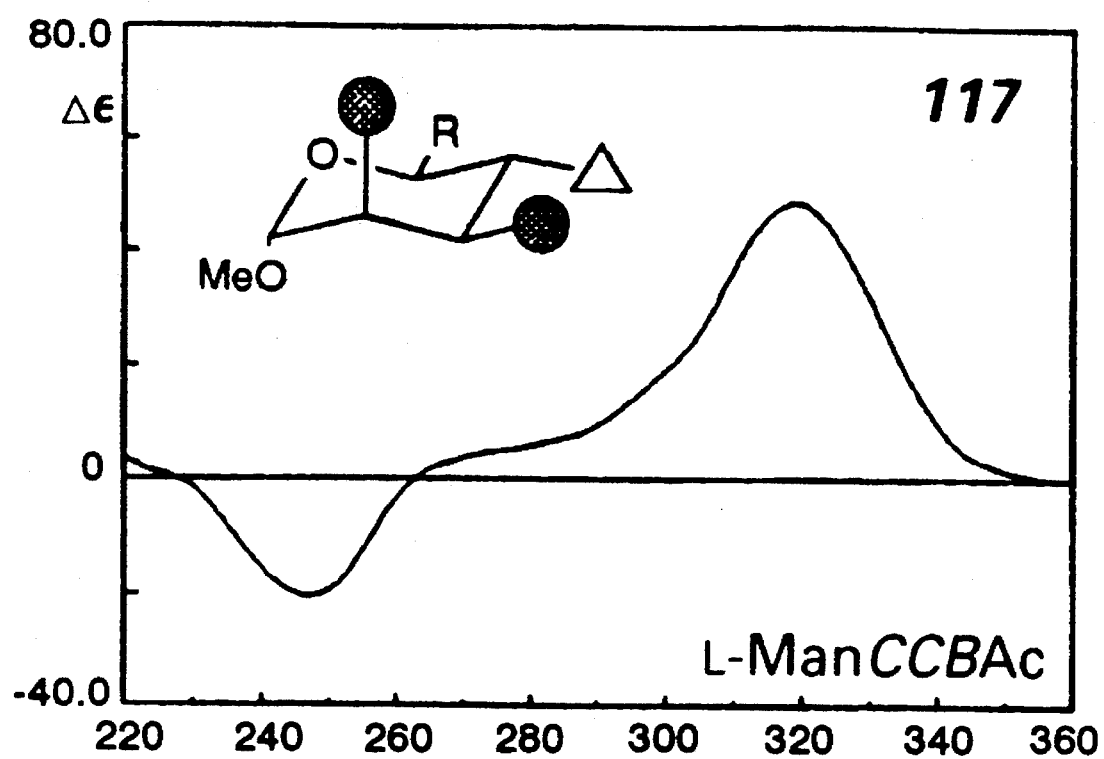
Figure 23D:
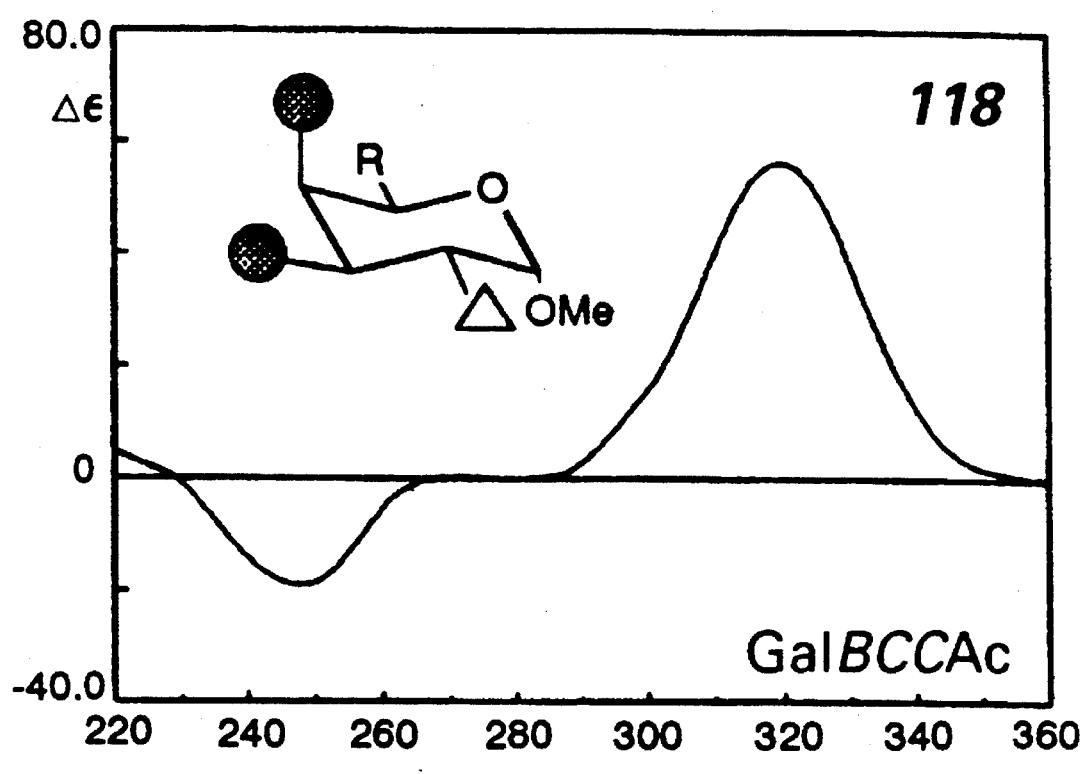
Figure 23E:
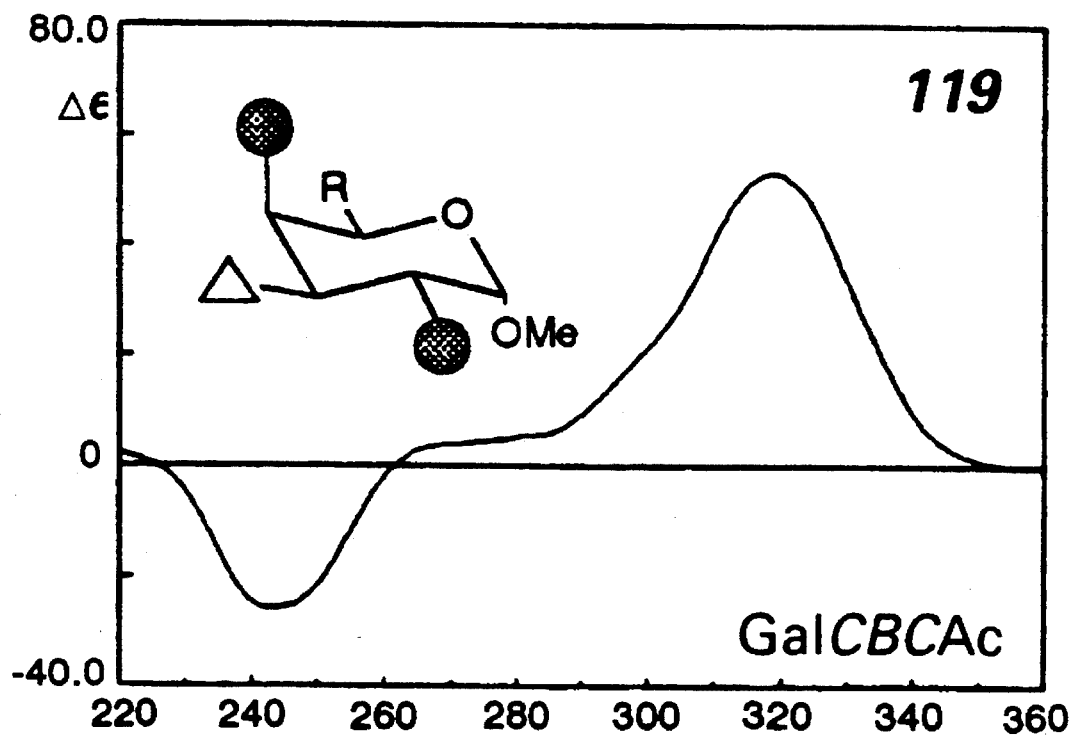
Figure 23F:
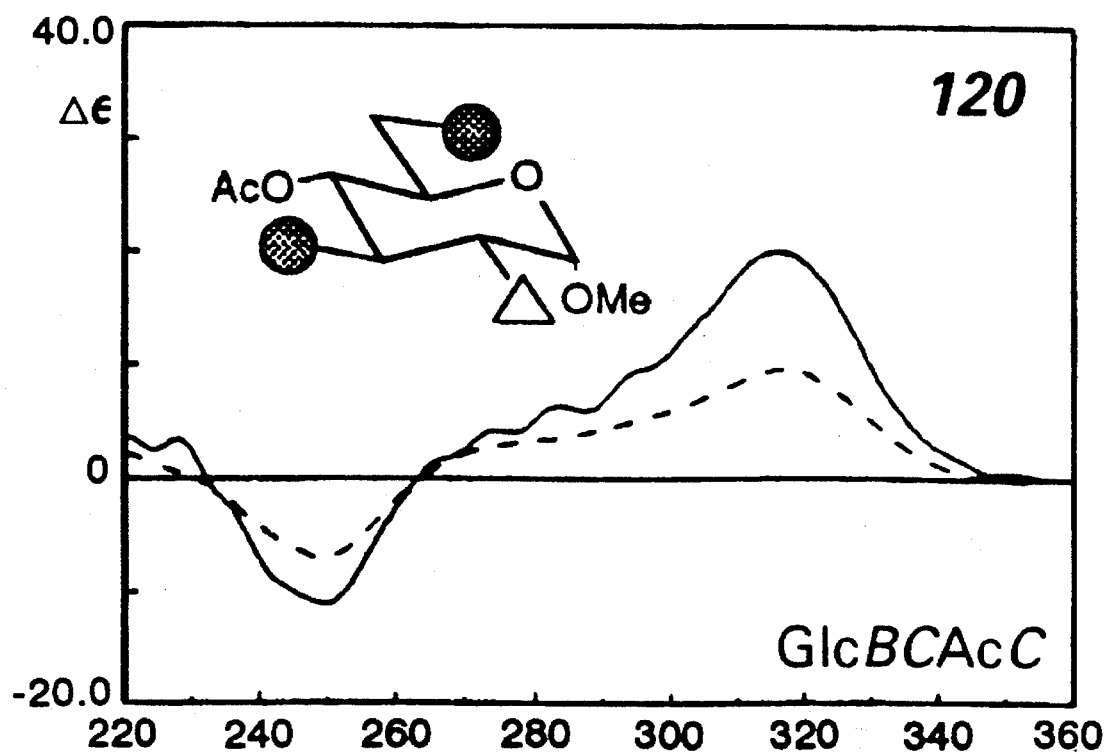
Figure 24A:
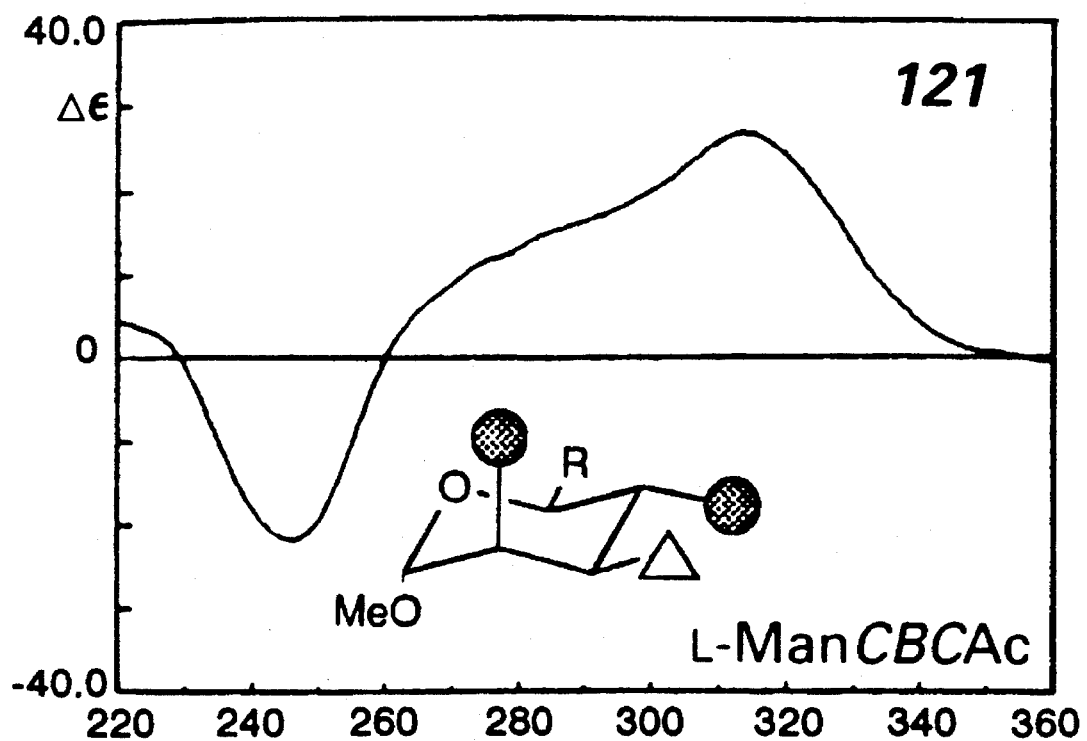
FIGS. 24a–f are a continuation of the $BC_2$ CD spectra of FIGS. 18a–f.
Figure 24B:
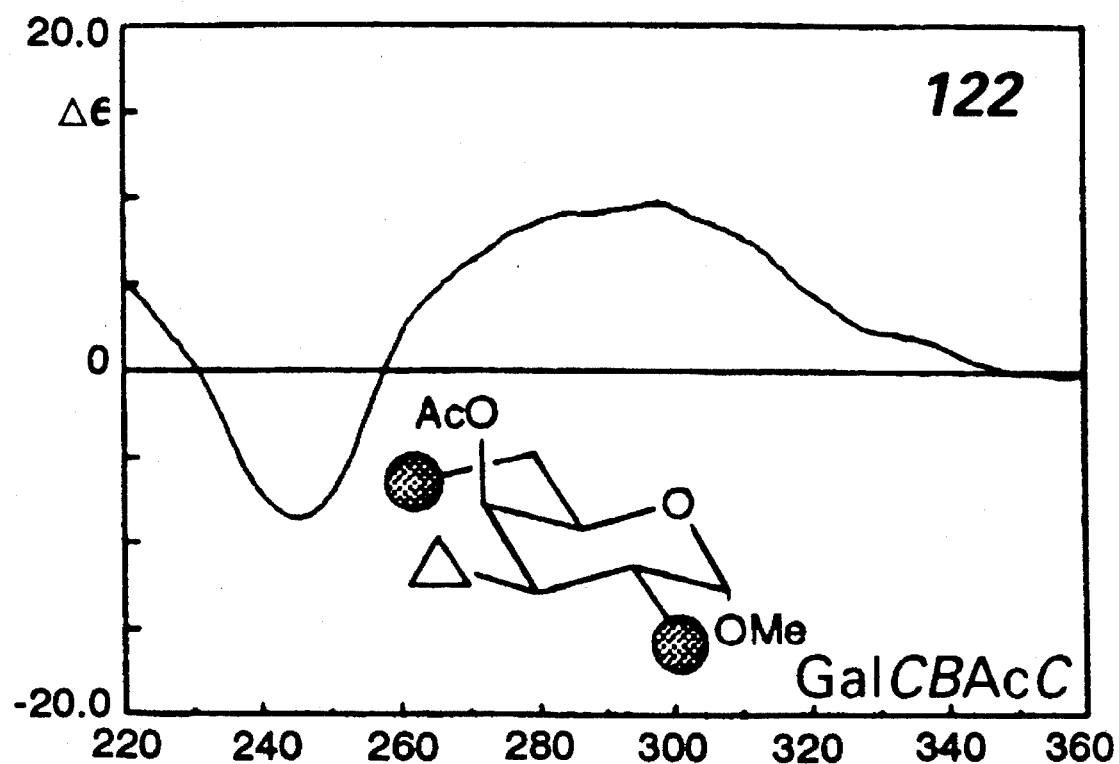
Figure 24C:
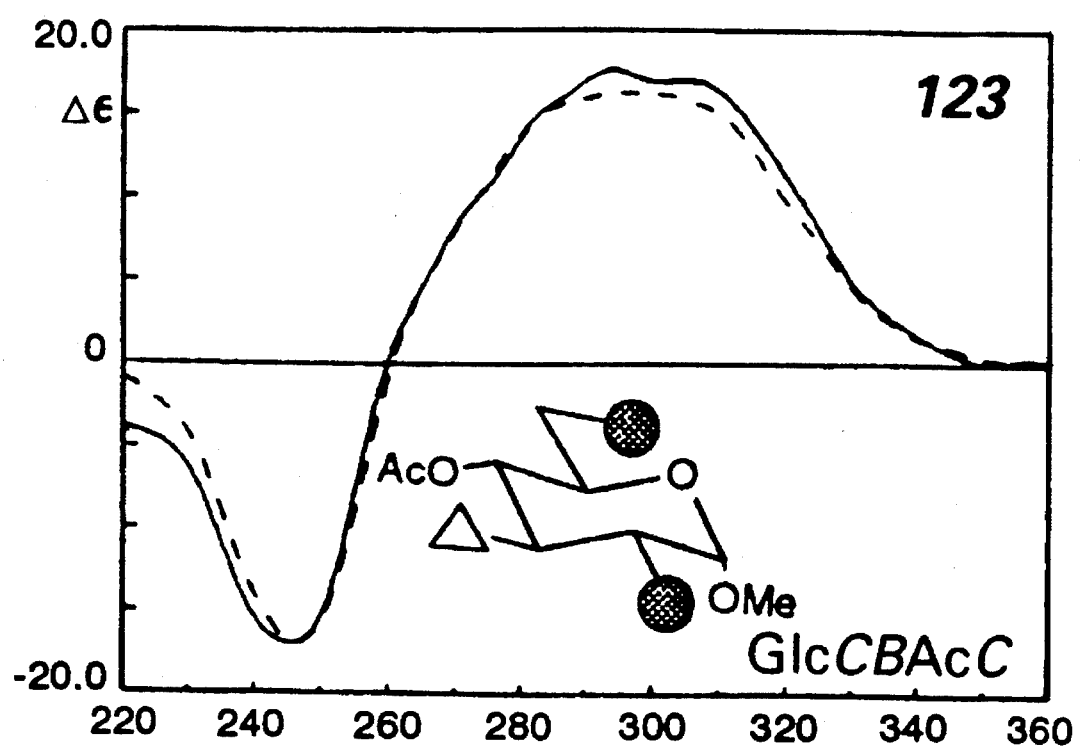
Figure 24D:
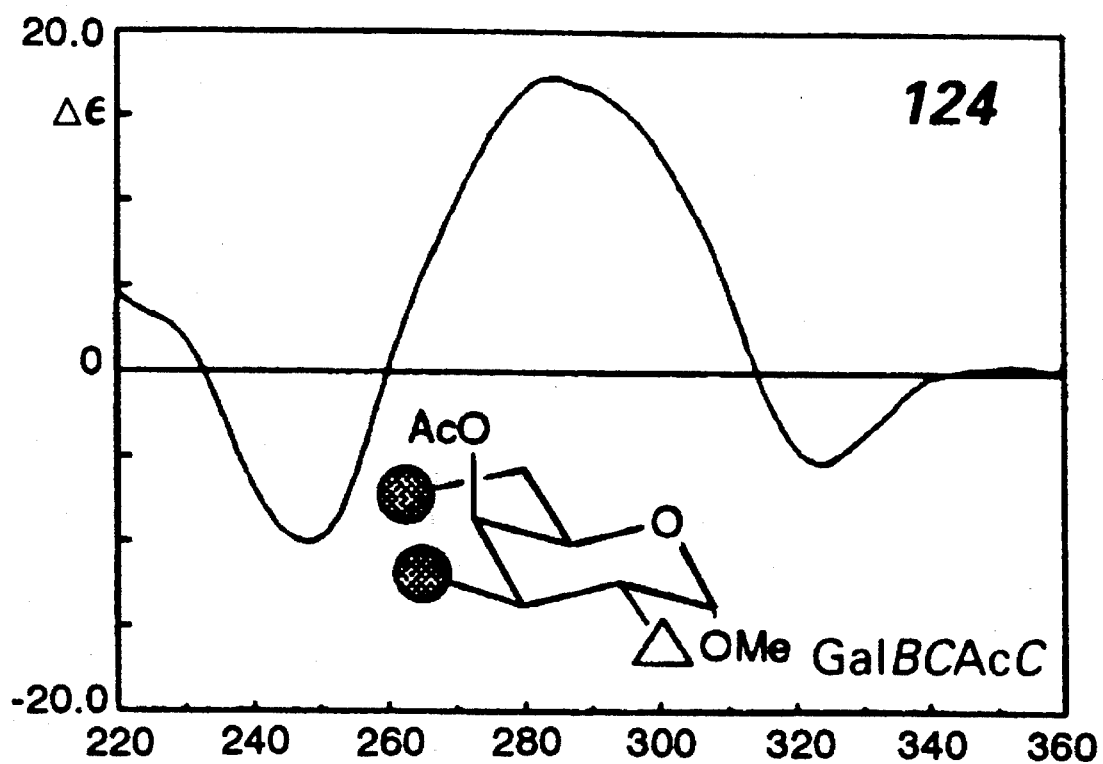
Figure 24E:
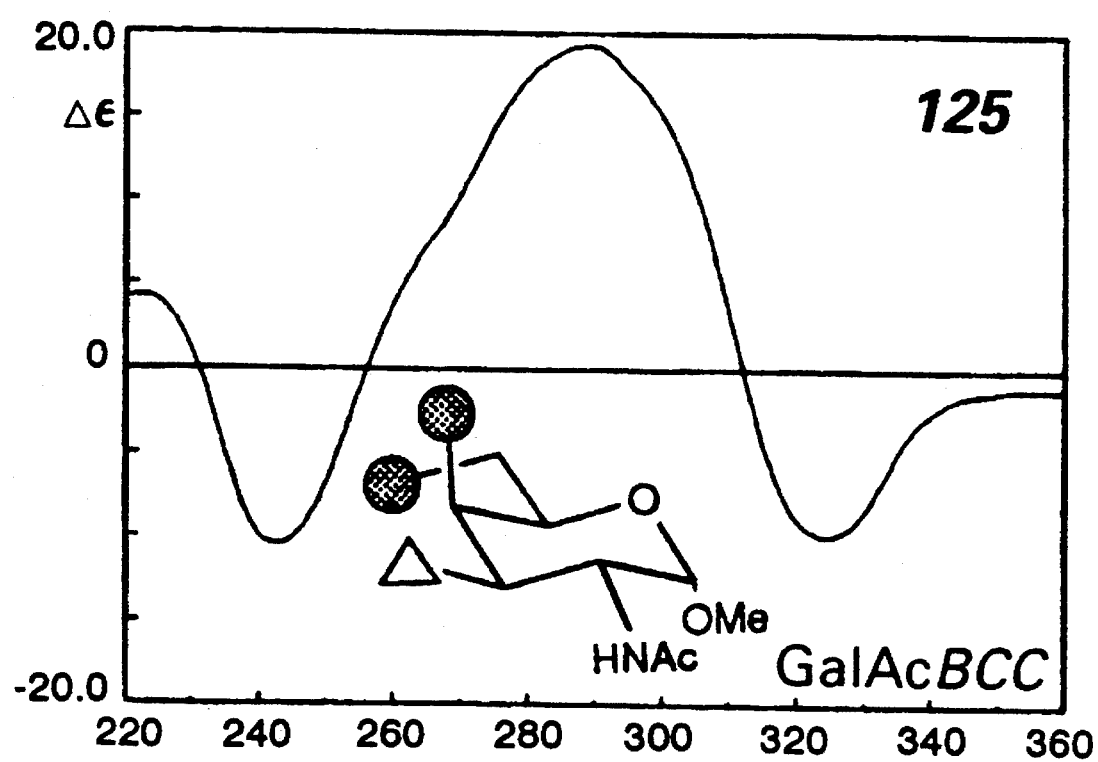
Figure 24F:
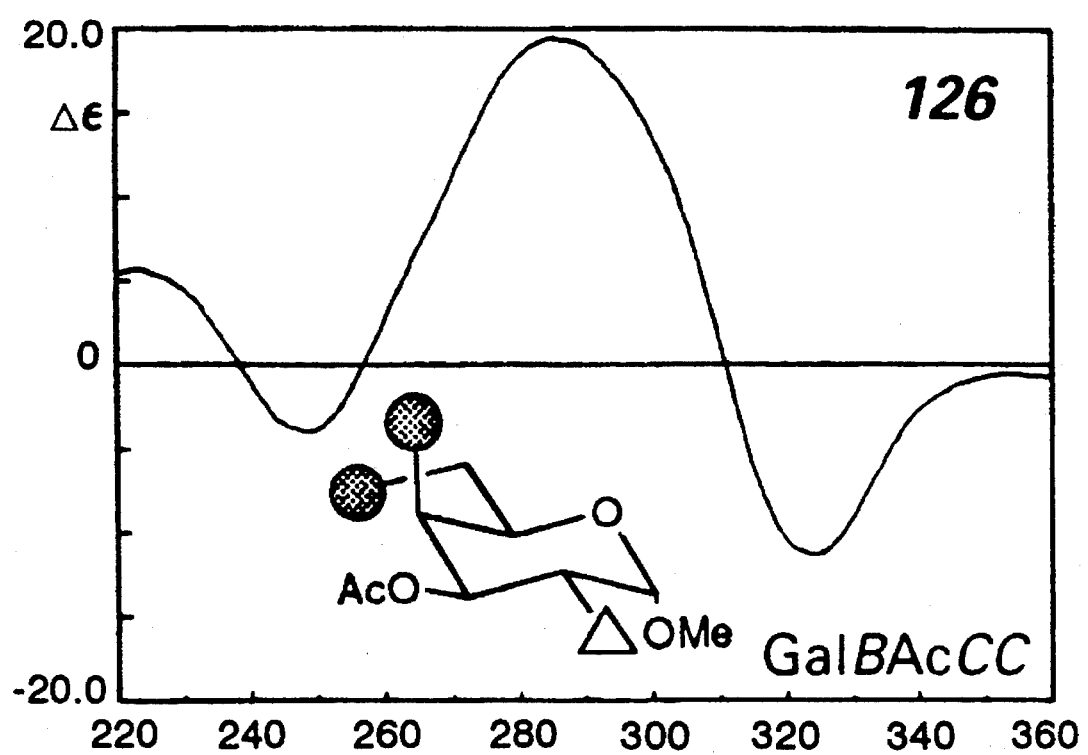

Calculated data are presented in Table 2 (tri- and tetrabenzoates) and in FIGS. 4a–f through 24-a–f together with observed spectra from authentic samples which have been prepared synthetically or obtained as derivatization products from commercially avilable di-, tri-, or tetrasaccharides. In FIGS. 4a–f through 24a–f, each calculated spectrum corresponds to the derivative given at the bottom right and is depicted by the solid line. The agreement between calculated and observed spectra (broken and dotted lines) is very good for all except a few examples. For example, discrepancies are observed in some glucose derivatives, where the calculated spectra are very weak. In such cases, the three equatorial chromophores at C-2, 3 and 4 adopt a nearly symmetrical orientation with respect to the pyranoside ring. Equal pairwise interactions of opposite signs result in a weak net spectrum, making deviations arising from conformational differences about the C5–C6 bond [8] and other effects more pronounced. See, for example G1cBCBB (FIG. 4f, Spectra 6) and GLcBCC (FIG. 6f, Spectra 18).

Naturally, experimental curves are the reference spectra of choice, and we are continuing to expand the experimental data base. Calculated spectra can also be used as reference spectra with a reasonable degree of confidence, but care should be taken to consider alternative structures which have closely related spectra. The configuration of the anomeric methyl group, α or β, give rise to the only small differences in CD curves [11]. While the current derivatization procedures yield β-methyl glycosides, most of the synthetic standards have been prepared from the α-methyl anomer. A number of derivatives having β-configuration, however, have been prepared and compared with the corresponding α derivatives. The small degree of variation observed between α and β in these cases can serve to indicate the amount of variation to be expected in other cases between derivatization products (β) and synthetic standards having α configuration.

6. Structure Identification using the CD Data Base.

Derivatization products can be classified according to the numbers of each chromophore present on the basis of UV analysis, as outlined above in Table 1. The CD data has been divided into these different classes to allow for easy comparison of the various isomers in each class. Tri- and Tetra-p-bromobenzoates. First, when UV analysis indicates the presence of bromobenzoate chromophores only, MS must be used to determined the number of these chromophores. Such compounds are derived from the terminal sugar units of oligosaccharides, and thus will always be obtained in derivatization product mixtures. As the CD curves of these derivatives generally vary only in sign and intensity, the data for these have been tabulated (see Table 2). The difference in ϵ values between extrema, or amplitude (a), is included in this table for comparison.

$B_3C$, $BC_3$, and $B_2C_2$ Tetrachromophoric Derivatives. The spectra for each of these classes have been grouped together in FIGS. 4a–f through 10a–f. The spectra have been arranged in such a way that similar spectra, i.e., those having Cotton effects with the same sign, are nearby to facilitate comparison. While these spectra correspond to linked and branched gluco-, galacto, and mannopyranosides, they are also applicable to N-benzoylated compounds which are obtained from GlcNAc and GalNac residues as described above (see Scheme 5).

$B_2C$ and $BC_2$ Trichromophoric Derivatives. These spectra are arranged in FIGS. 11a–f through 24a–f in a similar manner as those described above. Unlike the tetrachromophoric spectra, however, the trichromophoric spectra correspond to a wide variety of sugars depending on the functionality of the position lacking a chromophore, e.g. deoxy, N-acetyl, O-acetyl, and O-methyl. The spectra were calculated for the O-acetyl derivative indicated at the bottom right of each, but are applicable to cases where the non-chromophoric functionality is different, including deoxy sugars. Many of the structures shown in these figures correspond to commonly encountered sugar components (i.e., fucose, rhamnose, GlcNAc, and GalNAc), a number of which have been prepared synthetically or obtained from model studies. Calculations for derivatives lacking a chromophore at the 6-position correspond not only to 6-deoxyhexopyranosides but to pentopyranosides as well. Thus, for example, L-fucose (R—$CH_3$, FIGS. 13a–f) and D-arabinopyranose (R—H) derivatives are expected to have similar spectra, as are xylopyranose and quinovose (6-deoxyglucose) derivatives. While HPLC retention time can clearly differentiate 2-deoxy from 2-acetamide derivatives, differentiation between 6-deoxyhexopyranose and the corresponding pentopyranose derivatives having chromophores in the same orientation requires either MS ($CH_3$ vs. H) or an additional sugar analysis.

7. Analysis of CD Spectra 1–126. A majority of the tetrachromophoric components can be uniquely characterized by their CD spectra. For the more numerous trichromophoric derivatives, two or more possible structures correspond to a number of spectral types. In many cases, careful analysis of the absolute relative intensities of constituent Cotton effects makes it possible to differentiate between spectra having similar shapes.

$B_3C$ Isomers (Spectra 1–12, FIGS. 4a–f, 5a–f). These spectra correspond to the 12 possible components obtainable from hexopyranosides bearing a single linkage. In GalBBBC (1) and ManBBBC (7), the spatial arrangement of the 3 benzoate groups which make the dominant contributions to the CDs are approximately enantiomeric, accounting for the nearly opposite CDs of these two derivatives. GalBBBC (1)/GlcBBCB (2) and ManBBBC (7)/GlcCBBB (8), respectively, have similar CDs but can be differentiated on the basis of their intensities. For the discriminations among 3–5 and among 9–12, the absolute intensities as well as the relative intensities between the extrema must be considered.

$BC_3$ Isomers (Spectra 13–24, FIGS. 6a–f,7a–f). These spectra correspond to the 12 possible components obtainable from hexopyranosides bearing three linkages. Spectrum 13 can be differentiated from 14/15, and similarly 19 from 20/21 by the more intense couplet in 13 and 19. Discrimination between 14 and 15, and between 20 and 21 is less obvious and requires comparisons of relative intensities at extrema. Thus an intensity ratio of 0.7 or higher between $D\epsilon_{323nm}$ favors structure 14 over 15 (ratio ca. 0.4). In the case of 16 and 17, both calculated curves 16a and 17a are of similar intensities at their $k_{extra}$; GalCBCC (16) and GalBCC (1), however, can be distinguished from the different shapes of experimental curves 16b and 17b.

$B_2C_2$ Isomers (Spectra 25–42, FIGS. 8a–f–10a–f). These spectra correspond to the 18 possible components obtainable from hexopyranosides bearing two linkages (branching sugars). They can be divided into several subgroups on the basis of overall shape, i.e., 25/26/28, 29/30, 31–36 and 37–39; overall 40–42 have shapes which are different from the others. Spectra within each subgroup can be characterized by differing intensities of their Cotton effects, e/g., 31/32, 36/33–35, and 39/37, 38. Discrimination within each subgroup, i.e., 25/26, 27/28, 29/30, 33/34/35 and 37/38 requires determination of experimental D$\epsilon$ values within the range 220–360 nm and comparison of the relative intensities of the various Cotton effects.

A comparison between calculated CDs 29a and 30a reveals a clear difference below 240 nm and above 300 nm. and above 300 nm. It may, however, be difficult to distinguish between ManCBBC 29 and ManBBCC 30 because although the agreement between 29a (calcd) and b (obs) is fair, the CD of an authentic ManBBCC sample has not yet been recorded. In spectrum 36, the agreement between calculated and experimental curves is also poor; in such cases the experimental curve should be used for comparison.

B$_2$C Isomers (Spectra 43–84, FIGS. 11a–f through 17a–f). These spectra correspond to 42 possible components derived from N-acetylated, deoxyhexopyranose, or pentopyranose sugars having a single linkage. Depending on the shape of the entire CD curve and relative intensities of the constituent Cotton effects, these 42 spectra have been further divided into three groups to facilitate comparison for structure elucidation.

1. Spectra 43–54.—CD curves in this subgroup are characterized by strong positive CE around 250 nm and a broad weak negative CE in the region 270–340 nm; in spectra 43–45, 51 and 53, a second very weak CE is present at 230 nm. Spectra 43–45 can be readily differentiated from 46–53 on the basis of their intense 250 nm CE D$\epsilon$>45). While differentiation between 43, 44, and 45 cannot be certain because the shapes and intensities of CD of all three cases are similar, they derive from different sugars, the identities of which can be readily determined using conventional sugar analyses; the same is true for cases 46–48 when the experimentally measured D$\epsilon$s at 250 nm fall within the range 25–35. While the differentiation between BlcABCB (49) and ManABCB (50) is not feasible, these two can be distinguished from 51–53 on the following grounds. Regardless of the similar positive CE around 250 nm for all 5 cases 49–53, only 51 and 52 display broad negative bands above 260 nm with distinctive shape with k$_{extra}$ around 311 nm, whereas only 53 exhibits an extremely weak negative band (D$\epsilon$–2) above 260 nm.

2. Spectra 55–60.—These 6 spectra possess similar shapes with a positive first CE at the shortest wavelength (k1) and two additional negative CEs at longer wavelength (k2, k3). The pairs 55/56, 57/58 and 59/60 can be clearly distinguished from the differences in respective D$\epsilon$ values, and also from the intensity ratios of D$\epsilon$k1/D$\epsilon$k$_2$ and D$\epsilon$k$_2$/D$\epsilon$k$_3$. As each pair consists of, for example, an L-fucose (R=Me) and D-rhamnose (R=Me) derivative, further differentiation here would simply require knowledge of which of these two sugars was present.

3. Spectra 61–72.—The CD curves of 61, 62 and 72 exhibit characteristic features that allow them to be distinguished from the others, but precise measurements down to 220 nm is necessary. The similarity between 63 and 64 again results from the nearly identical spatial arrangement of chromophores in D-fucose (R=Me) and L-rhamnose (R=Me) derivatives, respectively. This also applies to 67/68 and 70/71. Making a positive identification in these cases will again simply require knowledge of which of the two possible sugars is expected. The different intensity ratios of CEs at ca. 250 nm and ca. 300 clearly distinguishes 67/68/70/71 from 69.

4. Spectra 73–84.—The 12 cases belonging to this subgroup are characterized by 3 distinct bands: positive CE at ca. 235 nm (k1), negative CE at ca. 250 nm (k2), and a broad positive band centered around 310 nm (k3). A detailed examination reveals that in 73–76 and 79 the intensity ratio D$\epsilon$k$_2$/D$\epsilon$k$_2$ is about 6 or higher, while in cases 77/78/80–84 this ratio is 1—3. Although the pairs 73–74 and 75–76 have similar D$\epsilon$k2 ratios and D$\epsilon$k2 values, the four cases can be differentiated because ManABBC (73) and GlcABBC (75) have stronger positive $\epsilon$ 1 values of 10–15. While it may not be possible to distinguish GalABCB (78) from GlcBCAB (81), the former would likely derive from a 4-linked GalNAC while the latter corresponds to a 3-linked glucose residue which is either deoxygenated or substituted at position 4; MS can readily clarify any ambiguities. Analogously, the very similar 83 and 84 correspond to widely different sugar types.

BC$_2$ Isomers (Spectra 85–226 FIGS. 18a–f through 24a–f)—These spectra correspond to 42 possible components derived from N-acetylated, deoxyhexopyranose, or pentopyranose sugars having two linkages (branched). The spectra can be divided into seven subgroups.

1. Spectra 85–90.—These 11 CD spectra possess a very strong negative couplet; the negative wing with k$_{extra}$ at ca. 320 nm (k2) is of higher intensity than the positive wing at ca. 285 nm (k1). It is possible to discriminate 85–87 from 88–90 on the basis of the intensities at k1 and k2. The distinction among 85–87 is uncertain except for the weak negative CE around 235 nm in 86, but they should be readily differentiated by MS. In 88–90, differences are seen in the short wavelength of calculated curves; however, lack of experimental curves for 88 and 90 leads to uncertainty. Again MS can clarify the differences.

2. Spectra 91–96.—GalACBC (91) and GalCABA (96) are distinctly different from 92–95, the latter group being chracterized by a series of weak negative, positive, and negative CEs in the range 220–360 nm. Although pair 92/93 can be distinguished from pair 94/95, further differentiation within each pair is not possible without additional structural information.

3. Spectra 97–102.—The 4 structures 97–100 corresponding to two L-fucose and two D-rhamnose derivatives are found to have very similar CD patterns; only 100 can be differentiated by its smaller D$\epsilon$ value at 315 nm and the intensity ratio of D$\epsilon_{246}$/D$_{314}$. While most cases of similar spectra involve different sugars, the similarity between 97 and 99, both derived from L-fucose, makes it impossible to distinguish between 3,4- and 2,4-branched L-fucose components by this method. Differentiation between 101 and 102 which are both derived from mannose also appears to be difficult.

4. Spectra 103–111.—In these 9 cases, 103–107 and 108–111 show, respectively, intense positive couplets with Cotton effects at ca. 287 nm (k1) and 323 nm (k2). Further identification, however, requires careful estimation of not only the D$\epsilon$ of the 2 wings, but also the intensity ratio of D$\epsilon$k1/D$\epsilon$k2. From such measurements, 104 can reliably be differentiated from 103 and 105–107, and similarly 111 from 109 and 110.

5. Spectra 112–116.—These 5 cases are clearly differentiated by the relative intensities of their three major Cotton effects. Notable differences are also seen in the 220–250 nm range.

6. Spectra 117–120.—Despite the very poor agreement between calculated and experimental curves in GlcBCAC (120), this sugar should be readily distinguishable from cases 117–119 where no further differentiation is possible. Similarity between 118 and 119, both derived from D-fucose, makes it impossible to distinguish between 3,4- and 2,4- branched D-fucose components by this method as discussed above for the enantiometric L-fucose components (97 and 99).

7. Spectra 121–126.—Structures 121–123 can be readily identified from the distinctive shapes of the CD curves and different D$\epsilon$ values around 245 nm and 300 nm. In the last 3 cases, 124–126, similarities in the shape of CD curves and the close values of the strongest positive CE around 285 nm make differentiation strongly dependent upon the accuracy of measured D$\epsilon$ values and relative intensity ratios of the three CE's.

Experimental Details

General. All solvents and reagents were prepared or purified as follows: $CH_2Cl_2$ and pyridine were distilled from $CaH_2$, and DMAP was recrystallized from hexane/benzene. CHCl3 was dried by passing through a pipet column of neutral $Al_2O_3$, and MeOH was distilled from $Mg(OMe)_2$. HPLC grade ETOAC and hexane were used without distillation. The reagent p-BrBzCL was prepurified by dilution with hexane/$CHCL_3$ (5:1), followed by filtration and concentration under reduced pressures. The reagent p-MeOCnCL was prepared from the acid and thionyl chloride (1.2 eq.) in refluxing benzene (2 h). Benzene and excess reagent were removed in vacuo, and distillation in a sublimation apparatus (140° C./0.1 mm Hg) afforded the pure acid chloride. All silver salts were dried in vacuo prior to use.

All cleavage reactions were performed in special glass tubes (1.1 or 3.3 ml capacity) fitted with Teflon screw caps to confine HBr during the reactions (FIG. 1a). The vessels were easily constructed from a glass flow control valve by sealing off the tubing with a flame.

In case where sufficient amount of cleavage products (bromosugars, methyl glycosides) were obtained (e.g., those derived from lactose perbenzoate), structures were determined by 1H-NMR (Brucker WM 250, 250 MHz, in $CDCl_3$) as either mixtures or purified components obtained from $SiO_2$ chromatography. Exact mass of peracylated oligosaccharides and cleavage products were recorded on a JEOL instrument by EI or FAB, the latter employing 3-nitrobenzyl alcohol as a matrix.

Optimization of cleavage conditions by varying reagent ratios, time and temperature for sugar peracylates was monitored by HPLC injections after the methyl glycosidation step and p-methoxycinnamoylation step, and in some cases after the deprotection step. Analytical thin layer chromatography (TLC) plates (Analtech, silica gel GHLF) were used to visualize product mixtures of each step in the derivation scheme. Prior to measurements of UV/CD/MS, all compounds were purified by HPLC with a HYPERSIL-3 $\mu$m (4.6×150 mm) analytical column, monitoring peaks by UV detection at k254 nm. An isocratic or gradient elution with EtOAc/hexane mixtures was employed (see FIGS. 1 and 2 for specific conditions).

For UV and CD measurements, all samples were prepared as acetonitrile solutions at concentrations between 0.5–1.5× $10^{-5}$M Concentrations for bichromophoric derivatives were determined on the basis of the experimentally determined average p-methoxycinnamate UV $\epsilon$ values 24,000: di: $\epsilon$ 45,000. In the case of terminal sugars, the average tribenzoate $\epsilon$ of 57,000 and tetrabenzoate $\epsilon$ 76,000 was used.

UV measurements were performed on a Perkin Elmer 320 UV Spectrophotometer. CD spectra were recorded on JASCO 500A Spectropolarimeter driven by JASCO DP500N Data Processor (four scans were taken of each compound from 200–400 nm). After normalization of the CD spectra to $10\times10^{-5}$M, the curves were smoothed. The smoothing was performed using either a DFT (Discrete Fourier Transfer) or a FIR (Finite duration Impulse Response Filter) procedure.

1. Perbenzoylation of hexopyranose, deoxysugars and aminosugars (General Procedure).—Underivatized saccharides were first dried in vacuo at room temperature overnight. To a solution of the sugar in dry pyridine (1 ml for each 10 mg of saccharide) was placed a catalytic amount (~0.1 eq) of N,N-dimethylaminopyridine (DMAP) and dry AgoTf (3 eq/OH), followed by p-bromobenzoyl chloride (3 eq/OH). After stirring at rt 12 h in the dark under Ar, water (one drop/10 mg of starting sugar) was added and the reaction mixture stirred 1 h. The reaction mixture was then diluted with benzene, and insoluble materials were removed by filtration and washed with benzene. The filtrate and washing were concentrated to dryness, suspended in hexane/EtOAC (2:1), and passed over a Pasteur pipet filled with a slurry of neutral $Al_2O_3$ (activity II, 1 g/10 mg of starting sugar) in hexane/ETOAc (2:1). The $Al_2O_3$ column was washed with EtOAC (5 ml/1 g of $Al_2O_3$), and the eluent was concentrated to afford a crude product which was purified by preparative $SiO_2$ thin layer chromatography (PTLC) using 2:1 Hexane/EtOAc as eluent. The purified product was dissolved in benzene, frozen with a dry ice/acetone bath, then kept in vacuo for 1 h to afford a white powder suitable for cleavage reactions. Rf values were estimated by TLC (UV monitor).

α-Lactose octa-(p-bromobenzoate): Perbenzoylation of the sugar with pBrBzCl/AgoTf (13 equiv) afforded a single zone (Rf ~0.4, $C_6H_6$/EtOAC 3:2), isolated by preparative TLC. $^1$H-NMR (250 MHz, $CDCl_3$): 7.84–7.26 (m, 32H), 6.08 (d, 8.0 Hz, 1H, H-1), 5.86 (dd, 8.8, 9.5 Hz, 1H, H-3), 5.69 (dd, 3.2, 5.2 Hz, 1H, H-4'), 5.67–5.60 (m, 2H H-2 and H-2'), 5.37 (dd, 3.2, 10.4 Hz, 1H, H-3'), 4.87 (d, 7.8 Hz, 1H, H-1'), 4.52–4.49 (m, 2H), 4.23 (dd, 9.5, 9.1 Hz, 1H, H-4), 4.07–4.04 (m, 1H, H-5), 3.93 (m, 2H), 3.80–3.72 (dd, 1H).

Digitonin heptadeca-(p-bromobenzoate): A commercial sample of digitonin (Aldrich) containing several components by TLC was first purified as follows: (i) $Ac_2O$, pyr, rt, 5 h; (ii) $SiO_2$ chromatography; (iii) $K_2CO_3$, MeOH, rt, 4.5 h. Perbenzoylation as the purified digitonin (9.8 mg, 8.0 $\mu$mol) without AgOTf afforded a single zone (Rf ~0.5, 25 mg, 62%), isolated by PTLC with 2:1 hexane/EtOAc as eluent. $^1$H-NMR (250 NMz, $CDCl_3$): 7.96–7.25 (m, 66H), 6.90–6.85 (m, 2H), 5.82–5.20 (m, 12H) , 4.96–4.82 (2H) , 4.75–3.88 (20H), 3.85–3.28 (10H), 3.10–2.95 (m, 1H) 2.20–0.60 (30H). Sarasinoside C, undeca-(p-bromobenzoate).—Perbenzoylation of the sugar (4.1 mg, 3.6 $\mu$mol, from I. Kitagawa) with pBrBzCl/AgoTf (4.3 eq/OH) afforded a single zone (Rf ~0.7, 8.9 mg, 90%), isolated by PTLC. $^1$H-NMR (250 MHz, $CDCl_3$): 7.95–7.30 (42H), 7.10–6.93 (2H), 6.12–5.08 (12H), 4.81–4.68 (1H), 4.46–3.53 (15H), 3.32–2.88 (3H) 2.59–2.42 (m, 1H), 2.40–0.58 (45H). FAB MS (3-mitrobenzyl alcohol): m/e 3135 (M+K+, 1.1).

2. Trifluoroacetobrominolysis and subsequent derivatization procedures (Scheme 2).—To a solution of perbenzoate (~1 mg) in $CF_3CO)_2O$ (130 $\mu$l, 0.92 mmol) and oxalyl bromide (79 $\mu$l, 0.85 nmol) in a glass tube fitted with stir bar and septum under Ar was added, at −78° C., 48% HBR (41 $\mu$l, 0.36 mmol HBr and 1.76 mmol $H_2O$) via syringe (a Teflon tube connected to the syringe needle was used such that no contact of the aq HBr is made with the needle). The glass tube was immediately sealed (hand tight) with the Teflon screw cap and heated with an oil bath to 100° C. for 30–45 min. Afterwards, the hot glass vessel was immersed in a dry ice acetone bath until a frozen mass was observed, then the screw cap was removed carefully (HBr gas is released when the seal is broken). The screw cap was replaced with a rubber septum, and the reaction mixture was placed under an aspirator vacuum fitted with a $CaCl_2$ drying tube (5 min) to remove trifluoracetic acid and other gases (box in Scheme 2). The residue was freeze-dried with benzene to give a pale yellow powder which was converted to methyl glycosides. Methyl glycosidation of bromosugar cleavage products. In the same glass tube, the powder was dissolved in $MeOH/CHCl_3$ (2:3, 0.5 ml) and stirred with $Ag_2O$ (10 mg) at rt 1 hr in the dark. When completed, the reaction was concentrated to dryness, suspended in hexane/ETOAc (1:1), and passed through a Pasteur pipet column (0.5 g $SiO_2$). The eluate was concentrated and lyophilized with benzene (0.2 ml) to give a powder. An aliquot was dissolved in hexane/EtOAc (3:1) and purified by HPLC with subsequent UV/CD analysis.

The above procedure was carried out on lactose octa-p-bromobenzoate in sufficient quantity to allow for $^1$H-NMR characterization of the products (GlcBBOB and GalBBBB). These were found to be identical to authentic samples prepared synthetically.

Methyl β-D-glucopyranoside 2,3,6-tri-p-bromobenzoate (GlcBBOB). $^1$H-NMR (250 MHz, CDCl3): 8.00–7.48 (m, 12H), 5.43 (dd, 1H, H-3), 5.34 (dd, 1H, H-2), 4.82 (dd, 1H, H-6), 4.63 (d, 1H, H-1), 4.62 (dd, 1H, H-6'), 3.82 (ddt, 1H, H-5), 3.80 (m, 1H, H-4), 3.53 (s, 3H, OMe), 3.33 (bd, 1H, 4-OH).

Methyl β-D-glucopyranoside 2,3,6-tri-p-bromobenzoate (GlcBBOB). $^1$H NMR (250 MHz, $CDCL_3$): 8.00–7.48 (m, 12H), 5.43 (dd, 1H, H-3), 5.34 (dd, 1H, H-2), 4.82 (dd, 1H, H-6), 4.63 (d, 1H, H-1), 4.62 (dd, 1H, H-6'), 3.82 (ddt, 1H, H-5), 3.80 (m, 1H, H-4), 3.53 (s, 3H, OMe), 3.33 (bd, 1H, 4-OH).

Methyl β-D-galactopyranoside 2,3,4,6-tetra-p-bromobenzoate (GalBBBB). $^1$H NMR (250 MHz, $CDCL_3$): 7.92–7.77 (m, 6H), 7.63–7.49 (m, 8H), 7.40–4.39 (m 2H), 5.91 (d, 1 H, H-4), 5.69 (dd, 10.5, 7.9 Hz, 1H, H-2), 5.53 (dd, 10.5, 3.4 Hz, 1H, H-3), 4.71 (d, 7.9 Hz, 1H, H-1), 4.66 (m, 1H), 4.41–4.26 (m, 2H), 3.57 (s, 3H, OMe).

Methoxycinnamoylation.—To a solution of the powder, AgOTf (10 mg) and DMAP (2 mg) in pyridine/$CH_2Cl_2$ (0.1/0.9 ml) was placed p-methoxycinnamoyl chloride (10 mg) under Ar with stirring at rt for 4 h in the dark. After adding a drop of $H_2O$ and pyridine (0.5 ml), the mixture was stirred an additional 1 h, then concentrated to dryness, suspended in hexane/EtOAC (2:1), and passed through a pipet column of activity II neutral $Al_2O_3$ (1 g). The column was washed with the same solvent, and the eluate concentrated to give an oil which was purified by HPLC and analyzed by UV/CD.

3. General Bromoacetobrominolysis and subsequent derivatization procedures (Scheme 3, steps a/b2/c2/d). To the sugar perbenzoate (200 μg–400 mg) in a glass tube (1.1 ml capacity) fitted with a stir bar and septum under Ar was placed $BrCH_2COBr$ (83 μl) via syringe, the solution cooled to 0° C., then $H_2O$ (17 μl) was added via syringe (a Teflon tube was used on the needle tip for delivery of the aq HBr). A Teflon spindle valve was used to seal the tube, and the reactions proceeded at the times and temperatures described below. Reactions were then cooled to –78° C., and the seal was broken carefully (HBr gas released); the tube was immediately fitted with a septum and placed under an aspirator vacuum (5 min), followed by placement under high vacuum (30 min).

To the solid residue containing $BrCH_2CO_2H$ was added dry MeOH (0.2 ml) under Ar at 0° C., then AgOAC (5 mg) or AGOTf/TMU (8 mg/5 ul) was added with stirring 1 h in the dark. Silver salts were removed by filtration, the filtrate concentrated, and the residue which was suspended in hexane/EtOAc (2:1) was passed through a Pasteur pipet filled with a slurry of activity II neutral $Al_2O_3$ in hexane/EtOAC (2:1). The $Al_2O_3$ column was washed concentrated to give a residue which was lyophilized with benzene (0.2 ml). An aliquot can be removed for HPLC analysis.

Deprotection/cinnamoylation reactions: To a solution of the product mixture in MeOH (0.3 ml) was added thiourea (3 mg), and the mixture was stirred at rt for 2 h. $AgNO_3$ (10 mg) in $CH_3CN$ (0.5 ml) was then added with stirring for an additional 5 min to precipitate the thiourea. The mixture was diluted with $CH_2Cl_2$ (3 ml) and passed over a Pasteur pipet filled with $SiO_2$ (0.5 g). The $SiO_2$ column was washed with $CH_2Cl_2$/MeOH (9:1, 10 ml), and the eluate and washings were concentrated to dryness, then lyophilized with benzene (0.2 ml) to give an amorphous powder. An aliquot can be removed for HPLC analysis. To a solution of the product in pyridine (0.2 ml) was added AgOTf (5 mg), p-methoxycinnamoyl chloride (5 mg) and DMAP (cat) under Ar. The reaction proceeded at rt 12 h in the dark, then one drop of $H_2O$ was added, and the mixture was stirred an additional 1 h. The reaction mixture was concentrated to dryness, suspended in hexane/ETOAc (2:1), then passed through a Pasteur pipet filled with 1 g of a neutral $Al_2O_3$ slurry (activity II) in hexane/EtOAC (2:1). The $Al_2O_3$ column was washed with EtOAC (5 ml), and the eluate and washings were concentrated to afford a residue which was HPLC-purified. Purified products were isolated and analyzed by UV, CD and MS.

(a) Digitonin heptadeca-p-bromobenzoate (Scheme 4).

As described in the text, the earlier version of Scheme 3, steps a/b1/c1/d, was applied to digitonin [14]; the general scheme, steps a/b2/c2/d yield equally satisfactory results. Procedures for steps a/b1/c1/d are described in the following: Glycosidic cleavage reaction.—Under Ar atmosphere, bromoacetyl bromide (250 μl, 2.87 mmol) and water (50 μl, 2.78 mmol) were added to digitonin heptadeca-(p-bromobenzoate), 2.1 mg (0.42 mmol) in a glass tube (3.3 ml capacity) fitted with a septum at –78° C. After sealing the vessel with the Teflon cap, the mixture was stirred at 60° C. for 12 hr in an oil bath. The reaction mixture was again cooled to –78° C. and the Teflon valve was carefully opened. HBr gas was removed in vacuo under aspirator pressure (5 min) and then under hi-vacuum (30 min). The resulting solid was dissolved in 10 ml of cold hexane/EtOAc (3:1) and washed with cold saturated $NaHCO_3$ (2×5 ml), followed by cold $H_2O$ (2 ml). The organic layer was dried over $MgSO_4$, filtered, and concentrated to dryness. The residue was freeze-dried with benzene (0.3 ml) in vacuo for 1 hr to give a white amorphous powder.

One third of the powder (corresponding to 140 nmol of digitonin perbenzoate) was dissolved in $MeOH/CHCl_3$ (1:2, 0.6 ml) under Ar, $Ag_2CO_3$ (12 mg) and AgOTf (6 mg) were added, and the mixture stirred at room temperature for 1 hr in the dark. The reaction mixture was concentrated to dryness, suspended in 1 ml of hexane/EtOAc (3:1), and passed over a Pasteur pipet filled with a slurry of $SiO_2$ (0.4 g) in hexane/EtOAC (3:1). The $SiO_2$ column was washed with 5 ml of hexane/EtOAc (3:1), and the eluate concentrated to give an oily material.

Deprotection/cinnamoylation reactions.—To a solution of the methyl glycoside mixture in $CHCl_3$/MeOH (2:1, 0.6 ml)

was added NaHCO$_3$ (2 mg) and thiourea (2 mg), and the reaction stirred at 25° C. for 2 hr. After concentration to dryness, the residue was suspended in hexane/ETOAC (2:3) and passed over a Pasteur pipet filled with a slurry of SiO$_2$ (0.4 g) in hexane/ETOAC (3:1). The SiO$_2$ column was washed with 10 ml of hexane/ETOAC (2:3), and the eluent and washings were concentrated. The resulting residue was lyophilized with benzene (0.3 ml) as previously described to afford a white powder. To a solution of the product mixture in 0.5 ml of dry pyridine/CH$_2$Cl$_2$ (1:4) was placed AgOTf, DMAP, and p-methoxycinnamoyl chloride (9 mg) under Ar. The reaction stirred at room temperature for 5 hr in the dark. A drop of H$_2$O and pyridine (0.5 ml) were added, and the mixture stirred an additional 1 h. After concentration to dryness, the residue was suspended in hexane/ETOAC (3:1) and passed over a Pasteur pipet filled with a slurry of Al$_2$O$_3$ (activity II, 1 g) in hexane/ETOAc (3:1). The Al$_2$O$_3$ column was washed with 10 ml of hexane/ETOAC (3:1), and the eluate and washings were concentrated to afford a colorless oil which was analyzed by HPLC, UV and CD.

904 (M+H$^+$, 46), 872 (M$^+$–OMe, 7); GalNAcBBB: 824 (M+K$^+$, 7), 808 (M+Na$^+$, 17), 786 (M+H$^+$, 47), 754 (M$^+$–OMe, 28); GlcNAcBBC: 762 (M+H$^+$, 62).

TABLE 1

Classification of Derivatization Products by UV Absorbance Ratios.

| Class | $A_{245\,nm}/A_{310\,nm}$ | CD Data | Linkage Type |
|---|---|---|---|
| B$_n$ | ∞ | Table 2 | terminal |
| B$_3$C | ~2.8 | FIGS. 4–5 (Spectra 1–12) | single linkage |
| B$_2$C | ~1.5 | FIGS. 11–17 (Spectra 43–84) | " |
| B$_2$C$_2$ | 0.8–1.0 | FIGS. 8–10 (Spectra 25–42) | branching |
| BC$_2$ | 0.42–0.57 | FIGS. 18–24 (Spectra 85–126) | " |
| BC$_3$ | 0.30–0.43 | FIGS. 6–7 (Spectra 13–24) | 3-way branching |

TABLE 2

Calculated and observed CD data for methyl pyranoside Tetra- and Tri-p-bromobenzoates

| Entry | Compound | Calc.[a] | | A$_{calc.}$[b] | Obs.[c] | | A$_{obs.}$[b] |
|---|---|---|---|---|---|---|---|
| 1 | α-D-GlcBBBB | 225 (+10) | 250 (+31) | — | 221 (+2) | 249 (+20) | — |
| 2 | β-D-GlcBBBB | " | " | — | 233 (–7) | 251 (+25) | +32 |
| 3 | α-D-GalBBBB | 234 (–18) | 252 (+95) | +113 | 237 (–29) | 253 (+70) | +99[d] |
| 4 | α-D-GalNBBBB | " | " | " | 237 (–27) | 252 (+71) | +98[e] |
| 5 | β-D-GalBBBB | " | " | " | 237 (–26) | 252 (+74) | +100[d] |
| 6 | α-D-ManBBBB | 234 (+26) | 252 (–82) | –108 | 237 (+23) | 252 (–66) | –89[e] |
| 7 | α-D-GlcBBBA | 226 (+4) | 243 (+4) | — | | | |
| 8 | β-D-XylBBB | " | " | — | 235 (–3) | 251 (+7) | +10 |
| 9 | β-D-VIOBBB | " | " | — | 237 (–6) | 253 (+11) | +17 |
| 10 | α-D-GalBBBA | 233 (–30) | 252 (+119) | +149 | 236 (–42) | 253 (+95) | +137[d] |
| 11 | β-L-AraBBB | " | " | " | 236 (–32) | 253 (+101) | +133[d] |
| 12 | α-L-GalBBBA | 233 (+30) | 252 (–119) | –149 | | | |
| 13 | α-L-FucBBB | " | " | " | 236 (+30) | 252 (–100) | –130[e] |
| 14 | β-L-FucBBB | " | " | " | 233 (+29) | 251 (–99) | –128 |
| 15 | α-L-ManBBBA | 234 (–28) | 252 (+103) | +131 | | | |
| 16 | α-L-RhaBBB | " | " | " | 237 (–30) | 252 (+101) | +131[e] |
| 17 | α-D-GlcBBAB | 234 (–14) | 252 (+54) | +68 | 236 (–22) | 253 (+47) | +69[d] |
| 18 | α-D-GalBBAB | 234 (–15) | 253 (+40) | +55 | 234 (–14) | 253 (+31) | +45[d] |
| 19 | β-D-GalBBAB | " | " | " | 236 (–16) | 253 (+30) | +46[d] |
| 20 | α-D-ManBBAB | 229 (+8) | 252 (–31) | –39 | | | |
| 21 | α-D-GlcBABB | 247 (+14) | | — | 236 (–1) | 253 (+8) | +9[d] |
| 22 | α-D-GalBABB | 233 (+7) | 249 (+13) | — | | 253 (+6) | — |
| 23 | α-D-ManBABB | 221 (+2) | 250 (–11) | — | | | |
| 24 | α-D-GlcABBB | 239 (+16) | 252 (–12) | –28 | 236 (+11) | 253 (–22) | –33[d] |
| 25 | β-D-GlcOBBB | " | " | " | 236 (+11) | 253 (–19) | –30 |
| 26 | β-D-GlcABBB | " | " | " | 236 (+8) | 254 (–18) | –26 |
| 27 | α-D-GalABBB | 229 (+4) | 253 (+16) | — | | | |
| 28 | β-D-GalNAcBBB | " | " | — | | 253 (+2) | — |
| 29 | α-D-ManABBB | 237 (+19) | 253 (–20) | –39 | | | |

[a] Calculated CD by summation of corresponding pairwise interactions from the homo basis set [wavelength in nm (Δl)].
[b] "Amplitude" or difference in Δl values of the two extrema of excition-split CD curves (see ref. [19]).
[c] Experimentally measured CD in acetonitrile solution of c = 1 × 10$^{-5}$ M.
[d] ref. [17]
[e] ref. [18]

The above procedures have been carried out on 70 nmol digitonin perbenzoate with the same results [14].

(b) Sarasinoside undeca-p-bromobenzoate (Scheme 5).

To the sugar perbenzoate (260 μg, 84 nmol) was added BrCH$_2$COBr (83 μl) and H$_2$O (17 μl), and the reaction stirred at 50° C. for 12 h, then the mixture with AgOTf (6.7 mg)/TMU (5 μl) in MeOH (200 μl) for 1 h at rt. Subsequent conversion to bichromophoric derivatives was performed as described above. FAB MS (3-nitrobenzyl alcohol): GalN-BBBB: 926 (M+H$^+$, 100), 894 (M$^+$–OMe, 23); GlcNBBBC:

DATA RELATING TO THE FIGURES

FIG. 4. B$_3$C CD Spectra.

4A. 1. a. [calc]: 233(–22), 252(+128). b. [α-synth]: 234(–32.3), 252(+102.0), 285(–7.4).

4B. 2. b. [calc]: 233(–5), 252(+65). b. [α-synth]:230(–10.5), 252(+56.8), 311(–10.4).

4C. 3. a. [calc]: 239(+29), 255(–14), 310(–23).

4D. 4. a. [calc]: 234(+5), 253(–28), 285sh(–10), 314(–11).

4E. 5. a. [calc]: 240(+2), 285sh(–15), 310(–18).

4F. 6. a. [calc]: 228(−11), 247(+9), 305(+4). b. [α-synth]: 232(−0.8), 251(+13.5), 296(+0.7).

FIG. 5 B₃C CD Spectra (continued).

5A. 7. a. [calc]: 233(+22), 252(−113), 291(+11). b. [α-synth]: 234(+24.7), 252(−100.0), 287(+8.9), 309(+9.4).

5B. 8. a. [calc]: 226(+9), 252(−23), 270sh(+6), 284sh(+9), 307(+10). b. [α-synth]: 228(+6.3), 253(−24.5), 286sh(+7.5), 310(+8.7). c. [β-exp derivatization product]: 228(+2.3), 253(+29.5), 285sh(+11.4), 307(+14.2).

5C. 9. a. [calc]: 237(−24), 254(+31), 305(+23). b. [α-synth]: 238(−25.2), 254(+24.7), 284sh(+8.3), 295sh(+12), 311(+13.2). c. [β-exp derivatization product]: 237(−19.1), 254(+20.1), 311(+10.9).

5D. 10. a. [calc]: 230(+6), 284(+17), 296(+18), 309(+18). b. [α-synth]: 241(−7.3), 287sh(+14), 306(+15.4). c. [β-exp derivatization product]: 246(−5.7), 297(+13.3), 309(+13.6).

5E. 11. a. [calc]: 241(−7), 258sh(+10), 282sh(+15), 296sh(+16), 310(+16). b. [α-synth]: 241(−18.2), 259sh(+8.1), 285sh(+16), 297sh(+18), 309(+19).

5F. 12. a. [calc]: 225(+3), 250(−4), 270sh(+4), 292sh(+7), 304(+8). b. [α-synth]: 233(+2.1), 253(−11), 296(+5.8). c. β-GlcN(B)BBC [exp derivation product]: 236(+1.8), 253(−5.7), 305(+2.4).

FIG. 6. BC₃ CD Spectra.

6A. 13. a. [calc]: 286(−74), 322(+132). b. [α-synth]: 285(−85.6), 321(+125).

6B. 14. a. [calc]: 287(−43), 323(+62). b. [α-synth]: 248(+11.3), 289(−31.1), 323(+31.4).

6C. 15. a. [calc]: 288(−23), 322(+52). b. [α-synth]: 287(−15.5), 323(+46.7).

6D. 16. a. [calc]: 244(−21), 284sh(+17), 316(+32). b. [α-synth]: 245(+25.1), 284sh(+14.7), 317(+24.9).

6E. 17. a. [calc]: 249(−16), 285sh(+19), 313(+27). b. [α-synth]: 247(−17.7), 283(+16.9), 323(+19.7).

6F. 18. a. [calc]: 241(−10), 318(+20). b. [α-synth]: 248(−5.5), 285(−2.7), 320(+9.9).

FIG. 7 BC₃ CD Spectra (continued).

7A. 19. a. [calc]: 286(+63), 322(−101).

7B. 20. a. [calc]: 238(−15), 288(+21), 322(−51).

7C. 21. a. [calc]: 251(−8), 284sh(+28), 292(+30), 327(−28). b. [α-synth]: 249(−5.7), 290(+15.2), 327(−9.2).

7D. 22. a. [calc]: 247(+19), 319(−38). b. [α-synth]: 247(+17.2), 273(−2.1), 323(−36.7).

7E. 23. a. [calc]: 237(+2), 254(−3), 287(+8), 329(−7). b. [α-synth]: 250(−2), 290(+6.6), 331(−5.3).

7F. 24. a. [calc]: 246(+13), 288(−22).

FIG. 8. B₂C₂ CD Spectra.

8A. 25. a. [calc]: 251(−11), 286(+47), 323(−54). b. [α-synth]: 249(−12.1), 290(+46.4), 325(−49.3).

8B. 26. a. [calc]: 248(−15), 287(+37), 322(−71). b. [α-synth]: 287(+30.3), 323(−54.5).

8C. 27. a. [calc]: 249(+35), 319(−49). b. [α-synth]: 249(+37.3), 321(−45.7).

8D. 28. a. [calc]: 247(+31), 314(−26).

8E. 29. a. [calc]: 236(+22), 253(−44), 313(−16). b. [α-synth]: 236(+19.6), 253(−60.6), 313(−4.4).

8F. 30. a. [calc]: 252(−42), 284(−19), 323(+5).

FIG. 9 B₂C₂ CD Spectra (continued).

9A. 31. a. [calc]: 250(−23), 287(−43), 323(+54). b. [α-synth]: 251(+25.9], 289(−44.6), 325(+52.1). c. β-GlcCCBB (exp): 251(+24.5), 287(−45.4), 323(+57).

9B. 32. a. [calc]: 234(−11), 252(+54), 286(−18), 323(+15). b. [α-synth]: 233(−13.3), 252(+48.4), 286(−20.5), 299sh(−16.6), 325(+10.4).

9C. 33. a. [calc]: 235(+12), 255(−14), 287(−28), 321(+69). b. [α-synth]: 251(−21.2), 288(−23.7), 322(+67.9).

9D. 34. a. [calc]: 250(−16), 320(+54). b. [α-synth]: 248(−16.2), 284(−2.7), 321(+39.7).

9E. 35. a. [calc]: 247(−31), 319(+53). b. [α-synth: 248(−30), 321(+43.2).

9F. 36. a. [calc]: 229(+5), 250(−12), 295sh(+4), 317(+16). b. [α-synth: 233(+2.4), 252(−8.5), 293(+2.6), 317(+4.5).

FIG. 10 B₂C₂ CD spectra (continued).

10A. 37. a. [calc]: 236(−23), 253(+44), 290(+28), 329(−5). b. [α-synth: 238(−26.7), 254(+33), 290(+23.2), 326(−6.4).

10B. 38. a. [calc]: 2519+23), 283(+21), 292sh(+19), 324(−3). b. [α-synth: 237(−12.5), 253(+17.1), 290(+16.5).

10C. 39. a. [calc]: 235(−5), 251(+5), 285(+8), 293sh(+8), 330(−2). b. [α-synth: 231(−4.4), 253(+2.9), 269sh(+2.9), 292(+6.1), 306sh(+4.6), 329(−3.3).

10D. 40. a. [calc]: 236(−4), 252(+40), 296(+9). b. [α-synth: 237(+14.5), 253(+23.6), 302(+10.4).

10E. 41. a. [calc]: 228(+3), 251(−58), 2193(+19). b. [α-synth: 232(+5.4), 252(−53.7), 284sh(+15.7), 299sh(+16.8), 306(17.3).

10F. 42. a. [calc]: 223(+3), 233sh(+2), 251(−15), 284(−16). b. [α-synth: 236(+6.9), 253(−9.3), 283sh(−12.2), 294(−12.5), 325(+0.9).

FIG. 11. B₂C CD Spectra (continued).

11A. 43. D-XylpBBC (R=H) or D-QuiBBC (R=Me) a. [calc]: 233(−10), 252(+56), 306(−12). b. β-XylBBC [synth]: 231(−5.0), 251(+46.4), 310(−13.2).

11B. 44. a. [calc]: 220(+4), 233(−2), 251(+48), 304((−8). b. α-GalNAcBBC [synth]: 233(−4), 251(+34.3), 294(−6).

11C. 45. a. [calc]: 233(−16), 252(+56), 307(−4).

11D. 46. a. [calc]: 221(+8). 250(+26), 299(−9). b. β-GlcNAcCBB [exp]: 227(−4.9), 251(+30), 304(−10.3).

11E. 47. a. [calc]: 249(+28), 284(−11), 311(−11).

11F. 48. a. [calc]: 251(+35), 291(−6), 303(−5).

FIG. 12 B₂C CD Spectra (continued).

12A. 49. a. [calc]: 249(+20), 304(−8). b. α-GlcNAcBCB [synth]: 247(+17), 296sh(−8.2). c. β-GlcNABCB [exp]: 248(+21.5), 308(−7.6).

12B. 50. a. [calc]: 248(+22), 283sh(−6), 311(−7).

12C. 51. a. [calc]: 231(−2), 250(+22), 311(−13).

12D. 52. a. [calc]: 248(+20), 293sh(−11), 311(−14).

12E. 53. a. [calc]: 218(+7), 234(−3), 251(+18), 298(−2).

12F. 54. a. [calc]: 237(+12), 259(−1), 302(−2). b. [α-synth]: 238(+5.5), 280(+2.3), 320(+2).

FIG. 13 B₂C CD spectra (continued).

13A. 55. L-FucBBC (R=Me) or D-ArapBBC (R=H) a. [calc]: 236(+28), 254(−40), 306(−24). b. β-L-FucBBC [synth]: 237(+24.5), 253(−29.4), 311(−19.6).

13B. 56. D-RhaCBB (R=Me) a. [calc]: 237(−40), 310(−21).

13C. 57. L-FucCBB (R=Me or D-ArapCBB (R=H) a. [calc]: 236(+13), 253(−30), 283sh(−14), 310(−15). b. β-L-FucCBB [synth]: 236(+12.3), 253(−23.4), 283sh(−12.8), 310(− 14.7).

13D. 58. D-RhaBBc (R=Me) a. [calc]: 235(+5), 252(−30), 283sh(−14), 311(−15).

13E. 59. L-FucBCB (R=Me) or D-ArapBCB (R=H) a. [calc]: 236(+7), 251(−15), 284sh(−18), 297(−20), 308(−20). b. β-L-FucBCB [synth]: 237(+11.6), 252(−14.2), 300(−18.9), 311(−19.4).

13F. 60. D-RhaBCB (R=Me) a. [calc]: 236(+5), 254(−10), 286sh(−17), 303(−20), 311(−20).

FIG. 14. B₂C CD Spectra (continued).

14A. 61. a. [calc]: 249(−10), 284sh(−3), 299sh(−4), 314(−5).

14B. 62. a. [calc]: 248(−14), 315(−1).

14C. 63. D-FucBCB (R=Me) or L-ArapBCB (R=H) a. [calc]: 236(−7), 251(+15), 284sh(+18), 297(+20), 308(+20); see 59b.

14D. 64. L-RhaBCB (R=Me) a. [calc]: 236(−5), 254(+10), 286sh(+17), 303(+20), 311(+20).
14E. 65. a. [calc]: 238(−10), 309(+15).
14F. 66. a. [calc]: 225(+5), 250(−5), 307(+9).
FIG. 15. B₂C CD Spectra (continued).
15A. 67. L-RhaCBB (R=Me) a. [calc]: 237(−26), 253(+40), 310(+21).
15B. 68. D-FucBBC (R=Me) or L-ArapBBC (R=H) a. [calc]: 236(−28), 254(+40), 306(+24); see 55b.
15C. 69. a. [calc]: 236(−17), 252(+45), 305(+3).
15D. 70. D-FucCBB (R=Me) or L-ArapCBB (R=H) a. [calc]: 236(−13), 253(+30), 283sh(+14), 310(+15); see 57b.
15E. 71. L-RhaBBC (R=Me) a. [calc]: 235(−5), 252(+30), 283sh(+14), 311(+15).
15F. 72. D-XylpBCB (R=H or D-QuiBCB (R=Me) a. [calc]: 229(+4), 251(−8), 314(+2).
FIG. 16. B₂C CD Spectra (continued).
16A. 73. a. [calc]: 234(+16), 252(−54), 282sh(+8), 296(+9), 311sh(+8).
16B. 74. D-XylpCBB (R=H) or D-QuiCBB (R=Me) a. [calc]: 230(+6), 251(−52), 286sh(+8), 294sh(+8), 311(+9). b. β-XylCBB [synth]: 229(+5.9), 251(−43.6), 295sh(+12.9), 311(+13.2).
16C. 75. a. [calc]: 234(+11), 252(−46), 292(+7), 303(+7). b. β-GlcNAcBBB [exp]: 233(+12.3), 251(−39.5), 289(+8.5).
16D. 76. a. [calc]: 231(+3), 251(−43), 282sh(+4), 295(+5), 309sh(+4).
16E. 77. a. [calc]: 249(−23), 283sh(+11), 308(+12).
16F. 78. a. [calc]: 225(+4), 248(−20), 309(+13). b. α-GalNAcBCB [synth]: 226(+4.6), 249(−17.8), 293sh(+9.2), 311(+10.8).
FIG. 17. B₂C CD Spectra (continued).
17A. 79. a. [calc]: 250(−28), 291(+7), 311sh(+5).
17B. 80. a. [calc]: 248(−12), 284sh(+9), 308(+10).
17C. 81. a. [calc]: 229(+5), 250(−15), 284sh(+13), 310(+14). b. ]α-synth]: 250(−13.8), 284sh(+9.4), 294sh(+10.3), 309(+10.8).
17D. 82. a. [calc]: 233(+2), 251(−9), 280sh(+4), 303(+6), 311sh(+5).
17E. 83. a. [calc]: 234(+11), 252(−13), 283(+6), 297(+6) 311(+6). b. α-GalNAcCBB [synth]: 236(+6.1), 252(−13), 285(+6.2), 309(+5.8).
17F. 84. a. [calc]: 233(+11), 252(−13), 282(+5), 294sh(+4), 309sh(+4).
FIG. 18 BC₂ CD Spectra.
18A. 85. a. [calc]: 288(+39), 323(−61).
18B. 86. D-XylpBCC (R=H) or D-QuiBCC (R=Me) a. [calc]: 249(−8), 287(+44), 323(−56). b. β-XylBCC [synth]: 247(−6.7), 287(+35.0), 323(−40.4).
18C. 87. a. [calc]: 287(+47), 322(−62). b. [α-synth]: 288(+42.3), 323(−58.1).
18D. 88. D-RhaBCC (R=Me) a. [calc]: 236(−8), 287(+31), 321(−75).
18E. 89. L-FucCCB (R=Me) or D-ArapCCB (R=H) a. [calc]: 286(+27), 321(−70). b. β-L-FucCCB [synth]: 253(+6.0), 287(+21.5), 320(−65).
FIG. 19. BC₂ CD Spectra (continued).
19A. 90. a. [calc]: 233(+2), 285(+13), 321(−31).
19B. 91. a. [calc]: 244(+8), 282(+10), 321(−11).
19C. 92. a. [calc]: 285(+5), 326(−4).
19D. 93. a. [calc]: 282(+6), 322(−6).
19E. 94. a. [calc]: 244(−8), 283sh(+4), 291(+6), 332(−1).
19F. 95. D-XylpCBC (R=H) or D-QuiCBC (R=Me) a. [calc]: 240(−7), 285(+6), 293(+6), 327(−3).
19G. 96. a. [calc]: 247(+9), 283sh(+2), 308sh(−2), 319(−3).

FIG. 20 BC₂ CD Spectra (continued).
20A. 97. L-FucBCC (=Me) or D-ArapBCC (R=H) a. [calc]: 247(+19), 319(−56). b. β-L-FucBCC [synth]: 247(+19.8), 319(−46.6).
20B. 98. D-RhaCCB (R=Me) a. [calc]: 247(+20), 319(−49).
20C. 99. L-FucCBC (R=Me) or D-ArapCBC (R=H) a. [calc]: 243(+26), 319(−53).
20D. 100. D-RhaCBC (R=Me) a. [calc]: 246(+21), 314(−27).
20E. 101. a. [calc]: 244(+3), 298sh(−7), 314(−8).
20F. 102. a. [calc]: 245(+5), 280sh(−6), 299sh(−9), 312(−10).
FIG. 21. BC₂ CD spectra (continued).
21A. 103. a. [calc]: 287(−32), 323(+62). b. [α-synth]: 288(−32), 323(+57.6).
21B. 104. D-XylpCCB (R=H) or D-QuiCCB (R=Me) a. [calc]: 249(+6), 288(−46), 323(+51). b. β-XylCCB [synth]: 250('4), 287(−29.6), 323(+38.8).
21C. 105. D-FucCCB (R=Me) or L-ArapCCB (R=H) a.a [calc]: 286(−27), 321(+70); see 89b.
21D. 106. a. [calc]: 287(−39), 322(+61).
21E. 107. L-RhaBCC (R=Me) a. [calc]: 236(−31), 322(+75).
21F. 108. a. [calc]: 246(+4), 285(−22), 322(+37).
FIG. 22. BC₂ CD Spectra (continued).
22A. 109. a. [calc]: 247(+4), 286(−16), 321(+32).
22B. 110. a. [calc]: 240(+8), 286(−13), 321(+20). b. [α-synth]: 241(+6.7), 279sh(−12.7), 287(−13.4), 322(+18.5).
22C. 111. a. [calc]: 248(+6), 285(−16), 322(+16).
22D. 112. a. [calc]: 247(+3), 283(−16), 321(+8).
22E. 113. a. [calc]: 247(+12), 284(−12), 324(+3).
22F. 114. a. [calc]: 250(+4), 284(−9), 321(+6).
FIG. 23. BC₂ CD Spectra (continued).
23A. 115. a. [calc]: 242(−6), 284(−9), 321(+5).
23B. 116. a. [calc]: 242(−16), 283(−12), 320(+11).
23C. 117. L-RhaCCB (R=Me) a. [calc]: 247(−20), 319(+49).
23D. 118. D-FucBCC (R=Me) or L-ArapBCC (R=H) a. [calc]: 247(−19), 319(+56); see 97b.
23E. 119. D-FucCBC (R=Me) or L-ArapCBC (R=H) a. [calc]: 243(−26), 319(+53).
23F. 120. a. [calc]: 250(−11), 284sh(+6), 295sh(+9), 316(+20). b. [α-synth]: 250(−7.0), 280(+3.4), 317(+9.6).
FIG. 24. BC₂ CD Spectra (continued).
24A. 121. L-RhaCBC (R=Me) a. [calc]: 246(−21), 314(+27).
24B. 122. a. [calc]: 245(−9), 284sh(+9), 299(+10), 311sh(+7).
24C. 123. a. [calc]: 245(−17), 294(+18), 307sh(+17). b. [α-synth]: 246(−16.7), 297(+16.2).
24D. 124. a. [calc]: 248(−10), 284(+17), 323(−5).
24E. 125. a. [calc]: 243(−10), 289(+19), 324(−10).
24F. 126. a. [calc]: 249(−4), 286(+19), 324(−11).

REFERENCES

[1] V. Ginsberg, P. W. Robbins, (Eds.), Biology of Carbohydrates, Vol. 2, Wiley, N.Y. 1984.
[2] S. B. Mahato, S. K. Sarkar, G. Poddar, Phytochem. 1988, 27, 3067.
[3] B. Lindberg, Chem. Soc. Rev. 1981, 10, 409; C. J. Biermann, G. D. McGinnis, (Eds.), Analysis of Carbohydrates by GLC and MS, CRC Press, Boca Raton, Fla., 1989.
[4] R. Geyer, H. Geyer, S. Kuhnhardt, W. Mink, S. Stirm, Anal. Biochem. 1983, 133, 197.
[5] K. Nakanishi, M. Kuroyanagi, H. Nambu, E. M. Oltz, R. Takeda, G. L. Verdine, A. Zask, Pure Appl. Chem. 1984, 56, 1031.

[6] K. Nakanishi, M. H. Park, R. Takeda, J. T. Vasquez, W. T. Wiesler, Stereochemistry of Organic and Bioorganic Transformations; Bartmann, W., Ed.; Verlag Chemie: 1986; pp. 303–319.

[7] R. Takeda, A. Zask, K. Nakanishi, M. H. Park, J. Am. Chem. Soc. 1987, 109, 914.

[8] M. H. Park, R. Takeda, K. Nakanishi, Tetrahedron Lett. 1987, 28, 3823.

[9] M. Chang, H. V. Meyers, K. Nakanishi, M. Ojika, J. H. Park, M. H. Park, R. Takeda, J. T. Vazquez, W. T. Wiesler, Pure Appl. Chem. 1989, 61, 1193.

[10] W. T. Wiesler, J. T. Vazquez, K. Nakanishi, J. Am. Chem. Soc. 1987, 109, 5586.

[11] J. T. Vazquez, W. T. Wiesler, K. Nakanishi, Carbohydr. Res. 1988, 176, 175.

[12] H. V. Meyers, M. Ojika, W. T. Wiesler, K. Nakanishi, Carbohydr. Res. 1989 (in press).

[13] Jeanes, A.; Wilham, C. A.; Hilbert, G. E. J. Am. Chem. Soc. 1953, 75, 3667.

[14] M. Ojika, H. V. Meyers, M. Chang, K. Nakanishi, J. Am. Chem. Soc. (in press).

[15] L. Rosenfeld, C. E. Bellou, Carb. Res., 1974, 32, 287.

[16] C. F. H. Allen, J. A. Van Allen, Org. Syn., Coil. Vol. 1955, 3, 751; K. Ohno, N. Naruse, H. Takeuchi, Tetrahedron Lett. 1979, 3, 251.

[17] H. W. Liu, K. Nakanishi, J. Am. Chem. Soc. 1982, 104, 1178.

[18] J. Golik, H. W. Liu, M. DiNovi, J. Furukawa, K. Nakanishi, Carbohydr. Res. 1983, 118, 135.

[19] N. Harada, K. Nakanishi, 'Circular Dichroic Spectroscopy—Exciton Coupling in Organic Stereochemistry, University Science Books: Mill Valley, Calif., 1983.

What is claimed is:

1. A method for determining the structure of a carbohydrate sample, comprising:

(a) perbenzoylating a carboydrate sample with a perbenzoylating agent to protect free hydroxyl groups in the carbohydrate sample;

(b) cleaving the glycosidic linkages of the perbenzoylated carbohydrate sample by contracting the carbohydrate sample with an amount of $BrCH_2COBr/H_2O$ effective to cleave the carbohydrate sample forming bromocetyl esters and α-bromo pyranosides;

(c) treating the resulting products with AgOAc and methanol or AgOTf/TMU and methanol to effect glycosidation;

(d) treating the resulting products with thiourea to remove bromoacetate groups;

(e) cinnamoylating the resulting products to effect methoxycinnamoylation of free hydroxyl groups;

(f) separating the resulting benzoates with high-pressure liquid chromatography;

(g) performing mass, ultraviolate and circular dichroic spectroscopy on the separated benzoates; and (h) comparing the spectra so obtained with reference spectra or calculated values to identify the structure of the carbohydrate.

2. A method in accordance with claim 1 wherein the perbenzoylating agent is para-bromobenzoyl chloride.

3. A method in accordance with claim 2 wherein the perbenzoylating step is carried out in the presence of silver triflate and dimethylaminopyridine.

4. A method in accordance with claim 1 wherein the cleavage step is performed in a glass tube sealed with a Teflon (PTFE) spindle valve.

5. A method in accordance with claim 4 wherein the ratio of $BrCH_2COBr$ to water is between 1:1.2 and 4:1.

6. A method in accordance with claim 5 wherein the ratio of $BrCH_2COBr$ to water is about 1:2 and about 1:0.8.

7. A method in accordance with claim 6 wherein the cleavage step is carried out at a temperature between about 0° C. and about 75° C.

8. A method in accordance with claim 6 wherein the carbohydrate sample is an oligosaccharide.

9. A method in accordance with claim 6 wherein the carbohydrate sample is a polysaccharide.

10. A method in accordance with claim 7 wherein the methoxycinnamoylation step is accomplished using para-methoxycinnamoyl chloride in the presence of dimethylamino pyridine and silver triflate.

11. An apparatus for use in determining the structure of a carbohydrate, comprising:

at least one reaction vessel for reacting a carbohydrate sample with reagents to cleave the carbohydrates into subunits and introduce chromophoric entities onto the subunits;

means for introducing the reagents into the reaction vessel;

means for removing a sample from the reaction vessel;

means for separating benzoates resulting from introduction of chromophoric entities onto the subunits;

means for delivering a sample of the separated benzoates to each of a plurality of spectrophotometric instruments;

means for determining the mass spectrum of a sample of the resulting benzoates;

means for determining the ultraviolet spectrum of a sample of the resulting benzoates;

means for determining the circular dichroic spectrum of a sample of the resulting benzoates; and means for comparing the mass, ultraviolet and circular dichroic spectra to reference spectra or calculated values in order to determine the structure of the sample carbohydrate.

12. An apparatus in accordance with claim 11 wherein the reaction vessel is a glass tube having a Teflon (PTFE) spindle valve as a closure.

13. An apparatus in accordance with claim 11 wherein the means for separating benzoates is a high pressure liquid chromatograph.

14. An apparatus in accordance with claim 11 wherein the means for comparing the mass, ultraviolet and circular dichroic spectra with reference spectra or calculated values comprises:

means for converting mass, ultraviolet and circular dichroic spectra into a series of spectral signals;

means for storing reference spectra or calculates values in the form of a plurality of reference signals; and means activated by the spectral signal for comparing the series of spectral signals to each of the reference signals to determine whether a substantial similarity exists between the spectral signals and the reference signals and to indicate the structure of a carbohydrate sample based upon a substantial similarity between the spectral signals and the reference signals.

15. A method for cleaving a carbohydrate comprising (a) perbenzoylating the carbohydrate with a perbenzoylating agent to protect free hydroxyl groups in the carbohydrate;

(b) contacting the perbenzoylated carbohydrate with an amount of $BrCH_2COBr/H_2O$ effective to cleave the carbohydrate;

(c) treating the product of step (b) with AgOAc and methanol or AgOTf/TMU and methanol to effect glycosildation; and (d) treating the product of step (c) with thiourea to remove bromoacetate groups.

16. A method in accordance with claim 15 wherein the ratio of $BrCH_2COBr$ to water is between 1:1.2 and 4:1.

17. A method in accordance with claim 16 wherein the ratio of $BrCH_2COBr$ to water is between about 1:1.2 and about 1:0.8.

18. A method in accordance with claim 17 wherein the carbohydrate is an oligosaccharide, polysaccharide, or complex carbohydrate.

\* \* \* \* \*